US011771754B2

(12) United States Patent
Li et al.

(10) Patent No.: US 11,771,754 B2
(45) Date of Patent: Oct. 3, 2023

(54) MUTANT OF L1 PROTEIN OF HUMAN PAPILLOMAVIRUS TYPE 18

(71) Applicants: XIAMEN UNIVERSITY, Fujian (CN); XIAMEN INNOVAX BIOTECH CO., LTD., Fujian (CN)

(72) Inventors: Shaowei Li, Fujian (CN); Shuo Song, Fujian (CN); Maozhou He, Fujian (CN); Jingjie Shi, Fujian (CN); Ying Gu, Fujian (CN); Ningshao Xia, Fujian (CN)

(73) Assignees: XIAMEN UNIVERSITY, Fujian (CN); XIAMEN INNOVAX BIOTECH CO., LTD., Fujian (CN)

( * ) Notice: Subject to any disclaimer, the term of this patent is extended or adjusted under 35 U.S.C. 154(b) by 171 days.

(21) Appl. No.: 15/734,670

(22) PCT Filed: Jun. 4, 2019

(86) PCT No.: PCT/CN2019/089979
§ 371 (c)(1),
(2) Date: Dec. 3, 2020

(87) PCT Pub. No.: WO2019/233412
PCT Pub. Date: Dec. 12, 2019

(65) Prior Publication Data
US 2021/0228703 A1    Jul. 29, 2021

(30) Foreign Application Priority Data

Jun. 4, 2018 (CN) .......................... 201810566208.8

(51) Int. Cl.
*A61K 39/12* (2006.01)
*C07K 14/005* (2006.01)
*C12N 7/00* (2006.01)
*A61K 39/00* (2006.01)

(52) U.S. Cl.
CPC ............... *A61K 39/12* (2013.01); *C12N 7/00* (2013.01); *A61K 2039/53* (2013.01); *C12N 2710/20022* (2013.01); *C12N 2710/20023* (2013.01); *C12N 2710/20034* (2013.01); *C12N 2710/20071* (2013.01)

(58) Field of Classification Search
None
See application file for complete search history.

(56) References Cited

U.S. PATENT DOCUMENTS 8,748,127 B2 * 6/2014 Li .......................... A61K 39/12
                                                                435/252.8

FOREIGN PATENT DOCUMENTS

EP    2154149 A1    2/2010

OTHER PUBLICATIONS

PCT/CN2019/089979 International Search Report dated Aug. 26, 2019.
Varsani, et al., Chimeric Human Papillomavirus Type 16 (HPV-16) L1 Particles Presenting the Common Neutralizing Epitope for the L2 Minor Capsid Protein of HPV-6 and HPV-16, Journal of Virology, vol. 77, No. 15, Aug. 31, 2003, pp. 8386-8393, Am Soc for Microbiology.
EP 19815298 Extended European Search Report dated Mar. 1, 2022.
Chen, H-S., et al., Papillomavirus capsid proteins mutually impact structure; Virology, Elsevier, vol. 412, No. 2, pp. 378-383, Jauary 14, 2011.
Chen, H-S., et al., Study of infectious virus production from HPV18/16 capsid chimeras, Virology, Elsevier, vol. 405, No. 2, pp. 289-299, Sep. 30, 2010.

* cited by examiner

*Primary Examiner* — Agnieszka Boesen
(74) *Attorney, Agent, or Firm* — Honigman LLP; Thomas A. Wootton, Esq.

(57) ABSTRACT

The present invention relates to a mutated HPV18 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (for example, HPV18 and HPV45, or HPV18, HPV45 and HPV59), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

20 Claims, 11 Drawing Sheets
Specification includes a Sequence Listing.

MUTANT OF L1 PROTEIN OF HUMAN PAPILLOMAVIRUS TYPE 18

CROSS-REFERENCE TO RELATED APPLICATIONS

This application is a National Stage Application and claims priority under 35 U.S.C. § 371 to Patent Cooperation Treaty application PCT/CN2019/089979, filed Jun. 4, 2019, which claims the benefit of Chinese Patent Application No. 201810566208.8, filed Jun. 4, 2018, priority is claimed to both of these applications and the disclosures of these prior applications are considered part of the disclosure of this application and to the extent allowed the entire contents of the aforementioned applications are incorporated herein.

SEQUENCE LISTING

This application incorporates by reference in its entirety the Sequence Listing entitled "2020-12-03_235427-482188_ST25.txt" is 153,094 bytes in size and was created on Dec. 3, 2020, and filed electronically herewith.

TECHNICAL FIELD

The invention relates to the field of molecular virology and immunology. In particular, the invention relates to a mutated HPV18 L1 protein (or a variant thereof), a sequence encoding the same, a method for preparing the same, and a virus-like particle comprising the same, wherein the protein (or a variant thereof) and the virus-like particle can induce the generation of neutralizing antibodies against at least two HPV types (e.g. HPV18 and HPV45, or HPV18, HPV45 and HPV59), and therefore can be used to prevent infection by said at least two HPV types, and a disease caused by said infection, such as cervical cancer and condyloma acuminatum. The invention further relates to the use of the protein and the virus-like particle in the manufacture of a pharmaceutical composition or a vaccine for preventing infection by said at least two HPV types, and a disease caused by said infection, such as cervical cancer and condyloma acuminatum.

BACKGROUND ART

Human Papillomavirus (HPV) mainly causes warts in skin and mucosa. HPV types are divided into high-risk types and low-risk types depending on their association with tumorigenesis. Among them, infection by high-risk HPV types has been demonstrated to be the leading cause of genital cancer including cervical cancer in women; and low-risk HPV types mainly cause condyloma acuminatum. The most effective way to prevent and control HPV infection is to vaccinate HPV vaccines, particularly vaccines against high-risk HPV types causing cervical cancer.

Major capsid protein L1 of HPV has the characteristic of self-assembling into hollow Virus-Like Particle (VLP). HPV VLP has a symmetrical icosahedral structure composed of 72 pentamers of major capsid protein L1 (Doorbar, J. and P. H. Gallimore. 1987. J Virol, 61(9): 2793-9). HPV VLP is highly similar to natural HPV in terms of structure, retains most of the neutralizing epitopes of natural virus, and can induce the generation of high-titer neutralizing antibodies (Kirnbauer, R., F. Booy, et al. 1992 Proc Natl Acad Sci USA 89(24): 12180-4).

However, the existing studies show that HPV VLPs mainly induce the generation of neutralizing antibodies against the same HPV type, produce the protective immunity against the same HPV type, and only have low cross-protective effect among a few highly homologous HPV types (Sara L. Bissett, Giada Mattiuzzo, et al. 2014 Vaccine. 32:6548-6555). Therefore, the existing HPV vaccines have a very limited protection range. In general, VLP of one HPV type can only be used to prevent infection by the same HPV type. In this case, if it needs to broaden the protection range of HPV vaccines, the only way is to add VLPs of more HPV types in vaccines. Currently, the commercially available HPV vaccines, including Gardasil® from Merck (which is a quadrivalent vaccine against HPV16, 18, 6 and 11), Cervarix® from GSK (which is a bivalent vaccine against HPV16 and 18), and Gardasil®9 from Merck (which is a 9-valent vaccine against HPV6, 11, 16, 18, 31, 33, 45, 52 and 58), are prepared by combining VLPs of multiple HPV types. However, such a solution would greatly increase the production cost of HPV vaccines, and might cause safety problem due to an increase in immunizing dose.

Therefore, it is urgent in the art to develop HPV virus-like particles capable of inducing the generation of protective neutralizing antibodies against multiple HPV types, so as to prevent infection by multiple HPV types, and a disease caused by the infection, such as cervical cancer and condyloma acuminatum, more economically and effectively.

CONTENTS OF INVENTION

The invention is at least partially based on the inventors' surprising discovery: after substitution of a specific segment of L1 protein of Human Papillomavirus (HPV) Type 18 with the corresponding segment of L1 protein of a second HPV type (such as HPV45), the mutated HPV18 L1 protein thus obtained can induce the generation of high-titer neutralizing antibodies against HPV18 and the second HPV type (such as HPV45) in organisms, and its protection effect is comparable to that of a mixture of HPV18 VLP and VLP of the second HPV type, its protection effect against HPV18 is comparable to that of HPV18 VLP alone, and its protection effect against the second HPV type (such as HPV45) is comparable to that of the VLP of the second HPV type alone.

In addition, based on the substitution above, another specific segment of HPV18 L1 protein can be further substituted with the corresponding segment of L1 protein of a third HPV type (such as HPV59), and the mutated HPV18 L1 protein having double substitutions thus obtained can induce the generation of high-titer neutralizing antibodies against HPV18, the second HPV type (such as HPV45) and the third HPV type (such as HPV59); and its protection effect is comparable to that of a mixture of HPV18 VLP, VLP of the second HPV type and VLP of the third HPV type, its protection effect against HPV18 is comparable to that of HPV18 VLP alone, its protection effect against the second HPV type (such as HPV45) is comparable to that of the VLP of the second HPV type alone, and its protection effect against the third HPV type (such as HPV59) is comparable to that of the VLP of the third HPV type alone.

Therefore, in an aspect, the invention provides a mutated HPV18 L1 protein or a variant thereof, wherein as compared with a wild type HPV18 L1 protein, the mutated HPV18 L1 protein has the following mutations:

(1) N-terminal truncation of 40-80 amino acids, for example 40-50, 45-70, 50-70, 55-65, 60-70, 65-75, 60-80, or 70-80 amino acids; and (2) (a) substitution of amino acid residues at positions 235-243 of the wild type HPV18 L1 protein with amino acid residues at the corresponding positions of a L1 protein of a second type of wild-type HPV; or (b) substitution of amino acid residues at positions 327-346 of the wild type HPV18 L1 protein with amino acid residues at the corresponding positions of a L1 protein of a second type of wild-type HPV; or (c) substitution of amino acid residues at positions 114-123 of the wild type HPV18 L1 protein with amino acid residues at the corresponding positions of a L1 protein of a second type of wild-type HPV; or (d) substitution of amino acid residues at positions 176-202 of the wild type HPV18 L1 protein with amino acid residues at the corresponding positions of a L1 protein of a second type of wild-type HPV, and, the variant differs from the mutated HPV18 L1 protein only by substitution (preferably conservative substitution), addition or deletion of one or more (e.g. 1, 2, 3, 4, 5, 6, 7, 8 or 9) amino acids, and retains the function of the mutated HPV18 L1 protein, i.e. capability of inducing generation of neutralizing antibodies against at least two HPV types (e.g. HPV18 and HPV45, or HPV18, HPV45 and HPV59).

In some preferred embodiments, the mutated HPV18 L1 protein has the mutation as defined in (2) (a) or (2) (b), and optionally, further has the following mutation:

(3) substitution of amino acid residues at positions 112-123 of the wild type HPV18 L1 protein with amino acid residues at the corresponding positions of a L1 protein of a third type of wild-type HPV.

In some preferred embodiments, the mutated HPV18 L1 protein has the mutation as defined in (2) (c) or (2) (d), and optionally, further has the following mutation:

(4) substitution of amino acid residues at positions 410-421 of the wild type HPV18 L1 protein with amino acid residues at the corresponding positions of a L1 protein of a third type of wild-type HPV.

In some preferred embodiments, the mutated HPV18 L1 protein has the mutations as defined in (2) (c) and (2) (a), and optionally, further has the mutation as defined in (4).

In some preferred embodiments, the mutated HPV18 L1 protein has the following mutations: substitution of amino acid residues at positions 235-243 of the wild type HPV18 L1 protein with amino acid residues at the corresponding positions of a L1 protein of a second type of wild-type HPV, and substitution of amino acid residues at positions 112-123 of the wild type HPV18 L1 protein with amino acid residues at the corresponding positions of a L1 protein of a third type of wild-type HPV.

In some preferred embodiments, the mutated HPV18 L1 protein has the following mutations: substitution of amino acid residues at positions 327-346 of the wild type HPV18 L1 protein with amino acid residues at the corresponding positions of a L1 protein of a second type of wild-type HPV, and substitution of amino acid residues at positions 112-123 of the wild type HPV18 L1 protein with amino acid residues at the corresponding positions of a L1 protein of a third type of wild-type HPV.

In some preferred embodiments, the mutated HPV18 L1 protein has the following mutations: substitution of amino acid residues at positions 114-123 of the wild type HPV18 L1 protein with amino acid residues at the corresponding positions of a L1 protein of a second type of wild-type HPV, and substitution of amino acid residues at positions 410-421 of the wild type HPV18 L1 protein with amino acid residues at the corresponding positions of a L1 protein of a third type of wild-type HPV.

In some preferred embodiments, the mutated HPV18 L1 protein has the following mutations: substitution of amino acid residues at positions 176-202 of the wild type HPV18 L1 protein with amino acid residues at the corresponding positions of a L1 protein of a second type of wild-type HPV, and substitution of amino acid residues at positions 410-421 of the wild type HPV18 L1 protein with amino acid residues at the corresponding positions of a L1 protein of a third type of wild-type HPV.

In some preferred embodiments, the mutated HPV18 L1 protein has the following mutations: substitution of amino acid residues at positions 114-123 of the wild type HPV18 L1 protein with amino acid residues at the corresponding positions of a L1 protein of a second type of wild-type HPV, and substitution of amino acid residues at positions 235-243 of the wild type HPV18 L1 protein with amino acid residues at the corresponding positions of a L1 protein of a second type of wild-type HPV, and substitution of amino acid residues at positions 410-421 of the wild type HPV18 L1 protein with amino acid residues at the corresponding positions of a L1 protein of a third type of wild-type HPV.

In some preferred embodiments, the mutated HPV18 L1 protein has 45, 50, 52, 55, 58, 60, 62, 65, 68, 70, 72, 75 or 78 amino acids truncated at N-terminal, as compared with the wild type HPV18 L1 protein.

In some preferred embodiments, the mutated HPV18 L1 protein has 65 amino acids truncated at N-terminal, as compared with the wild type HPV18 L1 protein.

In some preferred embodiments, the second type of wild-type HPV is HPV45. In some preferred embodiments, the amino acid residues at the corresponding positions as described in (2) (a) are amino acid residues at positions 201-209 of a wild type HPV45 L1 protein. In some preferred embodiments, the amino acid residues at the corresponding positions as described in (2) (b) are amino acid residues at positions 293-314 of a wild type HPV45 L1 protein. In some preferred embodiments, the amino acid residues at the corresponding positions as described in (2) (c) are amino acid residues at positions 79-89 of a wild type HPV45 L1 protein. In some preferred embodiments, the amino acid residues at the corresponding positions as described in (2) (d) are amino acid residues at positions 142-168 of a wild type HPV45 L1 protein.

In some preferred embodiments, the third type of wild-type HPV is HPV59. In some preferred embodiments, the amino acid residues at the corresponding positions as described in (3) are amino acid residues at positions 51-62 of a wild type HPV59 L1 protein. In some preferred embodiments, the amino acid residues at the corresponding positions as described in (4) are amino acid residues at positions 349-360 of a wild type HPV59 L1 protein.

In some preferred embodiments, the wild type HPV18 L1 protein has an amino acid sequence as set forth in SEQ ID NO: 1 or 113.

In some preferred embodiments, the wild type HPV45 L1 protein has an amino acid sequence as set forth in SEQ ID NO: 2 or 115.

In some preferred embodiments, the wild type HPV59 L1 protein has an amino acid sequence as set forth in SEQ ID NO: 3.

In some preferred embodiments, the amino acid residues at positions 79-89 of the wild type HPV45 L1 protein have a sequence as set forth in SEQ ID NO: 39.

In some preferred embodiments, the amino acid residues at positions 142-168 of the wild type HPV45 L1 protein have a sequence as set forth in SEQ ID NO: 40.

In some preferred embodiments, the amino acid residues at positions 201-209 of the wild type HPV45 L1 protein have a sequence as set forth in SEQ ID NO: 41.

In some preferred embodiments, the amino acid residues at positions 293-314 of the wild type HPV45 L1 protein have a sequence as set forth in SEQ ID NO: 42.

In some preferred embodiments, the amino acid residues at positions 51-62 of the wild type HPV59 L1 protein have a sequence as set forth in SEQ ID NO: 43.

In some preferred embodiments, the amino acid residues at positions 349-360 of the wild type HPV59 L1 protein have a sequence as set forth in SEQ ID NO: 44.

In some preferred embodiments, the mutated HPV18 L1 protein has an amino acid sequence selected from the group consisting of: SEQ ID NO: 4, 5, 6, 7, 9, 13, 17, 18 and 19.

In some preferred embodiments, the mutated HPV18 L1 protein has an amino acid sequence selected from the group consisting of: SEQ ID NO: 6, 7, 9, 13, 17, 18 and 19.

In another aspect, the invention provides an isolated nucleic acid, encoding the mutated HPV18 L1 protein or a variant thereof as described above. In another aspect, the invention provides a vector comprising the isolated nucleic acid. In some preferred embodiments, the isolated nucleic acid according to the invention has a nucleotide sequence selected from the group consisting of: SEQ ID NO: 23, 24, 25, 26, 28, 32, 36, 37 and 38. In some more preferred embodiments, the isolated nucleic acid according to the invention has a nucleotide sequence selected from the group consisting of: SEQ ID NO: 25, 26, 28, 32, 36, 37 and 38.

Vectors useful for insertion of a polynucleotide of interest are well known in the art, including, but not limited to cloning vectors and expression vectors. In one embodiment, the vectors are, for example, plasmids, cosmids, phages, etc.

In another aspect, the invention further relates to a host cell comprising the isolated nucleic acid or the vector. The host cell includes, but is not limited to prokaryotic cells such as *E. coli* cells, and eukaryotic cells such as yeast cells, insect cells, plant cells and animal cells (such as mammalian cells, for example, mouse cells, human cells, etc.). The host cell according to the invention may also be a cell line, such as 293T cell.

In another aspect, the invention relates to a HPV virus-like particle, comprising or consisting of the mutated HPV18 L1 protein or a variant thereof according to the invention.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 235-243 of the wild type HPV18 L1 protein with the amino acid residues at positions 201-209 of a wild type HPV45 L1 protein.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 327-346 of the wild type HPV18 L1 protein with the amino acid residues at positions 293-314 of a wild type HPV45 L1 protein.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 114-123 of the wild type HPV18 L1 protein with the amino acid residues at positions 79-89 of a wild type HPV45 L1 protein.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 176-202 of the wild type HPV18 L1 protein with the amino acid residues at positions 142-168 of a wild type HPV45 L1 protein.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 235-243 of the wild type HPV18 L1 protein with the amino acid residues at positions 201-209 of a wild type HPV45 L1 protein, and substitution of the amino acid residues at positions 112-123 of the wild type HPV18 L1 protein with the amino acid residues at positions 51-62 of a wild type HPV59 L1 protein.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 327-346 of the wild type HPV18 L1 protein with the amino acid residues at positions 293-314 of a wild type HPV45 L1 protein, and substitution of the amino acid residues at positions 112-123 of the wild type HPV18 L1 protein with the amino acid residues at positions 51-62 of a wild type HPV59 L1 protein.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 114-123 of the wild type HPV18 L1 protein with the amino acid residues at positions 79-89 of a wild type HPV45 L1 protein, and substitution of the amino acid residues at positions 410-421 of the wild type HPV18 L1 protein with the amino acid residues at positions 349-360 of a wild type HPV59 L1 protein.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 176-202 of the wild type HPV18 L1 protein with the amino acid residues at positions 142-168 of a wild type HPV45 L1 protein, and substitution of the amino acid residues at positions 410-421 of the wild type HPV18 L1 protein with the amino acid residues at positions 349-360 of a wild type HPV59 L1 protein.

In some preferred embodiments, the HPV virus-like particle according to the invention comprises the mutated HPV18 L1 protein, which has N-terminal truncation of 40-80 amino acids, for example, 40-50, 45-70, 50-70, 55-65, 60-70, 65-75, 60-80 or 70-80 amino acids, e.g. 45, 50, 52, 55, 58, 60, 62, 65, 68, 70, 72, 75 or 78 amino acids, as compared to a wild type HPV18 L1 protein, and substitution of the amino acid residues at positions 114-123 of the wild type HPV18 L1 protein with the amino acid residues at positions 79-89 of a wild type HPV45 L1 protein, and substitution of the amino acid residues at positions 235-243 of the wild type HPV18 L1 protein with the amino acid residues at positions 201-209 of a wild type HPV45 L1 protein, and substitution of the amino acid residues at positions 410-421 of the wild type HPV18 L1 protein with the amino acid residues at positions 349-360 of a wild type HPV59 L1 protein.

In a particularly preferred embodiment, the HPV virus-like particle according to the invention comprises the mutated HPV18 L1 protein, which has a sequence as set forth in SEQ ID NO: 4, 5, 6, 7, 9, 13, 17, 18 or 19.

In another aspect, the invention further relates to a composition comprising the mutated HPV18 L1 protein or a variant thereof, the isolated nucleic acid, the vector, the host cell, or the HPV virus-like particle. In some preferred embodiments, the composition comprises the mutated HPV18 L1 protein or a variant thereof according to the invention. In some preferred embodiments, the composition comprises the HPV virus-like particle according to the invention.

In another aspect, the invention further relates to a pharmaceutical composition or vaccine, comprising the HPV virus-like particle according to the invention, and optionally a pharmaceutically acceptable carrier and/or excipient. The pharmaceutical composition or vaccine according to the invention can be used for preventing HPV infection, or a disease caused by HPV infection, such as cervical cancer and condyloma acuminatum.

In some preferred embodiments, the HPV virus-like particle is present in an amount effective for preventing HPV infection or a disease caused by HPV infection. In some preferred embodiments, the HPV infection is infection by one or more HPV types (e.g. HPV18 infection, HPV45 infection and/or HPV59 infection). In some preferred embodiments, the disease caused by HPV infection is selected from the group consisting of cervical cancer and condyloma acuminatum.

The pharmaceutical composition or vaccine according to the invention may be administrated by methods well known in the art, for example, but not limited to, orally or by injection. In the invention, a particularly preferred administration route is injection.

In some preferred embodiments, the pharmaceutical composition or vaccine according to the invention is administrated in a form of a unit dosage. For example, but not for limiting the invention, each unit dosage contains 5 μg-80 μg, preferably 20 μg-40 μg of HPV virus-like particle.

In another aspect, the invention relates to a method for preparing the mutated HPV18 L1 protein or a variant thereof as described above, comprising expressing the mutated HPV18 L1 protein or a variant thereof in a host cell, and then recovering the mutated HPV18 L1 protein or a variant thereof from a culture of the host cell.

In some preferred embodiments, the host cell is *E. coli*.

In some preferred embodiments, the method comprises the steps of: expressing the mutated HPV18 L1 protein or a variant thereof in *E. coli*, and then obtaining the mutated HPV18 L1 protein or a variant thereof by purifying a lysate supernatant of the *E. coli*. In some preferred embodiments, the mutated HPV18 L1 protein or a variant thereof is recovered from the lysate supernatant of the *E. coli* by chromatography (e.g. cation-exchange chromatography, hydroxyapatite chromatography and/or hydrophobic interaction chromatography).

In another aspect, the invention relates to a method for preparing a vaccine, comprising combining the HPV virus-like particle according to the invention with a pharmaceutically acceptable carrier and/or excipient.

In another aspect, the invention relates to a method for preventing HPV infection or a disease caused by HPV infection, comprising administering to a subject a prophylactically effective amount of the HPV virus-like particle or the pharmaceutical composition or vaccine according to the invention. In a preferred embodiment, the HPV infection is infection by one or more HPV types (e.g. HPV18 infection, HPV45 infection and/or HPV59 infection). In another preferred embodiment, the disease caused by HPV infection includes, but is not limited to cervical cancer and condyloma acuminatum. In another preferred embodiment, the subject is mammal, such as human.

In another aspect, the invention further relates to use of the mutated HPV18 L1 protein or a variant thereof or the HPV virus-like particle according to the invention in the manufacture of a pharmaceutical composition or vaccine for preventing HPV infection or a disease caused by HPV infection. In a preferred embodiment, the HPV infection is infection by one or more HPV types (e.g. HPV18 infection, HPV45 infection and/or HPV59 infection). In another preferred embodiment, the disease caused by HPV infection includes, but is not limited to, cervical cancer and condyloma acuminatum.

In another aspect, the invention further relates to the mutated HPV18 L1 protein or a variant thereof or the HPV virus-like particle according to the invention for the prevention of HPV infection or a disease caused by HPV infection. In a preferred embodiment, the HPV infection is infection by one or more HPV types (e.g. HPV18 infection, HPV45 infection and/or HPV59 infection). In another preferred embodiment, the disease caused by HPV infection includes, but is not limited to, cervical cancer and condyloma acuminatum.

DEFINITIONS OF TERMS IN PRESENT INVENTION

In the invention, unless otherwise specified, the scientific and technical terms used herein have the meanings generally understood by a person skilled in the art. Moreover, the laboratory operations of cell culture, molecular genetics, nucleic acid chemistry, and immunology used herein are the routine operations widely used in the corresponding fields. Meanwhile, in order to better understand the invention, the definitions and explanations of the relevant terms are provided as follows.

According to the invention, the term "a second type of wild-type HPV" refers to a wild-type HPV type other than HPV18. In the invention, a second type of wild-type HPV is preferably wild type HPV45. According to the invention, the term "a third type of wild-type HPV" refers to a wild-type HPV type other than HPV18 and the second type of wild-type HPV. In the invention, a third type of wild-type HPV is preferably wild type HPV59.

According to the invention, the expression "corresponding positions" refers to the equivalent positions of the sequences being compared when the sequences are optimally aligned, i.e. the sequences are aligned to obtain a highest percentage of identity.

According to the invention, the term "wild type HPV18 L1 protein" refers to the naturally-occurring major capsid protein L1 in Human Papillomavirus Type 18 (HPV18). The sequence of wild type HPV18 L1 protein is well known in the art, and can be found in public database (such as Accession No. ARS43428.1, ARS43407.1, ARS43401.1, AAP20601.1 and ABP99727.1 in NCBI database).

In the invention, when an amino acid sequence of wild type HPV18 L1 protein is mentioned, it is described by reference to the sequence as set forth in SEQ ID NO: 1. For example, the expression "amino acid residues at positions 235-243 of a wild type HPV18 L1 protein" refers to the amino acid residues at positions 235-243 of the polypeptide as set forth in SEQ ID NO: 1. However, a person skilled in the art understands that wild type HPV18 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV18 isolates, and have substantively the same biological function. Therefore, in the invention, the term "wild type HPV18 L1 protein" includes not only the protein as set forth in SEQ ID NO: 1, but also L1 protein of various HPV18 isolates (such as HPV18 L1 protein as set forth in ARS43428.1, ARS43407.1, ARS43401.1, AAP20601.1 and ABP99727.1). Moreover, when a sequence fragment of a wild type HPV18 L1 protein is described, it includes not only the sequence fragment of SEQ ID NO: 1, but also the corresponding sequence fragment of a L1 protein of various HPV18 isolates. For example, the expression "amino acid residues at positions 235-243 of a wild type HPV18 L1 protein" includes the amino acid residues at positions 235-243 of SEQ ID NO: 1, and the corresponding fragment of a L1 protein of various HPV18 isolates.

According to the invention, the term "wild type HPV45 L1 protein" refers to the naturally-occurring major capsid protein L1 in Human Papillomavirus Type 45 (HPV45). The sequence of wild type HPV45 L1 protein is well known in the art, and can be found in public database (such as Accession No. P36741.1, ALV85689.1, ABP99815.1, AGU90600.1 and ALV85649.1 in NCBI database).

In the invention, when an amino acid sequence of wild type HPV45 L1 protein is mentioned, it is described by reference to the sequence as set forth in SEQ ID NO: 2. For example, the expression "amino acid residues at positions 201-209 of a wild type HPV45 L1 protein" refers to the amino acid residues at positions 201-209 of the polypeptide as set forth in SEQ ID NO: 2. However, a person skilled in the art understands that wild type HPV45 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV45 isolates, and have substantively the same biological function. Therefore, in the invention, the term "wild type HPV45 L1 protein" includes not only the protein as set forth in SEQ ID NO: 2, but also L1 protein of various HPV45 isolates (such as HPV45 L1 protein as set forth in P36741.1, ALV85689.1, ABP99815.1, AGU90600.1 and ALV85649.1). Moreover, when a sequence fragment of a wild type HPV45 L1 protein is described, it includes not only the sequence fragment of SEQ ID NO: 2, but also the corresponding sequence fragment of a L1 protein of various HPV45 isolates. For example, the expression "amino acid residues at positions 201-209 of a wild type HPV45 L1 protein" includes the amino acid residues at positions 201-209 of SEQ ID NO: 2, and the corresponding fragment of a L1 protein of various HPV45 isolates.

According to the invention, the term "wild type HPV59 L1 protein" refers to the naturally-occurring major capsid protein L1 in Human Papillomavirus Type 59 (HPV59). The sequence of wild type HPV59 L1 protein is well known in the art, and can be found in public database (such as Accession No. CAA54856.1, AGU90656.1, AEP23088.1, AEP23087.1 and AGU90672.1 in NCBI database).

In the invention, when an amino acid sequence of wild type HPV59 L1 protein is mentioned, it is described by reference to the sequence as set forth in SEQ ID NO: 3. For example, the expression "amino acid residues at positions 51-62 of a wild type HPV59 L1 protein" refers to amino acid residues at positions 51-62 of the polypeptide as set forth in SEQ ID NO: 3. However, a person skilled in the art understands that wild type HPV59 may include various isolates, and there might be difference in the amino acid sequence of L1 protein among various isolates. Furthermore, a person skilled in the art understands that although there might be difference in sequence, the amino acid sequences of L1 protein have a very high identity (generally higher than 95%, e.g. higher than 96%, higher than 97%, higher than 98%, or higher than 99%) among different HPV59 isolates, and have substantively the same biological function. Therefore, in the invention, the term "wild type HPV59 L1 protein" includes not only the protein as set forth in SEQ ID NO: 3, but also L1 protein of various HPV59 isolates (such as HPV59 L1 protein as set forth in CAA54856.1, AGU90656.1, AEP23088.1, AEP23087.1 and AGU90672.1). Moreover, when a sequence fragment of a wild type HPV59 L1 protein is described, it includes not only the sequence fragment of SEQ ID NO: 3, but also the corresponding sequence fragment of L1 protein of various HPV59 isolates. For example, the expression "amino acid residues at positions 51-62 of a wild type HPV59 L1 protein" includes the amino acid residues at positions 51-62 of SEQ ID NO: 3, and the corresponding fragment of L1 protein of various HPV59 isolates.

According to the invention, the expression "corresponding sequence fragments" or "corresponding fragments" refers to the fragments that are located at equivalent positions of the sequences being compared when the sequences are optimally aligned, i.e. the sequences are aligned to obtain a highest percentage of identity.

According to the invention, the expression "N-terminal truncation of X amino acids" or "having X amino acids truncated at N-terminal" refers to substitution of the amino acid residues from positions 1 to X at the N-terminal of a protein with methionine residue encoded by an initiator codon (for initiating protein translation). For example, a HPV18 L1 protein having 65 amino acids truncated at N-terminal refers to a protein resulted from substituting the amino acid residues from positions 1 to 65 at the N-terminal of wild type HPV18 L1 protein with methionine residue encoded by an initiator codon.

According to the invention, the term "variant" refers to a protein, whose amino acid sequence has substitution (preferably conservative substitution), addition or deletion of one or more (e.g. 1, 2, 3, 4, 5, 6, 7, 8 or 9) amino acids, or has an identity of at least 90%, 95%, 96%, 97%, 98%, or 99%, as compared with the mutated HPV18 L1 protein according to the invention (for example, the protein as set forth in SEQ ID NO: 6, 7, 9, 13, 17, 18 or 19), and which retains a function of the mutated HPV18 L1 protein according to the invention. In the invention, the term "function of the mutated HPV18 L1 protein" refers to a capability of inducing generation of neutralizing antibodies against at least two HPV types (e.g. HPV18 and HPV45, or HPV18, HPV45 and HPV59). The term "identity" refers to a measure of similarity between nucleotide sequences or amino acid sequences. Generally, sequences were aligned to obtain a maximum matching. "Identity" has well-known meanings in the art and can be calculated by published algorithm (such as BLAST).

According to the invention, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two polypeptides has a lysine at a certain site), the two molecules are identical at the site. The percent identity between two sequences is a function of the number of identical sites shared by the two sequences over the total number of sites for comparison ×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percent identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at http://www.gcg.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "conservative substitution" refers to amino acid substitutions which would not disadvantageously affect or change the essential properties of a protein/polypeptide comprising the amino acid sequence. For example, a conservative substitution may be introduced by standard techniques known in the art such as site-directed mutagenesis and PCR-mediated mutagenesis. Conservative amino acid substitutions include substitutions wherein an amino acid residue is substituted with another amino acid residue having a similar side chain, for example, a residue physically or functionally similar (such as, having similar size, shape, charge, chemical property including the capability of forming covalent bond or hydrogen bond, etc.) to the corresponding amino acid residue. The families of amino acid residues having similar side chains have been defined in the art. These families include amino acids having basic side chains (for example, lysine, arginine and histidine), amino acids having acidic side chains (for example, aspartic acid and glutamic acid), amino acids having uncharged polar side chains (for example, glycine, asparagine, glutamine, serine, threonine, tyrosine, cysteine, tryptophan), amino acids having nonpolar side chains (for example, alanine, valine, leucine, isoleucine, proline, phenylalanine, methionine), amino acids having β-branched side chains (such as threonine, valine, isoleucine) and amino acids having aromatic side chains (for example, tyrosine, phenylalanine, tryptophan, histidine). Therefore, generally a conservative substitution refers to a substitution of a corresponding amino acid residue with another amino acid residue from the same side-chain family. Methods for identifying amino acid conservative substitutions are well known in the art (see, for example, Brummell et al., Biochem. 32: 1180-1187 (1993); Kobayashi et al., Protein Eng. 12(10): 879-884 (1999); and Burks et al., Proc. Natl. Acad. Sci. USA 94: 412-417 (1997), which are incorporated herein by reference).

According to the invention, the term "E. coli expression system" refers to an expression system consisting of E. coli (strain) and a vector, wherein the E. coli (strain) is derived from the commercially available strains, including, but not limited to: ER2566, BL21 (DE3), B834 (DE3), and BLR (DE3).

According to the invention, the term "vector" refers to a nucleic acid carrier tool which can have a polynucleotide inserted therein. When the vector allows for the expression of the protein encoded by the polynucleotide inserted therein, the vector is called an expression vector. The vector can have the carried genetic material elements expressed in a host cell by transformation, transduction, or transfection into the host cell. Vectors are well known by a person skilled in the art, including, but not limited to plasmids, phages, cosmids, etc.

According to the invention, the term "a pharmaceutically acceptable carrier and/or excipient" refers to a carrier and/or excipient that is pharmacologically and/or physiologically compatible to a subject and active ingredients, which is well known in the art (see, for example, Remington's Pharmaceutical Sciences. Edited by Gennaro A R, 19th ed. Pennsylvania: Mack Publishing Company, 1995), including, but not limited to: pH regulators, surfactants, adjuvants, and ionic strength enhancers. For example, pH regulators include, but are not limited to, phosphate buffers; surfactants include, but are not limited to: cation surfactants, anion surfactants, or non-ionic surfactants, e.g., Tween-80; adjuvants include, but are not limited to, aluminium adjuvant (e.g., aluminium hydroxide), and Freund's adjuvant (e.g., Freund's complete adjuvant); and ionic strength enhancers include, but are not limited to, NaCl.

According to the invention, the term "an effective amount" refers to an amount that can effectively achieve the intended purpose. For example, an amount effective for preventing a disease (such as HPV infection) refers to an amount effective for preventing, suppressing, or delaying the occurrence of a disease (such as HPV infection). The determination of such an effective amount is within the ability of a person skilled in the art.

According to the invention, the term "chromatography" includes, but is not limited to: ion exchange chromatography (such as cation-exchange chromatography), hydrophobic interaction chromatography, absorbent chromatography (such as hydroxyapatite chromatography), gel filtration chromatography (gel exclusion chromatography), and affinity chromatography.

According to the invention, the term "lysate supernatant" refers to a solution produced by the following steps: host cells (such as E. coli) are disrupted in a lysis buffer, and the insoluble substances are then removed from the lysed solution containing the disrupted host cells. Various lysis buffers are well known in the art, including, but not limited to Tris buffers, phosphate buffers, HEPES buffers, MOPS buffers, etc. In addition, the disrupting of a host cell can be accomplished by methods well known by a person skilled in the art, including, but not limited to homogenizer disrupting, ultrasonic treatment, grinding, high pressure extrusion, lysozyme treatment, etc. Methods for removing insoluble substances are also well known by a person skilled in the art, including, but not limited to filtration and centrifugation.

BENEFICIAL EFFECTS OF INVENTION

Studies show that although there is certain cross-protection between HPV18 and other HPV type(s) (such as HPV45 and HPV59), such cross-protection is very low, generally lower than one percent, even one thousandth of the protection level of VLP of the same HPV type. Therefore, a subject vaccinated with HPV18 vaccine, still has a high risk of being infected by other HPV type(s) (such as HPV45 and HPV59).

The invention provides a mutated HPV18 L1 protein and a HPV virus-like particle formed by the same. The HPV virus-like particle according to the invention can provide significant cross-protection against HPV18 and other HPV type(s) (such as HPV45 and HPV59). Especially, at the same immunizing dose, the HPV virus-like particle according to the invention can induce the generation of high-titer neutralizing antibodies against at least two HPV types (e.g. HPV18 and HPV45, or HPV18, HPV45 and HPV59) in organisms, and its effect is comparable to that of a mixture of VLPs of multiple HPV types (e.g. a mixture of HPV18 VLP and HPV45 VLP, or a mixture of HPV18 VLP, HPV45 VLP and HPV59 VLP). Therefore, the HPV virus-like particle according to the invention can be used to prevent infection by at least two HPV types (e.g. HPV18 and HPV45, or HPV18, HPV45 and HPV59) at the same time as well as diseases associated with the infection, and has significantly beneficial technical effects. This has particularly significant advantages in terms of extending the protection range of HPV vaccines and reducing the production cost of HPV vaccines.

The embodiments of the invention are further described in detail by reference to the drawings and examples. However, a person skilled in the art would understand that the following drawings and examples are intended for illustrating the invention only, rather than defining the scope of the invention. According to the detailed description of the following drawings and preferred embodiments, various purposes and advantages of the invention are apparent for a person skilled in the art.

DESCRIPTION OF DRAWINGS

FIG. 4A, VLP assembled by HPV18N65; FIG. 4S, VLP assembled by H18N65-45T1T3-59S5. The results showed that H18N65-45T1, H18N65-45T2, H18N65-45T3, H18N65-45T4, H18N65-45T5, H18N65-45T3-59S1, H18N65-45T3-59S2, H18N65-45T3-59S4, H18N65-45T3-59S5, H18N65-45T4-59S1, H18N65-45T4-59S2, H18N65-45T4-59S3, H18N65-45T4-59S5, H18N65-45T1-59S5, H18N65-45T2-59S5 and H18N65-45T1T3-59S5 were similar to HPV18N65, HPV45N27 and HPV59 L1, were able to assemble into VLPs with a radius of about 30 nm.

FIG. 5A, HPV18N65 VLP; FIG. 5B, HPV45N27 VLP; FIG. 5C, HPV59 VLP; FIG. 5D, H18N65-45T3 VLP; FIG. 5E, H18N65-45T4 VLP; FIG. 5F, H18N65-45T3-59S1 VLP; FIG. 5G, H18N65-45T4-59S1 VLP; FIG. 5H, H18N65-45T1T3-59S5 VLP. The results showed that the sedimentation coefficients of H18N65-45T3 VLP, H18N65-45T4 VLP and H18N65-45T1T3-59S5 VLP were 143.7S, 173.3S and 167.1S, respectively, which was similar to that of HPV18N65 VLP, HPV45N27 VLP and HPV59 VLP (HPV18N65 VLP, 142.2S; HPV45N27 VLP, 146.5S, and HPV59 VLP, 139.3S). This showed that H18N65-45T3, H18N65-45T4 and H18N65-45T1T3-59S5 were able to assemble into virus-like particles that were similar to wild type VLP in terms of size and morphology.

FIG. 6A, HPV18N65 VLP; FIG. 6B, HPV45N27 VLP; FIG. 6C, HPV59 VLP; FIG. 6D, H18N65-45T3 VLP; FIG. 6E, H18N65-45T4 VLP; FIG. 6F, H18N65-45T3-59S1 VLP; FIG. 6G, H18N65-45T4-59S1 VLP; FIG. 6H, H18N65-45T1T3-59S5 VLP. The results showed that all the VLPs formed by these proteins had very high thermostability.

FIG. 8A: Group of dose of 10 μg (at an immunizing dose of 10 μg, using aluminum adjuvant); FIG. 8B: Group of dose of 1 μg (at an immunizing dose of 1 μg, using aluminum adjuvant). The result showed that H18N65-45T4 VLP could induce the generation of high-titer neutralizing antibodies against HPV18 in mice, and its protective effect was comparable to that of HPV18N65 VLP alone and that of the mixed HPV18/HPV45 VLP at the same dose, and was significantly superior to that of HPV45N27 VLP alone at the same dose; and it could induce the generation of high-titer neutralizing antibodies against HPV45 in mice, and its protective effect was comparable to that of HPV45N27 VLP alone and that of the mixed HPV18/HPV45 VLP at the same dose, and was significantly superior to that of HPV18N65 VLP alone at the same dose. This showed that H18N65-45T4 VLP had good cross-immunogenicity and cross-protection against HPV18 and HPV45.

FIG. 8C: Group of dose of 10 μg (at an immunizing dose of 10 μg, using aluminum adjuvant); FIG. 8D: Group of dose of 1 μg (at an immunizing dose of 1 μg, using aluminum adjuvant). The result showed that H18N65-45T3-59S1 VLP, H18N65-45T4-59S1 VLP, H18N65-45T1-59S5 VLP, H18N65-45T2-59S5 VLP and H18N65-45T1T3-59S5 VLP could induce the generation of high-titer neutralizing antibodies against HPV18 in mice, and their protective effects were comparable to that of HPV18N65 VLP alone and that of the mixed HPV18/HPV45/HPV59 VLP at the same dose, and were significantly superior to that of HPV45N27 VLP alone or that of HPV59 VLP alone at the same dose; and H18N65-45T3-59S1 VLP, H18N65-45T4-59S1 VLP, H18N65-45T1-59S5 VLP, H18N65-45T2-59S5 VLP and H18N65-45T1T3-59S5 VLP could induce the generation of high-titer neutralizing antibodies against HPV45 in mice, and their protective effects were comparable to that of HPV45N27 VLP alone and that of the mixed HPV18/HPV45/HPV59 VLP at the same dose, and were significantly superior to that of HPV18N65 VLP alone or that of HPV59 VLP alone at the same dose; and H18N65-45T3-59S1 VLP, H18N65-45T4-59S1 VLP, H18N65-45T1-59S5 VLP, H18N65-45T2-59S5 VLP and H18N65-45T1T3-59S5 VLP could induce the generation of high-titer neutralizing antibodies against HPV59 in mice, and their protective effects were comparable to that of HPV59 VLP alone or that of the mixed HPV18/HPV45/HPV59 VLP at the same dose, and were significantly superior to that of HPV18N65 VLP alone or that of HPV45N27 VLP alone at the same dose. This showed that H18N65-45T3-59S1 VLP, H18N65-45T4-59S1 VLP, H18N65-45T1-59S5 VLP, H18N65-45T2-59S5 VLP and H18N65-45T1T3-59S5 VLP had good cross-immunogenicity and cross-protection against HPV18, HPV45 and HPV59.

SEQUENCE INFORMATION

Figure 1:
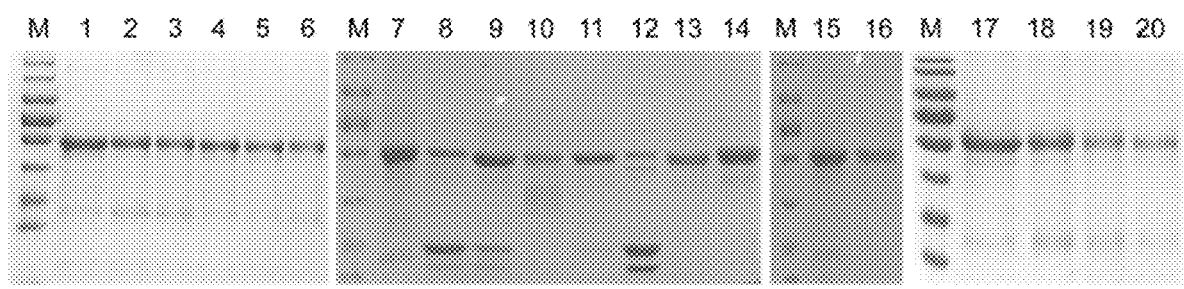
FIG. 1 shows the SDS-PAGE result of the purified mutated proteins in Example 1. Lane M: protein molecular weight marker; Lane 1: HPV18N65 (HPV18 L1 protein having 65 amino acids truncated at N-terminal); Lane 2: H18N65-45T1; Lane 3: H18N65-45T2; Lane 4: H18N65-45T3; Lane 5: H18N65-45T4; Lane 6: H18N65-45T5; Lane 7: HPV18N65; Lane 8: H18N65-45T3-5951; Lane 9: H18N65-45T3-5952; Lane 10: H18N65-45T3-5954; Lane 11: H18N65-45T3-5955; Lane 12: H18N65-45T4-5951; Lane 13: H18N65-45T4-5952; Lane 14: H18N65-45T4-5953; Lane 15: HPV18N65; Lane 16: H18N65-45T4-5955; Lane 17: HPV18N65; Lane 18: H18N65-45T1-5955; Lane 19: H18N65-45T2-5955; Lane 20: H18N65-45T1T3-5955. The result showed that after chromatographic purification, H18N65-45T1, H18N65-45T2, H18N65-45T3, H18N65-45T4, H18N65-45T5, H18N65-45T3-5951, H18N65-45T3-5952, H18N65-45T3-5954, H18N65-45T3-5955, H18N65-45T4-5951, H18N65-45T4-5952, H18N65-45T4-5953, H18N65-45T4-5955, H18N65-45T1-5955, H18N65-45T2-5955 and H18N65-45T1T3-5955 protein reached a purity of above 85%.

Some of the sequences involved in the invention are provided in the following Table 1.

TABLE 1

Description of sequences

| SEQ ID NO: | Description |
| --- | --- |
| 1 | wild type HPV18 L1 protein |
| 2 | wild type HPV45 L1 protein |
| 3 | wild type HPV59 L1 protein |
| 4 | the mutated HPV18 L1 protein comprising Segment 1 of HPV45 L1 protein, H18N65-45T1 |
| 5 | the mutated HPV18 L1 protein comprising Segment 2 of HPV45 L1 protein, H18N65-45T2 |
| 6 | the mutated HPV18 L1 protein comprising Segment 3 of HPV45 L1 protein, H18N65-45T3 |
| 7 | the mutated HPV18 L1 protein comprising Segment 4 of HPV45 L1 protein, H18N65-45T4 |
| 8 | the mutated HPV18 L1 protein comprising Segment 5 of HPV45 L1 protein, H18N65-45T5 |
| 9 | the mutated HPV18 L1 protein comprising Segment 3 of HPV45 L1 protein and Segment 1 of HPV59 L1 protein, H18N65-45T3-59S1 |
| 10 | the mutated HPV18 L1 protein comprising Segment 3 of HPV45 L1 protein and Segment 2 of HPV59 L1 protein, H18N65-45T3-59S2 |
| 11 | the mutated HPV18 L1 protein comprising Segment 3 of HPV45 L1 protein and Segment 4 of HPV59 L1 protein, H18N65-45T3-59S4 |
| 12 | the mutated HPV18 L1 protein comprising Segment 3 of HPV45 L1 protein and Segment 5 of HPV59 L1 protein, H18N65-45T3-59S5 |
| 13 | the mutated HPV18 L1 protein comprising Segment 4 of HPV45 L1 protein and Segment 1 of HPV59 L1 protein, H18N65-45T4-59S1 |
| 14 | the mutated HPV18 L1 protein comprising Segment 4 of HPV45 L1 protein and Segment 2 of HPV59 L1 protein, H18N65-45T4-59S2 |
| 15 | the mutated HPV18 L1 protein comprising Segment 4 of HPV45 L1 protein and Segment 3 of HPV59 L1 protein, H18N65-45T4-59S3 |
| 16 | the mutated HPV18 L1 protein comprising Segment 4 of HPV45 L1 protein and Segment 5 of HPV59 L1 protein, H18N65-45T4-59S5 |
| 17 | the mutated HPV18 L1 protein comprising Segment 1 of HPV45 L1 protein and Segment 5 of HPV59 L1 protein, H18N65-45T1-59S5 |
| 18 | the mutated HPV18 L1 protein comprising Segment 2 of HPV45 L1 protein and Segment 5 of HPV59 L1 protein, H18N65-45T2-59S5 |
| 19 | the mutated HPV18 L1 protein comprising Segment 1 and Segment 3 of HPV45 L1 protein and Segment 5 of HPV59 L1 protein, H18N65-45T1T3-59S5 |
| 20 | the DNA sequence encoding SEQ ID NO: 1 |
| 21 | the DNA sequence encoding SEQ ID NO: 2 |
| 22 | the DNA sequence encoding SEQ ID NO: 3 |
| 23 | the DNA sequence encoding SEQ ID NO: 4 |
| 24 | the DNA sequence encoding SEQ ID NO: 5 |
| 25 | the DNA sequence encoding SEQ ID NO: 6 |
| 26 | the DNA sequence encoding SEQ ID NO: 7 |
| 27 | the DNA sequence encoding SEQ ID NO: 8 |
| 28 | the DNA sequence encoding SEQ ID NO: 9 |
| 29 | the DNA sequence encoding SEQ ID NO: 10 |
| 30 | the DNA sequence encoding SEQ ID NO: 11 |
| 31 | the DNA sequence encoding SEQ ID NO: 12 |
| 32 | the DNA sequence encoding SEQ ID NO: 13 |
| 33 | the DNA sequence encoding SEQ ID NO: 14 |

TABLE 1-continued

Description of sequences

| SEQ ID NO: | Description |
|---|---|
| 34 | the DNA sequence encoding SEQ ID NO: 15 |
| 35 | the DNA sequence encoding SEQ ID NO: 16 |
| 36 | the DNA sequence encoding SEQ ID NO: 17 |
| 37 | the DNA sequence encoding SEQ ID NO: 18 |
| 38 | the DNA sequence encoding SEQ ID NO: 19 |
| 39 | the sequence of the amino acid residues at positions 79-89 of wild type HPV45 L1 protein, Segment 1 of HPV45 L1 protein |
| 40 | the sequence of the amino acid residues at positions 142-168 of wild type HPV45 L1 protein, Segment 2 of HPV45 L1 protein |
| 41 | the sequence of the amino acid residues at positions 201-209 of wild type HPV45 L1 protein, Segment 3 of HPV45 L1 protein |
| 42 | the sequence of the amino acid residues at positions 293-314 of wild type HPV45 L1 protein, Segment 4 of HPV45 L1 protein |
| 43 | the sequence of the amino acid residues at positions 51-62 of wild type HPV59 L1 protein, Segment 1 of HPV59 L1 protein |
| 44 | the sequence of the amino acid residues at positions 349-360 of wild type HPV59 L1 protein, Segment 5 of HPV59 L1 protein |
| 109 | the sequence of the amino acid residues at positions 379-387 of wild type HPV45 L1 protein, Segment 5 of HPV45 L1 protein |
| 110 | the sequence of the amino acid residues at positions 122-143 of wild type HPV59 L1 protein, Segment 2 of HPV59 L1 protein |
| 111 | the sequence of the amino acid residues at positions 264-290 of wild type HPV59 L1 protein, Segment 4 of HPV59 L1 protein |
| 112 | the sequence of the amino acid residues at positions 170-181 of wild type HPV59 L1 protein, Segment 3 of HPV59 L1 protein |
| 113 | the HPV18 L1 protein having 65 amino acids truncated at N-terminal, HPV18N65 |
| 114 | the DNA sequence encoding SEQ ID NO: 113 |
| 115 | the HPV45 L1 protein having 27 amino acids truncated at N-terminal, HPV45N27 |
| 116 | the DNA sequence encoding SEQ ID NO: 115 |

```
Sequence 1 (SEQ ID NO: 1):
MCLYTRVLILHYHLLPLYGPLYHPQPLPLHSILVYMVHIIICGHYIILF
LRNVNVFPIFLQMALWRPSDNTVYLPPPSVARVVNTDDYVTRTSIFYHA
GSSRLLTVGNPYFRVPAGGGNKQDIPKVSAYQYRVFRVQLPDPNKFGLP
DTSIYNPETQRLVWACAGVEIGRGQPLGVGLSGHPFYNKLDDTESSHAA
TSNVSEDVRDNVSVDYKQTQLCILGCAPAIGEHWAKGTACKSRPLSQGD
CPPLELKNTVLEDGDMVDTGYGAMDFSTLQDTKCEVPLDICQSICKYPD
YLQMSADPYGDSMFFCLRREQLFARHFWNRAGTMGDTVPQSLYIKGTGM
RASPGSCVYSPSPSGSIVTSDSQLFNKPYWLHKAQGHNNGVCWHNQLFV
TVVDTTRSTNLTICASTQSPVPGQYDATKFKQYSRHVEEYDLQFIFQLC
TITLTADVMSYIHSMNSSILEDWNFGVPPPPTTSLVDTYRFVQSVAIAC
QKDAAPAENKDPYDKLKFWNVDLKEKFSLDLDQYPLGRKELVQAGLRRK
PTIGPRKRSAPSATTASKPAKRVRVRARK Sequence 2 (SEQ ID NO: 2):
MAHNIIYGHGIIIFLKNVNVFPIFLQMALWRPSDSTVYLPPPSVARVVS
TDDYVSRTSIFYHAGSSRLLTVGNPYFRVVPNGAGNKQAVPKVSAYQYR
VFRVALPDPNKFGLPDSTIYNPETQRLVWACVGMEIGRGQPLGIGLSGH
PFYNKLDDTESAHAATAVITQDVRDNVSVDYKQTQLCILGCVPAIGEHW
AKGTLCKPAQLQPGDCPPLELKNTIIEDGDMVDTGYGAMDFSTLQDTKC
EVPLDICQSICKYPDYLQMSADPYGDSMFFCLRREQLFARHFWNRAGVM
GDTVPTDLYIKGTSANMRETPGSCVYSPSPSGSIITSDSQLFNKPYWLH
KAQGHNNGICWHNQLFVTVVDTTRSTNLTLCASTQNPVPSTYDPTKFKQ
YSRHVEEYDLQFIFQLCTITLTAEVMSYIHSMNSSILENWNFGVPPPPT
TSLVDTYRFVQSVAVTCQKDTTPPEKQDPYDKLKFWTVDLKEKFSSDLD
QYPLGRKFLVQAGLRRRPTIGPRKRPAASTSTASTASRPAKRVRIRSKK Sequence 3 (SEQ ID NO: 3):
MALWRSSDNKVYLPPPSVAKVVSTDEYVTRTSIFYHAGSSRLLTVGHPY
FKVPKGGNGRQDVPKVSAYQYRVFRVKLPDPNKFGLPDNTVYDPNSQRL
VWACVGVEIGRGQPLGVGLSGHPLYNKLDDTENSHVASAVDTKDTRDNV
SVDYKQTQLCIIGCVPAIGEHWTKGTACKPTTVVQGDCPPLELINTPIE
DGDMVDTGYGAMDFKLLQDNKSEVPLDICQSICKYPDYLQMSADAYGDS
MFFCLRREQVFARHFWNRSGTMGDQLPESLYIKGTDIRANPGSYLYSPS
PSGSVVTSDSQLFNKPYWLHKAQGLNNGICWHNQLFLTVVDTTRSTNLS
VCASTTSSIPNVYTPTSFKEYARHVEEFDLQFIFQLCKITLTTEVMSYI
HNMNTTILEDWNFGVTPPPTASLVDTYRFVQSAAVTCQKDTAPPVKQDP
YDKLKFWPVDLKERFSADLDQFPLGRKFLLQLGARPKPTIGPRKRAAPA
PTSTPSPKRVKRRKSSRK Sequence 4 (SEQ ID NO: 4):
MRPSDNTVYLPPPSVARVVNTDDYVTRTSIFYHAGSSRLLTVGNPYFRV
VPNGAGNKQAVPKVSAYQYRVFRVQLPDPNKFGLPDTSIYNPETQRLVW
```

ACAGVEIGRGQPLGVGLSGHPFYNKLDDTESSHAATSNVSEDVRDNVSV

DYKQTQLCILGCAPAIGEHWAKGTACKSRPLSQGDCPPLELKNTVLEDG

DMVDTGYGAMDFSTLQDTKCEVPLDICQSICKYPDYLQMSADPYGDSMF

FCLRREQLFARHFWNRAGTMGDTVPQSLYIKGTGMRASPGSCVYSPSPS

GSIVTSDSQLFNKPYWLHKAQGHNNGVCWHNQLFVTVVDTTRSTNLTIC

ASTQSPVPGQYDATKFKQYSRHVEEYDLQFIFQLCTITLTADVMSYIHS

MNSSILEDWNFGVPPPPTTSLVDTYRFVQSVAIACQKDAAPAENKDPYD

KLKFWNVDLKEKFSLDLDQYPLGRKFLVQAGLRRKPTIGPRKRSAPSAT

TASKPAKRVRVRARK

Sequence 5 (SEQ ID NO: 5):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGIGLSGHPFYNKLDDTESAHAATAVITQDVRDNVSVD

YKQTQLCILGCAPAIGEHWAKGTACKSRPLSQGDCPPLELKNTVLEDGD

MVDTGYGAMDFSTLQDTKCEVPLDICQSICKYPDYLQMSADPYGDSMFF

CLRREQLFARHFWNRAGTMGDTVPQSLYIKGTGMRASPGSCVYSPSPSG

SIVTSDSQLFNKPYWLHKAQGHNNGVCWHNQLFVTVVDTTRSTNLTICA

STQSPVPGQYDATKFKQYSRHVEEYDLQFIFQLCTITLTADVMSYIHSM

NSSILEDWNFGVPPPPTTSLVDTYRFVQSVAIACQKDAAPAENKDPYDK

LKFWNVDLKEKFSLDLDQYPLGRKFLVQAGLRRKPTIGPRKRSAPSATT

ASKPAKRVRVRARK

Sequence 6 (SEQ ID NO: 6):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWAKGTLCKPAQLQPGDCPPLELKNTVLEDGD

MVDTGYGAMDFSTLQDTKCEVPLDICQSICKYPDYLQMSADPYGDSMFF

CLRREQLFARHFWNRAGTMGDTVPQSLYIKGTGMRASPGSCVYSPSPSG

SIVTSDSQLFNKPYWLHKAQGHNNGVCWHNQLFVTVVDTTRSTNLTICA

STQSPVPGQYDATKFKQYSRHVEEYDLQFIFQLCTITLTADVMSYIHSM

NSSILEDWNFGVPPPPTTSLVDTYRFVQSVAIACQKDAAPAENKDPYDK

LKFWNVDLKEKFSLDLDQYPLGRKFLVQAGLRRKPTIGPRKRSAPSATT

ASKPAKRVRVRARK

Sequence 7 (SEQ ID NO: 7):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWAKGTACKSRPLSQGDCPPLELKNTVLEDGD

MVDTGYGAMDFSTLQDTKCEVPLDICQSICKYPDYLQMSADPYGDSMFF

CLRREQLFARHFWNRAGVMGDTVPTDLYIKGTSANMRETPGSCVYSPSP

SGSIVTSDSQLFNKPYWLHKAQGHNNGVCWHNQLFVTVVDTTRSTNLTI

CASTQSPVPGQYDATKFKQYSRHVEEYDLQFIFQLCTITLTADVMSYIH

SMNSSILEDWNFGVPPPPTTSLVDTYRFVQSVAIACQKDAAPAENKDPY

DKLKFWNVDLKEKFSLDLDQYPLGRKFLVQAGLRRKPTIGPRKRSAPSA

TTASKPAKRVRVRARK

Sequence 8 (SEQ ID NO: 8):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWAKGTACKSRPLSQGDCPPLELKNTVLEDGD

MVDTGYGAMDFSTLQDTKCEVPLDICQSICKYPDYLQMSADPYGDSMFF

CLRREQLFARHFWNRAGTMGDTVPQSLYIKGTGMRASPGSCVYSPSPSG

SIVTSDSQLFNKPYWLHKAQGHNNGVCWHNQLFVTVVDTTRSTNLTICA

STQNPVPSTYDPTKFKQYSRHVEEYDLQFIFQLCTITLTADVMSYIHSM

NSSILEDWNFGVPPPPTTSLVDTYRFVQSVAIACQKDAAPAENKDPYDK

LKFWNVDLKEKFSLDLDQYPLGRKFLVQAGLRRKPTIGPRKRSAPSATT

ASKPAKRVRVRARK

Sequence 9 (SEQ ID NO: 9):
MRPSDNTVYLPPPSVARVVNTDDYVTRTSIFYHAGSSRLLTVGNPYFKV

PKGGNGRQDVPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWAKGTLCKPAQLQPGDCPPLELKNTVLEDGD

MVDTGYGAMDFSTLQDTKCEVPLDICQSICKYPDYLQMSADPYGDSMFF

CLRREQLFARHFWNRAGTMGDTVPQSLYIKGTGMRASPGSCVYSPSPSG

SIVTSDSQLFNKPYWLHKAQGHNNGVCWHNQLFVTVVDTTRSTNLTICA

STQSPVPGQYDATKFKQYSRHVEEYDLQFIFQLCTITLTADVMSYIHSM

NSSILEDWNFGVPPPPTTSLVDTYRFVQSVAIACQKDAAPAENKDPYDK

LKFWNVDLKEKFSLDLDQYPLGRKFLVQAGLRRKPTIGPRKRSAPSATT

ASKPAKRVRVRARK

Sequence 10 (SEQ ID NO: 10):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPLYNKLDDTENSHVASAVDTKDTRDNVSVD

YKQTQLCILGCAPAIGEHWAKGTLCKPAQLQPGDCPPLELKNTVLEDGD

MVDTGYGAMDFSTLQDTKCEVPLDICQSICKYPDYLQMSADPYGDSMFF

CLRREQLFARHFWNRAGTMGDTVPQSLYIKGTGMRASPGSCVYSPSPSG

SIVTSDSQLFNKPYWLHKAQGHNNGVCWHNQLFVTVVDTTRSTNLTICA

-continued
STQSPVPGQYDATKFKQYSRHVEEYDLQFIFQLCTITLTADVMSYIHSM

NSSILEDWNFGVPPPPTTSLVDTYRFVQSVAIACQKDAAPAENKDPYDK

LKFWNVDLKEKFSLDLDQYPLGRKFLVQAGLRRKPTIGPRKRSAPSATT

ASKPAKRVRVRARK

Sequence 11 (SEQ ID NO: 11):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWAKGTLCKPAQLQPGDCPPLELKNTVLEDGD

MVDTGYGAMDFSTLQDTKCEVPLDICQSICKYPDYLQMSADPYGDSMFF

CLRREQLFARHFWNRSGTMGDQLPESLYIKGTDIRANPGSYLYSPSPSG

SIVTSDSQLFNKPYWLHKAQGHNNGVCWHNQLFVTVVDDTTRSTNLTICA

STQSPVPGQYDATKFKQYSRHVEEYDLQFIFQLCTITLTADVMSYIHSM

NSSILEDWNFGVPPPPTTSLVDTYRFVQSVAIACQKDAAPAENKDPYDK

LKFWNVDLKEKFSLDLDQYPLGRKFLVQAGLRRKPTIGPRKRSAPSATT

ASKPAKRVRVRARK

Sequence 12 (SEQ ID NO: 12):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWAKGTLCKPAQLQPGDCPPLELKNTVLEDGD

MVDTGYGAMDFSTLQDTKCEVPLDICQSICKYPDYLQMSADPYGDSMFF

CLRREQLFARHFWNRAGTMGDTVPQSLYIKGTGMRASPGSCVYSPSPSG

SIVTSDSQLFNKPYWLHKAQGHNNGVCWHNQLFVTVVDDTTRSTNLTICA

STTSSIPNVYTPTSFKQYSRHVEEYDLQFIFQLCTITLTADVMSYIHSM

NSSILEDWNFGVPPPPTTSLVDTYRFVQSVAIACQKDAAPAENKDPYDK

LKFWNVDLKEKFSLDLDQYPLGRKFLVQAGLRRKPTIGPRKRSAPSATT

ASKPAKRVRVRARK

Sequence 13 (SEQ ID NO: 13):
MRPSDNTVYLPPPSVARVVNTDDYVTRTSIFYHAGSSRLLTVGNPYFKV

PKGGNGRQDVPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWAKGTACKSRPLSQGDCPPLELKNTVLEDGD

MVDTGYGAMDFSTLQDTKCEVPLDICQSICKYPDYLQMSADPYGDSMFF

CLRREQLFARHFWNRAGVMGDTVPTDLYIKGTSANMRETPGSCVYSPSP

SGSIVTSDSQLFNKPYWLHKAQGHNNGVCWHNQLFVTVVDTTRSTNLTI

CASTQSPVPGQYDATKFKQYSRHVEEYDLQFIFQLCTITLTADVMSYIH

SMNSSILEDWNFGVPPPPTTSLVDTYRFVQSVAIACQKDAAPAENKDPY

DKLKFWNVDLKEKFSLDLDQYPLGRKFLVQAGLRRKPTIGPRKRSAPSA

TTASKPAKRVRVRARK

Sequence 14 (SEQ ID NO: 14):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPLYNKLDDTENSHVASAVDTKDTRDNVSVD

YKQTQLCILGCAPAIGEHWAKGTACKSRPLSQGDCPPLELKNTVLEDGD

MVDTGYGAMDFSTLQDTKCEVPLDICQSICKYPDYLQMSADPYGDSMFF

CLRREQLFARHFWHNQLFVTVVDDTTRSTNLTICASTQSPVPGQYDATKF

KQYSRHVEEYDLQFIFQLCTITLTADVMSYIHSMNSSILEDWNFGVPPP

PTTSLVDTYRFVQSVAIACQKDAAPAENKDPYDKLKFWNVDLKEKFSLD

LDQYPLGRKFLVQAGLRRKPTIGPRKRSAPSATTASKPAKRVRVRARK

Sequence 15 (SEQ ID NO: 15):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWTKGTACKPTTVVQGDCPPLELKNTVLEDGD

MVDTGYGAMDFSTLQDTKCEVPLDICQSICKYPDYLQMSADPYGDSMFF

CLRREQLFARHFWNRAGVMGDTVPTDLYIKGTSANMRETPGSCVYSPSP

SGSIVTSDSQLFNKPYWLHKAQGHNNGVCWHNQLFVTVVDTTRSTNLTI

CASTQSPVPGQYDATKFKQYSRHVEEYDLQFIFQLCTITLTADVMSYIH

SMNSSILEDWNFGVPPPPTTSLVDTYRFVQSVAIACQKDAAPAENKDPY

DKLKFWNVDLKEKFSLDLDQYPLGRKFLVQAGLRRKPTIGPRKRSAPSA

TTASKPAKRVRVRARK

Sequence 16 (SEQ ID NO: 16):
MRPSDNTVYLPPPSVARVVNTDDYVTRTSIFYHAGSSRLLTVGNPYFRV

PAGGGNKQDIPKVSAYQYRVFRVQLPDPNKFGLPDTSIYNPETQRLVWA

CAGVEIGRGQPLGVGLSGHPFYNKLDDTESSHAATSNVSEDVRDNVSVD

YKQTQLCILGCAPAIGEHWAKGTACKSRPLSQGDCPPLELKNTVLEDGD

MVDTGYGAMDFSTLQDTKCEVPLDICQSICKYPDYLQMSADPYGDSMFF

CLRREQLFARHFWNRAGVMGDTVPTDLYIKGTSANMRETPGSCVYSPSP

SGSIVTSDSQLFNKPYWLHKAQGHNNGVCWHNQLFVTVVDTTRSTNLTI

CASTTSSIPNVYTPTSFKQYSRHVEEYDLQFIFQLCTITLTADVMSYIH

SMNSSILEDWNFGVPPPPTTSLVDTYRFVQSVAIACQKDAAPAENKDPY

DKLKFWNVDLKEKFSLDLDQYPLGRKFLVQAGLRRKPTIGPRKRSAPSA

TTASKPAKRVRVRARK

Sequence 17 (SEQ ID NO: 17):
MRPSDNTVYLPPPSVARVVNTDDYVTRTSIFYHAGSSRLLTVGNPYFRV
VPNGAGNKQAVPKVSAYQYRVFRVQLPDPNKFGLPDTSIYNPETQRLVW
ACAGVEIGRGQPLGVGLSGHPFYNKLDDTESSHAATSNVSEDVRDNVSV
DYKQTQLCILGCAPAIGEHWAKGTACKSRPLSQGDCPPLELKNTVLEDG
DMVDTGYGAMDFSTLQDTKCEVPLDICQSICKYPDYLQMSADPYGDSMF
FCLRREQLFARHFWNRAGTMGDTVPQSLYIKGTGMRASPGSCVYSPSPS
GSIVTSDSQLFNKPYWLHKAQGHNNGVCWHNQLFVTVVDTTRSTNLTIC
ASTTSSIPNVYTPTSFKQYSRHVEEYDLQFIFQLCTITLTADVMSYIHS
MNSSILEDWNFGVPPPPTTSLVDTYRFVQSVAIACQKDAAPAENKDPYD
KLKFWNVDLKEKFSLDLDQYPLGRKFLVQAGLRRKPTIGPRKRSAPSAT
TASKPAKRVRVRARK Sequence 18 (SEQ ID NO: 18):
MRPSDNTVYLPPPSVARVVNTDDYVTRTSIFYHAGSSRLLTVGNPYFRV
PAGGGNKQDIPKVSAYQYRVFRVQLPDPNKFGLPDTSIYNPETQRLVWA
CAGVEIGRGQPLGIGLSGHPFYNKLDDTESAHAATAVITQDVRDNVSVD
YKQTQLCILGCAPAIGEHWAKGTACKSRPLSQGDCPPLELKNTVLEDGD
MVDTGYGAMDFSTLQDTKCEVPLDICQSICKYPDYLQMSADPYGDSMFF
CLRREQLFARHFWNRAGTMGDTVPQSLYIKGTGMRASPGSCVYSPSPSG
SIVTSDSQLFNKPYWLHKAQGHNNGVCWHNQLFVTVVDTTRSTNLTICA
STTSSIPNVYTPTSFKQYSRHVEEYDLQFIFQLCTITLTADVMSYIHSM
NSSILEDWNFGVPPPPTTSLVDTYRFVQSVAIACQKDAAPAENKDPYDK
LKFWNVDLKEKFSLDLDQYPLGRKFLVQAGLRRKPTIGPRKRSAPSATT
ASKPAKRVRVRARK Sequence 19 (SEQ ID NO: 19):
MRPSDNTVYLPPPSVARVVNTDDYVTRTSIFYHAGSSRLLTVGNPYFRV
VPNGAGNKQAVPKVSAYQYRVFRVQLPDPNKFGLPDTSIYNPETQRLVW
ACAGVEIGRGQPLGVGLSGHPFYNKLDDTESSHAATSNVSEDVRDNVSV
DYKQTQLCILGCAPAIGEHWAKGTLCKPAQLQPGDCPPLELKNTVLEDG
DMVDTGYGAMDFSTLQDTKCEVPLDICQSICKYPDYLQMSADPYGDSMF
FCLRREQLFARHFWNRAGTMGDTVPQSLYIKGTGMRASPGSCVYSPSPS
GSIVTSDSQLFNKPYWLHKAQGHNNGVCWHNQLFVTVVDTTRSTNLTIC
ASTTSSIPNVYTPTSFKQYSRHVEEYDLQFIFQLCTITLTADVMSYIHS
MNSSILEDWNFGVPPPPTTSLVDTYRFVQSVAIACQKDAAPAENKDPYD
KLKFWNVDLKEKFSLDLDQYPLGRKFLVQAGLRRKPTIGPRKRSAPSAT
TASKPAKRVRVRARK Sequence 20 (SEQ ID NO: 20):
ATGTGCCTGTATACACGGGTCCTGATATTACATTACCATCTACTACCTC
TGTATGGCCCATTGTATCACCCACAGCCCCTGCCTCTACACAGTATATT
GGTATACATGGTACACATTATTATTTGTGGCCATTATATTATTTTATTC
CTAAGAAACGTAAACGTGTTCCCTATTTTTTTGCAGATGGCTTTGTGGC
GGCCTAGTGACAATACCGTATATCTTCCACCTCCTTCTGTGGCAAGAGT
TGTAAATACCGATGATTACGTGACTCGCACAAGCATATTTTATCATGCT
GGCAGCTCTAGATTATTAACTGTTGGTAATCCATATTTTAGGGTTCCTG
CAGGTGGTGGCAATAAGCAGGATATTCCTAAGGTTTCTGCATACCAATA
TAGAGTATTTAGGGTGCAGTTACCTGACCCAAATAAATTTGGTTTACCT
GATACTAGTATTTATAATCCTGAAACACAACGTTTAGTGTGGGCCTGTG
CTGGAGTGGAAATTGGCCGTGGTCAGCCTTTAGGTGTTGGCCTTAGTGG
GCATCCATTTTATAATAAATTAGATGACACTGAAAGTTCCCATGCCGCC
ACGTCTAATGTTTCTGAGGACGTTAGGGACAATGTGTCTGTAGATTATA
AGCAGACACAGTTATGTATTTTGGGCTGTGCCCCTGCTATTGGGGAACA
CTGGGCTAAAGGCACTGCTTGTAAATCGCGTCCTTTATCACAGGGCGAT
TGCCCCCCTTTAGAACTTAAAAACACAGTTTTGGAAGATGGTGATATGG
TAGATACTGGATATGGTGCCATGGACTTTAGTACATTGCAAGATACTAA
ATGTGAGGTACCATTGGATATTTGTCAGTCTATTTGTAAATATCCTGAT
TATTTACAAATGTCTGCAGATCCTTATGGGGATTCCATGTTTTTTTGCT
TACGGCGTGAGCAGCTTTTTGCTAGGCATTTTTGGAATAGAGCAGGTAC
TATGGGTGACACTGTGCCTCAATCCTTATATATTAAAGGCACAGGTATG
CGTGCTTCACCTGGCAGCTGTGTGTATTCTCCCTCTCCAAGTGGCTCTA
TTGTTACCTCTGACTCCCAGTTGTTTAATAAACCATATTGGTTACATAA
GGCACAGGGTCATAACAATGGTGTTTGCTGGCATAATCAATTATTTGTT
ACTGTGGTAGATACCACTCGCAGTACCAATTTAACAATATGTGCTTCTA
CACAGTCTCCTGTACCTGGGCAATATGATGCTACCAAATTTAAGCAGTA
TAGCAGACATGTTGAGGAATATGATTTGCAGTTTATTTTTCAGTTGTGT
ACTATTACTTTAACTGCAGATGTTATGTCCTATATTCATAGTATGAATA
GCAGTATTTTAGAGGATTGGAACTTTGGTGTTCCCCCCCCGCCAACTAC
TAGTTTGGTGGATACATATCGTTTTGTACAATCTGTTGCTATTGCCTGT
CAAAAGGATGCTGCACCGGCTGAAAATAAGGATCCCTATGATAAGTTAA
AGTTTTGGAATGTGGATTTAAAGGAAAAGTTTTCTTTAGACTTAGATCA
ATATCCCCTTGGACGTAAATTTTTGGTTCAGGCTGGATTGCGTCGCAAG
CCCACCATAGGCCCTCGCAAACGTTCTGCTCCATCTGCCACTACGGCTT
CTAAACCTGCCAAGCGTGTGCGTGTACGTGCCAGGAAGTAA Sequence 21 (SEQ ID NO: 21):
ATGGCACACAATATTATTTATGGCCATGGTACTATTATTTTCCTAAAAA
ACGTAAACGTATTCCCTATTTTTTTGCAGATGGCCCTGTGGAGGCCCAG
CGACAGCACCGTGTACCTGCCCCCCCCCAGCGTGGCCAGGGTGGTGAGC
ACCGACGACTACGTGAGCAGGACCAGCATCTTCTACCACGCCGGCAGCA
GCAGGCTGCTGACCGTGGGCAACCCCTACTTCAGGGTGGTGCCCAACGG
CGCCGGCAACAAGCAGGCCGTGCCCAAGGTGAGCGCCTACCAGTACAGG -continued
GTGTTCAGGGTGGCCCTGCCCGACCCCAACAAGTTCGGCCTGCCCGACA
GCACCATCTACAACCCCGAGACCCAGAGGCTGGTGTGGGCCTGCGTGGG
CATGGAGATCGGCAGGGGCCAGCCCCTGGGCATCGGCCTGAGCGGCCAC
CCCTTCTACAACAAGCTGGACGACACCGAGAGCGCCCACGCCGCCACCG
CCGTGATCACCCAGGACGTGAGGGACAACGTGAGCGTGGACTACAAGCA
GACCCAGCTGTGCATCCTGGGCTGCGTGCCCGCCATCGGCGAGCACTGG
GCCAAGGGCACCCTGTGCAAGCCCGCCCAGCTGCAGCCCGGCGACTGCC
CCCCCCTGGAGCTGAAGAACACCATCATCGAGGACGGCGACATGGTGGA
CACCGGCTACGGCGCCATGGACTTCAGCACCCTGCAGGACACCAAGTGC
GAGGTGCCCCTGGACATCTGCCAGAGCATCTGCAAGTACCCCGACTACC
TGCAGATGAGCGCCGACCCCTACGGCGACAGCATGTTCTTCTGCCTGAG
GAGGGAGCAGCTGTTCGCCAGGCACTTCTGGAACAGGGCCGGCGTGATG
GGCGACACCGTGCCCACCGACCTGTACATCAAGGGCACCAGCGCCAACA
TGAGGGAGACCCCCGGCAGCTGCGTGTACAGCCCCAGCCCCAGCGGCAG
CATCATCACCAGCGACAGCCAGCTGTTCAACAAGCCCTACTGGCTGCAC
AAGGCCCAGGGCCACAACAACGGCATCTGCTGGCACAACCAGCTGTTCG
TGACCGTGGTGGACACCACCAGGAGCACCAACCTGACCCTGTGCGCCAG
CACCCAGAACCCCGTGCCCAGCACCTACGACCCCACCAAGTTCAAGCAG
TACAGCAGGCACGTGGAGGAGTACGACCTGCAGTTCATCTTCCAGCTGT
GCACCATCACCCTGACCGCCGAGGTGATGAGCTACATCCACAGCATGAA
CAGCAGCATCCTGGAGAACTGGAACTTCGGCGTGCCCCCCCCCCCCACC
ACCAGCCTGGTGGACACCTACAGGTTCGTGCAGAGCGTGGCCGTGACCT
GCCAGAAGGACACCACCCCCCCGAGAAGCAGGACCCCTACGACAAGCT
GAAGTTCTGGACCGTGGACCTGAAGGAGAAGTTCAGCAGCGACCTGGAC
CAGTACCCCCTGGGCAGGAAGTTCCTGGTGCAGGCCGGCCTGAGGAGGA
GGCCCACCATCGGCCCCAGGAAGAGGCCCGCCGCCAGCACCAGCACCGC
CAGCACCGCCAGCAGGCCCGCCAAGAGGGTGAGGATCAGGAGCAAGAAG
TGA Sequence 22 (SEQ ID NO: 22):
ATGGCCCTGTGGAGGAGCAGCGACAACAAGGTGTACCTGCCCCCCCCCA
GCGTGGCCAAGGTGGTGAGCACCGACGAGTACGTGACCAGGACCAGCAT
CTTCTACCACGCCGGCAGCAGCAGGCTGCTGACCGTGGGCCACCCCTAC
TTCAAGGTGCCCAAGGGCGGCAACGGCAGGCAGGACGTGCCCAAGGTGA
GCGCCTACCAGTACAGGGTGTTCAGGGTGAAGCTGCCCGACCCCAACAA
GTTCGGCCTGCCCGACAACACCGTGTACGACCCCAACAGCCAGAGGCTG
GTGTGGGCCTGCGTGGGCGTGGAGATCGGCAGGGGCCAGCCCCTGGGCG
TGGGCCTGAGCGGCCACCCCCTGTACAACAAGCTGGACGACACCGAGAA
CAGCCACGTGGCCAGCGCCGTGGACACCAAGGACACCAGGGACAACGTG
AGCGTGGACTACAAGCAGACCCAGCTGTGCATCATCGGCTGCGTGCCCG -continued
CCATCGGCGAGCACTGGACCAAGGGCACCGCCTGCAAGCCCACCACCGT
GGTGCAGGGCGACTGCCCCCCCCTGGAGCTGATCAACACCCCCATCGAG
GACGGCGACATGGTGGACACCGGCTACGGCGCCATGGACTTCAAGCTGC
TGCAGGACAACAAGAGCGAGGTGCCCCTGGACATCTGCCAGAGCATCTG
CAAGTACCCCGACTACCTGCAGATGAGCGCCGACGCCTACGGCGACAGC
ATGTTCTTCTGCCTGAGGAGGGAGCAGGTGTTCGCCAGGCACTTCTGGA
ACAGGAGCGGCACCATGGGCGACCAGCTGCCCGAGAGCCTGTACATCAA
GGGCACCGACATCAGGGCCAACCCCGGCAGCTACCTGTACAGCCCCAGC
CCCAGCGGCAGCGTGGTGACCAGCGACAGCCAGCTGTTCAACAAGCCCT
ACTGGCTGCACAAGGCCCAGGGCCTGAACAACGGCATCTGCTGGCACAA
CCAGCTGTTCCTGACCGTGGTGGACACCACCAGGAGCACCAACCTGAGC
GTGTGCGCCAGCACCACCAGCAGCATCCCCAACGTGTACACCCCCACCA
GCTTCAAGGAGTACGCCAGGCACGTGGAGGAGTTCGACCTGCAGTTCAT
CTTCCAGCTGTGCAAGATCACCCTGACCACCGAGGTGATGAGCTACATC
CACAACATGAACACCACCATCCTGGAGGACTGGAACTTCGGCGTGACCC
CCCCCCCCACCGCCAGCCTGGTGGACACCTACAGGTTCGTGCAGAGCGC
CGCCGTGACCTGCCAGAAGGACACCGCCCCCCCCGTGAAGCAGGACCCC
TACGACAAGCTGAAGTTCTGGCCCGTGGACCTGAAGGAGAGGTTCAGCG
CCGACCTGGACCAGTTCCCCCTGGGCAGGAAGTTCCTGCTGCAGCTGGG
CGCCAGGCCCAAGCCCACCATCGGCCCCAGGAAGAGGGCCGCCCCCGCC
CCCACCAGCACCCCCAGCCCCAAGAGGGTGAAGAGGAGGAAGAGCAGCA
GGAAGTGA Sequence 23 (SEQ ID NO: 23):
ATGCGGCCTAGTGACAATACCGTATATCTTCCACCTCCTTCTGTGGCAA
GAGTTGTAAATACCGATGATTACGTGACTAGGACCAGCATCTTCTACCA
CGCCGGCAGCAGCAGGCTGCTGACCGTGGGCAACCCCTACTTCAGGGTG
GTGCCCAACGGCGCCGGCAACAAGCAGGCCGTGCCCAAGGTGAGCGCCT
ACCAGTACAGGGTGTTCAGGGTGCAGTTACCTGACCCAAATAAATTTGG
TTTACCTGATACTAGTATTTATAATCCTGAAACACAACGTTTAGTGTGG
GCCTGTGCTGGAGTGGAAATTGGCCGTGGTCAGCCTTTAGGTGTTGGCC
TTAGTGGGCATCCATTTTATAATAAATTAGATGACACTGAAAGTTCCCA
TGCCGCCACGTCTAATGTTTCTGAGGACGTTAGGGACAATGTGTCTGTA
GATTATAAGCAGACACAGTTATGTATTTTGGGCTGTGCCCCTGCTATTG
GGGAACACTGGGCTAAAGGCACTGCTTGTAAATCGCGTCCTTTATCACA
GGGCGATTGCCCCCCTTTAGAACTTAAAAACACAGTTTTGGAAGATGGT
GATATGGTAGATACTGGATATGGTGCCATGGACTTTAGTACATTGCAAG
ATACTAAATGTGAGGTACCATTGGATATTTGTCAGTCTATTTGTAAATA
TCCTGATTATTTACAAATGTCTGCAGATCCTTATGGGGATTCCATGTTT
TTTTGCTTACGGCGTGAGCAGCTTTTTGCTAGGCATTTTGGAATAGAG
CAGGTACTATGGGTGACACTGTGCCTCAATCCTTATATATTAAAGGCAC

AGGTATGCGTGCTTCACCTGGCAGCTGTGTGTATTCTCCCTCTCCAAGT

GGCTCTATTGTTACCTCTGACTCCCAGTTGTTTAATAAACCATATTGGT

TACATAAGGCACAGGGTCATAACAATGGTGTTTGCTGGCATAATCAATT

ATTTGTTACTGTGGTAGATACCACTCGCAGTACCAATTTAACAATATGT

GCTTCTACACAGTCTCCTGTACCTGGGCAATATGATGCTACCAAATTTA

AGCAGTATAGCAGACATGTTGAGGAATATGATTTGCAGTTTATTTTTCA

GTTGTGTACTATTACTTTAACTGCAGATGTTATGTCCTATATTCATAGT

ATGAATAGCAGTATTTTAGAGGATTGGAACTTGGTGTTCCCCCCCGC

CAACTACTAGTTTGGTGGATACATATCGTTTTGTACAATCTGTTGCTAT

TGCCTGTCAAAAGGATGCTGCACCGGCTGAAAATAAGGATCCCTATGAT

AAGTTAAAGTTTTGGAATGTGGATTTAAAGGAAAAGTTTTCTTTAGACT

TAGATCAATATCCCCTTGGACGTAAATTTTTGGTTCAGGCTGGATTGCG

TCGCAAGCCCACCATAGGCCCTCGCAAACGTTCTGCTCCATCTGCCACT

ACGGCTTCTAAACCTGCCAAGCGTGTGCGTGTACGTGCCAGGAAGTAA

Sequence 24 (SEQ ID NO: 24):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAGATCGGCAGGGGCCAGCCCCTGGGCATCGGCCTGA

GCGGCCACCCCTTCTACAACAAGCTGGACGACACCGAGAGCGCCCACGC

CGCCACCGCCGTGATCACCCAGGACGTGAGGGACAACGTGAGCGTGGAC

TACAAGCAGACCCAGCTGTGCATCCTGGGCTGCGCCCCTGCTATTGGG

AACACTGGGCTAAAGGCACTGCTTGTAAATCGCGTCCTTTATCACAGGG

CGATTGCCCCCCTTTAGAACTTAAAAACACAGTTTTGGAAGATGGTGAT

ATGGTAGATACTGGATATGGTGCCATGGACTTTAGTACATTGCAAGATA

CTAAATGTGAGGTACCATTGGATATTGTCAGTCTATTTGTAAATATCC

TGATTATTTACAAATGTCTGCAGATCCTTATGGGGATTCCATGTTTTTT

TGCTTACGGCGTGAGCAGCTTTTTGCTAGGCATTTTTGGAATAGAGCAG

GTACTATGGGTGACACTGTGCCTCAATCCTTATATATTAAAGGCACAGG

TATGCGTGCTTCACCTGGCAGCTGTGTGTATTCTCCCTCTCCAAGTGGC

TCTATTGTTACCTCTGACTCCCAGTTGTTTAATAAACCATATTGGTTAC

ATAAGGCACAGGGTCATAACAATGGTGTTTGCTGGCATAATCAATTATT

TGTTACTGTGGTAGATACCACTCGCAGTACCAATTTAACAATATGTGCT

TCTACACAGTCTCCTGTACCTGGGCAATATGATGCTACCAAATTTAAGC

AGTATAGCAGACATGTTGAGGAATATGATTTGCAGTTTATTTTTCAGTT

GTGTACTATTACTTTAACTGCAGATGTTATGTCCTATATTCATAGTATG

AATAGCAGTATTTTAGAGGATTGGAACTTTGGTGTTCCCCCCCGCCAA

CTACTAGTTTGGTGGATACATATCGTTTTGTACAATCTGTTGCTATTGC

CTGTCAAAAGGATGCTGCACCGGCTGAAAATAAGGATCCCTATGATAAG

TTAAAGTTTTGGAATGTGGATTTAAAGGAAAAGTTTTCTTTAGACTTAG

ATCAATATCCCCTTGGACGTAAATTTTTGGTTCAGGCTGGATTGCGTCG

CAAGCCCACCATAGGCCCTCGCAAACGTTCTGCTCCATCTGCCACTACG

GCTTCTAAACCTGCCAAGCGTGTGCGTGTACGTGCCAGGAAGTAA

Sequence 25 (SEQ ID NO: 25):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCCGCCATCGGCG

AGCACTGGGCCAAGGGCACCCCTGTGCAAGCCCGCCCAGCTGCAGCCCGG

CGACTGCCCCCCCCTGGAGCTGAAGAACACCGTTTTGGAAGATGGTGAT

ATGGTAGATACTGGATATGGTGCCATGGACTTTAGTACATTGCAAGATA

CTAAATGTGAGGTACCATTGGATATTTGTCAGTCTATTTGTAAATATCC

TGATTATTTACAAATGTCTGCAGATCCTTATGGGGATTCCATGTTTTTT

TGCTTACGGCGTGAGCAGCTTTTTGCTAGGCATTTTTGGAATAGAGCAG

GTACTATGGGTGACACTGTGCCTCAATCCTTATATATTAAAGGCACAGG

TATGCGTGCTTCACCTGGCAGCTGTGTGTATTCTCCCTCTCCAAGTGGC

TCTATTGTTACCTCTGACTCCCAGTTGTTTAATAAACCATATTGGTTAC

ATAAGGCACAGGGTCATAACAATGGTGTTTGCTGGCATAATCAATTATT

TGTTACTGTGGTAGATACCACTCGCAGTACCAATTTAACAATATGTGCT

TCTACACAGTCTCCTGTACCTGGGCAATATGATGCTACCAAATTTAAGC

AGTATAGCAGACATGTTGAGGAATATGATTTGCAGTTTATTTTTCAGTT

GTGTACTATTACTTTAACTGCAGATGTTATGTCCTATATTCATAGTATG

AATAGCAGTATTTTAGAGGATTGGAACTTTGGTGTTCCCCCCCGCCAA

CTACTAGTTTGGTGGATACATATCGTTTTGTACAATCTGTTGCTATTGC

CTGTCAAAAGGATGCTGCACCGGCTGAAAATAAGGATCCCTATGATAAG

TTAAAGTTTTGGAATGTGGATTTAAAGGAAAAGTTTTCTTTAGACTTAG

ATCAATATCCCCTTGGACGTAAATTTTTGGTTCAGGCTGGATTGCGTCG

CAAGCCCACCATAGGCCCTCGCAAACGTTCTGCTCCATCTGCCACTACG

GCTTCTAAACCTGCCAAGCGTGTGCGTGTACGTGCCAGGAAGTAA

Sequence 26 (SEQ ID NO: 26):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCTGCTATTGGGG

AACACTGGGCTAAAGGCACTGCTTGTAAATCGCGTCCTTTATCACAGGG

CGATTGCCCCCCTTTAGAACTTAAAAACACAGTTTTGGAAGATGGTGAT

ATGGTAGATACTGGATACGGCGCCATGGACTTCAGCACCCTGCAGGACA

CCAAGTGCGAGGTGCCCCTGGACATCTGCCAGAGCATCTGCAAGTACCC

CGACTACCTGCAGATGAGCGCCGACCCCTACGGCGACAGCATGTTCTTC

TGCCTGAGGAGGGAGCAGCTGTTCGCCAGGCACTTCTGGAACAGGGCCG

GCGTGATGGGCGACACCGTGCCCACCGACCTGTACATCAAGGGCACCAG

CGCCAACATGAGGGAGACCCCCGGCAGCTGCGTGTACAGCCCCAGCCCC

AGCGGCAGCATCGTTACCTCTGACTCCCAGTTGTTTAATAAACCATATT

GGTTACATAAGGCACAGGGTCATAACAATGGTGTTTGCTGGCATAATCA

ATTATTTGTTACTGTGGTAGATACCACTCGCAGTACCAATTTAACAATA

TGTGCTTCTACACAGTCTCCTGTACCTGGCAATATGATGCTACCAAAT

TTAAGCAGTATAGCAGACATGTTGAGGAATATGATTTGCAGTTTATTTT

TCAGTTGTGTACTATTACTTTAACTGCAGATGTTATGTCCTATATTCAT

AGTATGAATAGCAGTATTTTAGAGGATTGGAACTTTGGTGTTCCCCCCC

CGCCAACTACTAGTTTGGTGGATACATATCGTTTTGTACAATCTGTTGC

TATTGCCTGTCAAAAGGATGCTGCACCGGCTGAAAATAAGGATCCCTAT

GATAAGTTAAAGTTTTGGAATGTGGATTTAAAGGAAAAGTTTTCTTTAG

ACTTAGATCAATATCCCCTTGGACGTAAATTTTTGGTTCAGGCTGGATT

GCGTCGCAAGCCCACCATAGGCCCTCGCAAACGTTCTGCTCCATCTGCC

ACTACGGCTTCTAAACCTGCCAAGCGTGTGCGTGTACGTGCCAGGAAGT

AA

Sequence 27 (SEQ ID NO: 27):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCTGCTATTGGGG

AACACTGGGCTAAAGGCACTGCTTGTAAATCGCGTCCTTTATCACAGGG

CGATTGCCCCCCTTTAGAACTTAAAAACACAGTTTTGGAAGATGGTGAT

ATGGTAGATACTGGATATGGTGCCATGGACTTTAGTACATTGCAAGATA

CTAAATGTGAGGTACCATTGGATATTTGTCAGTCTATTTGTAAATATCC

TGATTATTTACAAATGTCTGCAGATCCTTATGGGATTCCATGTTTTTTT

GCTTACGGCGTGAGCAGCTTTTTGCTAGGCATTTTTGGAATAGAGCAGG

TACTATGGGTGACACTGTGCCTCAATCCTTATATATTAAAGGCACAGGT

ATGCGTGCTTCACCTGGCAGCTGTGTGTATTCTCCCTCTCCAAGTGGCT

CTATTGTTACCTCTGACTCCCAGTTGTTTAATAAACCATATTGGTTACA

TAAGGCACAGGGTCATAACAATGGTGTTTGCTGGCATAATCAATTATTT

GTTACTGTGGTAGATACCACTCGCAGTACCAATTTAACAATATGCGCCA

GCACCCAGAACCCCGTGCCCAGCACCTACGACCCCACCAAGTTCAAGCA

GTACAGCAGGCACGTGGAGGAGTACGACCTGCAGTTCATCTTCCAGCTG

TGCACCATCACCCTGACCGCCGATGTTATGTCCTATATTCATAGTATGA

ATAGCAGTATTTTAGAGGATTGGAACTTTGGTGTTCCCCCCCCGCCAAC

TACTAGTTTGGTGGATACATATCGTTTTGTACAATCTGTTGCTATTGCC

TGTCAAAAGGATGCTGCACCGGCTGAAAATAAGGATCCCTATGATAAGT

TAAAGTTTTGGAATGTGGATTTAAAGGAAAAGTTTTCTTTAGACTTAGA

TCAATATCCCCTTGGACGTAAATTTTTGGTTCAGGCTGGATTGCGTCGC

AAGCCCACCATAGGCCCTCGCAAACGTTCTGCTCCATCTGCCACTACGG

CTTCTAAACCTGCCAAGCGTGTGCGTGTACGTGCCAGGAAGTAA

Sequence 28 (SEQ ID NO: 28):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTCAAGGTG

CCCAAGGGCGGCAACGGCAGGCAGGACGTGCCCAAGGTGAGCGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCCGCCATCGGCG

AGCACTGGGCCAAGGGCACCCTGTGCAAGCCCGCCAGCTGCAGCCCGG

CGACTGCCCCCCCCTGGAGCTGAAGAACACCGTTTTGGAAGATGGTGAT

ATGGTAGATACTGGATATGGTGCCATGGACTTTAGTACATTGCAAGATA

CTAAATGTGAGGTACCATTGGATATTTGTCAGTCTATTTGTAAATATCC

TGATTATTTACAAATGTCTGCAGATCCTTATGGGGATTCCATGTTTTTT

TGCTTACGGCGTGAGCAGCTTTTTGCTAGGCATTTTTGGAATAGAGCAG

GTACTATGGGTGACACTGTGCCTCAATCCTTATATATTAAAGGCACAGG

TATGCGTGCTTCACCTGGCAGCTGTGTGTATTCTCCCTCTCCAAGTGGC

TCTATTGTTACCTCTGACTCCCAGTTGTTTAATAAACCATATTGGTTAC

ATAAGGCACAGGGTCATAACAATGGTGTTTGCTGGCATAATCAATTATT

TGTTACTGTGGTAGATACCACTCGCAGTACCAATTTAACAATATGTGCT

TCTACACAGTCTCCTGTACCTGGGCAATATGATGCTACCAAATTTAAGC

AGTATAGCAGACATGTTGAGGAATATGATTTGCAGTTTATTTTTCAGTT

GTGTACTATTACTTTAACTGCAGATGTTATGTCCTATATTCATAGTATG

AATAGCAGTATTTTAGAGGATTGGAACTTTGGTGTTCCCCCCCGCCAA

CTACTAGTTTGGTGGATACATATCGTTTTGTACAATCTGTTGCTATTGC

CTGTCAAAAGGATGCTGCACCGGCTGAAAATAAGGATCCCTATGATAAG

TTAAAGTTTTGGAATGTGGATTTAAAGGAAAAGTTTTCTTTAGACTTAG

ATCAATATCCCCTTGGACGTAAATTTTTGGTTCAGGCTGGATTGCGTCG

CAAGCCCACCATAGGCCCTCGCAAACGTTCTGCTCCATCTGCCACTACG

GCTTCTAAACCTGCCAAGCGTGTGCGTGTACGTGCCAGGAAGTAA

Sequence 29 (SEQ ID NO: 29):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGCGTGGAGATCGGCAGGGGCCAGCCCCTGGGCGTGGGCCTGA

GCGGCCACCCCCTGTACAACAAGCTGGACGACACCGAGAACAGCCACGT

GGCCAGCGCCGTGGACACCAAGGACACCAGGGACAACGTGAGCGTGGAC

TACAAGCAGACCCAGCTGTGCATCTTGGGCTGTGCCCCCGCCATCGGCG

AGCACTGGGCCAAGGGCACCCTGTGCAAGCCCGCCCAGCTGCAGCCCGG

CGACTGCCCCCCCCTGGAGCTGAAGAACACCGTTTTGGAAGATGGTGAT

ATGGTAGATACTGGATATGGTGCCATGGACTTTAGTACATTGCAAGATA

CTAAATGTGAGGTACCATTGGATATTTGTCAGTCTATTTGTAAATATCC

TGATTATTTACAAATGTCTGCAGATCCTTATGGGGATTCCATGTTTTTT

TGCTTACGGCGTGAGCAGCTTTTTGCTAGGCATTTTTGGAATAGAGCAG

GTACTATGGGTGACACTGTGCCTCAATCCTTATATATTAAAGGCACAGG

TATGCGTGCTTCACCTGGCAGCTGTGTGTATTCTCCCTCTCCAAGTGGC

TCTATTGTTACCTCTGACTCCCAGTTGTTTAATAAACCATATTGGTTAC

ATAAGGCACAGGGTCATAACAATGGTGTTTGCTGGCATAATCAATTATT

TGTTACTGTGGTAGATACCACTCGCAGTACCAATTTAACAATATGTGCT

TCTACACAGTCTCCTGTACCTGGGCAATATGATGCTACCAAATTTAAGC

AGTATAGCAGACATGTTGAGGAATATGATTTGCAGTTTATTTTTCAGTT

GTGTACTATTACTTTAACTGCAGATGTTATGTCCTATATTCATAGTATG

AATAGCAGTATTTTAGAGGATTGGAACTTTGGTGTTCCCCCCCGCCAA

CTACTAGTTTGGTGGATACATATCGTTTTGTACAATCTGTTGCTATTGC

CTGTCAAAAGGATGCTGCACCGGCTGAAAATAAGGATCCCTATGATAAG

TTAAAGTTTTGGAATGTGGATTTAAAGGAAAAGTTTTCTTTAGACTTAG

ATCAATATCCCCTTGGACGTAAATTTTTGGTTCAGGCTGGATTGCGTCG

CAAGCCCACCATAGGCCCTCGCAAACGTTCTGCTCCATCTGCCACTACG

GCTTCTAAACCTGCCAAGCGTGTGCGTGTACGTGCCAGGAAGTAA

Sequence 30 (SEQ ID NO: 30):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCCGCCATCGGCG

AGCACTGGGCCAAGGGCACCCTGTGCAAGCCCGCCCAGCTGCAGCCCGG

CGACTGCCCCCCCCTGGAGCTGAAGAACACCGTTTTGGAAGATGGTGAT

ATGGTAGATACTGGATATGGTGCCATGGACTTTAGTACATTGCAAGATA

CTAAATGTGAGGTACCATTGGATATTTGTCAGTCTATTTGTAAATATCC

TGATTATTTACAAATGTCTGCAGATCCTTATGGGGATTCCATGTTTTTT

TGCTTACGGCGTGAGCAGCTTTTCGCCAGGCACTTCTGGAACAGGAGCG

GCACCATGGGCGACCAGCTGCCCGAGAGCCTGTACATCAAGGGCACCGA

CATCAGGGCCAACCCCGGCAGCTACCTGTACAGCCCCAGCCCCAGCGGC

TCTATTGTTACCTCTGACTCCCAGTTGTTTAATAAACCATATTGGTTAC

ATAAGGCACAGGGTCATAACAATGGTGTTTGCTGGCATAATCAATTATT

TGTTACTGTGGTAGATACCACTCGCAGTACCAATTTAACAATATGTGCT

TCTACACAGTCTCCTGTACCTGGGCAATATGATGCTACCAAATTTAAGC

AGTATAGCAGACATGTTGAGGAATATGATTTGCAGTTTATTTTTCAGTT

GTGTACTATTACTTTAACTGCAGATGTTATGTCCTATATTCATAGTATG

AATAGCAGTATTTTAGAGGATTGGAACTTTGGTGTTCCCCCCCGCCAA

CTACTAGTTTGGTGGATACATATCGTTTTGTACAATCTGTTGCTATTGC

CTGTCAAAAGGATGCTGCACCGGCTGAAAATAAGGATCCCTATGATAAG

TTAAAGTTTTGGAATGTGGATTTAAAGGAAAAGTTTTCTTTAGACTTAG

ATCAATATCCCCTTGGACGTAAATTTTTGGTTCAGGCTGGATTGCGTCG

CAAGCCCACCATAGGCCCTCGCAAACGTTCTGCTCCATCTGCCACTACG

GCTTCTAAACCTGCCAAGCGTGTGCGTGTACGTGCCAGGAAGTAA

Sequence 31 (SEQ ID NO: 31):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCCGCCATCGGCG

AGCACTGGGCCAAGGGCACCCTGTGCAAGCCCGCCCAGCTGCAGCCCGG

CGACTGCCCCCCCCTGGAGCTGAAGAACACCGTTTTGGAAGATGGTGAT

ATGGTAGATACTGGATATGGTGCCATGGACTTTAGTACATTGCAAGATA

CTAAATGTGAGGTACCATTGGATATTTGTCAGTCTATTTGTAAATATCC

TGATTATTTACAAATGTCTGCAGATCCTTATGGGGATTCCATGTTTTTT

TGCTTACGGCGTGAGCAGCTTTTTGCTAGGCATTTTTGGAATAGAGCAG

GTACTATGGGTGACACTGTGCCTCAATCCTTATATATTAAAGGCACAGG

TATGCGTGCTTCACCTGGCAGCTGTGTGTATTCTCCCTCTCCAAGTGGC

TCTATTGTTACCTCTGACTCCCAGTTGTTTAATAAACCATATTGGTTAC

ATAAGGCACAGGGTCATAACAATGGTGTTTGCTGGCATAATCAATTATT

TGTTACTGTGGTAGATACCACTCGCAGTACCAATTTAACAATATGCGCC

AGCACCACCAGCAGCATCCCCAACGTGTACACCCCCACCAGCTTCAAGC

AGTATAGCAGACATGTTGAGGAATATGATTTGCAGTTTATTTTTCAGTT

GTGTACTATTACTTTAACTGCAGATGTTATGTCCTATATTCATAGTATG

AATAGCAGTATTTTAGAGGATTGGAACTTTGGTGTTCCCCCCCCGCCAA

CTACTAGTTTGGTGGATACATATCGTTTTGTACAATCTGTTGCTATTGC

CTGTCAAAAGGATGCTGCACCGGCTGAAAATAAGGATCCCTATGATAAG

TTAAAGTTTTGGAATGTGGATTTAAAGGAAAAGTTTTCTTTAGACTTAG

ATCAATATCCCCTTGGACGTAAATTTTTGGTTCAGGCTGGATTGCGTCG

CAAGCCCACCATAGGCCCTCGCAAACGTTCTGCTCCATCTGCCACTACG

GCTTCTAAACCTGCCAAGCGTGTGCGTGTACGTGCCAGGAAGTAA

Sequence 32 (SEQ ID NO: 32):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCTACTTCAAGGTG

CCCAAGGGCGGCAACGGCAGGCAGGACGTGCCCAAGGTGAGCGCCTACC

AGTACAGGGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCTGCTATTGGGG

AACACTGGGCTAAAGGCACTGCTTGTAAATCGCGTCCTTTATCACAGGG

CGATTGCCCCCCTTTAGAACTTAAAAACACAGTTTTGGAAGATGGTGAT

ATGGTAGATACTGGATACGGCGCCATGGACTTCAGCACCCTGCAGGACA

CCAAGTGCGAGGTGCCCCTGGACATCTGCCAGAGCATCTGCAAGTACCC

CGACTACCTGCAGATGAGCGCCGACCCCTACGGCGACAGCATGTTCTTC

TGCCTGAGGAGGGAGCAGCTGTTCGCCAGGCACTTCTGGAACAGGGCCG

GCGTGATGGGCGACACCGTGCCCACCGACCTGTACATCAAGGGCACCAG

CGCCAACATGAGGGAGACCCCCGGCAGCTGCGTGTACAGCCCCAGCCCC

AGCGGCAGCATCGTTACCTCTGACTCCCAGTTGTTTAATAAACCATATT

GGTTACATAAGGCACAGGGTCATAACAATGGTGTTTGCTGGCATAATCA

ATTATTTGTTACTGTGGTAGATACCACTCGCAGTACCAATTTAACAATA

TGTGCTTCTACACAGTCTCCTGTACCTGGGCAATATGATGCTACCAAAT

TTAAGCAGTATAGCAGACATGTTGAGGAATATGATTTGCAGTTTATTTT

TCAGTTGTGTACTATTACTTTAACTGCAGATGTTATGTCCTATATTCAT

AGTATGAATAGCAGTATTTTAGAGGATTGGAACTTTGGTGTTCCCCCCC

CGCCAACTACTAGTTTGGTGGATACATATCGTTTTGTACAATCTGTTGC

TATTGCCTGTCAAAAGGATGCTGCACCGGCTGAAAATAAGGATCCCTAT

GATAAGTTAAAGTTTTGGAATGTGGATTTAAAGGAAAAGTTTTCTTTAG

ACTTAGATCAATATCCCCTTGGACGTAAATTTTTGGTTCAGGCTGGATT

GCGTCGCAAGCCCACCATAGGCCCTCGCAAACGTTCTGCTCCATCTGCC

ACTACGGCTTCTAAACCTGCCAAGCGTGTGCGTGTACGTGCCAGGAAGT

AA

Sequence 33 (SEQ ID NO: 33):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGCGTGGAGATCGGCAGGGGCCAGCCCCTGGGCGTGGGCCTGA

GCGGCCACCCCCTGTACAACAAGCTGGACGACACCGAGAACAGCCACGT

GGCCAGCGCCGTGGACACCAAGGACACCAGGGACAACGTGAGCGTGGAC

TACAAGCAGACCCAGCTGTGCATCTTGGGCTGTGCCCCTGCTATTGGGG

AACACTGGGCTAAAGGCACTGCTTGTAAATCGCGTCCTTTATCACAGGG

CGATTGCCCCCCTTTAGAACTTAAAAACACAGTTTTGGAAGATGGTGAT

ATGGTAGATACTGGATACGGCGCCATGGACTTCAGCACCCTGCAGGACA

CCAAGTGCGAGGTGCCCCTGGACATCTGCCAGAGCATCTGCAAGTACCC

CGACTACCTGCAGATGAGCGCCGAcCCCTACGGCGACAGCATGTTCTTC

TGCCTGAGGAGGGAGCAGCTGTTCGCCAGGCACTTCTGGAACAGGGCCG

GCGTGATGGGCGACACCGTGCCCACCGACCTGTACATCAAGGGCACCAG

CGCCAACATGAGGGAGACCCCCGGCAGCTGCGTGTACAGCCCCAGCCCC

AGCGGCAGCATCGTTACCTCTGACTCCCAGTTGTTTAATAAACCATATT

GGTTACATAAGGCACAGGGTCATAACAATGGTGTTTGCTGGCATAATCA

ATTATTTGTTACTGTGGTAGATACCACTCGCAGTACCAATTTAACAATA

TGTGCTTCTACACAGTCTCCTGTACCTGGGCAATATGATGCTACCAAAT

TTAAGCAGTATAGCAGACATGTTGAGGAATATGATTTGCAGTTTATTTT

TCAGTTGTGTACTATTACTTTAACTGCAGATGTTATGTCCTATATTCAT

AGTATGAATAGCAGTATTTTAGAGGATTGGAACTTTGGTGTTCCCCCCC

CGCCAACTACTAGTTTGGTGGATACATATCGTTTTGTACAATCTGTTGC

TATTGCCTGTCAAAAGGATGCTGCACCGGCTGAAAATAAGGATCCCTAT

GATAAGTTAAAGTTTTGGAATGTGGATTTAAAGGAAAAGTTTTCTTTAG

ACTTAGATCAATATCCCCTTGGACGTAAATTTTTGGTTCAGGCTGGATT

GCGTCGCAAGCCCACCATAGGCCCTCGCAAACGTTCTGCTCCATCTGCC

ACTACGGCTTCTAAACCTGCCAAGCGTGTGCGTGTACGTGCCAGGAAGT

AA

Sequence 34 (SEQ ID NO: 34):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCCGCCATCGGCG

AGCACTGGACCAAGGGCACCGCCTGCAAGCCCACCACCGTGGTGCAGGG

CGACTGCCCCCCCCTGGAGCTGAAAACACAGTTTTGGAAGATGGTGAT

ATGGTAGATACTGGATACGGCGCCATGGACTTCAGCACCCTGCAGGACA

CCAAGTGCGAGGTGCCCCTGGACATCTGCCAGAGCATCTGCAAGTACCC

CGACTACCTGCAGATGAGCGCCGAccccTACGGCGACAGCATGTTCTTC

TGCCTGAGGAGGGAGCAGCTGTTCGCCAGGCACTTCTGGAACAGGGCCG

GCGTGATGGGCGACACCGTGCCCACCGACCTGTACATCAAGGGCACCAG

CGCCAACATGAGGGAGACCCCCGGCAGCTGCGTGTACAGCCCCAGCCCC

AGCGGCAGCATCGTTACCTCTGACTCCCAGTTGTTTAATAAACCATATT

GGTTACATAAGGCACAGGGTCATAACAATGGTGTTTGCTGGCATAATCA

ATTATTTGTTACTGTGGTAGATACCACTCGCAGTACCAATTTAACAATA

TGTGCTTCTACACAGTCTCCTGTACCTGGGCAATATGATGCTACCAAAT

TTAAGCAGTATAGCAGACATGTTGAGGAATATGATTTGCAGTTTATTTT

TCAGTTGTGTACTATTACTTTAACTGCAGATGTTATGTCCTATATTCAT

AGTATGAATAGCAGTATTTTAGAGGATTGGAACTTTGGTGTTCCCCCCC

CGCCAACTACTAGTTTGGTGGATACATATCGTTTTGTACAATCTGTTGC

TATTGCCTGTCAAAAGGATGCTGCACCGGCTGAAAATAAGGATCCCTAT

GATAAGTTAAAGTTTTGGAATGTGGATTTAAAGGAAAAGTTTTCTTTAG

ACTTAGATCAATATCCCCTTGGACGTAAATTTTTGGTTCAGGCTGGATT

GCGTCGCAAGCCCACCATAGGCCCTCGCAAACGTTCTGCTCCATCTGCC

ACTACGGCTTCTAAACCTGCCAAGCGTGTGCGTGTACGTGCCAGGAAGT

AA

Sequence 35 (SEQ ID NO: 35):
ATGCGGCCTAGTGACAATACCGTATATCTTCCACCTCCTTCTGTGGCAA

GAGTTGTAAATACCGATGATTACGTGACTCGCACAAGCATATTTTATCA

TGCTGGCAGCTCTAGATTATTAACTGTTGGTAATCCATATTTTAGGGTT

CCTGCAGGTGGTGGCAATAAGCAGGATATTCCTAAGGTTTCTGCATACC

AATATAGAGTATTTAGGGTGCAGTTACCTGACCCAAATAAATTTGGTTT

ACCTGATACTAGTATTTATAATCCTGAAACACAACGTTTAGTGTGGGCC

TGTGCTGGAGTGGAAATTGGCCGTGGTCAGCCTTTAGGTGTTGGCCTTA

GTGGGCATCCATTTTATAATAAATTAGATGACACTGAAAGTTCCCATGC

CGCCACGTCTAATGTTTCTGAGGACGTTAGGGACAATGTGTCTGTAGAT

TATAAGCAGACACAGTTATGTATTTTGGGCTGTGCCCCTGCTATTGGGG

AACACTGGGCTAAAGGCACTGCTTGTAAATCGCGTCCTTTATCACAGGG

CGATTGCCCCCCTTTAGAACTTAAAAACACAGTTTTGGAAGATGGTGAT

ATGGTAGATACTGGATACGGCGCCATGGACTTCAGCACCCTGCAGGACA

CCAAGTGCGAGGTGCCCCTGGACATCTGCCAGAGCATCTGCAAGTACCC

CGACTACCTGCAGATGAGCGCCGAcCCCTACGGCGACAGCATGTTCTTC

TGCCTGAGGAGGGAGCAGCTGTTCGCCAGGCACTTCTGGAACAGGGCCG

GCGTGATGGGCGACACCGTGCCCACCGACCTGTACATCAAGGGCACCAG

CGCCAACATGAGGGAGACCCCCGGCAGCTGCGTGTACAGCCCCAGCCCC

AGCGGCAGCATCGTTACCTCTGACTCCCAGTTGTTTAATAAACCATATT

GGTTACATAAGGCACAGGGTCATAACAATGGTGTTTGCTGGCATAATCA

ATTATTTGTTACTGTGGTAGATACCACTCGCAGTACCAATTTAACAATA

TGCGCCAGCACCACCAGCAGCATCCCCAACGTGTACACCCCCACCAGCT

TCAAGCAGTATAGCAGACATGTTGAGGAATATGATTTGCAGTTTATTTT

-continued
TCAGTTGTGTACTATTACTTTAACTGCAGATGTTATGTCCTATATTCAT
AGTATGAATAGCAGTATTTTAGAGGATTGGAACTTTGGTGTTCCCCCCC
CGCCAACTACTAGTTTGGTGGATACATATCGTTTGTACAATCTGTTGC
TATTGCCTGTCAAAAGGATGCTGCACCGGCTGAAAATAAGGATCCCTAT
GATAAGTTAAAGTTTTGGAATGTGGATTTAAAGGAAAAGTTTTCTTTAG
ACTTAGATCAATATCCCCTTGGACGTAAATTTTTGGTTCAGGCTGGATT
GCGTCGCAAGCCCACCATAGGCCCTCGCAAACGTTCTGCTCCATCTGCC
ACTACGGCTTCTAAACCTGCCAAGCGTGTGCGTGTACGTGCCAGGAAGT
AA Sequence 36 (SEQ ID NO: 36):
ATGCGGCCTAGTGACAATACCGTATATCTTCCACCTCCTTCTGTGGCAA
GAGTTGTAAATACCGATGATTACGTGACTAGGACCAGCATCTTCTACCA
CGCCGGCAGCAGCAGGCTGCTGACCGTGGGCAACCCCTACTTCAGGGTG
GTGCCCAACGGCGCCGGCAACAAGCAGGCCGTGCCCAAGGTGAGCGCCT
ACCAGTACAGGGTGTTCAGGGTGCAGTTACCTGACCCAAATAAATTTGG
TTTACCTGATACTAGTATTTATAATCCTGAAACACAACGTTTAGTGTGG
GCCTGTGCTGGAGTGGAAATTGGCCGTGGTCAGCCTTTAGGTGTTGGCC
TTAGTGGGCATCCATTTTATAATAAATTAGATGACACTGAAAGTTCCCA
TGCCGCCACGTCTAATGTTTCTGAGGACGTTAGGGACAATGTGTCTGTA
GATTATAAGCAGACACAGTTATGTATTTTGGGCTGTGCCCCTGCTATTG
GGGAACACTGGGCTAAAGGCACTGCTTGTAAATCGCGTCCTTTATCACA
GGGCGATTGCCCCCCTTTAGAACTTAAAAACACAGTTTTGGAAGATGGT
GATATGGTAGATACTGGATATGGTGCCATGGACTTTAGTACATTGCAAG
ATACTAAATGTGAGGTACCATTGGATATTGTCAGTCTATTTGTAAATA
TCCTGATTATTTACAAATGTCTGCAGATCCTTATGGGGATTCCATGTTT
TTTTGCTTACGGCGTGAGCAGCTTTTTGCTAGGCATTTTTGGAATAGAG
CAGGTACTATGGGTGACACTGTGCCTCAATCCTTATATATTAAAGGCAC
AGGTATGCGTGCTTCACCTGGCAGCTGTGTGTATTCTCCCTCTCCAAGT
GGCTCTATTGTTACCTCTGACTCCCAGTTGTTTAATAAACCATATTGGT
TACATAAGGCACAGGGTCATAACAATGGTGTTTGCTGGCATAATCAATT
ATTTGTTACTGTGGTAGATACCACTCGCAGTACCAATTTAACAATATGC
GCCAGCACCACCAGCAGCATCCCCAACGTGTACACCCCCACCAGCTTCA
AGCAGTATAGCAGACATGTTGAGGAATATGATTTGCAGTTTATTTTCA
GTTGTGTACTATTACTTTAACTGCAGATGTTATGTCCTATATTCATAGT
ATGAATAGCAGTATTTTAGAGGATTGGAACTTTGGTGTTCCCCCCCGC
CAACTACTAGTTTGGTGGATACATATCGTTTGTACAATCTGTTGCTAT
TGCCTGTCAAAAGGATGCTGCACCGGCTGAAAATAAGGATCCCTATGAT
AAGTTAAAGTTTTGGAATGTGGATTTAAAGGAAAAGTTTTCTTTAGACT
TAGATCAATATCCCCTTGGACGTAAATTTTTGGTTCAGGCTGGATTGCG
TCGCAAGCCCACCATAGGCCCTCGCAAACGTTCTGCTCCATCTGCCACT
ACGGCTTCTAAACCTGCCAAGCGTGTGCGTGTACGTGCCAGGAAGTAA Sequence 37 (SEQ ID NO: 37):
ATGCGGCCTAGTGACAATACCGTATATCTTCCACCTCCTTCTGTGGCAA
GAGTTGTAAATACCGATGATTACGTGACTCGCACAAGCATATTTTATCA
TGCTGGCAGCTCTAGATTATTAACTGTTGGTAATCCATATTTTAGGGTT
CCTGCAGGTGGTGGCAATAAGCAGGATATTCCTAAGGTTTCTGCATACC
AATATAGAGTATTTAGGGTGCAGTTACCTGACCCAAATAAATTTGGTTT
ACCTGATACTAGTATTTATAATCCTGAAACACAACGTTTAGTGTGGGCC
TGTGCTGGAGTGGAGATCGGCAGGGGCCAGCCCCTGGGCATCGGCCTGA
GCGGCCACCCCTTCTACAACAAGCTGGACGACACCGAGAGCGCCCACGC
CGCCACCGCCGTGATCACCCAGGACGTGAGGGACAACGTGAGCGTGGAC
TACAAGCAGACCCAGCTGTGCATCCTGGGCTGCGCCCCTGCTATTGGGG
AACACTGGGCTAAAGGCACTGCTTGTAAATCGCGTCCTTTATCACAGGG
CGATTGCCCCCCTTTAGAACTTAAAAACACAGTTTTGGAAGATGGTGAT
ATGGTAGATACTGGATATGGTGCCATGGACTTTAGTACATTGCAAGATA
CTAAATGTGAGGTACCATTGGATATTGTCAGTCTATTTGTAAATATCC
TGATTATTTACAAATGTCTGCAGATCCTTATGGGGATTCCATGTTTTTT
TGCTTACGGCGTGAGCAGCTTTTTGCTAGGCATTTTTGGAATAGAGCAG
GTACTATGGGTGACACTGTGCCTCAATCCTTATATATTAAAGGCACAGG
TATGCGTGCTTCACCTGGCAGCTGTGTGTATTCTCCCTCTCCAAGTGGC
TCTATTGTTACCTCTGACTCCCAGTTGTTTAATAAACCATATTGGTTAC
ATAAGGCACAGGGTCATAACAATGGTGTTTGCTGGCATAATCAATTATT
TGTTACTGTGGTAGATACCACTCGCAGTACCAATTTAACAATATGCGCC
AGCACCACCAGCAGCATCCCCAACGTGTACACCCCCACCAGCTTCAAGC
AGTATAGCAGACATGTTGAGGAATATGATTTGCAGTTTATTTTTCAGTT
GTGTACTATTACTTTAACTGCAGATGTTATGTCCTATATTCATAGTATG
AATAGCAGTATTTTAGAGGATTGGAACTTTGGTGTTCCCCCCCCGCCAA
CTACTAGTTTGGTGGATACATATCGTTTGTACAATCTGTTGCTATTGC
CTGTCAAAAGGATGCTGCACCGGCTGAAAATAAGGATCCCTATGATAAG
TTAAAGTTTTGGAATGTGGATTTAAAGGAAAAGTTTTCTTTAGACTTAG
ATCAATATCCCCTTGGACGTAAATTTTTGGTTCAGGCTGGATTGCGTCG
CAAGCCCACCATAGGCCCTCGCAAACGTTCTGCTCCATCTGCCACTACG
GCTTCTAAACCTGCCAAGCGTGTGCGTGTACGTGCCAGGAAGTAA Sequence 38 (SEQ ID NO: 38):
ATGCGGCCTAGTGACAATACCGTATATCTTCCACCTCCTTCTGTGGCAA
GAGTTGTAAATACCGATGATTACGTGACTAGGACCAGCATCTTCTACCA
CGCCGGCAGCAGCAGGCTGCTGACCGTGGGCAACCCCTACTTCAGGGTG
GTGCCCAACGGCGCCGGCAACAAGCAGGCCGTGCCCAAGGTGAGCGCCT

```
ACCAGTACAGGGTGTTCAGGGTGCAGTTACCTGACCCAAATAAATTTGG
TTTACCTGATACTAGTATTTATAATCCTGAAACACAACGTTTAGTGTGG
GCCTGTGCTGGAGTGGAAATTGGCCGTGGTCAGCCTTTAGGTGTTGGCC
TTAGTGGGCATCCATTTTATAATAAATTAGATGACACTGAAAGTTCCCA
TGCCGCCACGTCTAATGTTTCTGAGGACGTTAGGGACAATGTGTCTGTA
GATTATAAGCAGACACAGTTATGTATTTTGGGCTGTGCCCCCGCCATCG
GCGAGCACTGGGCCAAGGGCACCCTGTGCAAGCCCGCCCAGCTGCAGCC
CGGCGACTGCCCCCCCCTGGAGCTGAAGAACACCGTTTTGGAAGATGGT
GATATGGTAGATACTGGATATGGTGCCATGGACTTTAGTACATTGCAAG
ATACTAAATGTGAGGTACCATTGGATATTTGTCAGTCTATTTGTAAATA
TCCTGATTATTTACAAATGTCTGCAGATCCTTATGGGGATTCCATGTTT
TTTTGCTTACGGCGTGAGCAGCTTTTTGCTAGGCATTTTTGGAATAGAG
CAGGTACTATGGGTGACACTGTGCCTCAATCCTTATATATTAAAGGCAC
AGGTATGCGTGCTTCACCTGGCAGCTGTGTGTATTCTCCCTCTCCAAGT
GGCTCTATTGTTACCTCTGACTCCCAGTTGTTTAATAAACCATATTGGT
TACATAAGGCACAGGGTCATAACAATGGTGTTTGCTGGCATAATCAATT
ATTTGTTACTGTGGTAGATACCACTCGCAGTACCAATTTAACAATATGC
GCCAGCACCACCAGCAGCATCCCCAACGTGTACACCCCCACCAGCTTCA
AGCAGTATAGCAGACATGTTGAGGAATATGATTTGCAGTTTATTTTTCA
GTTGTGTACTATTACTTTAACTGCAGATGTTATGTCCTATATTCATAGT
ATGAATAGCAGTATTTTAGAGGATTGGAACTTTGGTGTTCCCCCCCCGC
CAACTACTAGTTTGGTGGATACATATCGTTTTGTACAATCTGTTGCTAT
TGCCTGTCAAAAGGATGCTGCACCGGCTGAAAATAAGGATCCCTATGAT
AAGTTAAAGTTTTGGAATGTGGATTTAAAGGAAAAGTTTTCTTTAGACT
TAGATCAATATCCCCTTGGACGTAAATTTTTGGTTCAGGCTGGATTGCG
TCGCAAGCCCACCATAGGCCCTCGCAAACGTTCTGCTCCATCTGCCACT
ACGGCTTCTAAACCTGCCAAGCGTGTGCGTGTACGTGCCAGGAAGTAA
```

Sequence 39 (SEQ ID NO: 39)
VPNGAGNKQAV

Sequence 40 (SEQ ID NO: 40):
IGLSGHPFYNKLDDTESAHAATAVITQ

Sequence 41 (SEQ ID NO: 41)
LCKPAQLQP

Sequence 42 (SEQ ID NO: 42):
VMGDTVPTDLYIKGTSANMRET

Sequence 43 (SEQ ID NO: 43)
KVPKGGNGRQDV

Sequence 44 (SEQ ID NO: 44)
TSSIPNVYTPTS

Sequence 109 (SEQ ID NO: 109)
NPVPSTYDP

Sequence 110 (SEQ ID NO: 110):
LYNKLDDTENSHVASAVDTKDT

Sequence 111 (SEQ ID NO: 111):
SGTMGDQLPESLYIKGTDIRANPGSYL

Sequence 112 (SEQ ID NO: 112)
TKGTACKPTTVV

Sequence 113 (SEQ ID NO: 113):
MRPSDNTVYLPPPSVARVVNTDDYVTRTSIFYHAGSSRLLTVGNPYFRV
PAGGGNKQDIPKVSAYQYRVFRVQLPDPNKFGLPDTSIYNPETQRLVWA
CAGVEIGRGQPLGVGLSGHPFYNKLDDTESSHAATSNVSEDVRDNVSVD
YKQTQLCILGCAPAIGEHWAKGTACKSRPLSQGDCPPLELKNTVLEDGD
MVDTGYGAMDFSTLQDTKCEVPLDICQSICKYPDYLQMSADPYGDSMFF
CLRREQLFARHFWNRAGTMGDTVPQSLYIKGTGMRASPGSCVYSPSPSG
SIVTSDSQLFNKPYWLHKAQGHNNGVCWHNQLFVTVVDTTRSTNLTICA
STQSPVPGQYDATKFKQYSRHVEEYDLQFIFQLCTITLTADVMSYIHSM
NSSILEDWNFGVPPPPTTSLVDTYRFVQSVAIACQKDAAPAENKDPYDK
LKFWNVDLKEKFSLDLDQYPLGRKFLVQAGLRRKPTIGPRKRSAPSATT
ASKPAKRVRVRARK Sequence 114 (SEQ ID NO: 114):
```
ATGCGGCCTAGTGACAATACCGTATATCTTCCACCTCCTTCTGTGGCAA
GAGTTGTAAATACCGATGATTACGTGACTCGCACAAGCATATTTTATCA
TGCTGGCAGCTCTAGATTATTAACTGTTGGTAATCCATATTTTAGGGTT
CCTGCAGGTGGTGGCAATAAGCAGGATATTCCTAAGGTTTCTGCATACC
AATATAGAGTATTTAGGGTGCAGTTACCTGACCCAAATAAATTTGGTTT
ACCTGATACTAGTATTTATAATCCTGAAACACAACGTTTAGTGTGGGCC
TGTGCTGGAGTGGAAATTGGCCGTGGTCAGCCTTTAGGTGTTGGCCTTA
GTGGGCATCCATTTTATAATAAATTAGATGACACTGAAAGTTCCCATGC
CGCCACGTCTAATGTTTCTGAGGACGTTAGGGACAATGTGTCTGTAGAT
TATAAGCAGACACAGTTATGTATTTTGGGCTGTGCCCCTGCTATTGGGG
AACACTGGGCTAAAGGCACTGCTTGTAAATCGCGTCCTTTATCACAGGG
CGATTGCCCCCCTTTAGAACTTAAAAACACAGTTTTGGAAGATGGTGAT
ATGGTAGATACTGGATATGGTGCCATGGACTTTAGTACATTGCAAGATA
CTAAATGTGAGGTACCATTGGATATTTGTCAGTCTATTTGTAAATATCC
```

```
TGATTATTTACAAATGTCTGCAGATCCTTATGGGGATTCCATGTTTTTT

TGCTTACGGCGTGAGCAGCTTTTTGCTAGGCATTTTTGGAATAGAGCAG

GTACTATGGGTGACACTGTGCCTCAATCcTTATATATTAAAGGCACAGG

TATGCGTGCTTCACCTGGCAGCTGTGTGTATTCTCCCTCTCCAAGTGGC

TCTATTGTTACCTCTGACTCCCAGTTGTTTAATAAACCATATTGGTTAC

ATAAGGCACAGGGTCATAACAATGGTGTTTGCTGGCATAATCAATTATT

TGTTACTGTGGTAGATACCACTCGCAGTACCAATTTAACAATATGTGCT

TCTACACAGTCTCCTGTACCTGGGCAATATGATGCTACCAAATTTAAGC

AGTATAGCAGACATGTTGAGGAATATGATTTGCAGTTTATTTTTCAGTT

GTGTACTATTACTTTAACTGCAGATGTTATGTCCTATATTCATAGTATG

AATAGCAGTATTTTAGAGGATTGGAACTTTGGTGTTCCCCCCCCGCCAA

CTACTAGTTTGGTGGATACATATCGTTTTGTACAATCTGTTGCTATTGC

CTGTCAAAAGGATGCTGCACCGGCTGAAAATAAGGATCCCTATGATAAG

TTAAAGTTTTGGAATGTGGATTTAAAGGAAAAGTTTTCTTTAGACTTAG

ATCAATATCCCCTTGGACGTAAATTTTTGGTTCAGGCTGGATTGCGTCG

CAAGCCCACCATAGGCCCTCGCAAACGTTCTGCTCCATCTGCCACTACG

GCTTCTAAACCTGCCAAGCGTGTGCGTGTACGTGCCAGGAAGTAA

Sequence 115 (SEQ ID NO: 115):
MALWRPSDSTVYLPPPSVARVVSTDDYVSRTSIFYHAGSSRLLTVGNPY

FRVVPNGAGNKQAVPKVSAYQYRVFRVALPDPNKFGLPDSTIYNPETQR

LVWACVGMEIGRGQPLGIGLSGHPFYNKLDDTESAHAATAVITQDVRDN

VSVDYKQTQLCILGCVPAIGEHWAKGTLCKPAQLQPGDCPPLELKNTII

EDGDMVDTGYGAMDFSTLQDTKCEVPLDICQSICKYPDYLQMSADPYGD

SMFFCLRREQLFARHFWNRAGVMGDTVPTDLYIKGTSANMRETPGSCVY

SPSPSGSIITSDSQLFNKPYWLHKAQGHNNGICWHNQLFVTVVDTTRST

NLTLCASTQNPVPSTYDPTKFKQYSRHVEEYDLQFIFQLCTITLTAEVM

SYIHSMNSSILENWNFGVPPPPTTSLVDTYRFVQSVAVTCQKDTTPPEK

QDPYDKLKFWTVDLKEKFSSDLDQYPLGRKFLVQAGLRRRPTIGPRKRP

AASTSTASTASRPAKRVRIRSKK

Sequence 116 (SEQ ID NO: 116):
ATGGCCCTGTGGAGGCCCAGCGACAGCACCGTGTACCTGCCCCCCCCA

GCGTGGCCAGGGTGGTGAGCACCGACGACTACGTGAGCAGGACCAGCAT

CTTCTACCACGCCGGCAGCAGCAGGCTGCTGACCGTGGGCAACCCCTAC

TTCAGGGTGGTGCCCAACGGCGCCGGCAACAAGCAGGCCGTGCCCAAGG

TGAGCGCCTACCAGTACAGGGTGTTCAGGGTGGCCCTGCCCGACCCCAA

CAAGTTCGGCCTGCCCGACAGCACCATCTACAACCCCGAGACCCAGAGG

CTGGTGTGGGCCTGCGTGGGCATGGAGATCGGCAGGGGCCAGCCCCTGG

GCATCGGCCTGAGCGGCCACCCCTTCTACAACAAGCTGGACGACACCGA

GAGCGCCCACGCCGCCACCGCCGTGATCACCCAGGACGTGAGGGACAAC
```

```
                                           -continued
GTGAGCGTGGACTACAAGCAGACCCAGCTGTGCATCCTGGGCTGCGTGC

CCGCCATCGGCGAGCACTGGGCCAAGGGCACCCTGTGCAAGCCCGCCCA

GCTGCAGCCCGGCGACTGCCCCCCCCTGGAGCTGAAGAACACCATCATC

GAGGACGGCGACATGGTGGACACCGGCTACGGCGCCATGGACTTCAGCA

CCCTGCAGGACACCAAGTGCGAGGTGCCCCTGGACATCTGCCAGAGCAT

CTGCAAGTACCCCGACTACCTGCAGATGAGCGCCGACCCCTACGGCGAC

AGCATGTTCTTCTGCCTGAGGAGGGAGCAGCTGTTCGCCAGGCACTTCT

GGAACAGGGCCGGCGTGATGGGCGACACCGTGCCCACCGACCTGTACAT

CAAGGGCACCAGCGCCAACATGAGGGAGACCCCCGGCAGCTGCGTGTAC

AGCCCCAGCCCCAGCGGCAGCATCATCACCAGCGACAGCCAGCTGTTCA

ACAAGCCCTACTGGCTGCACAAGGCCCAGGGCCACAACAACGGCATCTG

CTGGCACAACCAGCTGTTCGTGACCGTGGTGGACACCACCAGGAGCACC

AACCTGACCCTGTGCGCCAGCACCCAGAACCCCGTGCCCAGCACCTACG

ACCCCACCAAGTTCAAGCAGTACAGCAGGCACGTGGAGGAGTACGACCT

GCAGTTCATCTTCCAGCTGTGCACCATCACCCTGACCGCCGAGGTGATG

AGCTACATCCACAGCATGAACAGCAGCATCCTGGAGAACTGGAACTTCG

GCGTGCCCCCCCCCCCACCACCAGCCTGGTGGACACCTACAGGTTCGT

GCAGAGCGTGGCCGTGACCTGCCAGAAGGACACCACCCCCCCCGAGAAG

CAGGACCCCTACGACAAGCTGAAGTTCTGGACCGTGGACCTGAAGGAGA

AGTTCAGCAGCGACCTGGACCAGTACCCCCTGGGCAGGAAGTTCCTGGT

GCAGGCCGGCCTGAGGAGGAGGCCCACCATCGGCCCCAGGAAGAGGCCC

GCCGCCAGCACCAGCACCGCCAGCACCGCCAGCAGGCCCGCCAAGAGGG

TGAGGATCAGGAGCAAGAAGTGA
```

Specific Modes for Carrying Out the Invention

The present invention is further described by reference to the examples as follows, wherein the examples are used only for the purpose of illustrating the present invention, rather than limiting the present invention.

Unless indicated otherwise, the molecular biological experimental methods and immunological assays used in the present invention are carried out substantially in accordance with the methods as described in J. Sambrook et al., Molecular Cloning: A Laboratory Manual (Second Edition), Cold Spring Harbor Laboratory Press, 1989, and F. M. Ausubel et al., Short Protocols in Molecular Biology, 3rd Edition, John Wiley & Sons, Inc., 1995; and restriction enzymes are used under the conditions recommended by the manufacturers. Those skilled in the art understand that the examples are used for illustrating the present invention, but not intended to limit the protection scope of the present invention.

Example 1. Expression and Purification of the Mutated HPV18 L1 Proteins

Construction of Expression Vectors

Gibson assembly (Gibson D G, Young L, Chuang R Y, Venter J C, Hutchison C A, Smith H O. Enzymatic assembly of DNA molecules up to several hundred kilobases. Nat Methods. 2009; 6:343-5. doi: 10.1038/nmeth.1318) was used to construct the expression vector encoding the mutated HPV18 L1 protein comprising a specific segment from HPV45 L1 protein and/or a specific segment from HPV59

L1 protein. In brief, a short fragment comprising mutations and a long fragment comprising no mutation were first obtained by PCR, and Gibson assembly system was then used to ligate the two fragments to form a ring.

The initial template used comprised the plasmid pTO-T7-HPV18N65L1 (encoding the HPV18 L1 protein having 65 amino acids truncated at N-terminal, and the protein was designated as HPV18N65; abbreviated as 18L1N65 in Table 2), the plasmid pTO-T7-HPV45L1N27C (encoding the HPV45 L1 protein having 27 amino acids truncated at N-terminal, and the protein was designated as HPV45N27; abbreviated as 45L1N27 in Table 2), the plasmid pTO-T7-H18N65-45T1 (encoding the mutated protein H18N65-45T1; abbreviated as H18N65-45T1 in Table 2), the plasmid pTO-T7-H18N65-45T2 (encoding the mutated protein H18N65-45T2; abbreviated as H18N65-45T2 in Table 2), the plasmid pTO-T7-H18N65-45T3 (encoding the mutated protein H18N65-45T3; abbreviated as H18N65-45T3 in Table 2), the plasmid pTO-T7-H18N65-45T4 (encoding the mutated protein H18N65-45T4; abbreviated as H18N65-45T4 in Table 2), the plasmid pTO-T7-H18N65-45T3-59S5 (encoding the mutated protein H18N65-45T3-59S5; abbreviated as H18N65-45T3-59S5 in Table 2) and the plasmid pTO-T7-HPV59L1 (encoding the HPV59 L1 protein; abbreviated as 59L1 in Table 2). The templates and primers for each PCR were shown in Table 2, and the amplification conditions for PCR for amplifying the short fragment were as followed: denaturation at 94° C. for 10 min; 25 cycles (denaturation at 94° C. for 50 sec, annealing at a given temperature for a certain period of time, and extension at 72° C. for 1 min); and final extension at 72° C. for 10 min. The amplification conditions for PCR for amplifying the long fragment were as followed: denaturation at 94° C. for 10 min; 25 cycles (denaturation at 94° C. for 50 sec, annealing at a given temperature for a certain period of time, and extension at 72° C. for 7.5 min); and final extension at 72° C. for 10 min. The temperature and time of annealing were listed in Table 2. The sequences of the PCR primers used were listed in Table 3.

The amplification product was subjected to electrophoresis, the fragment of interest was then recovered by using DNA Extraction Kit (BEYOTIME, Cat. No. D0033), and its concentration was determined. The short fragment and long fragment obtained by amplification were mixed at a molar ratio of 2:1 (a total volume of 3 μL), and 3 μL of 2× Gibson Assembly Master Mix (purchased from NEB, containing T5 exonuclease, Phusion DNA polymerase, Taq DNA ligase) was then added, and reacted at 50° C. for 1 h.

The assembled product (6 μL) was used to transform 40 μL competent *E. coli* ER2566 (purchased from New England Biolabs) prepared by the Calcium chloride method. The transformed *E. coli* were spread onto solid LB medium (components of LB medium: 10 g/L peptone, 5 g/L yeast powder, 10 g/L NaCl, the same hereinafter) containing kanamycin (at a final concentration of 25 μg/mL, the same hereinafter), and were subjected to static culture at 37° C. for 10-12 h until single colonies could be observed clearly. Single colony was picked and inoculated into a tube containing 4 mL liquid LB medium (containing kanamycin), and cultured with shaking at 220 rpm for 10 h at 37° C., and then 1 ml bacterial solution was taken and stored at −70° C. Plasmids were extracted from *E. coli*, and T7 primer was used to sequence the nucleotide sequences of the fragments of interest inserted into the plasmids. The sequencing result showed that the nucleotide sequences of the fragments of interest inserted into the constructed plasmids (expression vectors) were SEQ ID NO: 23, 24, 25, 26, 27, 28, 29, 30, 31, 32, 33, 34, 35, 36, 37 and 38, respectively, and their encoded amino acid sequences were SEQ ID NO: 4, 5, 6, 7, 8, 9, 10, 11, 12, 13, 14, 15, 16, 17, 18 and 19, respectively (the corresponding proteins were designated as H18N65-45T1, H18N65-45T2, H18N65-45T3, H18N65-45T4, H18N65-45T5, H18N65-45T3-5951, H18N65-45T3-5952, H18N65-45T3-5954, H18N65-45T3-5955, H18N65-45T4- 5951, H18N65-45T4-5952, H18N65-45T4-5953, H18N65-45T4-5955, H18N65-45T1-5955, H18N65-45T2- 5955 and H18N65-45T1T3-5955, respectively).

The mutated protein H18N65-45T1 differs from HPV18N65 by: the substitution of the amino acid residues from positions 114-123 of wild type HPV18 L1 protein with the amino acid residues from positions 79-89 of wild type HPV45 L1 protein. The mutated protein H18N65-45T2 differs from HPV18N65 by: the substitution of the amino acid residues from positions 176-202 of wild type HPV18 L1 protein with the amino acid residues from positions 142-168 of wild type HPV45 L1 protein. The mutated protein H18N65-45T3 differs from HPV18N65 by: the substitution of the amino acid residues from positions 235-243 of wild type HPV18 L1 protein with the amino acid residues from positions 201-209 of wild type HPV45 L1 protein. The mutated protein H18N65-45T4 differs from HPV18N65 by: the substitution of the amino acid residues from positions 327-346 of wild type HPV18 L1 protein with the amino acid residues from positions 293-314 of wild type HPV45 L1 protein. The mutated protein H18N65-45T5 differs from HPV18N65 by: the substitution of the amino acid residues from positions 411-419 of wild type HPV18 L1 protein with the amino acid residues from positions 379-387 of wild type HPV45 L1 protein.

The mutated protein H18N65-45T3-5951 differs from HPV18N65 by: the substitution of the amino acid residues from positions 235-243 of wild type HPV18 L1 protein with the amino acid residues from positions 201-209 of wild type HPV45 L1 protein, and the substitution of the amino acid residues from positions 112-123 of wild type HPV18 L1 protein with the amino acid residues from positions 51-62 of wild type HPV59 L1 protein. The mutated protein H18N65-45T3-59S2 differs from HPV18N65 by: the substitution of the amino acid residues from positions 235-243 of wild type HPV18 L1 protein with the amino acid residues from positions 201-209 of wild type HPV45 L1 protein, and the substitution of the amino acid residues from positions 183-204 of wild type HPV18 L1 protein with the amino acid residues from positions 122-143 of wild type HPV59 L1 protein. The mutated protein H18N65-45T3-59S4 differs from HPV18N65 by: the substitution of the amino acid residues from positions 235-243 of wild type HPV18 L1 protein with the amino acid residues from positions 201-209 of wild type HPV45 L1 protein, and the substitution of the amino acid residues from positions 325-351 of wild type HPV18 L1 protein with the amino acid residues from positions 264-290 of wild type HPV59 L1 protein. The mutated protein H18N65-45T3-59S5 differs from HPV18N65 by: the substitution of the amino acid residues from positions 235-243 of wild type HPV18 L1 protein with the amino acid residues from positions 201-209 of wild type HPV45 L1 protein, and the substitution of the amino acid residues from positions 410-421 of wild type HPV18 L1 protein with the amino acid residues from positions 349-360 of wild type HPV59 L1 protein.

The mutated protein H18N65-45T4-59S1 differs from HPV18N65 by: the substitution of the amino acid residues from positions 327-346 of wild type HPV18 L1 protein with the amino acid residues from positions 293-314 of wild type HPV45 L1 protein, and the substitution of the amino acid residues from positions 112-123 of wild type HPV18 L1 protein with the amino acid residues from positions 51-62 of wild type HPV59 L1 protein. The mutated protein H18N65-45T4-59S2 differs from HPV18N65 by: the substitution of the amino acid residues from positions 327-346 of wild type HPV18 L1 protein with the amino acid residues from positions 293-314 of wild type HPV45 L1 protein, and the substitution of the amino acid residues from positions 183-204 of wild type HPV18 L1 protein with the amino acid residues from positions 122-143 of wild type HPV59 L1 protein. The mutated protein H18N65-45T4-59S3 differs from HPV18N65 by: the substitution of the amino acid residues from positions 327-346 of wild type HPV18 L1 protein with the amino acid residues from positions 293-314 of wild type HPV45 L1 protein, and the substitution of the amino acid residues from positions 231-242 of wild type HPV18 L1 protein with the amino acid residues from positions 170-181 of wild type HPV59 L1 protein. The mutated protein H18N65-45T4-59S5 differs from HPV18N65 by: the substitution of the amino acid residues from positions 327-346 of wild type HPV18 L1 protein with the amino acid residues from positions 293-314 of wild type HPV45 L1 protein, and the substitution of the amino acid residues from positions 410-421 of wild type HPV18 L1 protein with the amino acid residues from positions 349-360 of wild type HPV59 L1 protein.

The mutated protein H18N65-45T1-59S5 differs from HPV18N65 by: the substitution of the amino acid residues from positions 114-123 of wild type HPV18 L1 protein with the amino acid residues from positions 79-89 of wild type HPV45 L1 protein, and the substitution of the amino acid residues from positions 410-421 of wild type HPV18 L1 protein with the amino acid residues from positions 349-360 of wild type HPV59 L1 protein. The mutated protein H18N65-45T2-59S5 differs from HPV18N65 by: the substitution of the amino acid residues from positions 176-202 of wild type HPV18 L1 protein with the amino acid residues from positions 142-168 of wild type HPV45 L1 protein, and the substitution of the amino acid residues from positions 410-421 of wild type HPV18 L1 protein with the amino acid residues from positions 349-360 of wild type HPV59 L1 protein. The mutated protein H18N65-45T1T3-59S5 differs from HPV18N65 by: the substitution of the amino acid residues from positions 114-123 of wild type HPV18 L1 protein with the amino acid residues from positions 79-89 of wild type HPV45 L1 protein, and the substitution of the amino acid residues from positions 235-243 of wild type HPV18 L1 protein with the amino acid residues from positions 201-209 of wild type HPV45 L1 protein, and the substitution of the amino acid residues from positions 410-421 of wild type HPV18 L1 protein with the amino acid residues from positions 349-360 of wild type HPV59 L1 protein.

TABLE 2

PCR templates and primers for constructing expression vectors

| Template | Upstream primer | Downstream primer | Product | Temperature/ Time of annealing |
|---|---|---|---|---|
| 18L1N65 | G-V-H18N65-45T1-F | G-V-H18N65-45T1-R | H18N65-45T1 long fragment | 56° C./50 s |
| 45L1N27 | G-H18N65-45T1-F | G-H18N65-45T1-R | H18N65-45T1 short fragment | 56° C./30 s |
| 18L1N65 | G-V-H18N65-45T2-F | G-V-H18N65-45T2-R | H18N65-45T2 long fragment | 56° C./50 s |
| 45L1N27 | G-H18N65-45T2-F | G-H18N65-45T2-R | H18N65-45T2 short fragment | 56° C./30 s |
| 18L1N65 | G-V-H18N65-45T3-F | G-V-H18N65-45T3-R | H18N65-45T3 long fragment | 56° C./50 s |
| 45L1N27 | G-H18N65-45T3-F | G-H18N65-45T3-R | H18N65-45T3 short fragment | 56° C./30 s |
| 18L1N65 | G-V-H18N65-45T4-F | G-V-H18N65-45T4-R | H18N65-45T4 long fragment | 56° C./50 s |
| 45L1N27 | G-H18N65-45T4-F | G-H18N65-45T4-R | H18N65-45T4 short fragment | 56° C./30 s |
| 18L1N65 | G-V-H18N65-45T5-F | G-V-H18N65-45T5-R | H18N65-45T5 long fragment | 56° C./50 s |
| 45L1N27 | G-H18N65-45T5-F | G-H18N65-45T5-R | H18N65-45T5 short fragment | 56° C./30 s |
| H18N65-45T3 | G-V-H18N65-45T3-59S1-F | G-V-H18N65-45T3-59S1-R | H18N65-45T3-59S1 long fragment | 56° C./50 s |
| 59L1 | G-H18N65-45T3-59S1-F | G-H18N65-45T3-59S1-R | H18N65-45T3-59S1 short fragment | 56° C./30 s |
| H18N65-45T3 | G-V-H18N65-45T3-59S2-F | G-V-H18N65-45T3-59S2-R | H18N65-45T3-59S2 long fragment | 56° C./50 s |
| 59L1 | G-H18N65-45T3-59S2-F | G-H18N65-45T3-59S2-R | H18N65-45T3-59S2 short fragment | 56° C./30 s |
| H18N65-45T3 | G-V-H18N65-45T3-59S4-F | G-V-H18N65-45T3-59S4-R | H18N65-45T3-59S4 long fragment | 56° C./50 s |
| 59L1 | G-H18N65-45T3-59S4-F | G-H18N65-45T3-59S4-R | H18N65-45T3-59S4 short fragment | 56° C./30 s |
| H18N65-45T3 | G-V-H18N65-45T3-59S5-F | G-V-H18N65-45T3-59S5-R | H18N65-45T3-59S5 long fragment | 56° C./50 s |
| 59L1 | G-H18N65-45T3-59S5-F | G-H18N65-45T3-59S5-R | H18N65-45T3-59S5 short fragment | 56° C./30 s |
| H18N65-45T4 | G-V-H18N65-45T4-59S1-F | G-V-H18N65-45T4-59S1-R | H18N65-45T4-59S1 long fragment | 56° C./50 s |

TABLE 2-continued PCR templates and primers for constructing expression vectors

| Template | Upstream primer | Downstream primer | Product | Temperature/Time of annealing |
|---|---|---|---|---|
| 59L1 | G-H18N65-45T4-59S1-F | G-H18N65-45T4-59S1-R | H18N65-45T4-59S1 short fragment | 56° C./30 s |
| H18N65-45T4 | G-V-H18N65-45T4-59S2-F | G-V-H18N65-45T4-59S2-R | H18N65-45T4-59S2 long fragment | 56° C./50 s |
| 59L1 | G-H18N65-45T4-59S2-F | G-H18N65-45T4-59S2-R | H18N65-45T4-59S2 short fragment | 56° C./30 s |
| H18N65-45T4 | G-V-H18N65-45T4-59S3-F | G-V-H18N65-45T4-59S3-R | H18N65-45T4-59S3 long fragment | 56° C./50 s |
| 59L1 | G-H18N65-45T4-59S3-F | G-H18N65-45T4-59S3-R | H18N65-45T4-59S3 short fragment | 56° C./30 s |
| H18N65-45T4 | G-V-H18N65-45T4-59S5-F | G-V-H18N65-45T4-59S5-R | H18N65-45T4-59S5 long fragment | 56° C./50 s |
| 59L1 | G-H18N65-45T4-59S5-F | G-H18N65-45T4-59S5-R | H18N65-45T4-59S5 short fragment | 56° C./30 s |
| H18N65-45T1 | G-V-H18N65-45T1-59S5-F | G-V-H18N65-45T1-59S5-R | H18N65-45T1-59S5 long fragment | 56° C./50 s |
| 59L1 | G-H18N65-45T1-59S5-F | G-H18N65-45T1-59S5-R | H18N65-45T1-59S5 short fragment | 56° C./30 s |
| H18N65-45T2 | G-V-H18N65-45T2-59S5-F | G-V-H18N65-45T2-59S5-R | H18N65-45T2-59S5 long fragment | 56° C./50 s |
| 59L1 | G-H18N65-45T2-59S5-F | G-H18N65-45T2-59S5-R | H18N65-45T2-59S5 short fragment | 56° C./30 s |
| H18N65-45T3-59S5 | G-V-H18N65-45T1T3-59S5-F | G-V-H18N65-45T1T3-59S5-R | H18N65-45T1T3-59S5 long fragment | 56° C./50 s |
| 45L1N27 | G-H18N65-45T1T3-59S5-F | G-H18N65-45T1T3-59S5-R | H18N65-45T1T3-59S5 short fragment | 56° C./30 s |

TABLE 3

Sequences of the primers used (SEQ ID NOs: 45-108)

| SEQ ID NO: | Primer name | Primer sequence (5'-3') |
|---|---|---|
| 45 | G-V-H18N65-45T1-F | CAGTTACCTGACCCAAATAAATT |
| 46 | G-V-H18N65-45T1-R | AGTCACGTAATCATCGGTAT |
| 47 | G-H18N65-45T1-F | TAAATACCGATGATTACGTGACTAGGACCAGCATCTTCTACCAC |
| 48 | G-H18N65-45T1-F | AATTTATTTGGGTCAGGTAACTGCACCCTGAACACCCTGTACTGG |
| 49 | G-V-H18N65-45T2-F | GCCCCTGCTATTGGGGAACACTGGGCT |
| 50 | G-V-H18N65-45T2-R | CACTCCAGCACAGGCCCACACTAAAC |
| 51 | G-H18N65-45T2-F | GTGTGGGCCTGTGCTGGAGTGGAGATCGGCAGGGGCCAG |
| 52 | G-H18N65-45T2-R | CAGTGTTCCCCAATAGCAGGGGCGCAGCCCAGGATGCACAGCT |
| 53 | G-V-H18N65-45T3-F | GTTTTGGAAGATGGTGATATGGT |
| 54 | G-V-H18N65-45T3-R | GGCACAGCCCAAAATACATAACT |
| 55 | G-H18N65-45T3-F | AGTTATGTATTTTGGGCTGTGCCCCCGCCATCGGCGAGCACTGGG |
| 56 | G-H18N65-45T3-R | ACCATATCACCATCTTCCAAAACGGTGTTCTTCAGCTCCAGGGG |
| 57 | G-V-H18N65-45T4-F | GTTACCTCTGACTCCCAGTTGTT |
| 58 | G-V-H18N65-45T4-R | TCCAGTATCTACCATATCACCATCTT |
| 59 | G-H18N65-45T4-F | GATGGTGATATGGTAGATACTGGATACGGCGCCATGGACTTCAGCAC |

TABLE 3-continued

Sequences of the primers used (SEQ ID NOs: 45-108)

| SEQ ID NO: | Primer name | Primer sequence (5'-3') |
|---|---|---|
| 60 | G-H18N65-45T4-R | AACAACTGGGAGTCAGAGGTAACGATGCTGCCGCTGGGGCTGGGGCT |
| 61 | G-V-H18N65-45T5-F | GATGTTATGTCCTATATTCAT |
| 62 | G-V-H18N65-45T5-R | TATTGTTAAATTGGTACTGCGAG |
| 63 | G-H18N65-45T5-F | CTCGCAGTACCAATTTAACAATATGCGCCAGCACCCAGAACCCCG |
| 64 | G-H18N65-45T5-R | CTATGAATATAGGACATAACATCGGCGGTCAGGGTGATGGTGCAC |
| 65 | G-V-H18N65-45T3-59S1-F | GCATACCAATATAGAGTATTTAG |
| 66 | G-V-H18N65-45T3-59S1-R | ATATGGATTACCAACAGTTAATAAT |
| 67 | G-H18N65-45T3-59S1-F | TATTAACTGTTGGTAATCCATATTTCAAGGTGCCCAAGGGCGGC |
| 68 | G-H18N65-45T3-59S1-R | CCTAAATACTCTATATTGGTATGCGCTCACCTTGGGCACGTCCTGC |
| 69 | G-V-H18N65-45T3-59S2-F | TTGGGCTGTGCCCCCGCCATCGG |
| 70 | G-V-H18N65-45T3-59S2-R | AGCACAGGCCCACACTAAACGTTGT |
| 71 | G-H18N65-45T3-59S2-F | CAACGTTTAGTGTGGGCCTGTGCTGGCGTGGAGATCGGCAGGGGC |
| 72 | G-H18N65-45T3-59S2-R | GCCGATGGCGGGGGCACAGCCCAAGATGCACAGCTGGGTCTGCTTGT |
| 73 | G-V-H18N65-45T3-59S4-F | GGCTCTATTGTTACCTCTGACTC |
| 74 | G-V-H18N65-45T3-59S4-R | AAGCTGCTCACGCCGTAAGCAAAAA |
| 75 | G-H18N65-45T3-59S4-F | TGCTTACGGCGTGAGCAGCTTTTCGCCAGGCACTTCTGGAACAG |
| 76 | G-H18N65-45T3-59S4-R | GGAGTCAGAGGTAACAATAGAGCCGCTGGGGCTGGGGCTGTACAGGT |
| 77 | G-V-H18N65-45T3-59S5-F | CAGTATAGCAGACATGTTGAGG |
| 78 | G-V-H18N65-45T3-59S5-R | TATTGTTAAATTGGTACTGCGAG |
| 79 | G-H18N65-45T3-59S5-F | ACTCGCAGTACCAATTTAACAATATGCGCCAGCACCACCAGCAGCAT |
| 80 | G-H18N65-45T3-59S5-R | TTCCTCAACATGTCTGCTATACTGCTTGAAGCTGGTGGGGGTGT |
| 81 | G-V-H18N65-45T4-59S1-F | GCATACCAATATAGAGTATTTAG |
| 82 | G-V-H18N65-45T4-59S1-R | ATTACCAACAGTTAATAATCTAGAGC |
| 83 | G-H18N65-45T4-59S1-F | GATTATTAACTGTTGGTAATCCCTACTTCAAGGTGCCCAAGGGCGG |
| 84 | G-H18N65-45T4-59S1-R | ATTTGGGTCAGGTAACTGCACCCTGAACACCCTGTACTGGTAGGCGC |
| 85 | G-V-H18N65-45T4-59S2-F | TTATGTATTTTGGGCTGTGCCCCTG |
| 86 | G-V-H18N65-45T4-59S2-R | AGCACAGGCCCACACTAAACGTT |
| 87 | G-H18N65-45T4-59S2-F | GTTTAGTGTGGGCCTGTGCTGGCGTGGAGATCGGCAGGGGCCAGCCC |
| 88 | G-H18N65-45T4-59S2-R | GCAGGGGCACAGCCCAAAATACATAACTGGGTCTGCTTGTAGTCCAC |
| 89 | G-V-H18N65-45T4-59S3-F | AAAAACACAGTTTTGGAAGATGGTG |

TABLE 3-continued

Sequences of the primers used (SEQ ID NOs: 45-108)

| SEQ ID NO: | Primer name | Primer sequence (5'-3') |
|---|---|---|
| 90 | G-V-H18N65-45T4-59S3-R | GGCACAGCCCAAAATACATAACT |
| 91 | G-H18N65-45T4-59S3-F | TTATGTATTTTGGGCTGTGCCCCCGCCATCGGCGAGCACTGGAC |
| 92 | G-H18N65-45T4-59S3-R | ACCATCTTCCAAAACTGTGTTTTTCAGCTCCAGGGGGGGCAGTCGC |
| 93 | G-V-H18N65-45T4-59S5-F | CAGTATAGCAGACATGTTGAGG |
| 94 | G-V-H18N65-45T4-59S5-R | TATTGTTAAATTGGTACTGCGGTGGT |
| 95 | G-H18N65-45T4-59S5-F | CAGTACCAATTTAACAATATGCGCCAGCACCACCAGCAGCATCCCC |
| 96 | G-H18N65-45T4-59S5-R | ATATTCCTCAACATGTCTGCTATACTGCTTGAAGCTGGTGGGGGTGT |
| 97 | G-V-H18N65-45T1-59S5-F | CAGTATAGCAGACATGTTGAGG |
| 98 | G-V-H18N65-45T1-59S5-R | TATTGTTAAATTGGTACTGCGAG |
| 99 | G-H18N65-45T1-59S5-F | ACTCGCAGTACCAATTTAACAATATGCGCCAGCACCACCAGCAGCAT |
| 100 | G-H18N65-45T1-59S5-R | TTCCTCAACATGTCTGCTATACTGCTTGAAGCTGGTGGGGTGT |
| 101 | G-V-H18N65-45T2-59S5-F | CAGTATAGCAGACATGTTGAGG |
| 102 | G-V-H18N65-45T2-59S5-R | TATTGTTAAATTGGTACTGCGAG |
| 103 | G-H18N65-45T2-59S5-F | ACTCGCAGTACCAATTTAACAATATGCGCCAGCACCACCAGCAGCAT |
| 104 | G-H18N65-45T2-59S5-R | TTCCTCAACATGTCTGCTATACTGCTTGAAGCTGGTGGGGTGT |
| 105 | G-V-H18N65-45T1T3-59S5-F | CAGTTACCTGACCCAAATAAATT |
| 106 | G-V-H18N65-45T1T3-59S5-R | AGTCACGTAATCATCGGTAT |
| 107 | G-H18N65-45T1T3-59S5-F | TAAATACCGATGATTACGTGACTAGGACCAGCATCTTCTACCAC |
| 108 | G-H18N65-45T1T3-59S5-R | AATTTATTTGGGTCAGGTAACTGCACCCTGAACACCCTGTACTGG |

Expression of the Mutated Proteins on a Large Scale

The E. coli solutions comprising the recombinant plasmid pTO-T7-H18N65-45T1, pTO-T7-H18N65-45T2, pTO-T7-H18N65-45T3, pTO-T7-H18N65-45T4, pTO-T7-H18N65-45T5, pTO-T7-H18N65-45T3-59S1, pTO-T7-H18N65-45T3-59S2, pTO-T7-H18N65-45T3-59S4, pTO-T7-H18N65-45T3-59S5, pTO-T7-H18N65-45T4-59S1, pTO-T7-H18N65-45T4-59S2, pTO-T7-H18N65-45T4-59S3, pTO-T7-H18N65-45T4-59S5, pTO-T7-H18N65-45T1-59S5, pTO-T7-H18N65-45T2-59S5 and pTO-T7-H18N65-45T1T3-59S5, respectively, were taken from −70° C. refrigerator, were inoculated in 100 mL LB liquid medium containing kanamycin, and incubated at 200 rpm and 37° C. for about 8 h. Then, the culture was transferred to 500 mL LB medium containing kanamycin (1 ml bacterial solution was transferred), and was further incubated. When the bacterial concentration reached an OD$_{600}$ of about 0.6, the culturing temperature was lowered to 25° C. and 500 μL IPTG was added to each culture bottle. The incubation was further performed for 8 h. After the incubation was finished, the bacteria were collected by centrifugation. The bacteria expressing H18N65-45T1, H18N65-45T2, H18N65-45T3, H18N65-45T4, H18N65-45T5, H18N65-45T3-59S1, H18N65-45T3-59S2, H18N65-45T3-59S4, H18N65-45T3-59S5, H18N65-45T4-59S1, H18N65-45T4-59S2, H18N65-45T4-59S3, H18N65-45T4-59S5, H18N65-45T1-59S5, H18N65-45T2-59S5 and H18N65-45T1T3-59S5 protein were obtained, respectively.

Disruption of Bacteria Expressing the Mutated Proteins

The bacteria obtained above were re-suspended at a ratio of 1 g bacteria to 10 mL lysis buffer (20 mM Tris buffer, pH7.2, 300 mM NaCl). The bacteria were disrupted by using an ultrasonic apparatus for 30 min. The lysis solution containing the disrupted bacteria were centrifuged at 13500 rpm (30000 g) for 15 min, and the supernatant (i.e. the supernatant of disrupted bacteria) was obtained.

Chromatographic Purification of the Mutated Protein

Equipment: AKTA Explorer 100 preparative liquid chromatography system produced by GE Healthcare (i.e. the original Amershan Pharmacia Co.)

Chromatographic media: SP Sepharose 4 Fast Flow (GE Healthcare Co.), CHT-II (purchased from Bio-RAD) and Butyl Sepharose 4 Fast Flow (GE Healthcare Co.)

Buffer: Buffer A (20 mM phosphate buffer, pH8.0, 20 mM DTT); and Buffer B (20 mM phosphate buffer, pH8.0, 20 mM DTT, 2M NaCl). The buffers containing different concentrations of NaCl used in the following elution protocol were prepared by mixing Buffer A and Buffer B at a certain ratio.

Sample: the supernatants of disrupted bacteria containing H18N65-45T1, H18N65-45T2, H18N65-45T3, H18N65-45T4, H18N65-45T5, H18N65-45T3-5951, H18N65-45T3-5952, H18N65-45T3-59S4, H18N65-45T3-5955, H18N65-45T4-5951, H18N65-45T4-5952, H18N65-45T4-5953, H18N65-45T4-59S5, H18N65-45T1-59S5, H18N65-45T2-5955, and H18N65-45T1T3-5955, respectively, as obtained above.

Elution Protocol:

(1) Cation exchange purification of the supernatant of disrupted bacteria by SP Sepharose 4 Fast Flow: the sample was loaded on the column, undesired proteins were then eluted with a buffer containing 400 mM NaCl (80% Buffer A+20% Buffer B), followed by the elution of the protein of interest with a buffer containing 800 mM NaCl (60% Buffer A+40% Buffer B), and the fraction eluted with the buffer containing 800 mM NaCl was collected;

(2) Chromatographic purification of the elution fraction obtained in the step (1) by CHTII (hydroxyapatite chromatography): the elution fraction obtained in the step (1) was diluted so that the NaCl concentration was decreased to 0.5 M; the sample was loaded on the column, undesired proteins were then eluted with a buffer containing 500 mM NaCl (75% Buffer A+25% Buffer B), followed by the elution of the protein of interest with a buffer containing 1000 mM NaCl (50% Buffer A+50% Buffer B), and the fraction eluted with the buffer containing 1000 mM NaCl was collected;

(3) Chromatographic purification of the elution fraction obtained in the step (2) by HIC (hydrophobic interaction chromatography): the sample was loaded on the column, undesired proteins were then eluted with a buffer containing 1000 mM NaCl, followed by the elution of the protein of interest with a buffer containing 200 mM NaCl (90% Buffer A+10% Buffer B), and the fraction eluted with the buffer containing 200 mM NaCl was collected.

150 µL of elution fraction obtained in the step (3) was added to 30 µL of 6× Loading Buffer (1 L of which contained 300 ml of 1M TB 6.8, 600 ml of 100% glycerol, 120 g of SDS, 6 g of bromophenol blue, and 50 ml of β-mercaptoethanol). The resultant solution was mixed well and incubated in 80° C. water bath for 10 min. 10 µl of the resultant sample was then subjected to 10% SDS-PAGE at 120V for 120 min; and the electrophoretic bands were stained by Coomassie brilliant blue. The electrophoretic result was shown in FIG. 1. The result showed that after said purification steps, H18N65-45T1, H18N65-45T2, H18N65-45T3, H18N65-45T4, H18N65-45T5, H18N65-45T3-59S1, H18N65-45T3-59S2, H18N65-45T3-59S4, H18N65-45T3-59S5, H18N65-45T4-59S1, H18N65-45T4-59S2, H18N65-45T4-59S3, H18N65-45T4-59S5, H18N65-45T1-59S5, H18N65-45T2-59S5 and H18N65-45T1T3-59S5 protein had a purity of above 85%.

By similar methods, HPV18N65 protein (SEQ ID NO: 113) was prepared and purified by using *E. coli* and the plasmid pTO-T7-HPV18N65L1; HPV45N27 protein (SEQ ID NO: 115) was prepared and purified by using *E. coli* and the plasmid pTO-T7-HPV45L1N27C; and HPV59 L1 protein (SEQ ID NO: 3) was prepared and purified by using *E. coli* and the plasmid pTO-T7-HPV59L1.

Western Blot Assay of the Mutated Proteins

Figure 2:
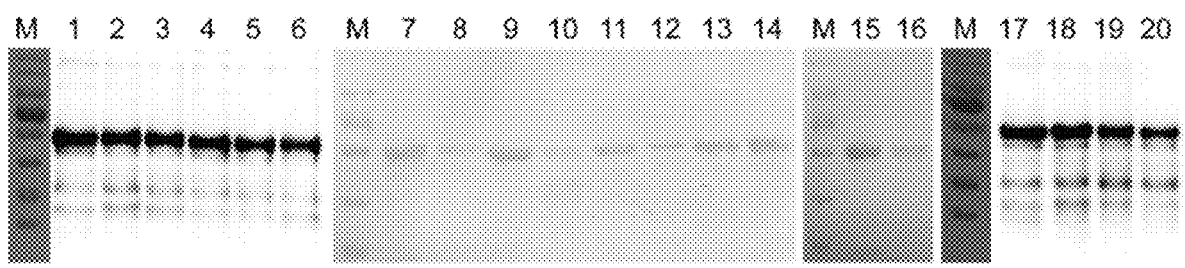
FIG. 2 shows the Western Blot result of H18N65-45T1, H18N65-45T2, H18N65-45T3, H18N65-45T4, H18N65-45T5, H18N65-45T3-5951, H18N65-45T3-5952, H18N65-45T3-5954, H18N65-45T3-5955, H18N65-45T4-5951, H18N65-45T4-5952, H18N65-45T4-5953, H18N65-45T4-5955, H18N65-45T1-5955, H18N65-45T2-5955 and H18N65-45T1T3-5955 prepared in Example 1, as determined by using a broad-spectrum antibody 4B3. Lane M: protein molecular weight marker; Lane 1: HPV18N65; Lane 2: H18N65-45T1; Lane 3: H18N65-45T2; Lane 4: H18N65-45T3; Lane 5: H18N65-45T4; Lane 6: H18N65-45T5; Lane 7: HPV18N65; Lane 8: H18N65-45T3-59S1; Lane 9: H18N65-45T3-59S2; Lane 10: H18N65-45T3-59S4; Lane 11: H18N65-45T3-59S5; Lane 12: H18N65-45T4-59S1; Lane 13: H18N65-45T4-59S2; Lane 14: H18N65-45T4-59S3; Lane 15: HPV18N65; Lane 16: H18N65-45T4-59S5; Lane 17: HPV18N65; Lane 18: H18N65-45T1-59S5; Lane 19: H18N65-45T2-59S5; Lane 20: H18N65-45T1T3-59S5. The result showed that the mutated proteins H18N65-45T1, H18N65-45T2, H18N65-45T3, H18N65-45T4, H18N65-45T5, H18N65-45T3-59S1, H18N65-45T3-59S2, H18N65-45T3-59S4, H18N65-45T3-59S5, H18N65-45T4-59S1, H18N65-45T4-59S2, H18N65-45T4-59S3, H18N65-45T4-59S5, H18N65-45T1-59S5, H18N65-45T2-59S5 and H18N65-45T1T3-59S5 could be specifically recognized by the broad-spectrum antibody 4B3.

The H18N65-45T1, H18N65-45T2, H18N65-45T3, H18N65-45T4, H18N65-45T5, H18N65-45T3-5951, H18N65-45T3-5952, H18N65-45T3-5954, H18N65-45T3-5955, H18N65-45T4-5951, H18N65-45T4-5952, H18N65-45T4-5953, H18N65-45T4-5955, H18N65-45T1-5955, H18N65-45T2-5955, and H18N65-45T1T3-59S5 protein purified by the method above were subjected to electrophoresis. After electrophoresis, Western Blot assay was carried out by using a broad-spectrum antibody 4B3 against HPV L1 protein, and the result was shown in FIG. 2. The result showed that H18N65-45T1, H18N65-45T2, H18N65-45T3, H18N65-45T4, H18N65-45T5, H18N65-45T3-5951, H18N65-45T3-5952, H18N65-45T3-5954, H18N65-45T3-5955, H18N65-45T4-5951, H18N65-45T4-5952, H18N65-45T4-5953, H18N65-45T4- 5955, H18N65-45T1-5955, H18N65-45T2-5955 and H18N65-45T1T3-5955 could be specifically recognized by the broad-spectrum antibody 4B3.

Example 2: Assembly of HPV Virus-Like Particles and Morphological Detection of Particles Assembly of HPV Virus-Like Particles A given volume (about 2 ml) of the protein H18N65-45T1, H18N65-45T2, H18N65-45T3, H18N65-45T4, H18N65-45T5, H18N65-45T3-5951, H18N65-45T3-5952, H18N65-45T3-5954, H18N65-45T3-5955, H18N65-45T4-5951, H18N65-45T4-5952, H18N65-45T4-5953, H18N65-45T4-5955, H18N65-45T1-5955, H18N65-45T2-5955, or H18N65-45T1T3-5955, was dialyzed to (1) 2 L storage buffer (20 mM sodium phosphate buffer pH 6.5, 0.5 M NaCl); (2) 2 L renaturation buffer (50 mM sodium phosphate buffer pH 6.0, 2 mM CaCl$_2$), 2 mM MgCl$_2$, 0.5 M NaCl); and (3) 20 mM sodium phosphate buffer pH 7.0, 0.5 M NaCl, successively. The dialysis was performed in each of the three buffers for 12 h.

By similar methods, the HPV18N65, HPV45N27 and HPV59 L1 protein were assembled into HPV18N65 VLP, HPV45N27 VLP and HPV59 VLP, respectively.

Molecular Sieve Chromatographic Analysis

Figure 3A:
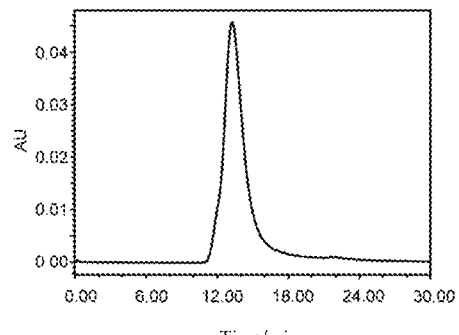
FIGS. 3A-3S show the results of the samples comprising the protein HPV18N65 (FIG. 3A), HPV45N27 (FIG. 3B), HPV59 L1 (FIG. 3C), H18N65-45T1 (FIG. 3D), H18N65-45T2 (FIG. 3E), H18N65-45T3 (FIG. 3F), H18N65-45T4 (FIG. 3G), H18N65-45T5 (FIG. 3H), H18N65-45T3-59S1 (FIG. 3I), H18N65-45T3-59S2 (FIG. 3J), H18N65-45T3-59S4 (FIG. 3K), H18N65-45T3-59S5 (FIG. 3L), H18N65-45T4-59S1 (FIG. 3M), H18N65-45T4-59S2 (FIG. 3N), H18N65-45T4-59S3 (FIG. 3O), H18N65-45T4-59S5 (FIG. 3P), H18N65-45T1-59S5 (FIG. 3Q), H18N65-45T2-59S5 (FIG. 3R), and H18N65-45T1T3-59S5 (FIG. 3S), as analyzed by molecular sieve chromatography. The results showed that the first protein peak of the samples comprising the protein H18N65-45T1, H18N65-45T2, H18N65-45T3, H18N65-45T4, H18N65-45T5, H18N65-45T3-59S1, H18N65-45T3-59S2, H18N65-45T3-59S4, H18N65-45T3-59S5, H18N65-45T4-59S1, H18N65-45T4-59S2, H18N65-45T4-59S3, H18N65-45T4-59S5, H18N65-45T1-59S5, H18N65-45T2-59S5, or H18N65-45T1T3-59S5 appeared at about 13 min, which was comparable to that of VLP assembled by HPV18N65 L1 protein (HPV18N65 VLP), VLP assembled by HPV45N27 protein (HPV45N27 VLP) and VLP assembled by HPV59 L1 protein (HPV59 VLP). This showed that all these proteins were able to assemble into VLPs.
Figure 3B:
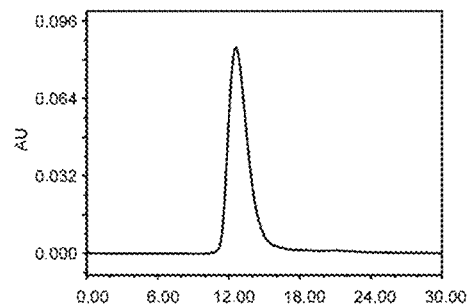
Figure 3C:
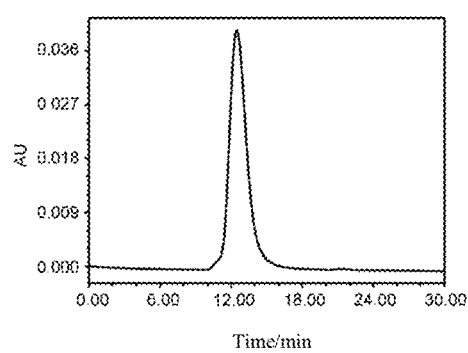
Figure 3D:
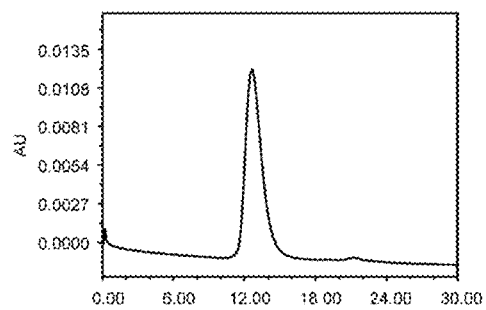
Figure 3E:
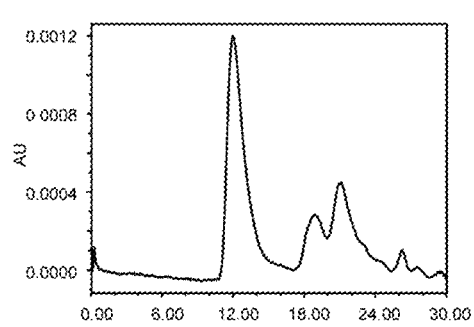
Figure 3F:
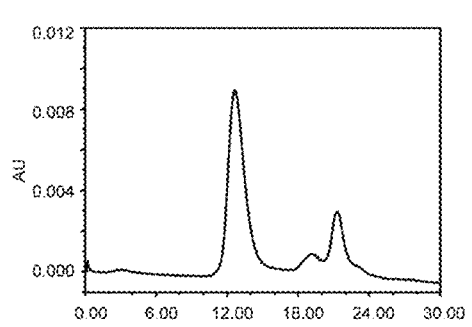
Figure 3G:
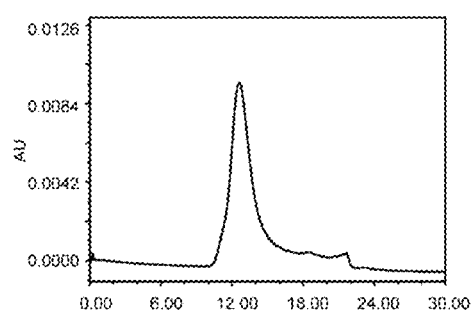
Figure 3H:
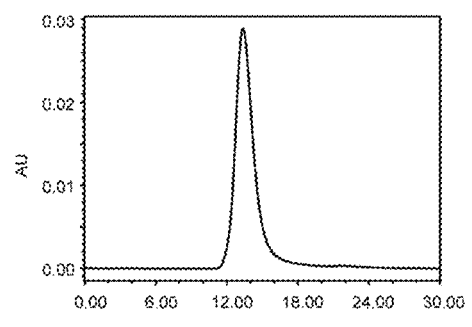
Figure 3I:
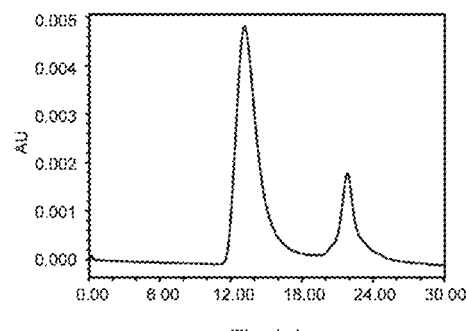
Figure 3J:
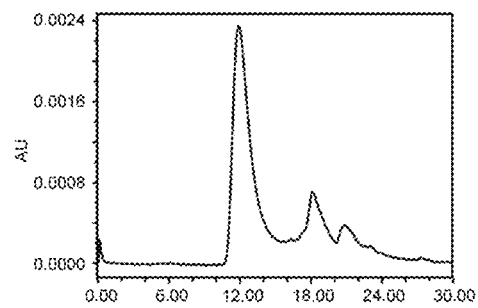
Figure 3K:
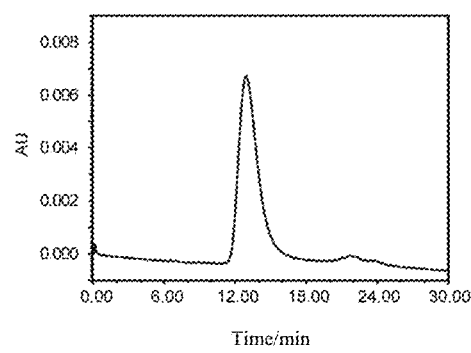
Figure 3L:
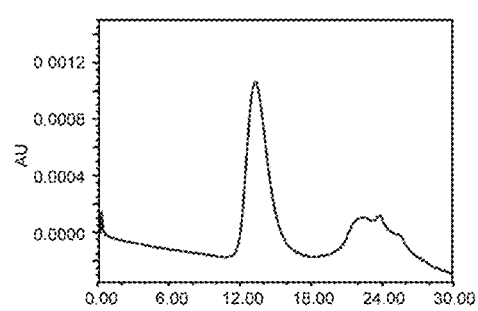
Figure 3M:
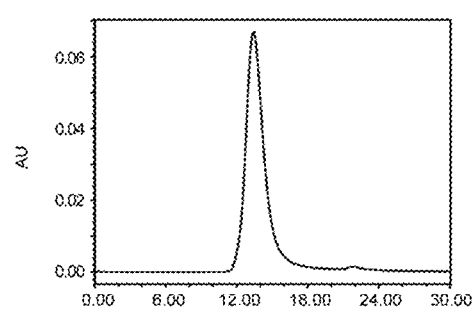
Figure 3N:
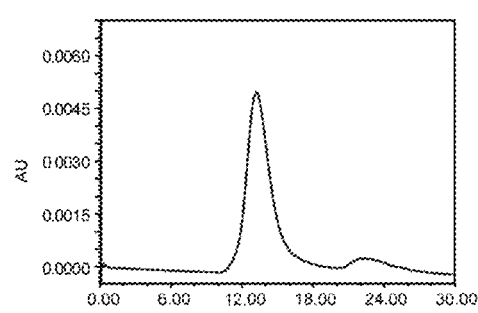
Figure 3O:
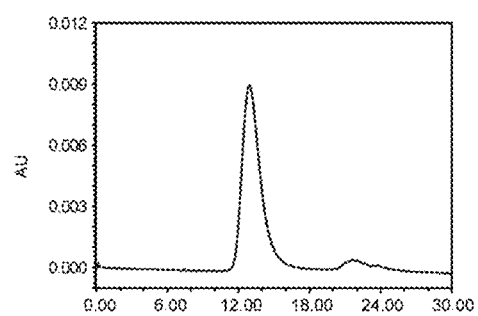
Figure 3P:
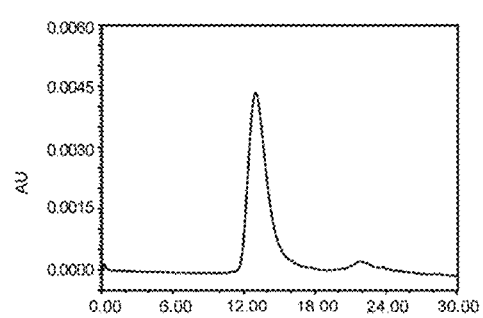
Figure 3Q:
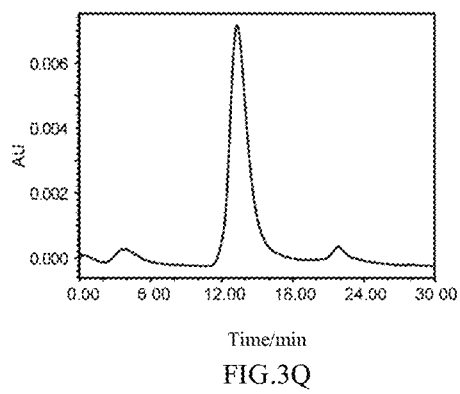
Figure 3R:
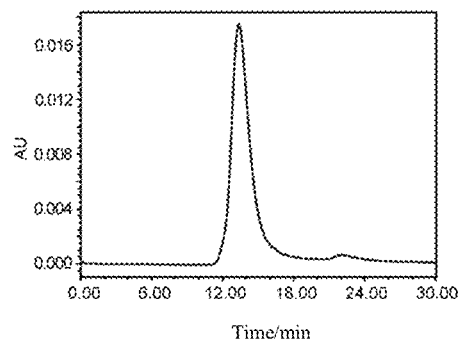
Figure 3S:
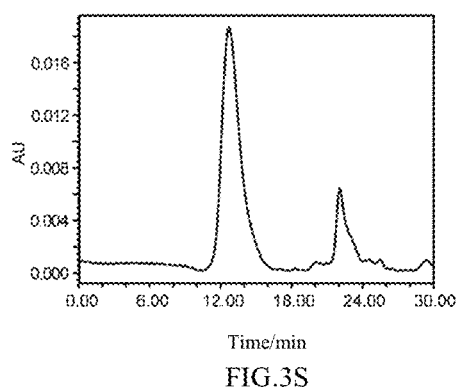

The dialyzed sample was subjected to molecular sieve chromatographic analysis by 1120 Compact LC High Performance Liquid Chromatographic System (Agilent Technologies), wherein the analytical column used was TSK Gel PW5000×1 7.8×300 mm. The analysis results were shown in FIGS. 3A-3S. The results showed that the first protein peak of the samples comprising the protein H18N65-45T1, H18N65-45T2, H18N65-45T3, H18N65-45T4, H18N65-45T5, H18N65-45T3-5951, H18N65-45T3-5952, H18N65-45T3-5954, H18N65-45T3-5955, H18N65-45T4-5951, H18N65-45T4-5952, H18N65-45T4- 5953, H18N65-45T4-5955, H18N65-45T1-5955, H18N65-45T2-5955 or H18N65-45T1T3-5955 appeared at about 13 min, which was comparable to that of HPV18N65 VLP, HPV45N27 VLP and HPV59 VLP. This showed that all these protein were able to assemble into VLPs.

Morphological Test of Virus-Like Particles

Figure 4A:
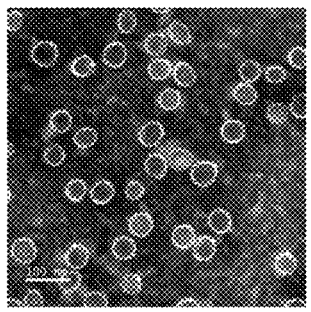
FIGS. 4A-4S show the transmission electron microscopy (TEM) photographs (taken at 100,000× magnification, Bar=0.1 μm) of various VLP samples.
Figure 4B:
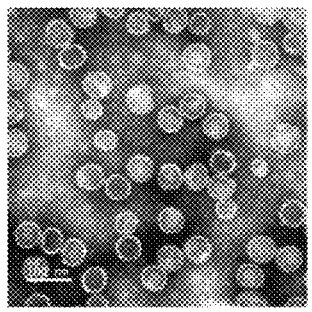
FIG. 4B, VLP assembled by HPV45N27.
Figure 4C:
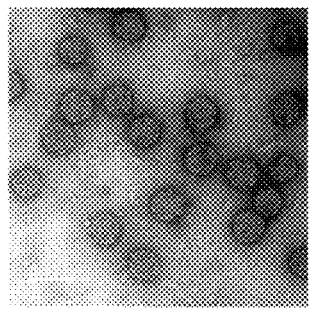
FIG. 4C, VLP assembled by HPV59 L1.
Figure 4D:
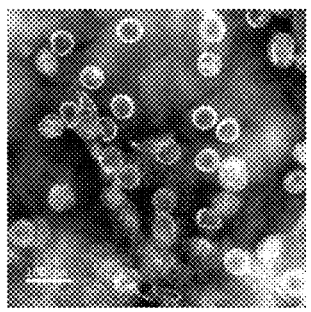
FIG. 4D, VLP assembled by H18N65-45T1.
Figure 4E:
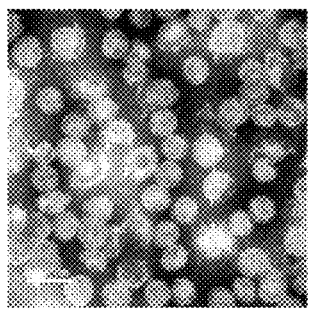
FIG. 4E, VLP assembled by H18N65-45T2.
Figure 4F:
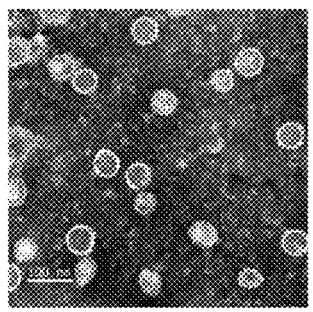
FIG. 4F, VLP assembled by H18N65-45T3.
Figure 4G:
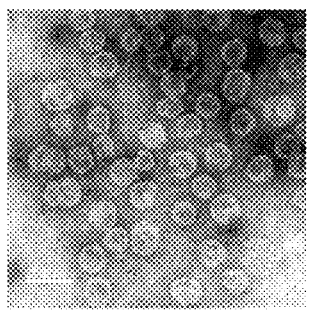
FIG. 4G, VLP assembled by H18N65-45T4.
Figure 4H:
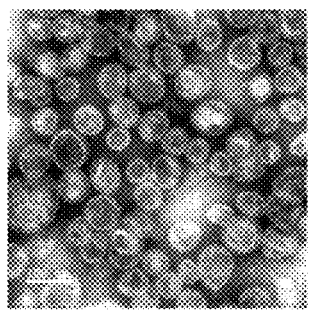
FIG. 4H, VLP assembled by H18N65-45T5.
Figure 4I:
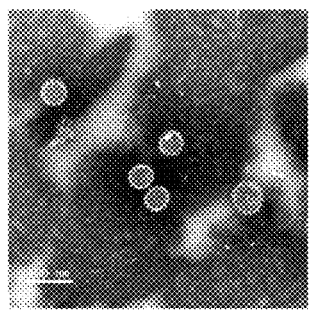
FIG. 4I, VLP assembled by H18N65-45T3-59S1.
Figure 4J:
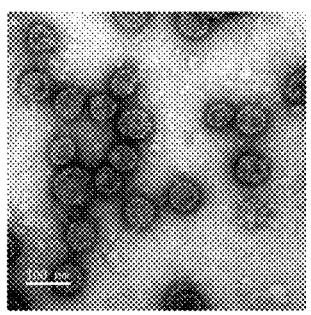
FIG. 4J, VLP assembled by H18N65-45T3-59S2.
Figure 4K:
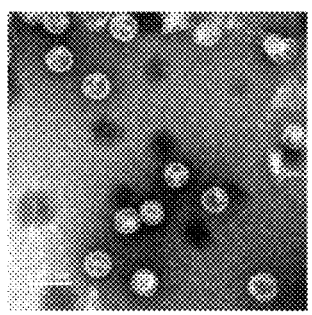
FIG. 4K, VLP assembled by H18N65-45T3-59S4.
Figure 4L:
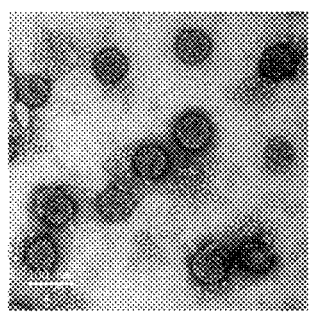
FIG. 4L, VLP assembled by H18N65-45T3-59S5.
Figure 4M:
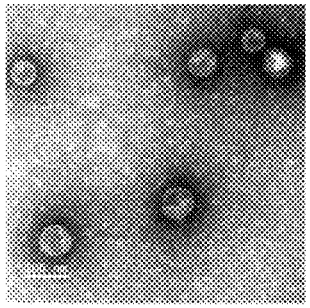
FIG. 4M, VLP assembled by H18N65-45T4-59S1.
Figure 4N:
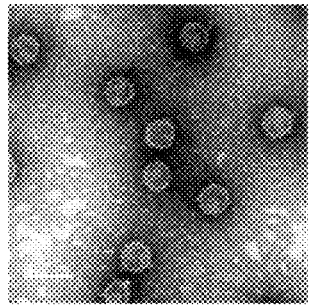
FIG. 4N, VLP assembled by H18N65-45T4-59S2.
Figure 4O:
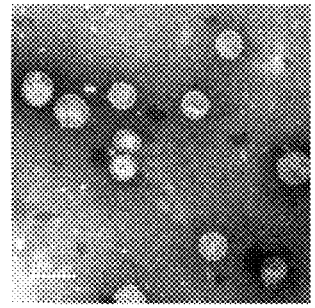
FIG. 4O, VLP assembled by H18N65-45T4-59S3.
Figure 4P:
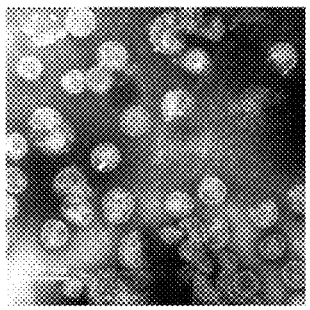
FIG. 4P, VLP assembled by H18N65-45T4-59S5.
Figure 4Q:
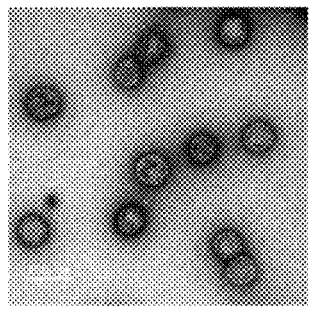
FIG. 4Q, VLP assembled by H18N65-45T1-59S5.
Figure 4R:
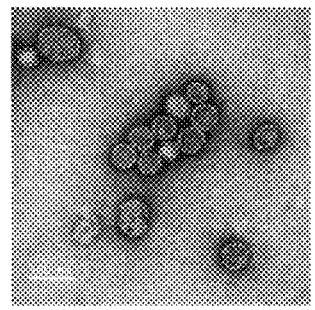
FIG. 4R, VLP assembled by H18N65-45T2-59S5.
Figure 4S:
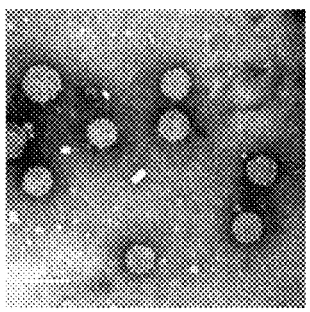
Figure 5A:
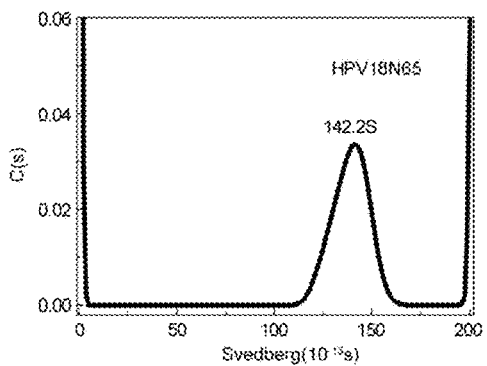
FIGS. 5A-5H show the results of sedimentation velocity analysis of HPV18N65 VLP, HPV45N27 VLP, HPV59 VLP, H18N65-45T3 VLP, H18N65-45T4 VLP, H18N65-45T3-59S1 VLP, H18N65-45T4-59S1 VLP and H18N65-45T1T3-59S5 VLP.
Figure 5B:
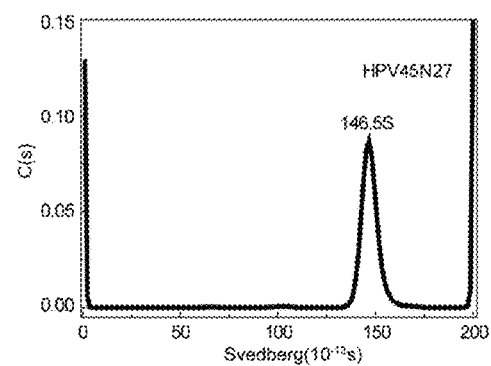
Figure 5C:
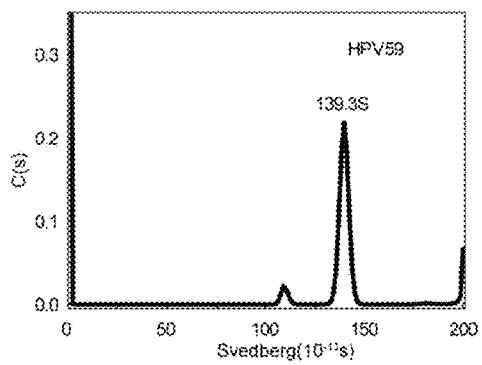
Figure 5D:
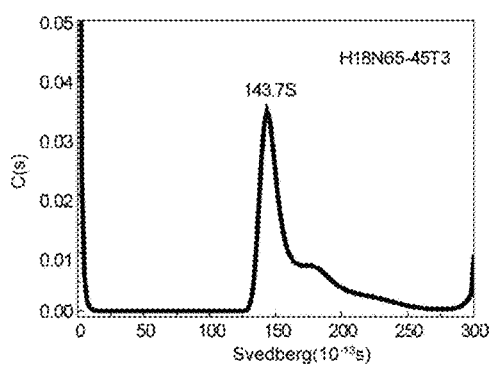
Figure 5E:
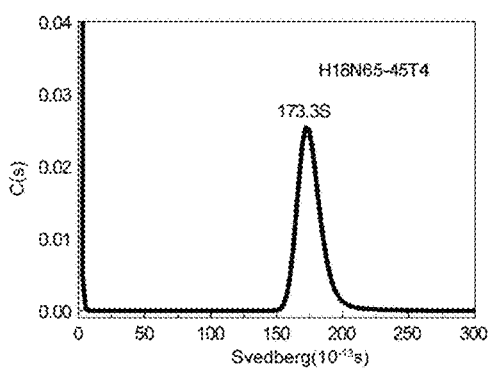
Figure 5F:
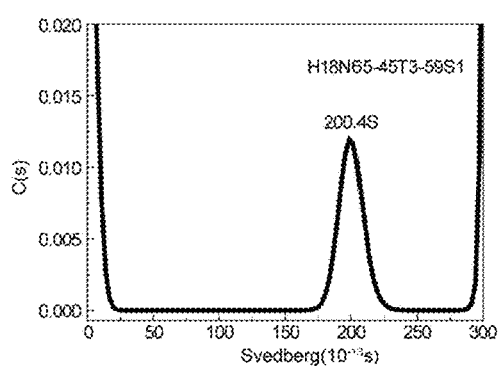
Figure 5G:
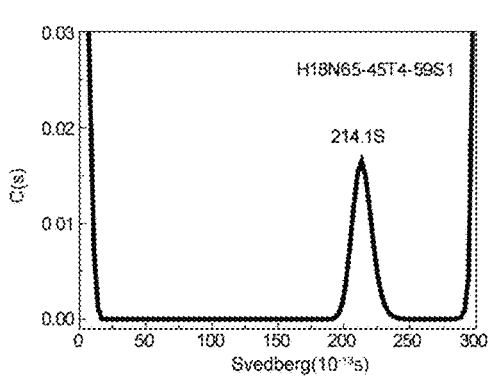
Figure 5H:
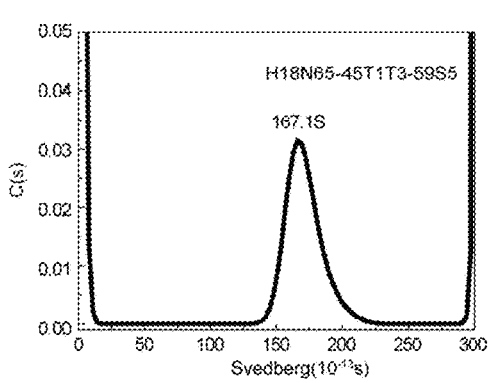
Figure 6A:
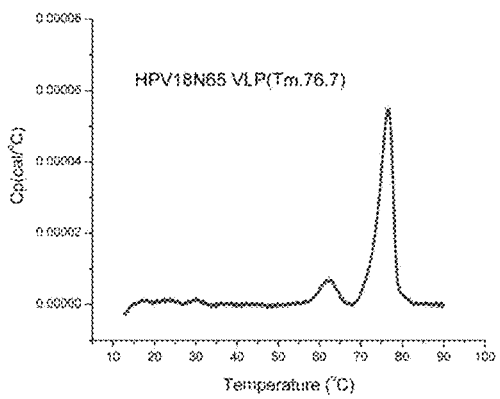
FIGS. 6A-6H show the detection results of thermostability of HPV18N65 VLP, HPV45N27 VLP, HPV59 VLP, H18N65-45T3 VLP, H18N65-45T4 VLP, H18N65-45T3-59S1 VLP, H18N65-45T4-59S1 VLP, and H18N65-45T1T3-59S5 VLP.
Figure 6B:
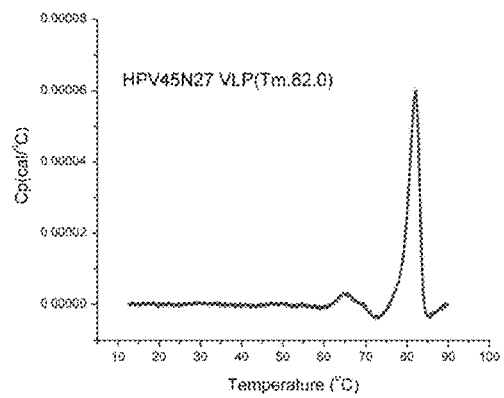
Figure 6C:
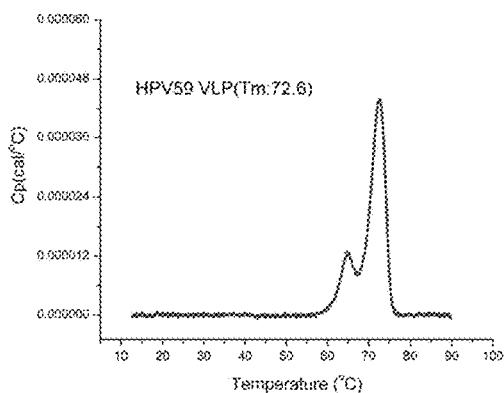
Figure 6D:
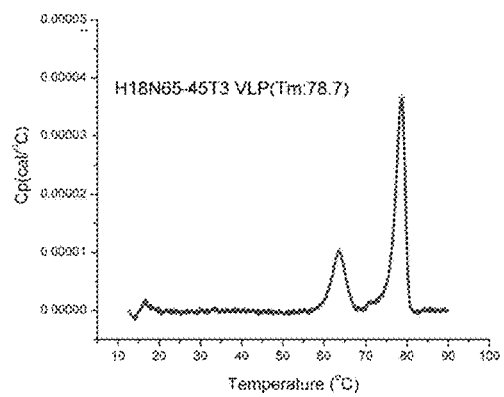
Figure 6E:
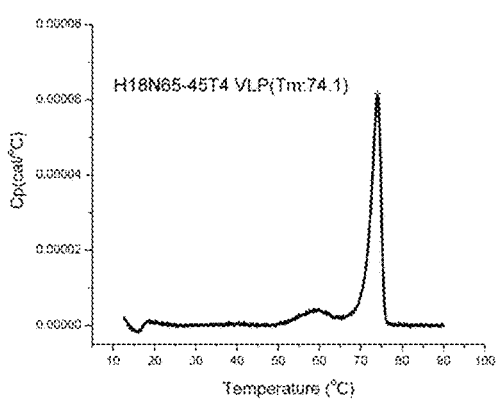
Figure 6F:
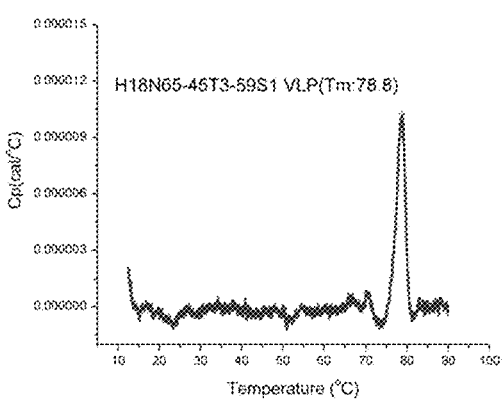
Figure 6G:
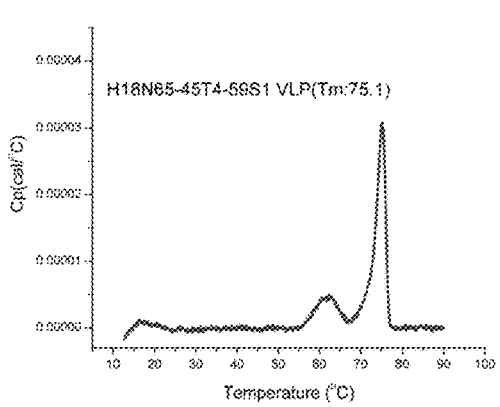
Figure 6H:
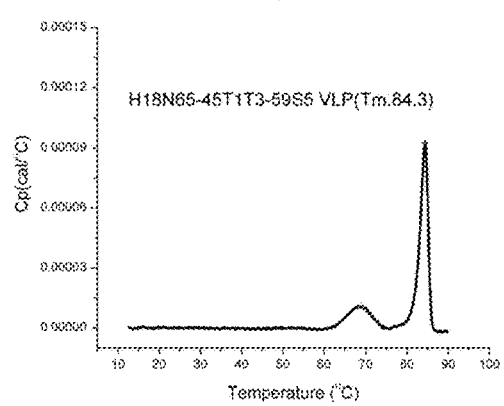

A 100 µL sample comprising VLP was observed by transmission electron microscope (TEM). The apparatus used was a 100 kV Transmission Electron Microscope supplied by JEOL Ltd. (100,000× magnification). In brief, a 13.5 μL of sample was negatively stained with 2% phosphotungstic acid (pH 7.0), fixed on a carbon-coated copper grid, and then observed by TEM. The results were shown in FIGS. 4A-4S. The results showed that H18N65-45T1, H18N65-45T2, H18N65-45T3, H18N65-45T4, H18N65-45T5, H18N65-45T3-59S1, H18N65-45T3-59S2, H18N65-45T3-59S4, H18N65-45T3-59S5, H18N65-45T4-59S1, H18N65-45T4-59S2, H18N65-45T4-59S3, H18N65-45T4-59S5, H18N65-45T1-59S5, H18N65-45T2-59S5 and H18N65-45T1T3-59S5 were able to assemble into virus-like particles. In addition, the results also showed that the particles assembled by these mutated proteins had a radius of about 30 nm, and were uniform in size. The particles assembled by wild type HPV18N65, HPV45N27 and HPV59 L1 also had a radius of about 30 nm, and were uniform in size. This indicated that these mutated proteins were similar to the L1 protein of HPV18, HPV45 and HPV59, and were able to assemble into VLPs with a uniform size.

Sedimentation Velocity Analysis

The apparatus for sedimentation velocity analysis was Beckman XL-A Analytical Ultracentrifuge, equipped with optical inspection system and An-50Ti and An-60Ti rotor. The sedimentation coefficients of HPV18N65 VLP, HPV45N27 VLP, HPV59 VLP, H18N65-45T3 VLP, H18N65-45T4 VLP, H18N65-45T3-59S1 VLP, H18N65-45T4-59S1 VLP and H18N65-45T1T3-59S5 VLP were analyzed by sedimentation velocity method. The results were shown in FIGS. 5A-5H. The results showed that the sedimentation coefficient of H18N65-45T3 VLP, H18N65-45T4 VLP and H18N65-45T1T3-59S5 VLP was 143.7S, 173.3S and 167.1S, respectively, which was similar to that of HPV18N65 VLP, HPV45N27 VLP and HPV59 VLP (HPV18N65 VLP, 142.2S; HPV45N27 VLP, 146.5S, and HPV59 VLP, 139.3S). This showed that H18N65-45T3 VLP, H18N65-45T4 VLP and H18N65-45T1T3-59S5 VLP were able to assemble into virus-like particles that were similar to wild type VLP in terms of size and morphology.

Example 3: Evaluation of Thermostability of Virus-Like Particles

The VLPs formed by protein HPV18N65, HPV45N27, HPV59, H18N65-45T3, H18N65-45T4, H18N65-45T3-59S1, H18N65-45T4-59S1, and H18N65-45T1T3-59S5 were evaluated for their thermostability by using a differential scanning calorimeter VP Capillary DSC purchased from GE Company (i.e. the original MicroCal Co.), wherein the storage buffer for the protein was used as control, and the proteins were scanned at a heating rate of 1.5° C./min within a temperature range of 10° C.-90° C. The detection results were shown in FIGS. 6A-6H. The results showed that all these VLPs formed by the proteins had very high thermostability.

Example 4: Evaluation 1 of Neutralizing Antibody Titer in Serum of Mice Vaccinated with Virus-Like Particles The immune protection of the VLPs formed by H18N65-45T1, H18N65-45T2, H18N65-45T3, H18N65-45T4, H18N65-45T5, H18N65-45T3-59S1, H18N65-45T3-59S2, H18N65-45T3-59S4, H18N65-45T3-59S5, H18N65-45T4-59S1, H18N65-45T4-59S2, H18N65-45T4-59S3, H18N65-45T4-59S5, H18N65-45T1-59S5, H18N65-45T2-59S5 and H18N65-45T1T3-59S5 was evaluated in mice. Animals for vaccination were BALB/c mice (ordinary grade), 5-6 weeks old (purchased from Shanghai SLAC Laboratory Animal Co. LTD.).

Figure 7A:
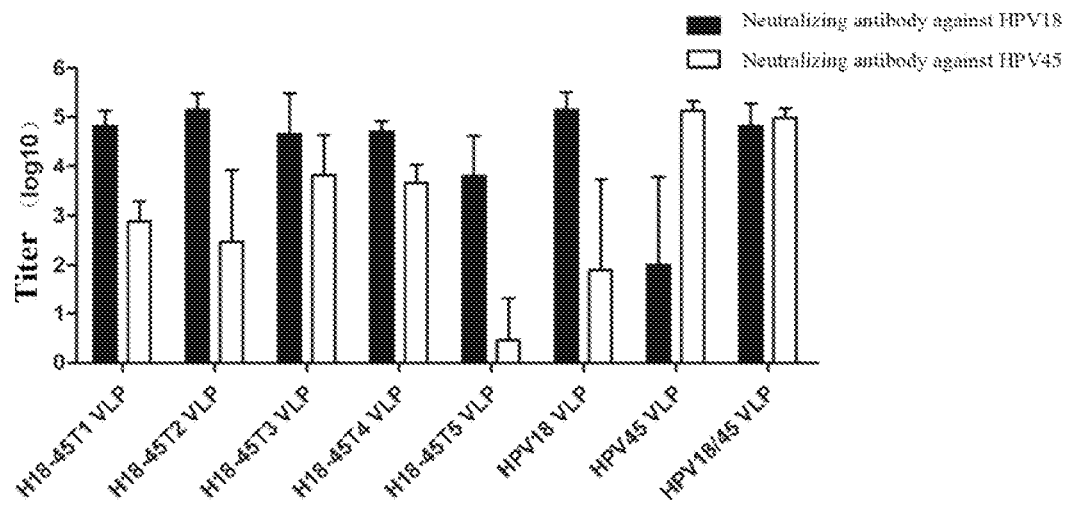
FIG. 7A shows the evaluation result of immune protection of H18N65-45T1 VLP, H18N65-45T2 VLP, H18N65-45T3 VLP, H18N65-45T4 VLP and H18N65-45T5 VLP in mice of the Experimental groups, and of HPV18N65 VLP, HPV45N27 VLP, and the mixed HPV18/HPV45 VLP in mice of the Control groups. The result showed that H18N65-45T1 VLP, H18N65-45T2, VLPH18N65-45T3 VLP and H18N65-45T4 VLP each retained the activity that could induce the generation of high-titer neutralizing antibodies against HPV18 in mice, and their protective effects against HPV18 were comparable to that of HPV18N65 VLP alone and that of the mixed HPV18/HPV45 VLP, and their activities that could induce the generation of neutralizing antibodies against HPV45 in mice were higher than that of HPV18N65 VLP alone. In particular, H18N65-45T3 VLP and H18N65-45T4 VLP each could induce the generation of high-titer neutralizing antibodies against HPV45 and HPV18 in mice; and their protective effects against HPV18 were comparable to that of HPV18N65 VLP alone and that of the mixed HPV18/HPV45 VLP, and were significantly higher than that of HPV45N27 VLP alone; and their protective effects against HPV45 were comparable to that of HPV45N27 VLP alone and that of the mixed HPV18/HPV45 VLP, and were significantly higher than that of HPV18N65 VLP alone. This showed that after mutation, H18N65-45T1 VLP, H18N65-45T2, VLPH18N65-45T3 VLP and H18N65-45T4 VLP retained their immunogenicity against HPV18, and their immunogenicity against HPV45 is also improved as compared to HPV18N65 VLP. Especially, H18N65-45T3 VLP and H18N65-45T4 VLP had good cross-immunogenicity and cross-protection against HPV18 and HPV45, and could be used as effective vaccines for preventing HPV18 infection and/or HPV45 infection, and could be used in place of a mixed vaccine comprising HPV18 VLP and HPV45 VLP.

The H18N65-45T1 VLP, H18N65-45T2 VLP, H18N65-45T3 VLP, H18N65-45T4 VLP, H18N65-45T5 VLP, HPV18N65 VLP, HPV45N27 VLP and a mixed HPV18/HPV45 VLP (i.e. a mixture of HPV18N65 VLP and HPV45N27 VLP) as prepared above were absorbed onto aluminum adjuvant, respectively. Mice were divided into 8 groups depending on immunogen, and each group included 5 mice. Vaccination procedure was as followed: the first vaccination at Week 0, and the booster vaccination at Weeks 2 and 4, respectively. Mice were vaccinated via intraperitoneal injection. The immunogens and doses thereof were shown in Table 4. At Week 8 after the first vaccination, venous blood was collected from eyeball, and serum was separated. The titers of neutralizing antibodies in the serum were determined. The detection result was shown in FIG. 7A. The result showed that H18N65-45T1 VLP, H18N65-45T2, VLPH18N65-45T3 VLP and H18N65-45T4 VLP each retained the activity that could induce the generation of high-titer neutralizing antibodies against HPV18 in mice, and their protective effects against HPV18 were comparable to that of HPV18N65 VLP alone and that of the mixed HPV18/HPV45 VLP, and their activities that could induce the generation of neutralizing antibodies against HPV45 in mice were higher than that of HPV18N65 VLP alone. In particular, H18N65-45T3 VLP and H18N65-45T4 VLP each could induce the generation of high-titer neutralizing antibodies against HPV45 and HPV18 in mice; and their protective effects against HPV18 were comparable to that of HPV18N65 VLP alone and that of the mixed HPV18/HPV45 VLP, and were significantly higher than that of HPV45N27 VLP alone; and their protective effects against HPV45 were comparable to that of HPV45N27 VLP alone and that of the mixed HPV18/HPV45 VLP, and were significantly higher than that of HPV18N65 VLP alone. This showed that after mutation, H18N65-45T1 VLP, H18N65-45T2, VLPH18N65-45T3 VLP and H18N65-45T4 VLP retained their immunogenicity against HPV18, and their immunogenicity against HPV45 is also improved as compared to HPV18N65 VLP. Especially, H18N65-45T3 VLP and H18N65-45T4 VLP had good cross-immunogenicity and cross-protection against HPV18 and HPV45, and could be used as effective vaccines for preventing HPV18 infection and/or HPV45 infection, and could be used in place of a mixed vaccine comprising HPV18 VLP and HPV45 VLP.

TABLE 4

| Vaccination schedule | | | | |
|---|---|---|---|---|
| Antigen for vaccination | Adjuvant | Immunizing dose | Number | Vaccination procedure (week) |
| H18N65-45T1 VLP | aluminum adjuvant | 5 μg | 5 | 0, 2, 4 |
| H18N65-45T2 VLP | aluminum adjuvant | 5 μg | 5 | 0, 2, 4 |
| H18N65-45T3 VLP | aluminum adjuvant | 5 μg | 5 | 0, 2, 4 |
| H18N65-45T4 VLP | aluminum adjuvant | 5 μg | 5 | 0, 2, 4 |
| H18N65-45T5 VLP | aluminum adjuvant | 5 μg | 5 | 0, 2, 4 |
| HPV18N65 VLP | aluminum adjuvant | 5 μg | 5 | 0, 2, 4 |
| HPV45N27 VLP | aluminum adjuvant | 5 μg | 5 | 0, 2, 4 |

TABLE 4-continued

Vaccination schedule

| Antigen for vaccination | Adjuvant | Immunizing dose | Number | Vaccination procedure (week) |
|---|---|---|---|---|
| HPV18/HPV45 VLP | aluminum adjuvant | 5 μg for each VLP | 5 | 0, 2, 4 |

Figure 7B:
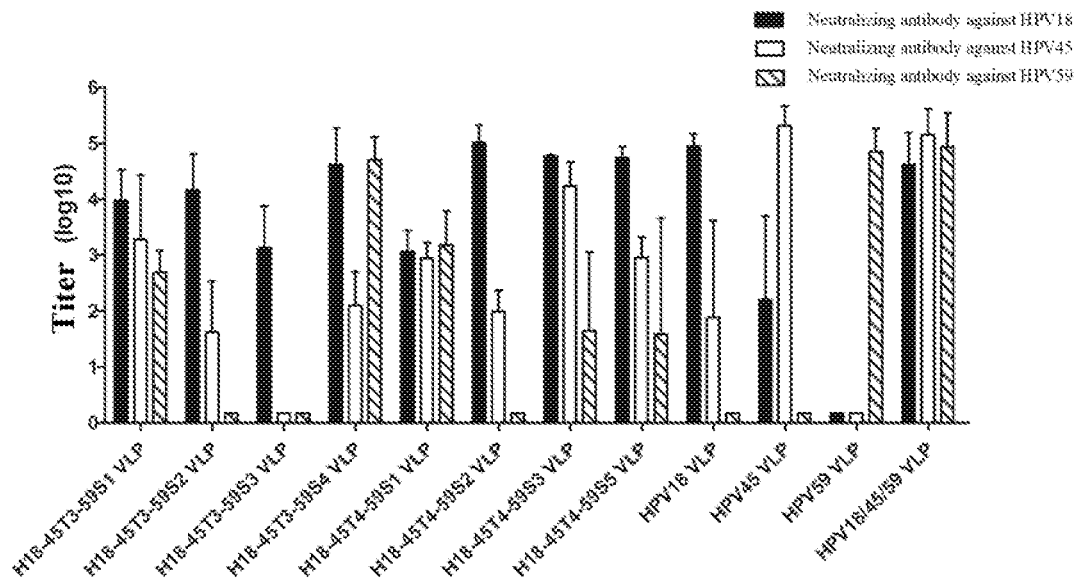
FIG. 7B shows the evaluation result of immune protection of H18N65-45T3-59S1 VLP, H18N65-45T3-59S2 VLP, H18N65-45T3-59S4 VLP, H18N65-45T3-59S5 VLP, H18N65-45T4-59S1 VLP, H18N65-45T4-59S2 VLP, H18N65-45T4-59S3 VLP and H18N65-45T4-59S5 VLP in mice of the Experimental groups, and of HPV18N65 VLP, HPV45N27 VLP, HPV59 VLP and the mixed HPV18/HPV45/HPV59 VLP in mice of the Control groups. The result showed that H18N65-45T3-59S1 VLP and H18N65-45T4-59S1 VLP each could induce the generation of high-titer neutralizing antibodies against HPV18, HPV45 and HPV59 in mice; and their protective effects against HPV18 were comparable to that of HPV18N65 VLP alone and that of the mixed HPV18/HPV45/HPV59 VLP, and were significantly higher than that of HPV45N27 VLP alone and that of HPV59 VLP alone; and their protective effects against HPV45 were comparable to that of HPV45N27 VLP alone and that of the mixed HPV18/HPV45/HPV59 VLP, and were significantly higher than that of HPV18N65 VLP alone and that of HPV59 VLP alone; and their protective effects against HPV59 were comparable to that of HPV59 VLP alone and that of the mixed HPV18/HPV45/HPV59 VLP, and were significantly higher than that of HPV45N27 VLP alone and that of HPV18N65 VLP alone. This showed that H18N65-45T3-59S1 VLP and H18N65-45T4-59S1 VLP had good cross-immunogenicity and cross-protection against HPV18, HPV45 and HPV59, and could be used as effective vaccines for preventing HPV18 infection, HPV45 infection and/or HPV59 infection, and could be used in place of a mixed vaccine comprising HPV18 VLP, HPV45 VLP and HPV59 VLP.

In addition, the H18N65-45T3-59S1 VLP, H18N65-45T3-59S2 VLP, H18N65-45T3-59S4 VLP, H18N65-45T3-59S5 VLP, H18N65-45T4-59S1 VLP, H18N65-45T4-59S2 VLP, H18N65-45T4-59S3 VLP, H18N65-45T4-59S5 VLP, HPV18N65 VLP, HPV45N27 VLP, HPV59 VLP and the mixed HPV18/HPV45/HPV59 VLP (i.e. a mixture of HPV18N65 VLP, HPV45N27 VLP and HPV59 VLP) as prepared above were absorbed onto aluminum adjuvant, respectively. Mice were divided into 12 groups depending on immunogen, and each group included 5 mice. Vaccination procedure was as followed: the first vaccination at Week 0, and the booster vaccination at Weeks 2 and 4, respectively. Mice were vaccinated via intraperitoneal injection. The immunogens and doses thereof were shown in Table 5. At Week 8 after the first vaccination, venous blood was collected from eyeball, and serum was separated. The titers of neutralizing antibodies in the serum were determined. The detection result was shown in FIG. 7B. The result showed that H18N65-45T3-59S1 VLP and H18N65-45T4-59S1 VLP each could induce the generation of high-titer neutralizing antibodies against HPV18, HPV45 and HPV59 in mice; and their protective effects against HPV18 were comparable to that of HPV18N65 VLP alone and that of the mixed HPV18/HPV45/HPV59 VLP, and were significantly higher than that of HPV45N27 VLP alone and that of HPV59 VLP alone; and their protective effects against HPV45 were comparable to that of HPV45N27 VLP alone and that of the mixed HPV18/HPV45/HPV59 VLP, and were significantly higher than that of HPV18N65 VLP alone and that of HPV59 VLP alone; and their protective effects against HPV59 were comparable to that of HPV59 VLP alone and that of the mixed HPV18/HPV45/HPV59 VLP, and were significantly higher than that of HPV45N27 VLP alone and that of HPV18N65 VLP alone. This showed that H18N65-45T3-59S1 VLP and H18N65-45T4-59S1 VLP had good cross-immunogenicity and cross-protection against HPV18, HPV45 and HPV59, and could be used as effective vaccines for preventing HPV18 infection, HPV45 infection and/or HPV59 infection, and could be used in place of a mixed vaccine comprising HPV18 VLP, HPV45 VLP and HPV59 VLP.

TABLE 5

Vaccination schedule

| Antigen for vaccination | Adjuvant | Immunizing dose | Number | Vaccination procedure (week) |
|---|---|---|---|---|
| H18N65-45T3-59S1 VLP | aluminum adjuvant | 5 μg | 5 | 0, 2, 4 |
| H18N65-45T3-59S2 VLP | aluminum adjuvant | 5 μg | 5 | 0, 2, 4 |
| H18N65-45T3-59S4 VLP | aluminum adjuvant | 5 μg | 5 | 0, 2, 4 |
| H18N65-45T3-59S5 VLP | aluminum adjuvant | 5 μg | 5 | 0, 2, 4 |
| H18N65-45T4-59S1 VLP | aluminum adjuvant | 5 μg | 5 | 0, 2, 4 |
| H18N65-45T4-59S2 VLP | aluminum adjuvant | 5 μg | 5 | 0, 2, 4 |
| H18N65-45T4-59S3 VLP | aluminum adjuvant | 5 μg | 5 | 0, 2, 4 |
| H18N65-45T4-59S5 VLP | aluminum adjuvant | 5 μg | 5 | 0, 2, 4 |
| HPV18N65 VLP | aluminum adjuvant | 5 μg | 5 | 0, 2, 4 |
| HPV45N27 VLP | aluminum adjuvant | 5 μg | 5 | 0, 2, 4 |
| HPV59 VLP | aluminum adjuvant | 5 μg | 5 | 0, 2, 4 |
| HPV18/HPV45/ HPV59 VLP | aluminum adjuvant | 5 μg for each VLP | 5 | 0, 2, 4 |

Example 5: Evaluation of $ED_{50}$ of Virus-Like Particles for Inducing Seroconversion In this experiment, virus-like particles used were H18N65-45T3-59S1 VLP, H18N65-45T4-59S1 VLP and H18N65-45T1T3-59S5 VLP.

6-Week old BalB/c female mice (8 mice) were vaccinated with aluminum adjuvant by single intraperitoneal injection, wherein H18N65-45T3-59S1 VLP, H18N65-45T4-59S1 VLP or H18N65-45T1T3-59S5 (at an immunizing dose of 0.300 μg, 0.100 μg, 0.033 μg, 0.011 μg or 0.004m) was used in the Experimental groups, and HPV45N27 VLP alone, HPV18N65 VLP alone, HPV59 VLP alone (at an immunizing dose of 0.300m, 0.100 μg, 0.033m, 0.011 μg or 0.004 μg) or the mixed HPV18/HPV45/HPV59 VLP (i.e. a mixture of HPV18N65 VLP, HPV45N27 VLP and HPV59 VLP, at an immunizing dose of 0.300m, 0.100 μg, 0.033m, 0.011 μg or 0.004 μg for each VLP) was used in the Control groups; the immunizing volume was 1 mL. In addition, the diluent used to dilute the vaccine was used as a blank control. 8 Mice were vaccinated in each group, and at Week 5 after vaccination, venous blood was collected from eyeball. Antibodies against HPV in the serum were detected, and by Reed-Muench method (Reed LJ MH. A simple method of estimating fifty percent endpoints. Am J Hyg. 1938; 27:493-7), $ED_{50}$ for inducing seroconversion (i.e. inducing the generation of antibodies in mice) was calculated for each sample. The results were shown in Tables 6-12.

TABLE 6

$ED_{50}$ of HPV18N65 VLP for inducing the generation of antibodies against HPV45, HPV18 and HPV59 (seroconversion) in mice

| Type | Immunizing dose (μg) | Total number of mice | Number of mice with positive conversion | Positive conversion rate | $ED_{50}$ (μg) |
|---|---|---|---|---|---|
| HPV18 | 0.300 | 8 | 6 | 83.33% | 0.138 |
| | 0.100 | 8 | 3 | 36.36% | |
| | 0.033 | 8 | 1 | 6.67% | |
| | 0.011 | 8 | 0 | 0.00% | |
| | 0.004 | 8 | 0 | 0.00% | |
| HPV45 | 0.300 | 8 | 0 | 100.00% | >0.3 |
| | 0.100 | 8 | 0 | 100.00% | |
| | 0.033 | 8 | 0 | 90.00% | |

TABLE 6-continued

ED$_{50}$ of HPV18N65 VLP for inducing the generation of antibodies against HPV45, HPV18 and HPV59 (seroconversion) in mice

| Type | Immunizing dose (μg) | Total number of mice | Number of mice with positive conversion | Positive conversion rate | ED$_{50}$ (μg) |
|---|---|---|---|---|---|
|  | 0.011 | 8 | 0 | 22.22% |  |
|  | 0.004 | 8 | 0 | 0.00% |  |
| HPV59 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |

TABLE 7

ED$_{50}$ of HPV45N27 VLP for inducing the generation of antibodies against HPV45, HPV18 and HPV59 (seroconversion) in mice

| Type | Immunizing dose (μg) | Total number of mice | Number of mice with positive conversion | Positive conversion rate | ED$_{50}$ (μg) |
|---|---|---|---|---|---|
| HPV18 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV45 | 0.300 | 8 | 7 | 95.83% | 0.021 |
|  | 0.100 | 8 | 8 | 94.12% |  |
|  | 0.033 | 8 | 7 | 80.00% |  |
|  | 0.011 | 8 | 1 | 10.00% |  |
|  | 0.004 | 8 | 0 | 0.00% |  |
| HPV59 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |

TABLE 8

ED$_{50}$ of HPV59 VLP for inducing the generation of antibodies against HPV45, HPV18 and HPV59 (seroconversion) in mice

| Type | Immunizing dose (μg) | Total number of mice | Number of mice with positive conversion | Positive conversion rate | ED$_{50}$ (μg) |
|---|---|---|---|---|---|
| HPV18 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV45 | 0.300 | 8 | 0 | 0.00% | >0.3 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV59 | 0.300 | 8 | 8 | 100.00% | 0.029 |
|  | 0.100 | 8 | 8 | 100.00% |  |
|  | 0.033 | 8 | 4 | 55.56% |  |
|  | 0.011 | 8 | 1 | 8.33% |  |
|  | 0.004 | 8 | 0 | 0.00% |  |

TABLE 9

ED$_{50}$ of the mixed HPV18/HPV45/HPV59 VLP for inducing the generation of antibodies against HPV45, HPV18 and HPV59 (seroconversion) in mice

| Type | Immunizing dose (μg) | Total number of mice | Number of mice with positive conversion | Positive conversion rate | ED$_{50}$ (μg) |
|---|---|---|---|---|---|
| HPV18 | 0.300 μg for each VLP | 8 | 6 | 86.67% | 0.088 |
|  | 0.100 μg for each VLP | 8 | 4 | 53.85% |  |
|  | 0.033 μg for each VLP | 8 | 3 | 21.43% |  |
|  | 0.011 μg for each VLP | 8 | 0 | 0.00% |  |
|  | 0.004 μg for each VLP | 8 | 0 | 0.00% |  |
| HPV45 | 0.300 μg for each VLP | 8 | 6 | 88.24% | 0.033 |
|  | 0.100 μg for each VLP | 8 | 6 | 69.23% |  |
|  | 0.033 μg for each VLP | 8 | 3 | 25.00% |  |
|  | 0.011 μg for each VLP | 8 | 0 | 0.00% |  |
|  | 0.004 μg for each VLP | 8 | 0 | 0.00% |  |
| HPV59 | 0.300 μg for each VLP | 8 | 6 | 91.30% | 0.025 |
|  | 0.100 μg for each VLP | 8 | 8 | 88.24% |  |
|  | 0.033 μg for each VLP | 8 | 6 | 63.64% |  |
|  | 0.011 μg for each VLP | 8 | 1 | 8.33% |  |
|  | 0.004 μg for each VLP | 8 | 0 | 0.00% |  |

TABLE 10

ED$_{50}$ of H18N65-45T3-59S1 VLP for inducing the generation of antibodies against HPV45, HPV18 and HPV59 (seroconversion) in mice

| Type | Immunizing dose (μg) | Total number of mice | Number of mice with positive conversion | Positive conversion rate | ED$_{50}$ (μg) |
|---|---|---|---|---|---|
| HPV18 | 0.300 | 8 | 7 | 94.12% | 0.057 |
|  | 0.100 | 8 | 7 | 81.82% |  |
|  | 0.033 | 8 | 2 | 20.00% |  |
|  | 0.011 | 8 | 0 | 0.00% |  |
|  | 0.004 | 8 | 0 | 0.00% |  |
| HPV45 | 0.300 | 8 | 2 | 53.85% | 0.244 |
|  | 0.100 | 8 | 4 | 33.33% |  |
|  | 0.033 | 8 | 1 | 5.56% |  |
|  | 0.011 | 8 | 0 | 0.00% |  |
|  | 0.004 | 8 | 0 | 0.00% |  |
| HPV59 | 0.300 | 8 | 7 | 90.91% | 0.152 |
|  | 0.100 | 8 | 0 | 25.00% |  |
|  | 0.033 | 8 | 2 | 16.67% |  |
|  | 0.011 | 8 | 1 | 4.35% |  |
|  | 0.004 | 8 | 0 | 0.00% |  |

TABLE 11

ED$_{50}$ of H18N65-45T4-59S1 VLP for inducing the generation of antibodies against HPV45, HPV18 and HPV59 (seroconversion) in mice

| Type | Immunizing dose (μg) | Total number of mice | Number of mice with positive conversion | Positive conversion rate | ED$_{50}$ (μg) |
|---|---|---|---|---|---|
| HPV18 | 0.300 | 8 | 6 | 75.00% | 0.208 |
|  | 0.100 | 8 | 0 | 0.00% |  |
|  | 0.033 | 8 | 0 | 0.00% |  |
|  | 0.011 | 8 | 0 | 0.00% |  |
|  | 0.004 | 8 | 0 | 0.00% |  |
| HPV45 | 0.300 | 8 | 4 | 55.56% | 0.264 |
|  | 0.100 | 8 | 0 | 7.69% |  |
|  | 0.033 | 8 | 1 | 5.00% |  |
|  | 0.011 | 8 | 0 | 0.00% |  |
|  | 0.004 | 8 | 0 | 0.00% |  |
| HPV59 | 0.300 | 8 | 6 | 77.78% | 0.191 |
|  | 0.100 | 8 | 1 | 10.00% |  |

TABLE 11-continued

ED$_{50}$ of H18N65-45T4-59S1 VLP for inducing the generation of antibodies against HPV45, HPV18 and HPV59 (seroconversion) in mice

| Type | Immunizing dose (μg) | Total number of mice | Number of mice with positive conversion | Positive conversion rate | ED$_{50}$ (μg) |
|---|---|---|---|---|---|
| | 0.033 | 8 | 0 | 0.00% | |
| | 0.011 | 8 | 0 | 0.00% | |
| | 0.004 | 8 | 0 | 0.00% | |

TABLE 12

ED$_{50}$ of H18N65-45T1T3-59S5 VLP for inducing the generation of antibodies against HPV45, HPV18 and HPV59 (seroconversion) in mice

| Type | Immunizing dose (μg) | Total number of mice | Number of mice with positive conversion | Positive conversion rate | ED$_{50}$ (μg) |
|---|---|---|---|---|---|
| HPV18 | 0.300 | 8 | 8 | 100.00% | 0.065 |
| | 0.100 | 8 | 5 | 70.00% | |
| | 0.033 | 8 | 2 | 18.18% | |
| | 0.011 | 8 | 0 | 0.00% | |
| | 0.004 | 8 | 0 | 0.00% | |
| HPV45 | 0.300 | 8 | 8 | 100.00% | 0.086 |
| | 0.100 | 8 | 3 | 54.55% | |
| | 0.033 | 8 | 2 | 21.43% | |
| | 0.011 | 8 | 1 | 5.26% | |
| | 0.004 | 8 | 0 | 0.00% | |
| HPV59 | 0.300 | 8 | 8 | 100.00% | 0.125 |
| | 0.100 | 8 | 3 | 37.50% | |
| | 0.033 | 8 | 0 | 0.00% | |
| | 0.011 | 8 | 0 | 0.00% | |
| | 0.004 | 8 | 0 | 0.00% | |

The results showed that 5 weeks after vaccination of mice, ED$_{50}$ of H18N65-45T3-59S1 VLP, H18N65-45T4-59S1 VLP and H18N65-45T1T3-59S5 VLP for inducing the generation of antibodies against HPV18 in mice was comparable to that of HPV18N65 VLP alone and that of the mixed HPV18/HPV45/HPV59 VLP, and was significantly superior to that of HPV45N27 VLP alone and that of HPV59 VLP alone; and ED$_{50}$ of H18N65-45T3-59S1 VLP, H18N65-45T4-59S1 VLP and H18N65-45T1T3-59S5 VLP for inducing the generation of antibodies against HPV45 in mice was comparable to that of HPV45N27 VLP alone and that of the mixed HPV18/HPV45/HPV59 VLP, and was significantly superior to that of HPV18N65 VLP alone and that of HPV59 VLP alone; and ED$_{50}$ of H18N65-45T3-59S1 VLP, H18N65-45T4-59S1 VLP and H18N65-45T1T3-59S5 VLP for inducing the generation of antibodies against HPV59 in mice was comparable to that of HPV59 VLP alone and that of the mixed HPV18/HPV45/HPV59 VLP, and was significantly superior to that of HPV45N27 VLP alone and that of HPV18N65 VLP alone. This showed that H18N65-45T3-59S1 VLP, H18N65-45T4-59S1 VLP and H18N65-45T1T3-59S5 VLP had good cross-immunogenicity and cross-protection against HPV18, HPV45 and HPV59.

Example 6: Evaluation 2 of Neutralizing Antibody Titer in Serum of Mice Vaccinated with Virus-Like Particles In this experiment, virus-like particle used was H18N65-45T4 VLP.

In this experiment, vaccination schedule was shown in Table 13. All the mice (6-week old BalB/c female mice) were divided into 2 groups: Group of dose of 10 μg (at an immunizing dose of 10 μg, using aluminum adjuvant), and Group of dose of 1 μg (at an immunizing dose of 1 μg, using aluminum adjuvant). Each group was further divided into 5 subgroups. The Control subgroups 1 and 2 were vaccinated with HPV45N27 VLP alone and HPV18N65 VLP alone, respectively, the Control subgroup 3 was vaccinated with the mixed HPV18/HPV45 VLP (i.e. a mixture of HPV18N65 VLP and HPV45N27 VLP, at a given immunizing dose for each VLP), and the Experimental subgroup was vaccinated with H18N65-45T4 VLP.

Figure 8A:
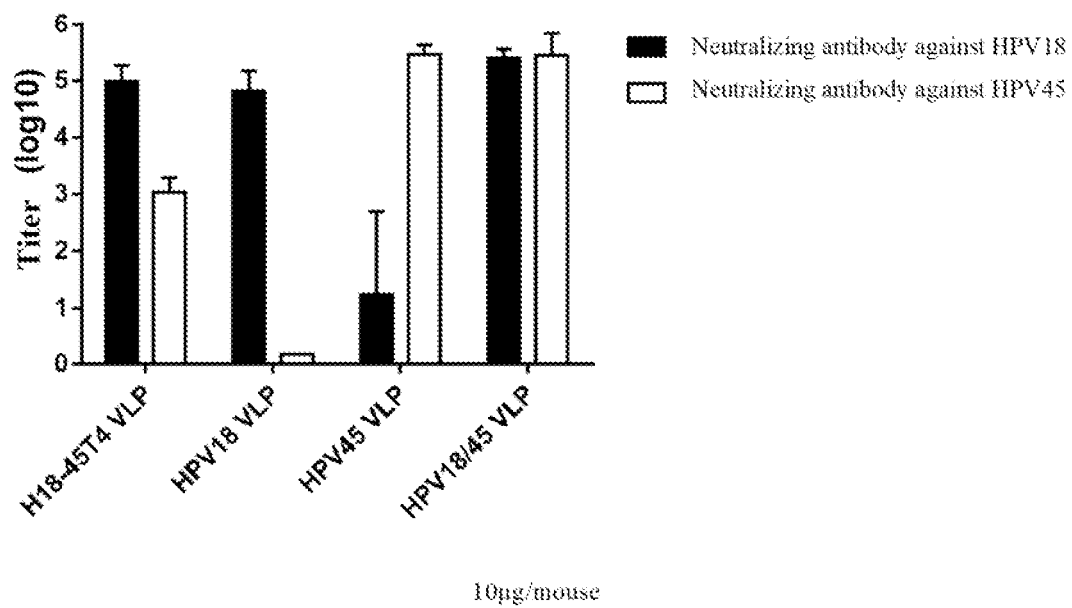
FIGS. 8A-8B show the result of neutralizing antibody titer in mouse serum after vaccination of mice with H18N65-45T4 VLP.
Figure 8B:
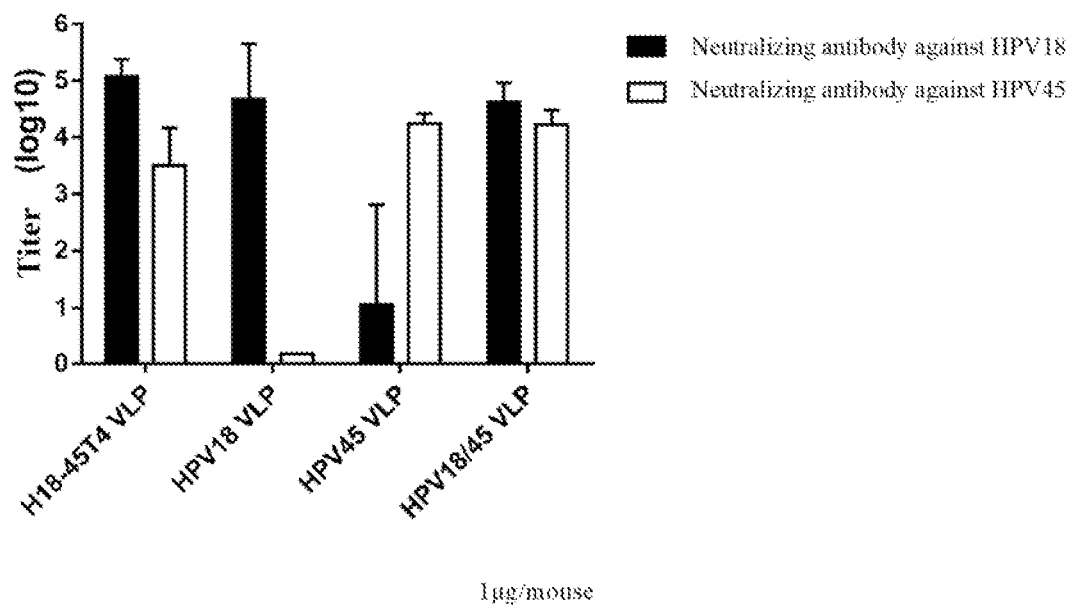

6 Mice/subgroup were vaccinated by intraperitoneal injection, at an immunizing dose of 10 μg, and 1 μg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV18 and HPV45 in serum were analyzed. The analysis results were shown in FIGS. 8A-8B. The result showed that H18N65-45T4 VLP could induce the generation of high-titer neutralizing antibodies against HPV18 in mice, and its protective effect was comparable to that of HPV18N65 VLP alone and that of the mixed HPV18/HPV45 VLP at the same dose, and was significantly superior to that of HPV45N27 VLP alone at the same dose; and it could induce the generation of high-titer neutralizing antibodies against HPV45 in mice, and its protective effect was comparable to that of HPV45N27 VLP alone and that of the mixed HPV18/HPV45 VLP at the same dose, and was significantly superior to that of HPV18N65 VLP alone at the same dose. This showed that H18N65-45T4 VLP had good cross-immunogenicity and cross-protection against HPV18 and HPV45.

TABLE 13

Vaccination schedule

| Group | Antigen for vaccination | Adjuvant | Immunizing dose | Number | Vaccination procedure (week) |
|---|---|---|---|---|---|
| Group of dose of 10 μg | HPV18N65 VLP | aluminum adjuvant | 10 μg | 6 | 0, 2, 4 |
| | HPV45N27 VLP | aluminum adjuvant | 10 μg | 6 | 0, 2, 4 |
| | HPV18/HPV45 VLP | aluminum adjuvant | 10 μg for each VLP | 6 | 0, 2, 4 |
| | H18N65-45T4 VLP | aluminum adjuvant | 10 μg | 6 | 0, 2, 4 |

TABLE 13-continued

| Group | Antigen for vaccination | Adjuvant | Immunizing dose | Number | Vaccination procedure (week) |
|---|---|---|---|---|---|
| Group of dose of 1 μg | HPV18N65 VLP | aluminum adjuvant | 1 μg | 6 | 0, 2, 4 |
| | HPV45N27 VLP | aluminum adjuvant | 1 μg | 6 | 0, 2, 4 |
| | HPV18/HPV45 VLP | aluminum adjuvant | 1 μg for each VLP | 6 | 0, 2, 4 |
| | H18N65-45T4 VLP | aluminum adjuvant | 1 μg | 6 | 0, 2, 4 |

Example 7: Evaluation 3 of Neutralizing Antibody Titer in Serum of Mice Vaccinated with Virus-Like Particles In this experiment, virus-like particles used were H18N65-45T3-59S1 VLP, H18N65-45T4-59S1 VLP, H18N65-45T1-59S5 VLP, H18N65-45T2-59S5 VLP and H18N65-45T1T3-59S5 VLP.

In this experiment, vaccination schedule was shown in Table 14. All the mice (6-week old BalB/c female mice) were divided into 2 groups: Group of dose of 10 μg (at an immunizing dose of 10 μg, using aluminum adjuvant), and Group of dose of 1 μg (at an immunizing dose of 1 μg, using aluminum adjuvant). Each group was further divided into 9 subgroups. The Control subgroups 1, 2 and 3 were vaccinated with HPV18N65 VLP alone, HPV45N27 VLP alone and HPV59 VLP alone, respectively, the Control subgroup 4 was vaccinated with the mixed HPV18/HPV45/HPV59 VLP (i.e. a mixture of HPV18N65 VLP, HPV45N27 VLP and HPV59 VLP, at a given immunizing dose for each VLP), and the Experimental subgroups 1, 2, 3, 4 and 5 were vaccinated with H18N65-45T3-59S1 VLP, H18N65-45T4-59S1 VLP, H18N65-45T1-59S5 VLP, H18N65-45T2-59S5 VLP and H18N65-45T1T3-59S5 VLP, respectively.

Figure 8C:
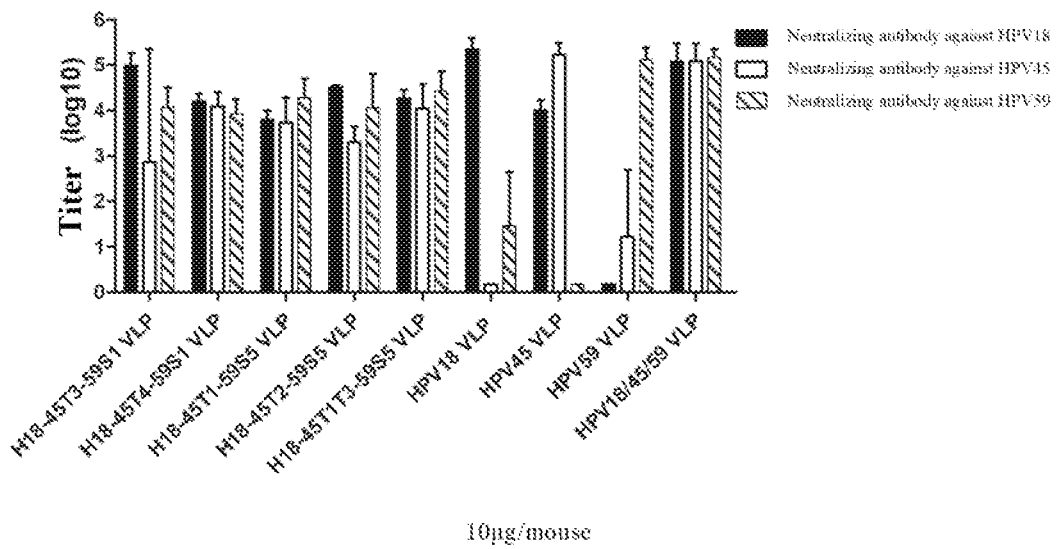
FIG. 8C-8D show the result of neutralizing antibody titer in mouse serum after vaccination of mice with H18N65-45T3-59S1 VLP, H18N65-45T4-59S1 VLP, H18N65-45T1-59S5 VLP, H18N65-45T2-59S5 VLP OR H18N65-45T1T3-59S5 VLP.
Figure 8D:
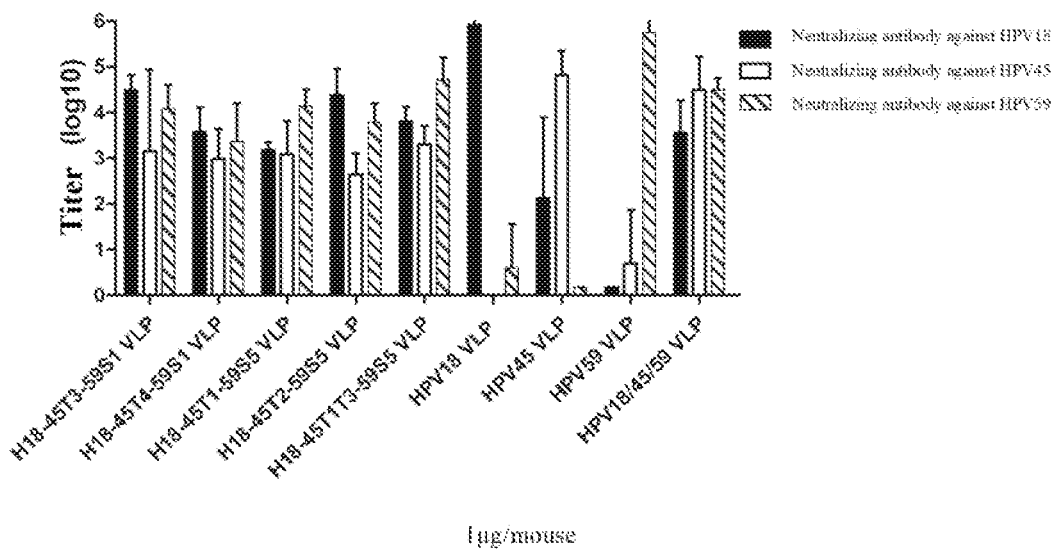

6 Mice/subgroup were vaccinated by intraperitoneal injection, at an immunizing dose of 10 μg and 1 μg, respectively, and an injection volume of 1 mL. All the mice were subjected to the first vaccination at Week 0, and then subjected to the booster vaccination at Weeks 2 and 4, respectively. At Week 8, blood sample was collected via orbital bleeding, and the titers of antibodies against HPV18, HPV45 and HPV59 in serum were analyzed. The analysis results were shown in FIGS. 8C-8D. The result showed that H18N65-45T3-59S1 VLP, H18N65-45T4-59S1 VLP, H18N65-45T1-59S5 VLP, H18N65-45T2-59S5 VLP and H18N65-45T1T3-59S5 VLP could induce the generation of high-titer neutralizing antibodies against HPV18 in mice, and their protective effects were comparable to that of HPV18N65 VLP alone and that of the mixed HPV18/HPV45/HPV59 VLP at the same dose, and were significantly superior to that of HPV45N27 VLP alone or that of HPV59 VLP alone at the same dose; and H18N65-45T3-59S1 VLP, H18N65-45T4-59S1 VLP, H18N65-45T1-59S5 VLP, H18N65-45T2-59S5 VLP and H18N65-45T1T3-59S5 VLP could induce the generation of high-titer neutralizing antibodies against HPV45 in mice, and their protective effects were comparable to that of HPV45N27 VLP alone and that of the mixed HPV18/HPV45/HPV59 VLP at the same dose, and were significantly superior to that of HPV18N65 VLP alone or that of HPV59 VLP alone at the same dose; and H18N65-45T3-59S1 VLP, H18N65-45T4-59S1 VLP, H18N65-45T1-59S5 VLP, H18N65-45T2-59S5 VLP and H18N65-45T1T3-59S5 VLP could induce the generation of high-titer neutralizing antibodies against HPV59 in mice, and their protective effects were comparable to that of HPV59 VLP alone or that of the mixed HPV18/HPV45/HPV59 VLP at the same dose, and were significantly superior to that of HPV18N65 VLP alone or that of HPV45N27 VLP alone at the same dose. This showed that H18N65-45T3-59S1 VLP, H18N65-45T4-59S1 VLP, H18N65-45T1-59S5 VLP, H18N65-45T2-59S5 VLP and H18N65-45T1T3-59S5 VLP had good cross-immunogenicity and cross-protection against HPV18, HPV45 and HPV59.

TABLE 14

| Group | Antigen for vaccination | Adjuvant | Immunizing dose | Number | Vaccination procedure (week) |
|---|---|---|---|---|---|
| Group of dose of 10 μg | HPV18N65 VLP | aluminum adjuvant | 10 μg | 6 | 0, 2, 4 |
| | HPV45N27 VLP | aluminum adjuvant | 10 μg | 6 | 0, 2, 4 |
| | HPV59 VLP | aluminum adjuvant | 10 μg | 6 | 0, 2, 4 |
| | HPV18/HPV45/HPV59 VLP | aluminum adjuvant | 10 μg for each VLP | 6 | 0, 2, 4 |
| | H18N65-45T3-59S1 VLP | aluminum adjuvant | 10 μg | 6 | 0, 2, 4 |
| | H18N65-45T4-59S1 VLP | aluminum adjuvant | 10 μg | 6 | 0, 2, 4 |

TABLE 14-continued

Vaccination schedule

| Group | Antigen for vaccination | Adjuvant | Immunizing dose | Number | Vaccination procedure (week) |
|---|---|---|---|---|---|
| | H18N65-45T1-59S5 VLP | aluminum adjuvant | 10 μg | 6 | 0, 2, 4 |
| | H18N65-45T2-59S5 VLP | aluminum adjuvant | 10 μg | 6 | 0, 2, 4 |
| | H18N65-45T1T3-59S5 VLP | aluminum adjuvant | 10 μg | 6 | 0, 2, 4 |
| Group of dose of 1 μg | HPV18N65 VLP | aluminum adjuvant | 1 μg | 6 | 0, 2, 4 |
| | HPV45N27 VLP | aluminum adjuvant | 1 μg | 6 | 0, 2, 4 |
| | HPV59 VLP | aluminum adjuvant | 1 μg | 6 | 0, 2, 4 |
| | HPV18/HPV45/HPV59 VLP | aluminum adjuvant | 1 μg for each VLP | 6 | 0, 2, 4 |
| | H18N65-45T3-59S1 VLP | aluminum adjuvant | 1 μg | 6 | 0, 2, 4 |
| | H18N65-45T4-59S1 VLP | aluminum adjuvant | 1 μg | 6 | 0, 2, 4 |
| | H18N65-45T1-59S5 VLP | aluminum adjuvant | 1 μg | 6 | 0, 2, 4 |
| | H18N65-45T2-59S5 VLP | aluminum adjuvant | 1 μg | 6 | 0, 2, 4 |
| | H18N65-45T1T3-59S5 VLP | aluminum adjuvant | 1 μg | 6 | 0, 2, 4 |

Although the specific embodiments of the present invention have been described in details, those skilled in the art would understand that, according to the teachings disclosed in the specification, various modifications and changes can be made thereto, and that such modifications and changes are within the scope of the present invention. The scope of the present invention is given by the appended claims and any equivalents thereof

The invention claimed is:

1. A mutated HPV18 L1 protein, wherein as compared with a wild type HPV18 L1 protein, (I) the mutated HPV18 L1 protein has the following mutations:
(1) N-terminal truncation of 40-80 amino acids; and
(2) (a) substitution of amino acid residues at positions of the wild type HPV18 L1 protein which correspond to positions 235-243 of SEQ ID NO: 1 with amino acid residues at the corresponding positions of a L1 protein of a second type of wild-type HPV; or
(b) substitution of amino acid residues at positions of the wild type HPV18 L1 protein which correspond to positions 327-346 of SEQ ID NO: 1 with amino acid residues at the corresponding positions of a L1 protein of a second type of wild-type HPV; or
(c) substitution of amino acid residues at positions of the wild type HPV18 L1 protein which correspond to positions 114-123 of SEQ ID NO: 1 with amino acid residues at the corresponding positions of a L1 protein of a second type of wild-type HPV; or
(d) substitution of amino acid residues at positions of the wild type HPV18 L1 protein which correspond to positions 176-202 of SEQ ID NO: 1 with amino acid residues at the corresponding positions of a L1 protein of a second type of wild-type HPV, or, (II) the mutated HPV18 L1 protein has the mutations as defined in (1) and (2) (a), and further has the following mutation:
(3) substitution of amino acid residues at positions of the wild type HPV18 L1 protein which correspond to positions 112-123 of SEQ ID NO: 1 with amino acid residues at the corresponding positions of a L1 protein of a third type of wild-type HPV;

or, (III) the mutated HPV18 L1 protein has the mutations as defined in (1) and (2) (b), and further has the following mutation:
(3) substitution of amino acid residues at positions of the wild type HPV 18 L1 protein which correspond to positions 112-123 of SEQ ID NO: 1 with amino acid residues at the corresponding positions of a L1 protein of a third type of wild-type HPV;

or, (IV) the mutated HPV18 L1 protein has the mutations as defined in (1) and (2) (c), and further has the following mutation:

(4) substitution of amino acid residues at positions of the wild type HPV18 L1 protein which correspond to positions 410-421 of SEQ ID NO: 1 with amino acid residues at the corresponding positions of a L1 protein of a third type of wild-type HPV;

or, (V) the mutated HPV18 L1 protein has the mutations as defined in (1) and (2) (d), and further has the mutation as defined in (4);

or, (VI) the mutated HPV18 L1 protein has the mutations as defined in (1), (2) (c) and (2) (a), and optionally, further has the mutation as defined in (4);

wherein said corresponding positions are determined by optimal alignment of the sequences being compared.

2. An isolated nucleic acid, encoding the mutated HPV18 L1 protein according to claim 1.

3. A vector comprising the isolated nucleic acid according to claim 2.

4. A host cell comprising the isolated nucleic acid according to claim 2 and/or a vector comprising the isolated nucleic acid according to claim 2.

5. An HPV virus-like particle, comprising or consisting of the mutated HPV18 L1 protein according to claim 1.

6. A composition, comprising:
the mutated HPV18 L1 protein according to claim 1, or
(ii) an isolated nucleic acid encoding the mutated HPV18 L1 protein as described in (i), or
(iii) a vector comprising the isolated nucleic acid as described in (ii), or
(iv) a host cell comprising the isolated nucleic acid as described in (ii) and/or the vector comprising the isolated nucleic acid as described in (iii), or
(v) a HPV virus-like particle comprising or consisting of the mutated HPV18 L1 protein as described in (i).

7. A pharmaceutical composition or vaccine, comprising the HPV virus-like particle according to claim 5, and optionally a pharmaceutically acceptable carrier and/or excipient.

8. A method for preparing the mutated HPV18 L1 protein according to claim 1, comprising expressing the mutated HPV18 L1 protein in a host cell, and then recovering the mutated HPV18 L1 protein from a culture of the host cell.

9. A method for preparing a vaccine, comprising combining the HPV virus-like particle according to claim 5 with a pharmaceutically acceptable carrier and/or excipient.

10. A method for preventing HPV infection or a disease caused by HPV infection, comprising administering to a subject a prophylactically effective amount of the HPV virus-like particle according to claim 5 or a pharmaceutical composition or vaccine comprising the HPV virus-like particle according to claim 5 and optionally a pharmaceutically acceptable carrier and/or excipient.

11. The mutated HPV18 L1 protein according to claim 1, wherein the mutated HPV18 L1 protein is characterized by one or more of the following items:
(i) the mutated HPV18 L1 protein has 45, 50, 52, 55, 58, 60, 62, 65, 68, 70, 72, 75 or 78 amino acids truncated at N-terminal, as compared with the wild type HPV18 L1 protein;

(ii) the second type of wild-type HPV is HPV45;
(iii) the amino acid residues at the corresponding positions as described in (2) (a) are amino acid residues at positions 201-209 of a wild type HPV45 L1 protein;
(iv) the amino acid residues at the corresponding positions as described in (2) (b) are amino acid residues at positions 293-314 of a wild type HPV45 L1 protein;
(v) the amino acid residues at the corresponding positions as described in (2) (c) are amino acid residues at positions 79-89 of a wild type HPV45 L1 protein;
(vi) the amino acid residues at the corresponding positions as described in (2) (d) are amino acid residues at positions 142-168 of a wild type HPV45 L1 protein;
(vii) the third type of wild-type HPV is HPV59;
(viii) the amino acid residues at the corresponding positions as described in (3) are amino acid residues at positions 51-62 of a wild type HPV59 L1 protein;
(ix) the amino acid residues at the corresponding positions as described in (4) are amino acid residues at positions 349-360 of a wild type HPV59 L1 protein;
(x) the wild type HPV18 L1 protein has an amino acid sequence as set forth in SEQ ID NO: 1;
(xi) the wild type HPV45 L1 protein has an amino acid sequence as set forth in SEQ ID NO: 2;
(xii) the wild type HPV59 L1 protein has an amino acid sequence as set forth in SEQ ID NO: 3.

12. The mutated HPV18 L1 protein according to claim 1, wherein the mutated HPV18 L1 protein has an amino acid sequence selected from the group consisting of: SEQ ID NO: 6, 7, 9, 13, 17, 18 and 19.

13. The isolated nucleic acid according to claim 2, wherein the isolated nucleic acid has a nucleotide sequence selected from the group consisting of: SEQ ID NO: 25, 26, 28, 32, 36, 37 and 38.

14. The pharmaceutical composition or vaccine according to claim 7, wherein the HPV virus-like particle is present in an amount effective for preventing HPV infection or a disease caused by HPV infection.

15. The pharmaceutical composition or vaccine according to claim 14, wherein the HPV infection is infection by one or more HPV types, and/or, the disease caused by HPV infection is selected from the group consisting of cervical cancer and condyloma acuminatum.

16. The pharmaceutical composition or vaccine according to claim 15, wherein the HPV infection is selected from: HPV18 infection, HPV45 infection, HPV59 infection and any combination thereof.

17. The method according to claim 8, wherein the host cell is *E. coli*.

18. The method according to claim 17, wherein the method comprises the steps of: expressing the mutated HPV18 L1 protein in *E. coli*, and then obtaining the mutated HPV18 L1 protein by purifying a lysate supernatant of the *E. coli*.

19. The method according to claim 10, wherein the HPV infection is infection by one or more HPV types, and/or, the disease caused by HPV infection is selected from the group consisting of cervical cancer and condyloma acuminatum.

20. The method according to claim 19, wherein the HPV infection is selected from: HPV18 infection, HPV45 infection, HPV59 infection and any combination thereof.

* * * * *

SEQUENCE LISTING

<160> NUMBER OF SEQ ID NOS: 116

<210> SEQ ID NO 1
<211> LENGTH: 568
<212> TYPE: PRT
<213> ORGANISM: Human papillomavirus type 18

<400> SEQUENCE: 1

Met Cys Leu Tyr Thr Arg Val Leu Ile Leu His Tyr His Leu Leu Pro
1               5                   10                  15

Leu Tyr Gly Pro Leu Tyr His Pro Gln Pro Leu Pro Leu His Ser Ile
                20                  25                  30

Leu Val Tyr Met Val His Ile Ile Ile Cys Gly His Tyr Ile Ile Leu
            35                  40                  45

Phe Leu Arg Asn Val Asn Val Phe Pro Ile Phe Leu Gln Met Ala Leu
        50                  55                  60

Trp Arg Pro Ser Asp Asn Thr Val Tyr Leu Pro Pro Ser Val Ala
65                  70                  75                  80

Arg Val Val Asn Thr Asp Asp Tyr Val Thr Arg Thr Ser Ile Phe Tyr
                85                  90                  95

His Ala Gly Ser Ser Arg Leu Leu Thr Val Gly Asn Pro Tyr Phe Arg
            100                 105                 110

Val Pro Ala Gly Gly Gly Asn Lys Gln Asp Ile Pro Lys Val Ser Ala
        115                 120                 125

```
Tyr Gln Tyr Arg Val Phe Arg Val Gln Leu Pro Asp Pro Asn Lys Phe
            130                 135                 140

Gly Leu Pro Asp Thr Ser Ile Tyr Asn Pro Glu Thr Gln Arg Leu Val
145                 150                 155                 160

Trp Ala Cys Ala Gly Val Glu Ile Gly Arg Gly Gln Pro Leu Gly Val
                    165                 170                 175

Gly Leu Ser Gly His Pro Phe Tyr Asn Lys Leu Asp Asp Thr Glu Ser
                180                 185                 190

Ser His Ala Ala Thr Ser Asn Val Ser Glu Asp Val Arg Asp Asn Val
            195                 200                 205

Ser Val Asp Tyr Lys Gln Thr Gln Leu Cys Ile Leu Gly Cys Ala Pro
210                 215                 220

Ala Ile Gly Glu His Trp Ala Lys Gly Thr Ala Cys Lys Ser Arg Pro
225                 230                 235                 240

Leu Ser Gln Gly Asp Cys Pro Pro Leu Glu Leu Lys Asn Thr Val Leu
                245                 250                 255

Glu Asp Gly Asp Met Val Asp Thr Gly Tyr Gly Ala Met Asp Phe Ser
                260                 265                 270

Thr Leu Gln Asp Thr Lys Cys Glu Val Pro Leu Asp Ile Cys Gln Ser
            275                 280                 285

Ile Cys Lys Tyr Pro Asp Tyr Leu Gln Met Ser Ala Asp Pro Tyr Gly
            290                 295                 300

Asp Ser Met Phe Phe Cys Leu Arg Arg Glu Gln Leu Phe Ala Arg His
305                 310                 315                 320

Phe Trp Asn Arg Ala Gly Thr Met Gly Asp Thr Val Pro Gln Ser Leu
                325                 330                 335

Tyr Ile Lys Gly Thr Gly Met Arg Ala Ser Pro Gly Ser Cys Val Tyr
                340                 345                 350

Ser Pro Ser Pro Ser Gly Ser Ile Val Thr Ser Asp Ser Gln Leu Phe
            355                 360                 365

Asn Lys Pro Tyr Trp Leu His Lys Ala Gln Gly His Asn Asn Gly Val
            370                 375                 380

Cys Trp His Asn Gln Leu Phe Val Thr Val Val Asp Thr Thr Arg Ser
385                 390                 395                 400

Thr Asn Leu Thr Ile Cys Ala Ser Thr Gln Ser Pro Val Pro Gly Gln
                405                 410                 415

Tyr Asp Ala Thr Lys Phe Lys Gln Tyr Ser Arg His Val Glu Glu Tyr
                420                 425                 430

Asp Leu Gln Phe Ile Phe Gln Leu Cys Thr Ile Thr Leu Thr Ala Asp
            435                 440                 445

Val Met Ser Tyr Ile His Ser Met Asn Ser Ser Ile Leu Glu Asp Trp
450                 455                 460

Asn Phe Gly Val Pro Pro Pro Thr Thr Ser Leu Val Asp Thr Tyr
465                 470                 475                 480

Arg Phe Val Gln Ser Val Ala Ile Ala Cys Gln Lys Asp Ala Ala Pro
                485                 490                 495

Ala Glu Asn Lys Asp Pro Tyr Asp Lys Leu Lys Phe Trp Asn Val Asp
                500                 505                 510

Leu Lys Glu Lys Phe Ser Leu Asp Leu Asp Gln Tyr Pro Leu Gly Arg
            515                 520                 525

Lys Phe Leu Val Gln Ala Gly Leu Arg Arg Lys Pro Thr Ile Gly Pro
530                 535                 540
```

```
Arg Lys Arg Ser Ala Pro Ser Ala Thr Thr Ala Ser Lys Pro Ala Lys
545                 550                 555                 560

Arg Val Arg Val Arg Ala Arg Lys
                565
```

<210> SEQ ID NO 2
<211> LENGTH: 539
<212> TYPE: PRT
<213> ORGANISM: Human papillomavirus type 45

<400> SEQUENCE: 2

```
Met Ala His Asn Ile Ile Tyr Gly His Gly Ile Ile Ile Phe Leu Lys
1               5                   10                  15

Asn Val Asn Val Phe Pro Ile Phe Leu Gln Met Ala Leu Trp Arg Pro
                20                  25                  30

Ser Asp Ser Thr Val Tyr Leu Pro Pro Ser Val Ala Arg Val Val
            35                  40                  45

Ser Thr Asp Asp Tyr Val Ser Arg Thr Ser Ile Phe Tyr His Ala Gly
        50                  55                  60

Ser Ser Arg Leu Leu Thr Val Gly Asn Pro Tyr Phe Arg Val Val Pro
65                  70                  75                  80

Asn Gly Ala Gly Asn Lys Gln Ala Val Pro Lys Val Ser Ala Tyr Gln
                85                  90                  95

Tyr Arg Val Phe Arg Val Ala Leu Pro Asp Pro Asn Lys Phe Gly Leu
                100                 105                 110

Pro Asp Ser Thr Ile Tyr Asn Pro Glu Thr Gln Arg Leu Val Trp Ala
            115                 120                 125

Cys Val Gly Met Glu Ile Gly Arg Gly Gln Pro Leu Gly Ile Gly Leu
        130                 135                 140

Ser Gly His Pro Phe Tyr Asn Lys Leu Asp Asp Thr Glu Ser Ala His
145                 150                 155                 160

Ala Ala Thr Ala Val Ile Thr Gln Asp Val Arg Asp Asn Val Ser Val
                165                 170                 175

Asp Tyr Lys Gln Thr Gln Leu Cys Ile Leu Gly Cys Val Pro Ala Ile
                180                 185                 190

Gly Glu His Trp Ala Lys Gly Thr Leu Cys Lys Pro Ala Gln Leu Gln
            195                 200                 205

Pro Gly Asp Cys Pro Pro Leu Glu Leu Lys Asn Thr Ile Ile Glu Asp
        210                 215                 220

Gly Asp Met Val Asp Thr Gly Tyr Gly Ala Met Asp Phe Ser Thr Leu
225                 230                 235                 240

Gln Asp Thr Lys Cys Glu Val Pro Leu Asp Ile Cys Gln Ser Ile Cys
                245                 250                 255

Lys Tyr Pro Asp Tyr Leu Gln Met Ser Ala Asp Pro Tyr Gly Asp Ser
                260                 265                 270

Met Phe Phe Cys Leu Arg Arg Glu Gln Leu Phe Ala Arg His Phe Trp
            275                 280                 285

Asn Arg Ala Gly Val Met Gly Asp Thr Val Pro Thr Asp Leu Tyr Ile
        290                 295                 300

Lys Gly Thr Ser Ala Asn Met Arg Glu Thr Pro Gly Ser Cys Val Tyr
305                 310                 315                 320

Ser Pro Ser Pro Ser Gly Ser Ile Ile Thr Ser Asp Ser Gln Leu Phe
                325                 330                 335

Asn Lys Pro Tyr Trp Leu His Lys Ala Gln Gly His Asn Asn Gly Ile
                340                 345                 350
```

```
Cys Trp His Asn Gln Leu Phe Val Thr Val Asp Thr Thr Arg Ser
            355                 360                 365

Thr Asn Leu Thr Leu Cys Ala Ser Thr Gln Asn Pro Val Pro Ser Thr
370                 375                 380

Tyr Asp Pro Thr Lys Phe Lys Gln Tyr Ser Arg His Val Glu Glu Tyr
385                 390                 395                 400

Asp Leu Gln Phe Ile Phe Gln Leu Cys Thr Ile Thr Leu Thr Ala Glu
                405                 410                 415

Val Met Ser Tyr Ile His Ser Met Asn Ser Ser Ile Leu Glu Asn Trp
                420                 425                 430

Asn Phe Gly Val Pro Pro Pro Thr Thr Ser Leu Val Asp Thr Tyr
            435                 440                 445

Arg Phe Val Gln Ser Val Ala Val Thr Cys Gln Lys Asp Thr Thr Pro
450                 455                 460

Pro Glu Lys Gln Asp Pro Tyr Asp Lys Leu Lys Phe Trp Thr Val Asp
465                 470                 475                 480

Leu Lys Glu Lys Phe Ser Ser Asp Leu Asp Gln Tyr Pro Leu Gly Arg
                485                 490                 495

Lys Phe Leu Val Gln Ala Gly Leu Arg Arg Arg Pro Thr Ile Gly Pro
            500                 505                 510

Arg Lys Arg Pro Ala Ala Ser Thr Ser Thr Ala Ser Thr Ala Ser Arg
            515                 520                 525

Pro Ala Lys Arg Val Arg Ile Arg Ser Lys Lys
530                 535

<210> SEQ ID NO 3
<211> LENGTH: 508
<212> TYPE: PRT
<213> ORGANISM: Human papillomavirus type 59

<400> SEQUENCE: 3

Met Ala Leu Trp Arg Ser Ser Asp Asn Lys Val Tyr Leu Pro Pro Pro
1               5                   10                  15

Ser Val Ala Lys Val Val Ser Thr Asp Glu Tyr Val Thr Arg Thr Ser
                20                  25                  30

Ile Phe Tyr His Ala Gly Ser Ser Arg Leu Leu Thr Val Gly His Pro
            35                  40                  45

Tyr Phe Lys Val Pro Lys Gly Gly Asn Gly Arg Gln Asp Val Pro Lys
        50                  55                  60

Val Ser Ala Tyr Gln Tyr Arg Val Phe Arg Val Lys Leu Pro Asp Pro
65                  70                  75                  80

Asn Lys Phe Gly Leu Pro Asp Asn Thr Val Tyr Asp Pro Asn Ser Gln
                85                  90                  95

Arg Leu Val Trp Ala Cys Val Gly Val Glu Ile Gly Arg Gly Gln Pro
            100                 105                 110

Leu Gly Val Gly Leu Ser Gly His Pro Leu Tyr Asn Lys Leu Asp Asp
        115                 120                 125

Thr Glu Asn Ser His Val Ala Ser Ala Val Asp Thr Lys Asp Thr Arg
    130                 135                 140

Asp Asn Val Ser Val Asp Tyr Lys Gln Thr Gln Leu Cys Ile Ile Gly
145                 150                 155                 160

Cys Val Pro Ala Ile Gly Glu His Trp Thr Lys Gly Thr Ala Cys Lys
                165                 170                 175

Pro Thr Thr Val Val Gln Gly Asp Cys Pro Pro Leu Glu Leu Ile Asn
```

```
            180                 185                 190
Thr Pro Ile Glu Asp Gly Asp Met Val Asp Thr Gly Tyr Gly Ala Met
            195                 200                 205

Asp Phe Lys Leu Leu Gln Asp Asn Lys Ser Glu Val Pro Leu Asp Ile
        210                 215                 220

Cys Gln Ser Ile Cys Lys Tyr Pro Asp Tyr Leu Gln Met Ser Ala Asp
225                 230                 235                 240

Ala Tyr Gly Asp Ser Met Phe Phe Cys Leu Arg Arg Glu Gln Val Phe
                245                 250                 255

Ala Arg His Phe Trp Asn Arg Ser Gly Thr Met Gly Asp Gln Leu Pro
            260                 265                 270

Glu Ser Leu Tyr Ile Lys Gly Thr Asp Ile Arg Ala Asn Pro Gly Ser
        275                 280                 285

Tyr Leu Tyr Ser Pro Ser Pro Ser Gly Ser Val Val Thr Ser Asp Ser
    290                 295                 300

Gln Leu Phe Asn Lys Pro Tyr Trp Leu His Lys Ala Gln Gly Leu Asn
305                 310                 315                 320

Asn Gly Ile Cys Trp His Asn Gln Leu Phe Leu Thr Val Val Asp Thr
                325                 330                 335

Thr Arg Ser Thr Asn Leu Ser Val Cys Ala Ser Thr Thr Ser Ser Ile
            340                 345                 350

Pro Asn Val Tyr Thr Pro Thr Ser Phe Lys Glu Tyr Ala Arg His Val
        355                 360                 365

Glu Glu Phe Asp Leu Gln Phe Ile Phe Gln Leu Cys Lys Ile Thr Leu
    370                 375                 380

Thr Thr Glu Val Met Ser Tyr Ile His Asn Met Asn Thr Thr Ile Leu
385                 390                 395                 400

Glu Asp Trp Asn Phe Gly Val Thr Pro Pro Thr Ala Ser Leu Val
                405                 410                 415

Asp Thr Tyr Arg Phe Val Gln Ser Ala Ala Val Thr Cys Gln Lys Asp
            420                 425                 430

Thr Ala Pro Pro Val Lys Gln Asp Pro Tyr Asp Lys Leu Lys Phe Trp
        435                 440                 445

Pro Val Asp Leu Lys Glu Arg Phe Ser Ala Asp Leu Asp Gln Phe Pro
    450                 455                 460

Leu Gly Arg Lys Phe Leu Leu Gln Leu Gly Ala Arg Pro Lys Pro Thr
465                 470                 475                 480

Ile Gly Pro Arg Lys Arg Ala Ala Pro Ala Pro Thr Ser Thr Pro Ser
                485                 490                 495

Pro Lys Arg Val Lys Arg Lys Ser Ser Arg Lys
            500                 505

<210> SEQ ID NO 4
<211> LENGTH: 505
<212> TYPE: PRT
<213> ORGANISM: Artificial Sequence
<220> FEATURE:
<223> OTHER INFORMATION: H18N65-45T1

<400> SEQUENCE: 4

Met Arg Pro Ser Asp Asn Thr Val Tyr Leu Pro Pro Pro Ser Val Ala
1               5                   10                  15

Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Arg
```

```
                35                  40                  45
Val Val Pro Asn Gly Ala Gly Asn Lys Gln Ala Val Pro Lys Val Ser
 50                  55                  60

Ala Tyr Gln Tyr Arg Val Phe Arg Val Gln Leu Pro Asp Pro Asn Lys
 65                  70                  75                  80

Phe Gly Leu Pro Asp Thr Ser Ile Tyr Asn Pro Glu Thr Gln Arg Leu
                 85                  90                  95

Val Trp Ala Cys Ala Gly Val Glu Ile Gly Arg Gly Gln Pro Leu Gly
                100                 105                 110

Val Gly Leu Ser Gly His Pro Phe Tyr Asn Lys Leu Asp Asp Thr Glu
                115                 120                 125

Ser Ser His Ala Ala Thr Ser Asn Val Ser Glu Asp Val Arg Asp Asn
                130                 135                 140

Val Ser Val Asp Tyr Lys Gln Thr Gln Leu Cys Ile Leu Gly Cys Ala
145                 150                 155                 160

Pro Ala Ile Gly Glu His Trp Ala Lys Gly Thr Ala Cys Lys Ser Arg
                165                 170                 175

Pro Leu Ser Gln Gly Asp Cys Pro Pro Leu Glu Leu Lys Asn Thr Val
                180                 185                 190

Leu Glu Asp Gly Asp Met Val Asp Thr Gly Tyr Gly Ala Met Asp Phe
                195                 200                 205

Ser Thr Leu Gln Asp Thr Lys Cys Glu Val Pro Leu Asp Ile Cys Gln
210                 215                 220

Ser Ile Cys Lys Tyr Pro Asp Tyr Leu Gln Met Ser Ala Asp Pro Tyr
225                 230                 235                 240

Gly Asp Ser Met Phe Phe Cys Leu Arg Arg Glu Gln Leu Phe Ala Arg
                245                 250                 255

His Phe Trp Asn Arg Ala Gly Thr Met Gly Asp Thr Val Pro Gln Ser
                260                 265                 270

Leu Tyr Ile Lys Gly Thr Gly Met Arg Ala Ser Pro Gly Ser Cys Val
                275                 280                 285

Tyr Ser Pro Ser Pro Ser Gly Ser Ile Val Thr Ser Asp Ser Gln Leu
                290                 295                 300

Phe Asn Lys Pro Tyr Trp Leu His Lys Ala Gln Gly His Asn Asn Gly
305                 310                 315                 320

Val Cys Trp His Asn Gln Leu Phe Val Thr Val Val Asp Thr Thr Arg
                325                 330                 335

Ser Thr Asn Leu Thr Ile Cys Ala Ser Thr Gln Ser Pro Val Pro Gly
                340                 345                 350

Gln Tyr Asp Ala Thr Lys Phe Lys Gln Tyr Ser Arg His Val Glu Glu
                355                 360                 365

Tyr Asp Leu Gln Phe Ile Phe Gln Leu Cys Thr Ile Thr Leu Thr Ala
                370                 375                 380

Asp Val Met Ser Tyr Ile His Ser Met Asn Ser Ser Ile Leu Glu Asp
385                 390                 395                 400

Trp Asn Phe Gly Val Pro Pro Pro Thr Thr Ser Leu Val Asp Thr
                405                 410                 415

Tyr Arg Phe Val Gln Ser Val Ala Ile Ala Cys Gln Lys Asp Ala Ala
                420                 425                 430

Pro Ala Glu Asn Lys Asp Pro Tyr Asp Lys Leu Lys Phe Trp Asn Val
                435                 440                 445

Asp Leu Lys Glu Lys Phe Ser Leu Asp Leu Asp Gln Tyr Pro Leu Gly
                450                 455                 460
```

```
Arg Lys Phe Leu Val Gln Ala Gly Leu Arg Arg Lys Pro Thr Ile Gly
465                 470                 475                 480

Pro Arg Lys Arg Ser Ala Pro Ser Ala Thr Thr Ala Ser Lys Pro Ala
            485                 490                 495

Lys Arg Val Arg Val Arg Ala Arg Lys
        500                 505

<210> SEQ ID NO 5
<211> LENGTH: 504
<212> TYPE: PRT
<213> ORGANISM: Artificial Sequence
<220> FEATURE:
<223> OTHER INFORMATION: H18N65-45T2

<400> SEQUENCE: 5

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Arg
        35                  40                  45

Val Pro Ala Gly Gly Gly Asn Lys Gln Asp Ile Pro Lys Val Ser Ala
    50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Ile
            100                 105                 110

Gly Leu Ser Gly His Pro Phe Tyr Asn Lys Leu Asp Asp Thr Glu Ser
        115                 120                 125

Ala His Ala Ala Thr Ala Val Ile Thr Gln Asp Val Arg Asp Asn Val
    130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
    210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
        275                 280                 285

Ser Pro Ser Pro Ser Gly Ser Ile Val Thr Ser Asp Ser Gln Leu Phe
    290                 295                 300

Asn Lys Pro Tyr Trp Leu His Lys Ala Gln Gly His Asn Asn Gly Val
305                 310                 315                 320
```

```
Cys Trp His Asn Gln Leu Phe Val Thr Val Asp Thr Thr Arg Ser
                325                 330                 335

Thr Asn Leu Thr Ile Cys Ala Ser Thr Gln Ser Pro Val Pro Gly Gln
            340                 345                 350

Tyr Asp Ala Thr Lys Phe Lys Gln Tyr Ser Arg His Val Glu Glu Tyr
            355                 360                 365

Asp Leu Gln Phe Ile Phe Gln Leu Cys Thr Ile Thr Leu Thr Ala Asp
        370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
                420                 425                 430

Ala Glu Asn Lys Asp Pro Tyr Asp Lys Leu Lys Phe Trp Asn Val Asp
            435                 440                 445

Leu Lys Glu Lys Phe Ser Leu Asp Leu Asp Gln Tyr Pro Leu Gly Arg
        450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Ala Ser Lys Pro Ala Lys
                485                 490                 495

Arg Val Arg Val Arg Ala Arg Lys
                500

<210> SEQ ID NO 6
<211> LENGTH: 504
<212> TYPE: PRT
<213> ORGANISM: Artificial Sequence
<220> FEATURE:
<223> OTHER INFORMATION: H18N65-45T3

<400> SEQUENCE: 6

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Gly Asn Lys Gln Asp Ile Pro Lys Val Ser Ala
        50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
                100                 105                 110

Gly Leu Ser Gly His Pro Phe Tyr Asn Lys Leu Asp Asp Thr Glu Ser
            115                 120                 125

Ser His Ala Ala Thr Ser Asn Val Ser Glu Asp Val Arg Asp Asn Val
        130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Leu Cys Lys Pro Ala Gln
                165                 170                 175
```

Leu Gln Pro Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
            195                 200                 205

Thr Leu Gln Asp Thr Lys Cys Glu Val Pro Leu Asp Ile Cys Gln Ser
210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
            275                 280                 285

Ser Pro Ser Pro Ser Gly Ser Ile Val Thr Ser Asp Ser Gln Leu Phe
            290                 295                 300

Asn Lys Pro Tyr Trp Leu His Lys Ala Gln Gly His Asn Asn Gly Val
305                 310                 315                 320

Cys Trp His Asn Gln Leu Phe Val Thr Val Val Asp Thr Thr Arg Ser
                325                 330                 335

Thr Asn Leu Thr Ile Cys Ala Ser Thr Gln Ser Pro Val Pro Gly Gln
            340                 345                 350

Tyr Asp Ala Thr Lys Phe Lys Gln Tyr Ser Arg His Val Glu Glu Tyr
            355                 360                 365

Asp Leu Gln Phe Ile Phe Gln Leu Cys Thr Ile Thr Leu Thr Ala Asp
            370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
            435                 440                 445

Leu Lys Glu Lys Phe Ser Leu Asp Leu Asp Gln Tyr Pro Leu Gly Arg
450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
                485                 490                 495

Arg Val Arg Val Arg Ala Arg Lys
            500

<210> SEQ ID NO 7
<211> LENGTH: 506
<212> TYPE: PRT
<213> ORGANISM: Artificial Sequence
<220> FEATURE:
<223> OTHER INFORMATION: H18N65-45T4

<400> SEQUENCE: 7

Met Arg Pro Ser Asp Asn Thr Val Tyr Leu Pro Pro Pro Ser Val Ala
1               5                   10                  15

Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Arg
            35                  40                  45

Val Pro Ala Gly Gly Asn Lys Gln Asp Ile Pro Lys Val Ser Ala
 50                  55                  60

Tyr Gln Tyr Arg Val Phe Arg Val Gln Leu Pro Asp Pro Asn Lys Phe
 65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
                100                 105                 110

Gly Leu Ser Gly His Pro Phe Tyr Asn Lys Leu Asp Asp Thr Glu Ser
            115                 120                 125

Ser His Ala Ala Thr Ser Asn Val Ser Glu Asp Val Arg Asp Asn Val
        130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Val Met Gly Asp Thr Val Pro Thr Asp Leu
            260                 265                 270

Tyr Ile Lys Gly Thr Ser Ala Asn Met Arg Glu Thr Pro Gly Ser Cys
        275                 280                 285

Val Tyr Ser Pro Ser Pro Ser Gly Ser Ile Val Thr Ser Asp Ser Gln
290                 295                 300

Leu Phe Asn Lys Pro Tyr Trp Leu His Lys Ala Gln Gly His Asn Asn
305                 310                 315                 320

Gly Val Cys Trp His Asn Gln Leu Phe Val Thr Val Asp Thr Thr
                325                 330                 335

Arg Ser Thr Asn Leu Thr Ile Cys Ala Ser Thr Gln Ser Pro Val Pro
            340                 345                 350

Gly Gln Tyr Asp Ala Thr Lys Phe Lys Gln Tyr Ser Arg His Val Glu
        355                 360                 365

Glu Tyr Asp Leu Gln Phe Ile Phe Gln Leu Cys Thr Ile Thr Leu Thr
370                 375                 380

Ala Asp Val Met Ser Tyr Ile His Ser Met Asn Ser Ser Ile Leu Glu
385                 390                 395                 400

Asp Trp Asn Phe Gly Val Pro Pro Pro Thr Thr Ser Leu Val Asp
                405                 410                 415

Thr Tyr Arg Phe Val Gln Ser Val Ala Ile Ala Cys Gln Lys Asp Ala
            420                 425                 430

Ala Pro Ala Glu Asn Lys Asp Pro Tyr Asp Lys Leu Lys Phe Trp Asn
        435                 440                 445

```
Val Asp Leu Lys Glu Lys Phe Ser Leu Asp Leu Asp Gln Tyr Pro Leu
450                 455                 460

Gly Arg Lys Phe Leu Val Gln Ala Gly Leu Arg Arg Lys Pro Thr Ile
465                 470                 475                 480

Gly Pro Arg Lys Arg Ser Ala Pro Ser Ala Thr Thr Ala Ser Lys Pro
                485                 490                 495

Ala Lys Arg Val Arg Val Arg Ala Arg Lys
                500                 505

<210> SEQ ID NO 8
<211> LENGTH: 504
<212> TYPE: PRT
<213> ORGANISM: Artificial Sequence
<220> FEATURE:
<223> OTHER INFORMATION: H18N65-45T5

<400> SEQUENCE: 8

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
                35                  40                  45

Val Pro Ala Gly Gly Gly Asn Lys Gln Asp Ile Pro Lys Val Ser Ala
50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
                100                 105                 110

Gly Leu Ser Gly His Pro Phe Tyr Asn Lys Leu Asp Asp Thr Glu Ser
                115                 120                 125

Ser His Ala Ala Thr Ser Asn Val Ser Glu Asp Val Arg Asp Asn Val
130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
                180                 185                 190

Glu Asp Gly Asp Met Val Asp Thr Gly Tyr Gly Ala Met Asp Phe Ser
                195                 200                 205

Thr Leu Gln Asp Thr Lys Cys Glu Val Pro Leu Asp Ile Cys Gln Ser
210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
                260                 265                 270

Tyr Ile Lys Gly Thr Gly Met Arg Ala Ser Pro Gly Ser Cys Val Tyr
                275                 280                 285

Ser Pro Ser Pro Ser Gly Ser Ile Val Thr Ser Asp Ser Gln Leu Phe
290                 295                 300
```

```
Asn Lys Pro Tyr Trp Leu His Lys Ala Gln Gly His Asn Asn Gly Val
305                 310                 315                 320

Cys Trp His Asn Gln Leu Phe Val Thr Val Asp Thr Thr Arg Ser
            325                 330                 335

Thr Asn Leu Thr Ile Cys Ala Ser Thr Gln Asn Pro Val Pro Ser Thr
            340                 345                 350

Tyr Asp Pro Thr Lys Phe Lys Gln Tyr Ser Arg His Val Glu Glu Tyr
            355                 360                 365

Asp Leu Gln Phe Ile Phe Gln Leu Cys Thr Ile Thr Leu Thr Ala Asp
            370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
            405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
            435                 440                 445

Leu Lys Glu Lys Phe Ser Leu Asp Leu Asp Gln Tyr Pro Leu Gly Arg
450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
            485                 490                 495

Arg Val Arg Val Arg Ala Arg Lys
            500

<210> SEQ ID NO 9
<211> LENGTH: 504
<212> TYPE: PRT
<213> ORGANISM: Artificial Sequence
<220> FEATURE:
<223> OTHER INFORMATION: H18N65-45T3-59S1

<400> SEQUENCE: 9

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Lys
        35                  40                  45

Val Pro Lys Gly Gly Asn Gly Arg Gln Asp Val Pro Lys Val Ser Ala
50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
            85                  90                  95

Trp Ala Cys Ala Gly Val Glu Ile Gly Arg Gly Gln Pro Leu Gly Val
            100                 105                 110

Gly Leu Ser Gly His Pro Phe Tyr Asn Lys Leu Asp Asp Thr Glu Ser
        115                 120                 125

Ser His Ala Ala Thr Ser Asn Val Ser Glu Asp Val Arg Asp Asn Val
    130                 135                 140

Ser Val Asp Tyr Lys Gln Thr Gln Leu Cys Ile Leu Gly Cys Ala Pro
145                 150                 155                 160
```

Ala Ile Gly Glu His Trp Ala Lys Gly Thr Leu Cys Lys Pro Ala Gln
            165                 170                 175

Leu Gln Pro Gly Asp Cys Pro Leu Glu Leu Lys Asn Thr Val Leu
        180                 185                 190

Glu Asp Gly Asp Met Val Asp Thr Gly Tyr Gly Ala Met Asp Phe Ser
            195                 200                 205

Thr Leu Gln Asp Thr Lys Cys Glu Val Pro Leu Asp Ile Cys Gln Ser
    210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
        275                 280                 285

Ser Pro Ser Pro Ser Gly Ser Ile Val Thr Ser Asp Ser Gln Leu Phe
    290                 295                 300

Asn Lys Pro Tyr Trp Leu His Lys Ala Gln Gly His Asn Asn Gly Val
305                 310                 315                 320

Cys Trp His Asn Gln Leu Phe Val Thr Val Asp Thr Thr Arg Ser
                325                 330                 335

Thr Asn Leu Thr Ile Cys Ala Ser Thr Gln Ser Pro Val Pro Gly Gln
            340                 345                 350

Tyr Asp Ala Thr Lys Phe Lys Gln Tyr Ser Arg His Val Glu Glu Tyr
        355                 360                 365

Asp Leu Gln Phe Ile Phe Gln Leu Cys Thr Ile Thr Leu Thr Ala Asp
    370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
        435                 440                 445

Leu Lys Glu Lys Phe Ser Leu Asp Leu Asp Gln Tyr Pro Leu Gly Arg
    450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
                485                 490                 495

Arg Val Arg Val Arg Ala Arg Lys
            500

<210> SEQ ID NO 10
<211> LENGTH: 504
<212> TYPE: PRT
<213> ORGANISM: Artificial Sequence
<220> FEATURE:
<223> OTHER INFORMATION: H18N65-45T3-59S2

<400> SEQUENCE: 10

Met Arg Pro Ser Asp Asn Thr Val Tyr Leu Pro Pro Pro Ser Val Ala
1               5                   10                  15

```
Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Arg
        35                  40                  45

Val Pro Ala Gly Gly Asn Lys Gln Asp Ile Pro Lys Val Ser Ala
50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Leu Tyr Asn Lys Leu Asp Asp Thr Glu Asn
        115                 120                 125

Ser His Val Ala Ser Ala Val Asp Thr Lys Asp Thr Arg Asp Asn Val
    130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Leu Cys Lys Pro Ala Gln
                165                 170                 175

Leu Gln Pro Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
        275                 280                 285

Ser Pro Ser Pro Ser Gly Ser Ile Val Thr Ser Asp Ser Gln Leu Phe
    290                 295                 300

Asn Lys Pro Tyr Trp Leu His Lys Ala Gln Gly His Asn Asn Gly Val
305                 310                 315                 320

Cys Trp His Asn Gln Leu Phe Val Thr Val Asp Thr Thr Arg Ser
                325                 330                 335

Thr Asn Leu Thr Ile Cys Ala Ser Thr Gln Ser Pro Val Pro Gly Gln
            340                 345                 350

Tyr Asp Ala Thr Lys Phe Lys Gln Tyr Ser Arg His Val Glu Glu Tyr
        355                 360                 365

Asp Leu Gln Phe Ile Phe Gln Leu Cys Thr Ile Thr Leu Thr Ala Asp
    370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
```

```
                435                 440                 445
Leu Lys Glu Lys Phe Ser Leu Asp Leu Asp Gln Tyr Pro Leu Gly Arg
450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
                485                 490                 495

Arg Val Arg Val Arg Ala Arg Lys
            500

<210> SEQ ID NO 11
<211> LENGTH: 504
<212> TYPE: PRT
<213> ORGANISM: Artificial Sequence
<220> FEATURE:
<223> OTHER INFORMATION: H18N65-45T3-59S4

<400> SEQUENCE: 11

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Gly Asn Lys Gln Asp Ile Pro Lys Val Ser Ala
        50                  55                  60

Tyr Gln Tyr Arg Val Phe Arg Val Gln Leu Pro Asp Pro Asn Lys Phe
65              70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Phe Tyr Asn Lys Leu Asp Asp Thr Glu Ser
        115                 120                 125

Ser His Ala Ala Thr Ser Asn Val Ser Glu Asp Val Arg Asp Asn Val
130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Leu Cys Lys Pro Ala Gln
                165                 170                 175

Leu Gln Pro Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ser Gly Thr Met Gly Asp Gln Leu Pro Glu Ser Leu
            260                 265                 270

Tyr Ile Lys Gly Thr Asp Ile Arg Ala Asn Pro Gly Ser Tyr Leu Tyr
        275                 280                 285

Ser Pro Ser Pro Ser Gly Ser Ile Val Thr Ser Asp Ser Gln Leu Phe
```

-continued

```
                290                 295                 300
Asn Lys Pro Tyr Trp Leu His Lys Ala Gln Gly His Asn Asn Gly Val
305                 310                 315                 320

Cys Trp His Asn Gln Leu Phe Val Thr Val Val Asp Thr Thr Arg Ser
                325                 330                 335

Thr Asn Leu Thr Ile Cys Ala Ser Thr Gln Ser Pro Val Pro Gly Gln
                340                 345                 350

Tyr Asp Ala Thr Lys Phe Lys Gln Tyr Ser Arg His Val Glu Glu Tyr
                355                 360                 365

Asp Leu Gln Phe Ile Phe Gln Leu Cys Thr Ile Thr Leu Thr Ala Asp
                370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
                420                 425                 430

Ala Glu Asn Lys Asp Pro Tyr Asp Lys Leu Lys Phe Trp Asn Val Asp
                435                 440                 445

Leu Lys Glu Lys Phe Ser Leu Asp Leu Asp Gln Tyr Pro Leu Gly Arg
                450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Ala Ser Lys Pro Ala Lys
                485                 490                 495

Arg Val Arg Val Arg Ala Arg Lys
                500
```

<210> SEQ ID NO 12
<211> LENGTH: 504
<212> TYPE: PRT
<213> ORGANISM: Artificial Sequence
<220> FEATURE:
<223> OTHER INFORMATION: H18N65-45T3-59S5

<400> SEQUENCE: 12

```
Met Arg Pro Ser Asp Asn Thr Val Tyr Leu Pro Pro Ser Val Ala
1                   5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
                35                  40                  45

Val Pro Ala Gly Gly Gly Asn Lys Gln Asp Ile Pro Lys Val Ser Ala
                50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
                100                 105                 110

Gly Leu Ser Gly His Pro Phe Tyr Asn Lys Leu Asp Asp Thr Glu Ser
                115                 120                 125

Ser His Ala Ala Thr Ser Asn Val Ser Glu Asp Val Arg Asp Asn Val
                130                 135                 140

Ser Val Asp Tyr Lys Gln Thr Gln Leu Cys Ile Leu Gly Cys Ala Pro
```

```
            145                 150                 155                 160
        Ala Ile Gly Glu His Trp Ala Lys Gly Thr Leu Cys Lys Pro Ala Gln
                        165                 170                 175

Leu Gln Pro Gly Asp Cys Pro Pro Leu Glu Leu Lys Asn Thr Val Leu
                        180                 185                 190

Glu Asp Gly Asp Met Val Asp Thr Gly Tyr Gly Ala Met Asp Phe Ser
                        195                 200                 205

Thr Leu Gln Asp Thr Lys Cys Glu Val Pro Leu Asp Ile Cys Gln Ser
                210                 215                 220

Ile Cys Lys Tyr Pro Asp Tyr Leu Gln Met Ser Ala Asp Pro Tyr Gly
        225                 230                 235                 240

Asp Ser Met Phe Phe Cys Leu Arg Arg Glu Gln Leu Phe Ala Arg His
                        245                 250                 255

Phe Trp Asn Arg Ala Gly Thr Met Gly Asp Thr Val Pro Gln Ser Leu
                        260                 265                 270

Tyr Ile Lys Gly Thr Gly Met Arg Ala Ser Pro Gly Ser Cys Val Tyr
                        275                 280                 285

Ser Pro Ser Pro Ser Gly Ser Ile Val Thr Ser Asp Ser Gln Leu Phe
                        290                 295                 300

Asn Lys Pro Tyr Trp Leu His Lys Ala Gln Gly His Asn Asn Gly Val
        305                 310                 315                 320

Cys Trp His Asn Gln Leu Phe Val Thr Val Val Asp Thr Thr Arg Ser
                        325                 330                 335

Thr Asn Leu Thr Ile Cys Ala Ser Thr Thr Ser Ser Ile Pro Asn Val
                        340                 345                 350

Tyr Thr Pro Thr Ser Phe Lys Gln Tyr Ser Arg His Val Glu Glu Tyr
                        355                 360                 365

Asp Leu Gln Phe Ile Phe Gln Leu Cys Thr Ile Thr Leu Thr Ala Asp
                        370                 375                 380

Val Met Ser Tyr Ile His Ser Met Asn Ser Ser Ile Leu Glu Asp Trp
        385                 390                 395                 400

Asn Phe Gly Val Pro Pro Pro Thr Thr Ser Leu Val Asp Thr Tyr
                        405                 410                 415

Arg Phe Val Gln Ser Val Ala Ile Ala Cys Gln Lys Asp Ala Ala Pro
                        420                 425                 430

Ala Glu Asn Lys Asp Pro Tyr Asp Lys Leu Lys Phe Trp Asn Val Asp
                        435                 440                 445

Leu Lys Glu Lys Phe Ser Leu Asp Leu Asp Gln Tyr Pro Leu Gly Arg
        450                 455                 460

Lys Phe Leu Val Gln Ala Gly Leu Arg Arg Lys Pro Thr Ile Gly Pro
        465                 470                 475                 480

Arg Lys Arg Ser Ala Pro Ser Ala Thr Thr Ala Ser Lys Pro Ala Lys
                        485                 490                 495

Arg Val Arg Val Arg Ala Arg Lys
                        500

<210> SEQ ID NO 13
<211> LENGTH: 506
<212> TYPE: PRT
<213> ORGANISM: Artificial Sequence
<220> FEATURE:
<223> OTHER INFORMATION: H18N65-45T4-59S1

<400> SEQUENCE: 13

Met Arg Pro Ser Asp Asn Thr Val Tyr Leu Pro Pro Pro Ser Val Ala
```

-continued

```
1               5                   10                  15
Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Lys
                35                  40                  45

Val Pro Lys Gly Gly Asn Gly Arg Gln Asp Val Pro Lys Val Ser Ala
 50                 55                  60

Tyr Gln Tyr Arg Val Phe Arg Val Gln Leu Pro Asp Pro Asn Lys Phe
 65                 70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
                100                 105                 110

Gly Leu Ser Gly His Pro Phe Tyr Asn Lys Leu Asp Asp Thr Glu Ser
                115                 120                 125

Ser His Ala Ala Thr Ser Asn Val Ser Glu Asp Val Arg Asp Asn Val
                130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
                180                 185                 190

Glu Asp Gly Asp Met Val Asp Thr Gly Tyr Gly Ala Met Asp Phe Ser
                195                 200                 205

Thr Leu Gln Asp Thr Lys Cys Glu Val Pro Leu Asp Ile Cys Gln Ser
210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Val Met Gly Asp Thr Val Pro Thr Asp Leu
                260                 265                 270

Tyr Ile Lys Gly Thr Ser Ala Asn Met Arg Glu Thr Pro Gly Ser Cys
                275                 280                 285

Val Tyr Ser Pro Ser Pro Ser Gly Ser Ile Val Thr Ser Asp Ser Gln
                290                 295                 300

Leu Phe Asn Lys Pro Tyr Trp Leu His Lys Ala Gln Gly His Asn Asn
305                 310                 315                 320

Gly Val Cys Trp His Asn Gln Leu Phe Val Thr Val Asp Thr Thr
                325                 330                 335

Arg Ser Thr Asn Leu Thr Ile Cys Ala Ser Thr Gln Ser Pro Val Pro
                340                 345                 350

Gly Gln Tyr Asp Ala Thr Lys Phe Lys Gln Tyr Ser Arg His Val Glu
                355                 360                 365

Glu Tyr Asp Leu Gln Phe Ile Phe Gln Leu Cys Thr Ile Thr Leu Thr
                370                 375                 380

Ala Asp Val Met Ser Tyr Ile His Ser Met Asn Ser Ser Ile Leu Glu
385                 390                 395                 400

Asp Trp Asn Phe Gly Val Pro Pro Pro Thr Thr Ser Leu Val Asp
                405                 410                 415

Thr Tyr Arg Phe Val Gln Ser Val Ala Ile Ala Cys Gln Lys Asp Ala
                420                 425                 430
```

```
Ala Pro Ala Glu Asn Lys Asp Pro Tyr Asp Lys Leu Lys Phe Trp Asn
            435                 440                 445

Val Asp Leu Lys Glu Lys Phe Ser Leu Asp Leu Asp Gln Tyr Pro Leu
    450                 455                 460

Gly Arg Lys Phe Leu Val Gln Ala Gly Leu Arg Arg Lys Pro Thr Ile
465                 470                 475                 480

Gly Pro Arg Lys Arg Ser Ala Pro Ser Ala Thr Thr Ala Ser Lys Pro
                485                 490                 495

Ala Lys Arg Val Arg Val Arg Ala Arg Lys
            500                 505

<210> SEQ ID NO 14
<211> LENGTH: 506
<212> TYPE: PRT
<213> ORGANISM: Artificial Sequence
<220> FEATURE:
<223> OTHER INFORMATION: H18N65-45T4-59S2

<400> SEQUENCE: 14

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Gly Asn Lys Gln Asp Ile Pro Lys Val Ser Ala
    50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Leu Tyr Asn Lys Leu Asp Asp Thr Glu Asn
        115                 120                 125

Ser His Val Ala Ser Ala Val Asp Thr Lys Asp Thr Arg Asp Asn Val
    130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
        195                 200                 205

Thr Leu Gln Asp Thr Lys Cys Glu Val Pro Leu Asp Ile Cys Gln Ser
    210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Val Met Gly Asp Thr Val Pro Thr Asp Leu
            260                 265                 270

Tyr Ile Lys Gly Thr Ser Ala Asn Met Arg Glu Thr Pro Gly Ser Cys
        275                 280                 285
```

```
Val Tyr Ser Pro Ser Pro Ser Gly Ser Ile Val Thr Ser Asp Ser Gln
    290                 295                 300

Leu Phe Asn Lys Pro Tyr Trp Leu His Lys Ala Gln Gly His Asn Asn
305                 310                 315                 320

Gly Val Cys Trp His Asn Gln Leu Phe Val Thr Val Val Asp Thr Thr
                325                 330                 335

Arg Ser Thr Asn Leu Thr Ile Cys Ala Ser Thr Gln Ser Pro Val Pro
            340                 345                 350

Gly Gln Tyr Asp Ala Thr Lys Phe Lys Gln Tyr Ser Arg His Val Glu
        355                 360                 365

Glu Tyr Asp Leu Gln Phe Ile Phe Gln Leu Cys Thr Ile Thr Leu Thr
    370                 375                 380

Ala Asp Val Met Ser Tyr Ile His Ser Met Asn Ser Ser Ile Leu Glu
385                 390                 395                 400

Asp Trp Asn Phe Gly Val Pro Pro Pro Thr Thr Ser Leu Val Asp
                405                 410                 415

Thr Tyr Arg Phe Val Gln Ser Val Ala Ile Ala Cys Gln Lys Asp Ala
            420                 425                 430

Ala Pro Ala Glu Asn Lys Asp Pro Tyr Asp Lys Leu Lys Phe Trp Asn
        435                 440                 445

Val Asp Leu Lys Glu Lys Phe Ser Leu Asp Leu Asp Gln Tyr Pro Leu
450                 455                 460

Gly Arg Lys Phe Leu Val Gln Ala Gly Leu Arg Arg Lys Pro Thr Ile
465                 470                 475                 480

Gly Pro Arg Lys Arg Ser Ala Pro Ser Ala Thr Thr Ala Ser Lys Pro
                485                 490                 495

Ala Lys Arg Val Arg Val Arg Ala Arg Lys
            500                 505

<210> SEQ ID NO 15
<211> LENGTH: 506
<212> TYPE: PRT
<213> ORGANISM: Artificial Sequence
<220> FEATURE:
<223> OTHER INFORMATION: H18N65-45T4-59S3

<400> SEQUENCE: 15

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Arg
        35                  40                  45

Val Pro Ala Gly Gly Asn Lys Gln Asp Ile Pro Lys Val Ser Ala
    50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Phe Tyr Asn Lys Leu Asp Asp Thr Glu Ser
        115                 120                 125

Ser His Ala Ala Thr Ser Asn Val Ser Glu Asp Val Arg Asp Asn Val
130                 135                 140
```

Ser Val Asp Tyr Lys Gln Thr Gln Leu Cys Ile Leu Gly Cys Ala Pro
145                 150                 155                 160

Ala Ile Gly Glu His Trp Thr Lys Gly Thr Ala Cys Lys Pro Thr Thr
            165                 170                 175

Val Val Gln Gly Asp Cys Pro Pro Leu Glu Leu Lys Asn Thr Val Leu
        180                 185                 190

Glu Asp Gly Asp Met Val Asp Thr Gly Tyr Gly Ala Met Asp Phe Ser
    195                 200                 205

Thr Leu Gln Asp Thr Lys Cys Glu Val Pro Leu Asp Ile Cys Gln Ser
210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Val Met Gly Asp Thr Val Pro Thr Asp Leu
            260                 265                 270

Tyr Ile Lys Gly Thr Ser Ala Asn Met Arg Glu Thr Pro Gly Ser Cys
        275                 280                 285

Val Tyr Ser Pro Ser Pro Ser Gly Ser Ile Val Thr Ser Asp Ser Gln
    290                 295                 300

Leu Phe Asn Lys Pro Tyr Trp Leu His Lys Ala Gln Gly His Asn Asn
305                 310                 315                 320

Gly Val Cys Trp His Asn Gln Leu Phe Val Thr Val Asp Thr Thr
                325                 330                 335

Arg Ser Thr Asn Leu Thr Ile Cys Ala Ser Thr Gln Ser Pro Val Pro
                340                 345                 350

Gly Gln Tyr Asp Ala Thr Lys Phe Lys Gln Tyr Ser Arg His Val Glu
        355                 360                 365

Glu Tyr Asp Leu Gln Phe Ile Phe Gln Leu Cys Thr Ile Thr Leu Thr
    370                 375                 380

Ala Asp Val Met Ser Tyr Ile His Ser Met Asn Ser Ser Ile Leu Glu
385                 390                 395                 400

Asp Trp Asn Phe Gly Val Pro Pro Pro Thr Thr Ser Leu Val Asp
                405                 410                 415

Thr Tyr Arg Phe Val Gln Ser Val Ala Ile Ala Cys Gln Lys Asp Ala
        420                 425                 430

Ala Pro Ala Glu Asn Lys Asp Pro Tyr Asp Lys Leu Lys Phe Trp Asn
    435                 440                 445

Val Asp Leu Lys Glu Lys Phe Ser Leu Asp Leu Asp Gln Tyr Pro Leu
450                 455                 460

Gly Arg Lys Phe Leu Val Gln Ala Gly Leu Arg Arg Lys Pro Thr Ile
465                 470                 475                 480

Gly Pro Arg Lys Arg Ser Ala Pro Ser Ala Thr Thr Ala Ser Lys Pro
                485                 490                 495

Ala Lys Arg Val Arg Val Arg Ala Arg Lys
                500                 505

<210> SEQ ID NO 16
<211> LENGTH: 506
<212> TYPE: PRT
<213> ORGANISM: Artificial Sequence
<220> FEATURE:
<223> OTHER INFORMATION: H18N65-45T4-59S5

<400> SEQUENCE: 16

```
Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Asn Lys Gln Asp Ile Pro Lys Val Ser Ala
    50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
                100                 105                 110

Gly Leu Ser Gly His Pro Phe Tyr Asn Lys Leu Asp Asp Thr Glu Ser
            115                 120                 125

Ser His Ala Ala Thr Ser Asn Val Ser Glu Asp Val Arg Asp Asn Val
            130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro
                165                 170                 175

Leu Ser Gln Gly Asp Cys Pro Pro Leu Glu Leu Lys Asn Thr Val Leu
                180                 185                 190

Glu Asp Gly Asp Met Val Asp Thr Gly Tyr Gly Ala Met Asp Phe Ser
            195                 200                 205

Thr Leu Gln Asp Thr Lys Cys Glu Val Pro Leu Asp Ile Cys Gln Ser
210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Val Met Gly Asp Thr Val Pro Thr Asp Leu
                260                 265                 270

Tyr Ile Lys Gly Thr Ser Ala Asn Met Arg Glu Thr Pro Gly Ser Cys
                275                 280                 285

Val Tyr Ser Pro Ser Pro Ser Gly Ser Ile Val Thr Ser Asp Ser Gln
    290                 295                 300

Leu Phe Asn Lys Pro Tyr Trp Leu His Lys Ala Gln Gly His Asn Asn
305                 310                 315                 320

Gly Val Cys Trp His Asn Gln Leu Phe Val Thr Val Val Asp Thr Thr
                325                 330                 335

Arg Ser Thr Asn Leu Thr Ile Cys Ala Ser Thr Thr Ser Ser Ile Pro
                340                 345                 350

Asn Val Tyr Thr Pro Thr Ser Phe Lys Gln Tyr Ser Arg His Val Glu
                355                 360                 365

Glu Tyr Asp Leu Gln Phe Ile Phe Gln Leu Cys Thr Ile Thr Leu Thr
370                 375                 380

Ala Asp Val Met Ser Tyr Ile His Ser Met Asn Ser Ser Ile Leu Glu
385                 390                 395                 400

Asp Trp Asn Phe Gly Val Pro Pro Pro Thr Thr Ser Leu Val Asp
                405                 410                 415
```

```
Thr Tyr Arg Phe Val Gln Ser Val Ala Ile Ala Cys Gln Lys Asp Ala
            420                 425                 430

Ala Pro Ala Glu Asn Lys Asp Pro Tyr Asp Lys Leu Lys Phe Trp Asn
        435                 440                 445

Val Asp Leu Lys Glu Lys Phe Ser Leu Asp Leu Asp Gln Tyr Pro Leu
    450                 455                 460

Gly Arg Lys Phe Leu Val Gln Ala Gly Leu Arg Arg Lys Pro Thr Ile
465                 470                 475                 480

Gly Pro Arg Lys Arg Ser Ala Pro Ser Ala Thr Thr Ala Ser Lys Pro
                485                 490                 495

Ala Lys Arg Val Arg Val Arg Ala Arg Lys
        500                 505

<210> SEQ ID NO 17
<211> LENGTH: 505
<212> TYPE: PRT
<213> ORGANISM: Artificial Sequence
<220> FEATURE:
<223> OTHER INFORMATION: H18N65-45T1-59S5

<400> SEQUENCE: 17

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Arg
        35                  40                  45

Val Val Pro Asn Gly Ala Gly Asn Lys Gln Ala Val Pro Lys Val Ser
    50                  55                  60

Ala Tyr Gln Tyr Arg Val Phe Arg Val Gln Leu Pro Asp Pro Asn Lys
65                  70                  75                  80

Phe Gly Leu Pro Asp Thr Ser Ile Tyr Asn Pro Glu Thr Gln Arg Leu
                85                  90                  95

Val Trp Ala Cys Ala Gly Val Glu Ile Gly Arg Gly Gln Pro Leu Gly
            100                 105                 110

Val Gly Leu Ser Gly His Pro Phe Tyr Asn Lys Leu Asp Asp Thr Glu
        115                 120                 125

Ser Ser His Ala Ala Thr Ser Asn Val Ser Glu Asp Val Arg Asp Asn
    130                 135                 140

Val Ser Val Asp Tyr Lys Gln Thr Gln Leu Cys Ile Leu Gly Cys Ala
145                 150                 155                 160

Pro Ala Ile Gly Glu His Trp Ala Lys Gly Thr Ala Cys Lys Ser Arg
                165                 170                 175

Pro Leu Ser Gln Gly Asp Cys Pro Pro Leu Glu Leu Lys Asn Thr Val
            180                 185                 190

Leu Glu Asp Gly Asp Met Val Asp Thr Gly Tyr Gly Ala Met Asp Phe
        195                 200                 205

Ser Thr Leu Gln Asp Thr Lys Cys Glu Val Pro Leu Asp Ile Cys Gln
    210                 215                 220

Ser Ile Cys Lys Tyr Pro Asp Tyr Leu Gln Met Ser Ala Asp Pro Tyr
225                 230                 235                 240

Gly Asp Ser Met Phe Phe Cys Leu Arg Arg Glu Gln Leu Phe Ala Arg
                245                 250                 255

His Phe Trp Asn Arg Ala Gly Thr Met Gly Asp Thr Val Pro Gln Ser
            260                 265                 270
```

```
Leu Tyr Ile Lys Gly Thr Gly Met Arg Ala Ser Pro Gly Ser Cys Val
            275                 280                 285

Tyr Ser Pro Ser Pro Ser Gly Ser Ile Val Thr Ser Asp Ser Gln Leu
290                 295                 300

Phe Asn Lys Pro Tyr Trp Leu His Lys Ala Gln Gly His Asn Asn Gly
305                 310                 315                 320

Val Cys Trp His Asn Gln Leu Phe Val Thr Val Asp Thr Thr Arg
                325                 330                 335

Ser Thr Asn Leu Thr Ile Cys Ala Ser Thr Thr Ser Ser Ile Pro Asn
            340                 345                 350

Val Tyr Thr Pro Thr Ser Phe Lys Gln Tyr Ser Arg His Val Glu Glu
            355                 360                 365

Tyr Asp Leu Gln Phe Ile Phe Gln Leu Cys Thr Ile Thr Leu Thr Ala
            370                 375                 380

Asp Val Met Ser Tyr Ile His Ser Met Asn Ser Ser Ile Leu Glu Asp
385                 390                 395                 400

Trp Asn Phe Gly Val Pro Pro Pro Thr Thr Ser Leu Val Asp Thr
                405                 410                 415

Tyr Arg Phe Val Gln Ser Val Ala Ile Ala Cys Gln Lys Asp Ala Ala
            420                 425                 430

Pro Ala Glu Asn Lys Asp Pro Tyr Asp Lys Leu Lys Phe Trp Asn Val
            435                 440                 445

Asp Leu Lys Glu Lys Phe Ser Leu Asp Leu Asp Gln Tyr Pro Leu Gly
            450                 455                 460

Arg Lys Phe Leu Val Gln Ala Gly Leu Arg Arg Lys Pro Thr Ile Gly
465                 470                 475                 480

Pro Arg Lys Arg Ser Ala Pro Ser Ala Thr Thr Ala Ser Lys Pro Ala
                485                 490                 495

Lys Arg Val Arg Val Arg Ala Arg Lys
                500                 505

<210> SEQ ID NO 18
<211> LENGTH: 504
<212> TYPE: PRT
<213> ORGANISM: Artificial Sequence
<220> FEATURE:
<223> OTHER INFORMATION: H18N65-45T2-59S5

<400> SEQUENCE: 18

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Pro Ala Gly Gly Gly Asn Lys Gln Asp Ile Pro Lys Val Ser Ala
50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Ile
            100                 105                 110

Gly Leu Ser Gly His Pro Phe Tyr Asn Lys Leu Asp Asp Thr Glu Ser
            115                 120                 125
```

```
Ala His Ala Ala Thr Ala Val Ile Thr Gln Asp Val Arg Asp Asn Val
        130                 135                 140
Ser Val Asp Tyr Lys Gln Thr Gln Leu Cys Ile Leu Gly Cys Ala Pro
145                 150                 155                 160
Ala Ile Gly Glu His Trp Ala Lys Gly Thr Ala Cys Lys Ser Arg Pro
                165                 170                 175
Leu Ser Gln Gly Asp Cys Pro Pro Leu Glu Leu Lys Asn Thr Val Leu
            180                 185                 190
Glu Asp Gly Asp Met Val Asp Thr Gly Tyr Gly Ala Met Asp Phe Ser
        195                 200                 205
Thr Leu Gln Asp Thr Lys Cys Glu Val Pro Leu Asp Ile Cys Gln Ser
210                 215                 220
Ile Cys Lys Tyr Pro Asp Tyr Leu Gln Met Ser Ala Asp Pro Tyr Gly
225                 230                 235                 240
Asp Ser Met Phe Phe Cys Leu Arg Arg Glu Gln Leu Phe Ala Arg His
                245                 250                 255
Phe Trp Asn Arg Ala Gly Thr Met Gly Asp Thr Val Pro Gln Ser Leu
            260                 265                 270
Tyr Ile Lys Gly Thr Gly Met Arg Ala Ser Pro Gly Ser Cys Val Tyr
        275                 280                 285
Ser Pro Ser Pro Ser Gly Ser Ile Val Thr Ser Asp Ser Gln Leu Phe
        290                 295                 300
Asn Lys Pro Tyr Trp Leu His Lys Ala Gln Gly His Asn Asn Gly Val
305                 310                 315                 320
Cys Trp His Asn Gln Leu Phe Val Thr Val Asp Thr Thr Arg Ser
                325                 330                 335
Thr Asn Leu Thr Ile Cys Ala Ser Thr Thr Ser Ser Ile Pro Asn Val
            340                 345                 350
Tyr Thr Pro Thr Ser Phe Lys Gln Tyr Ser Arg His Val Glu Glu Tyr
        355                 360                 365
Asp Leu Gln Phe Ile Phe Gln Leu Cys Thr Ile Thr Leu Thr Ala Asp
370                 375                 380
Val Met Ser Tyr Ile His Ser Met Asn Ser Ser Ile Leu Glu Asp Trp
385                 390                 395                 400
Asn Phe Gly Val Pro Pro Pro Thr Thr Ser Leu Val Asp Thr Tyr
                405                 410                 415
Arg Phe Val Gln Ser Val Ala Ile Ala Cys Gln Lys Asp Ala Ala Pro
            420                 425                 430
Ala Glu Asn Lys Asp Pro Tyr Asp Lys Leu Lys Phe Trp Asn Val Asp
        435                 440                 445
Leu Lys Glu Lys Phe Ser Leu Asp Leu Asp Gln Tyr Pro Leu Gly Arg
450                 455                 460
Lys Phe Leu Val Gln Ala Gly Leu Arg Arg Lys Pro Thr Ile Gly Pro
465                 470                 475                 480
Arg Lys Arg Ser Ala Pro Ser Ala Thr Thr Ala Ser Lys Pro Ala Lys
                485                 490                 495
Arg Val Arg Val Arg Ala Arg Lys
            500
```

<210> SEQ ID NO 19
<211> LENGTH: 505
<212> TYPE: PRT
<213> ORGANISM: Artificial Sequence
<220> FEATURE:
<223> OTHER INFORMATION: H18N65-45T1T3-59S5

<400> SEQUENCE: 19

```
Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
                20                  25                  30

His Ala Gly Ser Ser Arg Leu Leu Thr Val Gly Asn Pro Tyr Phe Arg
            35                  40                  45

Val Val Pro Asn Gly Ala Gly Asn Lys Gln Ala Val Pro Lys Val Ser
        50                  55                  60

Ala Tyr Gln Tyr Arg Val Phe Arg Val Gln Leu Pro Asp Pro Asn Lys
65                  70                  75                  80

Phe Gly Leu Pro Asp Thr Ser Ile Tyr Asn Pro Glu Thr Gln Arg Leu
                85                  90                  95

Val Trp Ala Cys Ala Gly Val Glu Ile Gly Arg Gly Gln Pro Leu Gly
                100                 105                 110

Val Gly Leu Ser Gly His Pro Phe Tyr Asn Lys Leu Asp Asp Thr Glu
            115                 120                 125

Ser Ser His Ala Ala Thr Ser Asn Val Ser Glu Asp Val Arg Asp Asn
130                 135                 140

Val Ser Val Asp Tyr Lys Gln Thr Gln Leu Cys Ile Leu Gly Cys Ala
145                 150                 155                 160

Pro Ala Ile Gly Glu His Trp Ala Lys Gly Thr Leu Cys Lys Pro Ala
                165                 170                 175

Gln Leu Gln Pro Gly Asp Cys Pro Pro Leu Glu Leu Lys Asn Thr Val
            180                 185                 190

Leu Glu Asp Gly Asp Met Val Asp Thr Gly Tyr Gly Ala Met Asp Phe
        195                 200                 205

Ser Thr Leu Gln Asp Thr Lys Cys Glu Val Pro Leu Asp Ile Cys Gln
210                 215                 220

Ser Ile Cys Lys Tyr Pro Asp Tyr Leu Gln Met Ser Ala Asp Pro Tyr
225                 230                 235                 240

Gly Asp Ser Met Phe Phe Cys Leu Arg Arg Glu Gln Leu Phe Ala Arg
                245                 250                 255

His Phe Trp Asn Arg Ala Gly Thr Met Gly Asp Thr Val Pro Gln Ser
            260                 265                 270

Leu Tyr Ile Lys Gly Thr Gly Met Arg Ala Ser Pro Gly Ser Cys Val
        275                 280                 285

Tyr Ser Pro Ser Pro Ser Gly Ser Ile Val Thr Ser Asp Ser Gln Leu
290                 295                 300

Phe Asn Lys Pro Tyr Trp Leu His Lys Ala Gln Gly His Asn Asn Gly
305                 310                 315                 320

Val Cys Trp His Asn Gln Leu Phe Val Thr Val Asp Thr Thr Arg
                325                 330                 335

Ser Thr Asn Leu Thr Ile Cys Ala Ser Thr Thr Ser Ser Ile Pro Asn
            340                 345                 350

Val Tyr Thr Pro Thr Ser Phe Lys Gln Tyr Ser Arg His Val Glu Glu
        355                 360                 365

Tyr Asp Leu Gln Phe Ile Phe Gln Leu Cys Thr Ile Thr Leu Thr Ala
370                 375                 380

Asp Val Met Ser Tyr Ile His Ser Met Asn Ser Ser Ile Leu Glu Asp
385                 390                 395                 400

Trp Asn Phe Gly Val Pro Pro Pro Pro Thr Thr Ser Leu Val Asp Thr
```

```
              405                 410                 415
Tyr Arg Phe Val Gln Ser Val Ala Ile Ala Cys Gln Lys Asp Ala Ala
        420                 425                 430

Pro Ala Glu Asn Lys Asp Pro Tyr Asp Lys Leu Lys Phe Trp Asn Val
            435                 440                 445

Asp Leu Lys Glu Lys Phe Ser Leu Asp Leu Asp Gln Tyr Pro Leu Gly
450                 455                 460

Arg Lys Phe Leu Val Gln Ala Gly Leu Arg Arg Lys Pro Thr Ile Gly
465                 470                 475                 480

Pro Arg Lys Arg Ser Ala Pro Ser Ala Thr Thr Ala Ser Lys Pro Ala
                485                 490                 495

Lys Arg Val Arg Val Arg Ala Arg Lys
                500                 505

<210> SEQ ID NO 20
<211> LENGTH: 1707
<212> TYPE: DNA
<213> ORGANISM: Human papillomavirus type 18

<400> SEQUENCE: 20
atgtgcctgt atacacgggt cctgatatta cattaccatc tactacctct gtatggccca       60
ttgtatcacc cacagcccct gcctctacac agtatattgg tatacatggt acacattatt      120
atttgtggcc attatattat tttattccta agaaacgtaa acgtgttccc tattttttg       180 cagatggctt tgtggcggcc tagtgacaat accgtatatc ttccacctcc ttctgtggca      240
agagttgtaa ataccgatga ttacgtgact cgcacaagca tatttatca tgctggcagc       300 tctagattat taactgttgg taatccatat tttagggttc ctgcaggtgg tggcaataag      360
caggatattc ctaaggtttc tgcataccaa tatagagtat ttagggtgca gttacctgac      420
ccaaataaat ttggtttacc tgatactagt atttataatc ctgaaacaca acgtttagtg      480
tgggcctgtg ctggagtgga aattggccgt ggtcagcctt taggtgttgg ccttagtggg      540 catccattt ataataaatt agatgacact gaaagttccc atgccgccac gtctaatgtt       600
tctgaggacg ttagggacaa tgtgtctgta gattataagc agacacagtt atgtattttg      660
ggctgtgccc ctgctattgg gaacactggg ctaaaggca ctgcttgtaa atcgcgtcct       720
ttatcacagg gcgattgccc cccttttgaa cttaaaaaca gttttggga agatggtgat       780 atggtagata ctggatatgg tgccatggac tttagtacat gcaagatac taaatgtgag      840 gtaccattgg atatttgtca gtctatttgt aaatatcctg attatttaca atgtctgca       900 gatccttatg gggattccat gttttttgc ttacggcgtg agcagctttt tgctaggcat       960
ttttggaata gagcaggtac tatgggtgac actgtgcctc aatccttata tattaaaggc     1020
acaggtatgc gtgcttcacc tggcagctgt gtgtattctc cctctccaag tggctctatt     1080
gttacctctg actcccagtt gtttaataaa ccatattggt tacataaggc acagggtcat     1140
aacaatggtg tttgctggca taatcaatta tttgttactg tggtagatac cactcgcagt     1200
accaatttaa caatatgtgc ttctacacag tctcctgtac ctgggcaata tgatgctacc     1260
aaatttaagc agtatagcag acatgttgag gaatatgatt tgcagtttat ttttcagttg     1320
tgtactatta ctttaactgc agatgttatg tcctatattc atagtatgaa tagcagtatt     1380
ttagaggatt ggaactttgg tgttccccc ccgccaacta ctagtttggt ggatacatat     1440
cgttttgtac aatctgttgc tattgcctgt caaaaggatg ctgcaccggc tgaaaataag     1500 gatcccctatg ataagttaaa gttttggaat gtggatttaa aggaaaagtt ttctttagac     1560
```

```
ttagatcaat atcccttgg acgtaaattt ttggttcagg ctggattgcg tcgcaagccc    1620
accataggcc ctcgcaaacg ttctgctcca tctgccacta cggcttctaa acctgccaag    1680
cgtgtgcgtg tacgtgccag gaagtaa                                       1707

<210> SEQ ID NO 21
<211> LENGTH: 1707
<212> TYPE: DNA
<213> ORGANISM: Human papillomavirus type 45

<400> SEQUENCE: 21
atgtgcctgt atacacgggt cctgatatta cattaccatc tactacctct gtatggccca      60
ttgtatcacc cacagcccct gcctctacac agtatattgg tatacatggt acacattatt     120
atttgtggcc attatattat tttattccta agaaacgtaa acgtgttccc tatttttttg     180
cagatggctt tgtggcggcc tagtgacaat accgtatatc ttccacctcc ttctgtggca     240
agagttgtaa ataccgatga ttacgtgact cgcacaagca tattttatca tgctggcagc     300
tctagattat taactgttgg taatccatat tttagggttc ctgcaggtgg tggcaataag     360
caggatattc ctaaggtttc tgcataccaa tatagagtat ttagggtgca gttacctgac     420
ccaaataaat ttggtttacc tgatactagt atttataatc ctgaaacaca acgtttagtg     480
tgggcctgtg ctggagtgga aattggccgt ggtcagcctt taggtgttgg ccttagtggg     540
catccatttt ataataaatt agatgacact gaaagttccc atgccgccac gtctaatgtt     600
tctgaggacg ttagggacaa tgtgtctgta gattataagc agacacagtt atgtatttg      660 ggctgtgccc ctgctattgg ggaacactgg gctaaaggca ctgcttgtaa atcgcgtcct     720
ttatcacagg gcgattgccc ccctttagaa cttaaaaaca cagttttgga agatggtgat     780
atggtagata ctggatatgg tgccatggac tttagtacat tgcaagatac taaatgtgag     840
gtaccattgg atatttgtca gtctatttgt aaatatcctg attatttaca aatgtctgca     900
gatccttatg gggattccat gttttttgc ttacggcgtg agcagctttt tgctaggcat     960
ttttggaata gagcaggtac tatgggtgac actgtgcctc aatccttata tattaaaggc    1020
acaggtatgc gtgcttcacc tggcagctgt gtgtattctc cctctccaag tggctctatt    1080
gttacctctg actcccagtt gtttaataaa ccatattggt tacataaggc acagggtcat    1140
aacaatggtg tttgctggca taatcaatta tttgttactg tggtagatac cactcgcagt    1200
accaatttaa caatatgtgc ttctacacag tctcctgtac ctgggcaata tgatgctacc    1260
aaatttaagc agtatagcag acatgttgag gaatatgatt tgcagtttat ttttcagttg    1320
tgtactatta ctttaactgc agatgttatg tcctatattc atagtatgaa tagcagtatt    1380
ttagaggatt ggaactttgg tgttcccccc cgccaactac tagtttggt ggatacatat    1440 cgttttgtac aatctgttgc tattgcctgt caaaaggatg ctgcaccggc tgaaaataag    1500
gatccctatg ataagttaaa gttttggaat gtggatttaa aggaaaagtt ttctttagac    1560
ttagatcaat atcccttgg acgtaaattt ttggttcagg ctggattgcg tcgcaagccc    1620
accataggcc ctcgcaaacg ttctgctcca tctgccacta cggcttctaa acctgccaag    1680
cgtgtgcgtg tacgtgccag gaagtaa                                       1707

<210> SEQ ID NO 22
<211> LENGTH: 1527
<212> TYPE: DNA
<213> ORGANISM: Human papillomavirus type 59
```

<400> SEQUENCE: 22

```
atggccctgt ggaggagcag cgacaacaag gtgtacctgc cccccccag cgtggccaag      60
gtggtgagca ccgacgagta cgtgaccagg accagcatct tctaccacgc cggcagcagc    120
aggctgctga ccgtgggcca cccctacttc aaggtgccca agggcggcaa cggcaggcag    180
gacgtgccca aggtgagcgc ctaccagtac agggtgttca gggtgaagct gcccgacccc    240
aacaagttcg gcctgcccga caacaccgtg tacgacccca cagccagag gctggtgtgg    300
gcctgcgtgg gcgtggagat cggcaggggc cagcccctgg gcgtgggcct gagcggccac    360
cccctgtaca acaagctgga cgacaccgag aacagccacg tggccagcgc cgtggacacc    420
aaggacacca gggacaacgt gagcgtggac tacaagcaga cccagctgtg catcatcggc    480
tgcgtgcccg ccatcggcga gcactggacc aagggcaccg cctgcaagcc caccaccgtg    540
gtgcagggcg actgcccccc cctggagctg atcaacaccc ccatcgagga cggcgacatg    600
gtggacaccg gctacggcgc catggacttc aagctgctgc aggacaacaa gagcgaggtg    660
cccctggaca tctgccagag catctgcaag taccccgact acctgcagat gagcgccgac    720
gcctacggcg acagcatgtt cttctgcctg aggagggagc aggtgttcgc caggcacttc    780
tggaacagga gcggcaccat gggcgaccag ctgcccgaga gcctgtacat caagggcacc    840
gacatcaggg ccaaccccgg cagctacctg tacagcccca gccccagcgg cagcgtggtg    900
accagcgaca gccagctgtt caacaagccc tactggctgc acaaggccca gggcctgaac    960
aacggcatct gctggcacaa ccagctgttc ctgaccgtgg tggacaccac caggagcacc   1020
aacctgagcg tgtgcgccag caccaccagc agcatcccca cgtgtacac ccccaccagc    1080
ttcaaggagt acgccaggca cgtggaggag ttcgacctgc agttcatctt ccagctgtgc    1140
aagatcaccc tgaccaccga ggtgatgagc tacatccaca acatgaacac caccatcctg   1200
gaggactgga acttcggcgt gaccccccc cccaccgcca gcctggtgga cacctacagg    1260
ttcgtgcaga gcgccgccgt gacctgccag aaggacaccg ccccccccgt gaagcaggac   1320
ccctacgaca agctgaagtt ctggcccgtg gacctgaagg agaggttcag cgccgacctg   1380
gaccagttcc ccctgggcag gaagttcctg ctgcagctgg cgccaggcc caagcccacc    1440
atcggcccca ggaagagggc cgccccccgcc cccaccagca cccccagccc caagagggtg   1500
aagaggagga gagcagcag gaagtga                                        1527
```

<210> SEQ ID NO 23
<211> LENGTH: 1518
<212> TYPE: DNA
<213> ORGANISM: Artificial Sequence
<220> FEATURE:
<223> OTHER INFORMATION: The DNA sequence encoding H18N65-45T1

<400> SEQUENCE: 23

```
atgcggccta gtgacaatac cgtatatctt ccacctcctt ctgtggcaag agttgtaaat     60
accgatgatt acgtgactag gaccagcatc ttctaccacg ccggcagcag caggctgctg   120
accgtgggca ccccctactt cagggtggtg cccaacggcg ccggcaacaa gcaggccgtg   180
cccaaggtga gcgcctacca gtacagggtg ttcagggtgc agttacctga cccaaataaa   240
tttggtttac ctgatactag tatttataat cctgaaacac aacgtttagt gtgggcctgt   300
gctggagtgg aaattggccg tggtcagcct ttaggtgttg ccttagtgg catccatt     360
tataataaat tagatgacac tgaaagttcc catgccgcca cgtctaatgt ttctgaggac   420
gttagggaca atgtgtctgt agattataag cagacacagt tatgtatttt gggctgtgcc    480
```

| | |
|---|---|
| cctgctattg gggaacactg ggctaaaggc actgcttgta aatcgcgtcc tttatcacag | 540 |
| ggcgattgcc cccctttaga acttaaaaac acagttttgg aagatggtga tatggtagat | 600 |
| actggatatg gtgccatgga ctttagtaca ttgcaagata ctaaatgtga ggtaccattg | 660 |
| gatatttgtc agtctatttg taaatatcct gattatttac aaatgtctgc agatccttat | 720 |
| ggggattcca tgttttttg cttacggcgt gagcagcttt tgctaggca tttttggaat | 780 |
| agagcaggta ctatgggtga cactgtgcct caatccttat atattaaagg cacaggtatg | 840 |
| cgtgcttcac ctgcagctg tgtgtattct ccctctccaa gtggctctat tgttacctct | 900 |
| gactcccagt tgtttaataa accatattgg ttacataagg cacagggtca taacaatggt | 960 |
| gtttgctggc ataatcaatt atttgttact gtggtagata ccactcgcag taccaattta | 1020 |
| acaatatgtg cttctacaca gtctcctgta cctgggcaat atgatgctac caaatttaag | 1080 |
| cagtatagca gacatgttga ggaatatgat ttgcagttta ttttcagtt gtgtactatt | 1140 |
| actttaactg cagatgttat gtcctatatt catagtatga atagcagtat tttagaggat | 1200 |
| tggaactttg gtgttccccc cccgccaact actagtttgg tggatacata tcgttttgta | 1260 |
| caatctgttg ctattgcctg tcaaaaggat gctgcaccgg ctgaaaataa ggatccctat | 1320 |
| gataagttaa agttttggaa tgtggattta aaggaaaagt tttctttaga cttagatcaa | 1380 |
| tatccccttg gacgtaaatt tttggttcag gctggattgc gtcgcaagcc caccataggc | 1440 |
| cctcgcaaac gttctgctcc atctgccact acggcttcta aacctgccaa gcgtgtgcgt | 1500 |
| gtacgtgcca ggaagtaa | 1518 |

<210> SEQ ID NO 24
<211> LENGTH: 1515
<212> TYPE: DNA
<213> ORGANISM: Artificial Sequence
<220> FEATURE:
<223> OTHER INFORMATION: The DNA sequence encoding H18N65-45T2

<400> SEQUENCE: 24

| | |
|---|---|
| atgcggccta gtgacaatac cgtatatctt ccacctcctt ctgtggcaag agttgtaaat | 60 |
| accgatgatt acgtgactcg cacaagcata ttttatcatg ctggcagctc tagattatta | 120 |
| actgttggta atccatattt tagggttcct gcaggtggtg caataagca ggatattcct | 180 |
| aaggtttctg cataccaata tagagtattt agggtgcagt tacctgaccc aaataaattt | 240 |
| ggtttacctg atactagtat ttataatcct gaaacacaac gtttagtgtg ggcctgtgct | 300 |
| ggagtggaga tcggcagggg ccagcccctg ggcatcggcc tgagcggcca ccccttctac | 360 |
| aacaagctgg acgacaccga gagcgcccac gccgccaccg ccgtgatcac ccaggacgtg | 420 |
| agggacaacg tgagcgtgga ctacaagcag acccagctgt gcatcctggg ctgcgccct | 480 |
| gctattgggg aacactgggc taaggcact gcttgtaaat cgcgtccttt atcacagggc | 540 |
| gattgccccc cttagaact aaaaacaca gttttggaag atggtgatat ggtagatact | 600 |
| ggatatggtg ccatggactt tagtacattg caagatacta atgtgaggt accattggat | 660 |
| atttgtcagt ctatttgtaa atatcctgat tatttacaaa tgtctgcaga tccttatggg | 720 |
| gattccatgt tttttgctt acggcgtgag cagcttttg ctaggcattt ttggaataga | 780 |
| gcaggtacta tgggtgacac tgtgcctcaa tccttatata ttaaaggcac aggtatgcgt | 840 |
| gcttcacctg cagctgtgt gtattctccc tctccaagtg gctctattgt tacctctgac | 900 |
| tcccagttgt ttaataaacc atattggtta cataaggcac agggtcataa caatggtgtt | 960 |

| | |
|---|---|
| tgctggcata atcaattatt tgttactgtg gtagatacca ctcgcagtac caatttaaca | 1020 |
| atatgtgctt ctacacagtc tcctgtacct gggcaatatg atgctaccaa atttaagcag | 1080 |
| tatagcagac atgttgagga atatgatttg cagtttattt ttcagttgtg tactattact | 1140 |
| ttaactgcag atgttatgtc ctatattcat agtatgaata gcagtatttt agaggattgg | 1200 |
| aactttggtg ttccccccccc gccaactact agtttggtgg atacatatcg ttttgtacaa | 1260 |
| tctgttgcta ttgcctgtca aaaggatgct gcaccggctg aaaataagga tcccctatgat | 1320 |
| aagttaaagt tttggaatgt ggatttaaag gaaaagtttt ctttagactt agatcaatat | 1380 |
| cccctttggac gtaaattttt ggttcaggct ggattgcgtc gcaagcccac cataggccct | 1440 |
| cgcaaacgtt ctgctccatc tgccactacg gcttctaaac ctgccaagcg tgtgcgtgta | 1500 |
| cgtgccagga agtaa | 1515 |

<210> SEQ ID NO 25
<211> LENGTH: 1515
<212> TYPE: DNA
<213> ORGANISM: Artificial Sequence
<220> FEATURE:
<223> OTHER INFORMATION: The DNA sequence encoding H18N65-45T3

<400> SEQUENCE: 25

| | |
|---|---|
| atgcggccta gtgacaatac cgtatatctt ccacctcctt ctgtggcaag agttgtaaat | 60 |
| accgatgatt acgtgactcg cacaagcata ttttatcatg ctggcagctc tagattatta | 120 |
| actgttggta atccatattt tagggttcct gcaggtggtg gcaataagca ggatattcct | 180 |
| aaggtttctg cataccaata tagagtattt agggtgcagt tacctgaccc aaataaattt | 240 |
| ggtttacctg atactagtat ttataatcct gaaacacaac gtttagtgtg ggcctgtgct | 300 |
| ggagtggaaa ttggccgtgg tcagccttta ggtgttggcc ttagtgggca tccattttat | 360 |
| aataaattag atgacactga agttcccat gccgccacgt ctaatgtttc tgaggacgtt | 420 |
| agggacaatg tgtctgtaga ttataagcag acacagttat gtattttggg ctgtgccccc | 480 |
| gccatcggcg agcactgggc caagggcacc ctgtgcaagc ccgcccagct gcagcccggc | 540 |
| gactgccccc ccctggagct gaagaacacc gttttggaag atggtgatat ggtagatact | 600 |
| ggatatggtg ccatggactt agtacattg caagatacta atgtgaggt accattggat | 660 |
| atttgtcagt ctatttgtaa atatcctgat tatttacaaa tgtctgcaga tcctatatggg | 720 |
| gattccatgt tttttttgctt acggcgtgag cagctttttg ctaggcattt ttggaataga | 780 |
| gcaggtacta tgggtgacac tgtgcctcaa tccttatata ttaaaggcac aggtatgcgt | 840 |
| gcttcacctg cagctgtgt gtattctccc tctccaagtg gctctattgt tacctctgac | 900 |
| tcccagttgt ttaataaacc atattggtta cataaggcac agggtcataa caatggtgtt | 960 |
| tgctggcata atcaattatt tgttactgtg gtagatacca ctcgcagtac caatttaaca | 1020 |
| atatgtgctt ctacacagtc tcctgtacct gggcaatatg atgctaccaa atttaagcag | 1080 |
| tatagcagac atgttgagga atatgatttg cagtttattt ttcagttgtg tactattact | 1140 |
| ttaactgcag atgttatgtc ctatattcat agtatgaata gcagtatttt agaggattgg | 1200 |
| aactttggtg ttccccccccc gccaactact agtttggtgg atacatatcg ttttgtacaa | 1260 |
| tctgttgcta ttgcctgtca aaaggatgct gcaccggctg aaaataagga tcccctatgat | 1320 |
| aagttaaagt tttggaatgt ggatttaaag gaaaagtttt ctttagactt agatcaatat | 1380 |
| cccctttggac gtaaattttt ggttcaggct ggattgcgtc gcaagcccac cataggccct | 1440 |
| cgcaaacgtt ctgctccatc tgccactacg gcttctaaac ctgccaagcg tgtgcgtgta | 1500 | cgtgccagga agtaa                                                          1515

<210> SEQ ID NO 26
<211> LENGTH: 1521
<212> TYPE: DNA
<213> ORGANISM: Artificial Sequence
<220> FEATURE:
<223> OTHER INFORMATION: The DNA sequence encoding H18N65-45T4

<400> SEQUENCE: 26
atgcggccta gtgacaatac cgtatatctt ccacctcctt ctgtggcaag agttgtaaat    60
accgatgatt acgtgactcg cacaagcata ttttatcatg ctggcagctc tagattatta   120
actgttggta atccatattt tagggttcct gcaggtggtg gcaataagca ggatattcct   180
aaggtttctg cataccaata tagagtattt agggtgcagt tacctgaccc aaataaattt   240
ggtttacctg atactagtat ttataatcct gaaacacaac gtttagtgtg ggcctgtgct   300
ggagtggaaa ttggccgtgg tcagccttta ggtgttggcc ttagtgggca tccattttat   360
aataaattag atgacactga agttcccat gccgccacgt ctaatgtttc tgaggacgtt    420
agggacaatg tgtctgtaga ttataagcag acacagttat gtattttggg ctgtgcccct   480
gctattgggg aacactgggc taaaggcact gcttgtaaat cgcgtccttt atcacagggc   540
gattgccccc ctttagaact aaaaacaca gttttggaag atggtgatat ggtagatact    600
ggatacggcg ccatggactt cagcaccctg caggacacca gtgcgaggt gcccctggac    660
atctgccaga gcatctgcaa gtaccccgac tacctgcaga tgagcgccga ccccctacggc  720
gacagcatgt tcttctgcct gaggagggag cagctgttcg ccaggcactt ctggaacagg   780
gccggcgtga tgggcgacac cgtgcccacc gacctgtaca tcaagggcac cagcgccaac   840
atgagggaga ccccggcag ctgcgtgtac agccccagcc cagcggcag catcgttacc     900
tctgactccc agttgtttaa taaaccatat tggttacata aggcacaggg tcataacaat   960
ggtgtttgct ggcataatca attatttgtt actgtggtag ataccactcg cagtaccaat  1020
ttaacaatat gtgcttctac acagtctcct gtacctgggc aatatgatgc taccaaattt  1080
aagcagtata gcagacatgt tgaggaatat gatttgcagt ttatttttca gttgtgtact  1140
attactttaa ctgcagatgt tatgtcctat attcatagta tgaatagcag tattttagag  1200
gattggaact ttggtgttcc ccccccgcca actactagtt tggtggatac atatcgtttt  1260
gtacaatctg ttgctattgc ctgtcaaaag gatgctgcac cggctgaaaa taaggatccc  1320
tatgataagt taaagttttg gaatgtggat ttaaaggaaa gttttctttt agacttagat  1380
caatatcccc ttggacgtaa attttggtt caggctggat tgcgtcgcaa gcccaccata   1440
ggccctcgca aacgttctgc tccatctgcc actacggctt ctaaacctgc caagcgtgtg  1500
cgtgtacgtg ccaggaagta a                                            1521

<210> SEQ ID NO 27
<211> LENGTH: 1515
<212> TYPE: DNA
<213> ORGANISM: Artificial Sequence
<220> FEATURE:
<223> OTHER INFORMATION: The DNA sequence encoding H18N65-45T5

<400> SEQUENCE: 27
atgcggccta gtgacaatac cgtatatctt ccacctcctt ctgtggcaag agttgtaaat    60
accgatgatt acgtgactcg cacaagcata ttttatcatg ctggcagctc tagattatta   120

```
actgttggta atccatattt tagggttcct gcaggtggtg gcaataagca ggatattcct      180
aaggtttctg cataccaata tagagtattt agggtgcagt tacctgaccc aaataaattt      240
ggtttacctg atactagtat ttataatcct gaaacacaac gtttagtgtg ggcctgtgct      300
ggagtggaaa ttggccgtgg tcagccttta ggtgttggcc ttagtgggca tccattttat      360
aataaattag atgacactga aagttcccat gccgccacgt ctaatgtttc tgaggacgtt      420
agggacaatg tgtctgtaga ttataagcag acacagttat gtattttggg ctgtgcccct      480
gctattgggg aacactgggc taaaggcact gcttgtaaat cgcgtccttt atcacagggc      540
gattgccccc ctttagaact aaaaacaca  gttttggaag atggtgatat ggtagatact      600
ggatatggtg ccatggactt tagtacattg caagatacta aatgtgaggt accattggat      660
atttgtcagt ctatttgtaa atatcctgat tatttacaaa tgtctgcaga tccttatggg      720
gattccatgt ttttttgctt acggcgtgag cagcttttg  ctaggcattt ttggaataga      780
gcaggtacta tgggtgacac tgtgcctcaa tccttatata ttaaaggcac aggtatgcgt      840
gcttcacctg gcagctgtgt gtattctccc tctccaagtg gctctattgt tacctctgac      900
tcccagttgt ttaataaacc atattggtta cataaggcac agggtcataa caatggtgtt      960
tgctggcata atcaattatt tgttactgtg gtagatacca ctcgcagtac caatttaaca     1020
atatgcgcca gcacccagaa ccccgtgccc agcacctacg accccaccaa gttcaagcag     1080
tacagcaggc acgtggagga gtacgacctg cagttcatct tccagctgtg caccatcacc     1140
ctgaccgccg atgttatgtc ctatattcat agtatgaata gcagtatttt agaggattgg     1200
aactttggtg ttccccccc  gccaactact agttggtgg  atacatatcg ttttgtacaa     1260
tctgttgcta ttgcctgtca aaaggatgct gcaccggctg aaaataagga tccctatgat     1320
aagttaaagt tttggaatgt ggatttaaag gaaaagtttt ctttagactt agatcaatat     1380 cccccttggac gtaaattttt ggttcaggct ggattgcgtc gcaagcccac cataggccct     1440
cgcaaacgtt ctgctccatc tgccactacg gcttctaaac ctgccaagcg tgtgcgtgta     1500
cgtgccagga agtaa                                                     1515
```

<210> SEQ ID NO 28
<211> LENGTH: 1515
<212> TYPE: DNA
<213> ORGANISM: Artificial Sequence
<220> FEATURE:
<223> OTHER INFORMATION: The DNA sequence encoding H18N65-45T3-59S1

<400> SEQUENCE: 28

```
atgcggccta gtgacaatac cgtatatctt ccacctcctt ctgtggcaag agttgtaaat       60
accgatgatt acgtgactcg cacaagcata ttttatcatg ctggcagctc tagattatta      120
actgttggta atccatattt caaggtgccc aagggcggca acggcaggca ggacgtgccc      180
aaggtgagcg cataccaata tagagtattt agggtgcagt tacctgaccc aaataaattt      240
ggtttacctg atactagtat ttataatcct gaaacacaac gtttagtgtg ggcctgtgct      300
ggagtggaaa ttggccgtgg tcagccttta ggtgttggcc ttagtgggca tccattttat      360
aataaattag atgacactga aagttcccat gccgccacgt ctaatgtttc tgaggacgtt      420
agggacaatg tgtctgtaga ttataagcag acacagttat gtattttggg ctgtgccccc      480
gccatcggcg agcactgggc caagggcacc ctgtgcaagc cgcccagct gcagcccggc      540 gactgccccc ccctggagct gaagaacacc gttttggaag atggtgatat ggtagatact      600
ggatatggtg ccatggactt tagtacattg caagatacta aatgtgaggt accattggat      660
```

| atttgtcagt ctatttgtaa atatcctgat tatttacaaa tgtctgcaga tccttatggg | 720 |
| gattccatgt ttttttgctt acggcgtgag cagcttttg ctaggcattt ttggaataga | 780 |
| gcaggtacta tgggtgacac tgtgcctcaa tccttatata ttaaaggcac aggtatgcgt | 840 |
| gcttcacctg gcagctgtgt gtattctccc tctccaagtg gctctattgt tacctctgac | 900 |
| tcccagttgt ttaataaacc atattggtta cataaggcac agggtcataa caatggtgtt | 960 |
| tgctggcata atcaattatt tgttactgtg gtagatacca ctcgcagtac caatttaaca | 1020 |
| atatgtgctt ctacacagtc tcctgtacct gggcaatatg atgctaccaa atttaagcag | 1080 |
| tatagcagac atgttgagga atatgatttg cagtttattt ttcagttgtg tactattact | 1140 |
| ttaactgcag atgttatgtc ctatattcat agtatgaata gcagtatttt agaggattgg | 1200 |
| aactttggtg ttccccccc gccaactact agtttggtgg atacatatcg ttttgtacaa | 1260 |
| tctgttgcta ttgcctgtca aaaggatgct gcaccggctg aaaataagga tccctatgat | 1320 |
| aagttaaagt tttggaatgt ggatttaaag gaaaagtttt ctttagactt agatcaatat | 1380 |
| ccccttggac gtaaattttt ggttcaggct ggattgcgtc gcaagcccac cataggccct | 1440 |
| cgcaaacgtt ctgctccatc tgccactacg gcttctaaac tgccaagcg tgtgcgtgta | 1500 |
| cgtgccagga agtaa | 1515 |

<210> SEQ ID NO 29
<211> LENGTH: 1515
<212> TYPE: DNA
<213> ORGANISM: Artificial Sequence
<220> FEATURE:
<223> OTHER INFORMATION: The DNA sequence encoding H18N65-45T3-59S2

<400> SEQUENCE: 29

| atgcggccta gtgacaatac cgtatatctt ccacctcctt ctgtggcaag agttgtaaat | 60 |
| accgatgatt acgtgactcg cacaagcata ttttatcatg ctggcagctc tagattatta | 120 |
| actgttggta atccatattt tagggttcct gcaggtggtg gcaataagca ggatattcct | 180 |
| aaggtttctg cataccaata tagagtattt agggtgcagt tacctgaccc aaataaattt | 240 |
| ggtttacctg atactagtat ttataatcct gaaacacaac gtttagtgtg ggcctgtgct | 300 |
| ggcgtggaga tcggcagggg ccagcccctg gcgtgggcc tgagcggcca ccccctgtac | 360 |
| aacaagctgg acgacaccga gaacagccac gtggccagcg ccgtgacac caaggacacc | 420 |
| agggacaacg tgagcgtgga ctacaagcag acccagctgt gcatcttggg ctgtgccccc | 480 |
| gccatcggcg agcactgggc caagggcacc ctgtgcaagc ccgcccagct gcagcccggc | 540 |
| gactgccccc ccctggagct gaagaacacc gttttggaag atggtgatat ggtagatact | 600 |
| ggatatggtg ccatggactt tagtacattg caagatacta atgtgaggt accattggat | 660 |
| atttgtcagt ctatttgtaa atatcctgat tatttacaaa tgtctgcaga tccttatggg | 720 |
| gattccatgt ttttttgctt acggcgtgag cagcttttg ctaggcattt ttggaataga | 780 |
| gcaggtacta tgggtgacac tgtgcctcaa tccttatata ttaaaggcac aggtatgcgt | 840 |
| gcttcacctg gcagctgtgt gtattctccc tctccaagtg gctctattgt tacctctgac | 900 |
| tcccagttgt ttaataaacc atattggtta cataaggcac agggtcataa caatggtgtt | 960 |
| tgctggcata atcaattatt tgttactgtg gtagatacca ctcgcagtac caatttaaca | 1020 |
| atatgtgctt ctacacagtc tcctgtacct gggcaatatg atgctaccaa atttaagcag | 1080 |
| tatagcagac atgttgagga atatgatttg cagtttattt ttcagttgtg tactattact | 1140 |

| | | |
|---|---|---|
| ttaactgcag atgttatgtc ctatattcat agtatgaata gcagtatttt agaggattgg | 1200 | |
| aactttggtg ttcccccccc gccaactact agtttggtgg atacatatcg ttttgtacaa | 1260 | |
| tctgttgcta ttgcctgtca aaaggatgct gcaccggctg aaaataagga tccctatgat | 1320 | |
| aagttaaagt tttggaatgt ggatttaaag gaaaagtttt ctttagactt agatcaatat | 1380 | |
| ccccttggac gtaaattttt ggttcaggct ggattgcgtc gcaagcccac cataggccct | 1440 | |
| cgcaaacgtt ctgctccatc tgccactacg gcttctaaac ctgccaagcg tgtgcgtgta | 1500 | |
| cgtgccagga agtaa | 1515 | |

<210> SEQ ID NO 30
<211> LENGTH: 1515
<212> TYPE: DNA
<213> ORGANISM: Artificial Sequence
<220> FEATURE:
<223> OTHER INFORMATION: The DNA sequence encoding H18N65-45T3-59S4

<400> SEQUENCE: 30

| | | |
|---|---|---|
| atgcggccta gtgacaatac cgtatatctt ccacctcctt ctgtggcaag agttgtaaat | 60 | |
| accgatgatt acgtgactcg cacaagcata ttttatcatg ctggcagctc tagattatta | 120 | |
| actgttggta atccatattt tagggttcct gcaggtggtg gcaataagca ggatattcct | 180 | |
| aaggtttctg cataccaata tagagtattt agggtgcagt tacctgaccc aaataaattt | 240 | |
| ggtttacctg atactagtat tttataatcct gaaacacaac gttagtgtg ggcctgtgct | 300 | |
| ggagtggaaa ttggccgtgg tcagccttta ggtgttggcc ttagtgggca tccattttat | 360 | |
| aataaattag atgacactga agttcccat gccgccacgt ctaatgtttc tgaggacgtt | 420 | |
| agggacaatg tgtctgtaga ttataagcag acacagttat gtattttggg ctgtgccccc | 480 | |
| gccatcggcg agcactgggc caagggcacc ctgtgcaagc cgcccagct gcagcccggc | 540 | |
| gactgccccc ccctggagct gaagaacacc gttttggaag atggtgatat ggtagatact | 600 | |
| ggatatggtg ccatggactt tagtacattg caagatacta atgtgaggt accattggat | 660 | |
| atttgtcagt ctatttgtaa atatcctgat tatttacaaa tgtctgcaga tccttatggg | 720 | |
| gattccatgt ttttttgctt acggcgtgag cagcttttcg ccaggcactt ctggaacagg | 780 | |
| agcggcacca tgggcgacca gctgcccgag agcctgtaca tcaagggcac cgacatcagg | 840 | |
| gccaaccccg gcagctacct gtacagcccc agcccagcg gctctattgt tacctctgac | 900 | |
| tcccagttgt ttaataaacc atattggtta cataaggcac agggtcataa caatggtgtt | 960 | |
| tgctggggcata atcaattatt tgttactgtg gtagatacca ctcgcagtac caatttaaca | 1020 | |
| atatgtgctt ctacacagtc tcctgtacct gggcaatatg atgctaccaa atttaagcag | 1080 | |
| tatagcagac atgttgagga atatgatttg cagtttattt ttcagttgtg tactattact | 1140 | |
| ttaactgcag atgttatgtc ctatattcat agtatgaata gcagtatttt agaggattgg | 1200 | |
| aactttggtg ttcccccccc gccaactact agtttggtgg atacatatcg ttttgtacaa | 1260 | |
| tctgttgcta ttgcctgtca aaaggatgct gcaccggctg aaaataagga tccctatgat | 1320 | |
| aagttaaagt tttggaatgt ggatttaaag gaaaagtttt ctttagactt agatcaatat | 1380 | |
| ccccttggac gtaaattttt ggttcaggct ggattgcgtc gcaagcccac cataggccct | 1440 | |
| cgcaaacgtt ctgctccatc tgccactacg gcttctaaac ctgccaagcg tgtgcgtgta | 1500 | |
| cgtgccagga agtaa | 1515 | |

<210> SEQ ID NO 31
<211> LENGTH: 1515

<212> TYPE: DNA
<213> ORGANISM: Artificial Sequence
<220> FEATURE:
<223> OTHER INFORMATION: The DNA sequence encoding H18N65-45T3-59S5

<400> SEQUENCE: 31

| | | | | | |
|---|---|---|---|---|---|
| atgcggccta | gtgacaatac | cgtatatctt | ccacctcctt | ctgtggcaag | agttgtaaat | 60 |
| accgatgatt | acgtgactcg | cacaagcata | ttttatcatg | ctggcagctc | tagattatta | 120 |
| actgttggta | atccatattt | tagggttcct | gcaggtggtg | gcaataagca | ggatattcct | 180 |
| aaggtttctg | cataccaata | tagagtattt | agggtgcagt | tacctgaccc | aaataaattt | 240 |
| ggtttacctg | tatactagtat | ttataatcct | gaaacacaac | gtttagtgtg | ggcctgtgct | 300 |
| ggagtggaaa | ttggccgtgg | tcagccttta | ggtgttggcc | ttagtgggca | tccattttat | 360 |
| aataaattag | atgacactga | agttcccat | gccgccacgt | ctaatgtttc | tgaggacgtt | 420 |
| agggacaatg | tgtctgtaga | ttataagcag | acacagttat | gtattttggg | ctgtgccccc | 480 |
| gccatcggcg | agcactgggc | caagggcacc | ctgtgcaagc | cgcccagct | gcagcccggc | 540 |
| gactgccccc | ccctggagct | gaagaacacc | gttttggaag | atggtgatat | ggtagatact | 600 |
| ggatatggtg | ccatggactt | tagtacattg | caagatacta | atgtgaggt | accattggat | 660 |
| atttgtcagt | ctatttgtaa | atatcctgat | tatttacaaa | tgtctgcaga | tccttatggg | 720 |
| gattccatgt | ttttttgctt | acggcgtgag | cagcttttg | ctaggcattt | ttggaataga | 780 |
| gcaggtacta | tgggtgacac | tgtgcctcaa | tccttatata | ttaaaggcac | aggtatgcgt | 840 |
| gcttcacctg | gcagctgtgt | gtattctccc | tctccaagtg | gctctattgt | tacctctgac | 900 |
| tcccagttgt | ttaataaacc | atattggtta | cataaggcac | agggtcataa | caatggtgtt | 960 |
| tgctggcata | tcaattatt | tgttactgtg | gtagatacca | ctcgcagtac | caatttaaca | 1020 |
| atatgcgcca | gcaccaccag | cagcatcccc | aacgtgtaca | cccccaccag | cttcaagcag | 1080 |
| tatagcagac | atgttgagga | atatgattg | cagtttattt | ttcagttgtg | tactattact | 1140 |
| ttaactgcag | atgttatgtc | ctatattcat | agtatgaata | gcagtatttt | agaggattgg | 1200 |
| aactttggtg | ttccccccc | gccaactact | agtttggtgg | atacatatcg | ttttgtacaa | 1260 |
| tctgttgcta | ttgcctgtca | aaaggatgct | gcaccggctg | aaaataagga | tcctatgat | 1320 |
| aagttaaagt | tttggaatgt | ggatttaaag | gaaaagtttt | ctttagactt | agatcaatat | 1380 |
| cccttggac | gtaaatttt | ggttcaggct | ggattgcgtc | gcaagccac | cataggccct | 1440 |
| cgcaaacgtt | ctgctccatc | tgccactacg | gcttctaaac | tgccaagcg | tgtgcgtgta | 1500 |
| cgtgccagga | agtaa | | | | | 1515 |

<210> SEQ ID NO 32
<211> LENGTH: 1521
<212> TYPE: DNA
<213> ORGANISM: Artificial Sequence
<220> FEATURE:
<223> OTHER INFORMATION: The DNA sequence encoding H18N65-45T4-59S1

<400> SEQUENCE: 32

| | | | | | |
|---|---|---|---|---|---|
| atgcggccta | gtgacaatac | cgtatatctt | ccacctcctt | ctgtggcaag | agttgtaaat | 60 |
| accgatgatt | acgtgactcg | cacaagcata | ttttatcatg | ctggcagctc | tagattatta | 120 |
| actgttggta | atccctactt | caaggtgccc | aagggcggca | acggcaggca | ggacgtgccc | 180 |
| aaggtgagcg | cctaccagta | cagggtattt | agggtgcagt | tacctgaccc | aaataaattt | 240 |
| ggtttacctg | tatactagtat | ttataatcct | gaaacacaac | gtttagtgtg | ggcctgtgct | 300 |

```
ggagtggaaa ttggccgtgg tcagcccttta ggtgttggcc ttagtgggca tccatttat      360 aataaattag atgacactga aagttcccat gccgccacgt ctaatgtttc tgaggacgtt      420
agggacaatg tgtctgtaga ttataagcag acacagttat gtattttggg ctgtgcccct     480
gctattgggg aacactgggc taaaggcact gcttgtaaat cgcgtccttt atcacagggc     540
gattgccccc ctttagaact taaaaacaca gttttggaag atggtgatat ggtagatact     600
ggatacggcg ccatggactt cagcaccctg caggacacca agtgcgaggt gcccctggac     660
atctgccaga gcatctgcaa gtaccccgac tacctgcaga tgagcgccga ccccctacggc   720 gacagcatgt tcttctgcct gaggagggag cagctgttcg ccaggcactt ctggaacagg    780
gccggcgtga tgggcgacac cgtgcccacc gacctgtaca tcaagggcac cagcgccaac    840
atgagggaga cccccggcag ctgcgtgtac agccccagcc ccagcggcag catcgttacc    900
tctgactccc agttgtttaa taaaccatat tggttacata aggcacaggg tcataacaat    960
ggtgtttgct ggcataatca attatttgtt actgtggtag ataccactcg cagtaccaat    1020
ttaacaatat gtgcttctac acagtctcct gtacctgggc aatatgatgc taccaaattt   1080
aagcagtata gcagacatgt tgaggaatat gatttgcagt ttattttca gttgtgtact    1140 attactttaa ctgcagatgt tatgtccttat attcatagta tgaatagcag tattttagag  1200
gattggaact ttggtgttcc ccccccgcca actactagtt tggtggatac atatcgtttt   1260
gtacaatctg ttgctattgc ctgtcaaaag gatgctgcac cggctgaaaa taaggatccc   1320
tatgataagt taaagttttg gaatgtggat ttaaaggaaa agttttcttt agacttagat    1380
caatatcccc ttggacgtaa attttttggtt caggctggat tgcgtcgcaa gcccaccata   1440
ggccctcgca acgttctgc tccatctgcc actacggctt ctaaacctgc caagcgtgtg    1500
cgtgtacgtg ccaggaagta a                                              1521

<210> SEQ ID NO 33
<211> LENGTH: 1521
<212> TYPE: DNA
<213> ORGANISM: Artificial Sequence
<220> FEATURE:
<223> OTHER INFORMATION: The DNA sequence encoding H18N65-45T4-59S2

<400> SEQUENCE: 33
atgcggccta gtgacaatac cgtatatctt ccacctcctt ctgtggcaag agttgtaaat      60
accgatgatt acgtgactcg cacaagcata ttttatcatg ctggcagctc tagattatta     120
actgttggta atccatattt taggttcct gcaggtggtg gcaataagca ggatattcct      180
aaggtttctg cataccaata tagagtattt agggtgcagt tacctgaccc aaataaattt     240
ggtttacctg atactagtat ttataatcct gaaacacaac gtttagtgtg gcctgtgct    300 ggcgtggaga tcggcagggg ccagcccctg ggcgtgggcc tgagcggcca ccccctgtac    360
aacaagctgg acgacaccga aacagccac gtggccagcg ccgtggacac caaggacacc    420
agggacaacg tgagcgtgga ctacaagcag acccagctgt gcatcttggg ctgtgcccct    480
gctattgggg aacactgggc taaaggcact gcttgtaaat cgcgtccttt atcacagggc    540
gattgccccc ctttagaact taaaaacaca gttttggaag atggtgatat ggtagatact    600
ggatacggcg ccatggactt cagcaccctg caggacacca agtgcgaggt gcccctggac    660
atctgccaga gcatctgcaa gtaccccgac tacctgcaga tgagcgccga ccccctacggc   720 gacagcatgt tcttctgcct gaggagggag cagctgttcg ccaggcactt ctggaacagg    780
gccggcgtga tgggcgacac cgtgcccacc gacctgtaca tcaagggcac cagcgccaac    840
```

| | |
|---|---|
| atgagggaga cccccggcag ctgcgtgtac agccccagcc ccagcggcag catcgttacc | 900 |
| tctgactccc agttgtttaa taaaccatat tggttacata aggcacaggg tcataacaat | 960 |
| ggtgtttgct ggcataatca attatttgtt actgtggtag ataccactcg cagtaccaat | 1020 |
| ttaacaatat gtgcttctac acagtctcct gtacctgggc aatatgatgc taccaaattt | 1080 |
| aagcagtata gcagacatgt tgaggaatat gatttgcagt ttattttca gttgtgtact | 1140 |
| attactttaa ctgcagatgt tatgtcctat attcatagta tgaatagcag tattttagag | 1200 |
| gattggaact ttggtgttcc ccccccgcca actactagtt tggtggatac atatcgtttt | 1260 |
| gtacaatctg ttgctattgc ctgtcaaaag gatgctgcac cggctgaaaa taaggatccc | 1320 |
| tatgataagt taaagttttg gaatgtggat ttaaaggaaa agttttcttt agacttagat | 1380 |
| caatatcccc ttggacgtaa attttggtt caggctggat tgcgtcgcaa gcccaccata | 1440 |
| ggccctcgca aacgttctgc tccatctgcc actacggctt ctaaacctgc caagcgtgtg | 1500 |
| cgtgtacgtg ccaggaagta a | 1521 |

<210> SEQ ID NO 34
<211> LENGTH: 1521
<212> TYPE: DNA
<213> ORGANISM: Artificial Sequence
<220> FEATURE:
<223> OTHER INFORMATION: The DNA sequence encoding H18N65-45T4-59S3

<400> SEQUENCE: 34

| | |
|---|---|
| atgcggccta gtgacaatac cgtatatctt ccacctcctt ctgtggcaag agttgtaaat | 60 |
| accgatgatt acgtgactcg cacaagcata ttttatcatg ctggcagctc tagattatta | 120 |
| actgttggta atccatattt tagggttcct gcaggtggtg gcaataagca ggatattcct | 180 |
| aaggtttctg cataccaata tagagtattt agggtgcagt tacctgaccc aaataaattt | 240 |
| ggtttacctg atactagtat ttataatcct gaaacacaac gtttagtgtg ggcctgtgct | 300 |
| ggagtggaaa ttggccgtgg tcagcccttt ggtgttggcc ttagtgggca tccatttat | 360 |
| aataaattag atgacactga agttcccat gccgccacgt ctaatgtttc tgaggacgtt | 420 |
| agggacaatg tgtctgtaga ttataagcag acacagttat gtatttgggg ctgtgccccc | 480 |
| gccatcggcg agcactggac caagggcacc gcctgcaagc ccaccaccgt ggtgcagggc | 540 |
| gactgccccc ccctggagct gaaaacaca gttttggaag atggtgatat ggtagatact | 600 |
| ggatacggcg ccatggactt cagcaccctg caggacacca gtgcgaggt gcccctggac | 660 |
| atctgccaga gcatctgcaa gtaccccgac tacctgcaga tgagcgccga cccctacggc | 720 |
| gacagcatgt tcttctgcct gaggagggag cagctgttcg ccaggcactt ctggaacagg | 780 |
| gccggcgtga tgggcgacac cgtgcccacc gacctgtaca tcaagggcac cagcgccaac | 840 |
| atgagggaga cccccggcag ctgcgtgtac agccccagcc ccagcggcag catcgttacc | 900 |
| tctgactccc agttgtttaa taaaccatat tggttacata aggcacaggg tcataacaat | 960 |
| ggtgtttgct ggcataatca attatttgtt actgtggtag ataccactcg cagtaccaat | 1020 |
| ttaacaatat gtgcttctac acagtctcct gtacctgggc aatatgatgc taccaaattt | 1080 |
| aagcagtata gcagacatgt tgaggaatat gatttgcagt ttattttca gttgtgtact | 1140 |
| attactttaa ctgcagatgt tatgtcctat attcatagta tgaatagcag tattttagag | 1200 |
| gattggaact ttggtgttcc ccccccgcca actactagtt tggtggatac atatcgtttt | 1260 |
| gtacaatctg ttgctattgc ctgtcaaaag gatgctgcac cggctgaaaa taaggatccc | 1320 |

| | |
|---|---|
| tatgataagt taaagttttg aatgtggat ttaaaggaaa agttttcttt agacttagat | 1380 |
| caatatcccc ttggacgtaa atttttggtt caggctggat tgcgtcgcaa gcccaccata | 1440 |
| ggccctcgca aacgttctgc tccatctgcc actacggctt ctaaacctgc caagcgtgtg | 1500 |
| cgtgtacgtg ccaggaagta a | 1521 |

<210> SEQ ID NO 35
<211> LENGTH: 1521
<212> TYPE: DNA
<213> ORGANISM: Artificial Sequence
<220> FEATURE:
<223> OTHER INFORMATION: The DNA sequence encoding H18N65-45T4-59S5

<400> SEQUENCE: 35

| | |
|---|---|
| atgcggccta gtgacaatac cgtatatctt ccacctcctt ctgtggcaag agttgtaaat | 60 |
| accgatgatt acgtgactcg cacaagcata ttttatcatg ctggcagctc tagattatta | 120 |
| actgttggta atccatattt tagggttcct gcaggtggtg caataagca ggatattcct | 180 |
| aaggtttctg cataccaata tagagtattt agggtgcagt tacctgaccc aaataaattt | 240 |
| ggtttacctg atactagtat ttataatcct gaaacacaac gtttagtgtg ggcctgtgct | 300 |
| ggagtggaaa ttggccgtgg tcagccttta ggtgttggcc ttagtgggca tccattttat | 360 |
| aataaattag atgacactga aagttcccat gccgccacgt ctaatgtttc tgaggacgtt | 420 |
| agggacaatg tgtctgtaga ttataagcag acacagttat gtattttggg ctgtgcccct | 480 |
| gctattgggg aacactgggc taaaggcact gcttgtaaat cgcgtccttt atcacagggc | 540 |
| gattgccccc ctttagaact taaaacacac gttttggaag atggtgatat ggtagatact | 600 |
| ggatacgcg ccatggactt cagcaccctg caggacacca gtgcgaggt gcccctggac | 660 |
| atctgccaga gcatctgcaa gtaccccgac tacctgcaga tgagcgccga cccctacggc | 720 |
| gacagcatgt tcttctgcct gaggagggag cagctgttcg ccaggcactt ctggaacagg | 780 |
| gccggcgtga tgggcgacac cgtgcccacc gacctgtaca tcaagggcac cagcgccaac | 840 |
| atgagggaga cccccggcag ctgcgtgtac agccccagcc cagcggcag catcgttacc | 900 |
| tctgactccc agttgtttaa taaaccatat tggttacata aggcacaggg tcataacaat | 960 |
| ggtgtttgct ggcataatca attatttgtt actgtggtag ataccactcg cagtaccaat | 1020 |
| ttaacaatat cgccagcac caccagcagc atccccaacg tgtacacccc caccagcttc | 1080 |
| aagcagtata gcagacatgt tgaggaatat gatttgcagt ttattttca gttgtgtact | 1140 |
| attactttaa ctgcagatgt tatgtcctat attcatagta tgaatagcag tattttagag | 1200 |
| gattggaact ttggtgttcc cccccgcca actactagtt tggtggatac atatcgtttt | 1260 |
| gtacaatctg ttgctattgc ctgtcaaaag gatgctgcac cggctgaaaa taaggatccc | 1320 |
| tatgataagt taaagttttg aatgtggat ttaaaggaaa agttttcttt agacttagat | 1380 |
| caatatcccc ttggacgtaa atttttggtt caggctggat tgcgtcgcaa gcccaccata | 1440 |
| ggccctcgca aacgttctgc tccatctgcc actacggctt ctaaacctgc caagcgtgtg | 1500 |
| cgtgtacgtg ccaggaagta a | 1521 |

<210> SEQ ID NO 36
<211> LENGTH: 1518
<212> TYPE: DNA
<213> ORGANISM: Artificial Sequence
<220> FEATURE:
<223> OTHER INFORMATION: The DNA sequence encoding H18N65-45T1-59S5

<400> SEQUENCE: 36

```
atgcggccta gtgacaatac cgtatatctt ccacctcctt ctgtggcaag agttgtaaat    60
accgatgatt acgtgactag gaccagcatc ttctaccacg ccggcagcag caggctgctg   120
accgtgggca accccctactt cagggtggtg cccaacggcg ccggcaacaa gcaggccgtg   180
cccaaggtga gcgcctacca gtacagggtg ttcagggtgc agttacctga cccaaataaa   240
tttggtttac ctgatactag tatttataat cctgaaacac aacgtttagt gtgggcctgt   300
gctggagtgg aaattggccg tggtcagcct ttaggtgttg gccttagtgg gcatccattt   360
tataataaat tagatgacac tgaaagttcc catgccgcca cgtctaatgt ttctgaggac   420
gttagggaca atgtgtctgt agattataag cagacacagt tatgtatttt gggctgtgcc   480
cctgctattg gggaacactg ggctaaaggc actgcttgta atcgcgtcc tttatcacag   540
ggcgattgcc ccccttttaga acttaaaaac acagttttgg aagatggtga tatggtagat   600
actggatatg gtgccatgga ctttagtaca ttgcaagata ctaaatgtga ggtaccattg   660
gatatttgtc agtctatttg taaatatcct gattatttac aaatgtctgc agatccttat   720
ggggattcca tgttttttttg cttacggcgt gagcagcttt ttgctaggca ttttttggaat   780
agagcaggta ctatgggtga cactgtgcct caatccttat atattaaagg cacaggtatg   840
cgtgcttcac ctggcagctg tgtgtattct ccctctccaa gtggctctat tgttacctct   900
gactcccagt tgtttaataa accatattgg ttacataagg cacagggtca taacaatggt   960
gtttgctggc ataatcaatt atttgttact gtggtagata ccactcgcag taccaattta   1020
acaatatgcg ccagcaccac cagcagcatc cccaacgtgt acacccccac cagcttcaag   1080
cagtatagca gacatgttga ggaatatgat ttgcagttta ttttttcagtt gtgtactatt   1140
actttaactg cagatgttat gtcctatatt catagtatga atagcagtat tttagaggat   1200
tggaacttttg tgttcccccc cccgccaact actagtttgg tggatacata tcgttttgta   1260
caatctgttg ctattgcctg tcaaaaggat gctgcaccgg ctgaaaataa ggatccctat   1320
gataagttaa agttttggaa tgtggattta aaggaaaagt tttctttaga cttagatcaa   1380
tatcccctg gacgtaaaatt tttggttcag gctggattgc gtcgcaagcc caccataggc   1440
cctcgcaaac gttctgctcc atctgccact acggcttcta aacctgccaa gcgtgtgcgt   1500
gtacgtgcca ggaagtaa                                                 1518
```

<210> SEQ ID NO 37
<211> LENGTH: 1515
<212> TYPE: DNA
<213> ORGANISM: Artificial Sequence
<220> FEATURE:
<223> OTHER INFORMATION: The DNA sequence encoding H18N65-45T2-59S5

<400> SEQUENCE: 37

```
atgcggccta gtgacaatac cgtatatctt ccacctcctt ctgtggcaag agttgtaaat    60
accgatgatt acgtgactcg cacaagcata ttttatcatg ctggcagctc tagattatta   120
actgttggta atccatattt tagggttcct gcaggtggtg gcaataagca ggatattcct   180
aaggtttctg cataccaata tagagtattt agggtgcagt tacctgaccc aaataaattt   240
ggtttacctg atactagtat ttataatcct gaaacacaac gtttagtgtg gcctgtgct   300
ggagtgggaga tcggcagggg ccagcccctg ggcatcggcc tgagcggcca ccccttctac   360
aacaagctgg acgacaccga gagcgcccac gccgccaccg ccgtgatcac ccaggacgtg   420
agggacaacg tgagcgtgga ctacaagcag acccagctgt gcatcctggg ctgcgcccct   480
```

```
gctattgggg aacactgggc taaaggcact gcttgtaaat cgcgtccttt atcacagggc    540
gattgccccc ctttagaact taaaaacaca gttttggaag atggtgatat ggtagatact    600
ggatatggtg ccatggactt tagtacattg caagatacta aatgtgaggt accattggat    660
atttgtcagt ctatttgtaa atatcctgat tatttacaaa tgtctgcaga tccttatggg    720
gattccatgt ttttttgctt acggcgtgag cagcttttg  ctaggcattt ttggaataga    780
gcaggtacta tgggtgacac tgtgcctcaa tccttatata ttaaaggcac aggtatgcgt    840
gcttcacctg gcagctgtgt gtattctccc tctccaagtg gctctattgt tacctctgac    900
tcccagttgt ttaataaacc atattggtta cataaggcac agggtcataa caatggtgtt    960
tgctggcata atcaattatt tgttactgtg gtagatacca ctcgcagtac caatttaaca   1020
atatgcgcca gcaccaccag cagcatcccc aacgtgtaca cccccaccag cttcaagcag   1080
tatagcagac atgttgagga atatgatttg cagtttattt ttcagttgtg tactattact   1140
ttaactgcag atgttatgtc ctatattcat agtatgaata gcagtatttt agaggattgg   1200
aactttggtg ttcccccccc gccaactact agtttggtgg atacatatcg ttttgtacaa   1260
tctgttgcta ttgcctgtca aaaggatgct gcaccggctg aaaataagga tccctatgat   1320
aagttaaagt tttggaatgt ggatttaaag gaaaagtttt ctttagactt agatcaatat   1380
ccccttggac gtaaattttt ggttcaggct ggattgcgtc gcaagcccac cataggccct   1440
cgcaaacgtt ctgctccatc tgccactacg gcttctaaac tgccaagcg  tgtgcgtgta   1500 cgtgccagga agtaa                                                    1515

<210> SEQ ID NO 38
<211> LENGTH: 1518
<212> TYPE: DNA
<213> ORGANISM: Artificial Sequence
<220> FEATURE:
<223> OTHER INFORMATION: The DNA sequence encoding H18N65-45T1T3-59S5

<400> SEQUENCE: 38
atgcggccta gtgacaatac cgtatatctt ccacctcctt ctgtggcaag agttgtaaat     60
accgatgatt acgtgactag gaccagcatc ttctaccacg ccggcagcag caggctgctg    120
accgtgggca cccctactt  cagggtggtg cccaacggcg ccggcaacaa gcaggccgtg    180
cccaaggtga cgcctacca  gtacaggatg ttcagggtgc agttacctga cccaaataaa    240
tttggtttac ctgatactag tatttataat cctgaaacac aacgtttagt gtgggcctgt    300
gctggagtgg aaattggccg tggtcagcct ttaggtgttg gccttagtgg catccatttt    360
tataataaat tagatgacac tgaaagttcc catgccgcca cgtctaatgt ttctgaggac    420
gttagggaca atgtgtctgt agattataag cagacacagt tatgtatttt gggctgtgcc    480
cccgccatcg gcgagcactg ggccaagggc accctgtgca agcccgccca gctgcagccc    540
ggcgactgcc ccccctgga  gctgaagaac accgttttgg aagatggtga tatggtagat    600
actggatatg gtgccatgga ctttagtaca ttgcaagata ctaaatgtga ggtaccattg    660
gatatttgtc agtctatttg taaatatcct gattatttac aaatgtctgc agatccttat    720
ggggattcca tgttttttg  cttacggcgt gagcagcttt tgctaggca  ttttggaat    780 agagcaggta ctatgggtga cactgtgcct caatccttat atattaaagg cacaggtatg    840
cgtgcttcac ctggcagctg tgtgtattct ccctctccaa gtggctctat tgttacctct    900
gactcccagt tgtttaataa accatattgg ttacataagg cacagggtca taacaatggt    960
gtttgctggc ataatcaatt atttgttact gtggtagata ccactcgcag taccaattta   1020
```

```
acaatatgcg ccagcaccac cagcagcatc cccaacgtgt acaccccac cagcttcaag    1080 cagtatagca gacatgttga ggaatatgat ttgcagttta ttttcagtt gtgtactatt    1140 actttaactg cagatgttat gtcctatatt catagtatga atagcagtat tttagaggat   1200
tggaactttg gtgttccccc cccgccaact actagtttgg tggatacata tcgttttgta   1260
caatctgttg ctattgcctg tcaaaaggat gctgcaccgg ctgaaaataa ggatccctat   1320
gataagttaa agttttggaa tgtggattta aaggaaaagt tttctttaga cttagatcaa   1380
tatccccttg gacgtaaaatt tttggttcag gctggattgc gtcgcaagcc caccataggc   1440
cctcgcaaac gttctgctcc atctgccact acggcttcta aacctgccaa gcgtgtgcgt   1500
gtacgtgcca ggaagtaa                                                  1518
```

<210> SEQ ID NO 39
<211> LENGTH: 11
<212> TYPE: PRT
<213> ORGANISM: Human papillomavirus type 45

<400> SEQUENCE: 39

Val Pro Asn Gly Ala Gly Asn Lys Gln Ala Val
1               5                   10

<210> SEQ ID NO 40
<211> LENGTH: 27
<212> TYPE: PRT
<213> ORGANISM: Human papillomavirus type 45

<400> SEQUENCE: 40

Ile Gly Leu Ser Gly His Pro Phe Tyr Asn Lys Leu Asp Asp Thr Glu
1               5                   10                  15

Ser Ala His Ala Ala Thr Ala Val Ile Thr Gln
            20                  25

<210> SEQ ID NO 41
<211> LENGTH: 9
<212> TYPE: PRT
<213> ORGANISM: Human papillomavirus type 45

<400> SEQUENCE: 41

Leu Cys Lys Pro Ala Gln Leu Gln Pro
1               5

<210> SEQ ID NO 42
<211> LENGTH: 22
<212> TYPE: PRT
<213> ORGANISM: Human papillomavirus type 45

<400> SEQUENCE: 42

Val Met Gly Asp Thr Val Pro Thr Asp Leu Tyr Ile Lys Gly Thr Ser
1               5                   10                  15

Ala Asn Met Arg Glu Thr
            20

<210> SEQ ID NO 43
<211> LENGTH: 12
<212> TYPE: PRT
<213> ORGANISM: Human papillomavirus type 59

<400> SEQUENCE: 43

Lys Val Pro Lys Gly Gly Asn Gly Arg Gln Asp Val
1               5                   10

-continued

```
<210> SEQ ID NO 44
<211> LENGTH: 12
<212> TYPE: PRT
<213> ORGANISM: Human papillomavirus type 59

<400> SEQUENCE: 44

Thr Ser Ser Ile Pro Asn Val Tyr Thr Pro Thr Ser
1               5                   10

<210> SEQ ID NO 45
<211> LENGTH: 23
<212> TYPE: DNA
<213> ORGANISM: Artificial Sequence
<220> FEATURE:
<223> OTHER INFORMATION: Primer

<400> SEQUENCE: 45
cagttacctg acccaaataa att                                             23

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46
agtcacgtaa tcatcggtat                                                 20

<210> SEQ ID NO 47
<211> LENGTH: 44
<212> TYPE: DNA
<213> ORGANISM: Artificial Sequence
<220> FEATURE:
<223> OTHER INFORMATION: Primer

<400> SEQUENCE: 47
taaataccga tgattacgtg actaggacca gcatcttcta ccac                      44

<210> SEQ ID NO 48
<211> LENGTH: 45
<212> TYPE: DNA
<213> ORGANISM: Artificial Sequence
<220> FEATURE:
<223> OTHER INFORMATION: Primer

<400> SEQUENCE: 48
aatttatttg ggtcaggtaa ctgcaccctg aacaccctgt actgg                     45

<210> SEQ ID NO 49
<211> LENGTH: 27
<212> TYPE: DNA
<213> ORGANISM: Artificial Sequence
<220> FEATURE:
<223> OTHER INFORMATION: Primer

<400> SEQUENCE: 49 gccccctgcta ttggggaaca ctgggct                                        27

<210> SEQ ID NO 50
<211> LENGTH: 26
<212> TYPE: DNA
<213> ORGANISM: Artificial Sequence
<220> FEATURE:
<223> OTHER INFORMATION: Primer
```

<400> SEQUENCE: 50
cactccagca caggcccaca ctaaac                                        26

<210> SEQ ID NO 51
<211> LENGTH: 39
<212> TYPE: DNA
<213> ORGANISM: Artificial Sequence
<220> FEATURE:
<223> OTHER INFORMATION: Primer

<400> SEQUENCE: 51
gtgtgggcct gtgctggagt ggagatcggc aggggccag                          39

<210> SEQ ID NO 52
<211> LENGTH: 43
<212> TYPE: DNA
<213> ORGANISM: Artificial Sequence
<220> FEATURE:
<223> OTHER INFORMATION: Primer

<400> SEQUENCE: 52
cagtgttccc caatagcagg ggcgcagccc aggatgcaca gct                     43

<210> SEQ ID NO 53
<211> LENGTH: 23
<212> TYPE: DNA
<213> ORGANISM: Artificial Sequence
<220> FEATURE:
<223> OTHER INFORMATION: Primer

<400> SEQUENCE: 53
gttttggaag atggtgatat ggt                                           23

<210> SEQ ID NO 54
<211> LENGTH: 23
<212> TYPE: DNA
<213> ORGANISM: Artificial Sequence
<220> FEATURE:
<223> OTHER INFORMATION: Primer

<400> SEQUENCE: 54
ggcacagccc aaaatacata act                                           23

<210> SEQ ID NO 55
<211> LENGTH: 45
<212> TYPE: DNA
<213> ORGANISM: Artificial Sequence
<220> FEATURE:
<223> OTHER INFORMATION: Primer

<400> SEQUENCE: 55
agttatgtat tttgggctgt gcccccgcca tcggcgagca ctggg                   45

<210> SEQ ID NO 56
<211> LENGTH: 44
<212> TYPE: DNA
<213> ORGANISM: Artificial Sequence
<220> FEATURE:
<223> OTHER INFORMATION: Primer

<400> SEQUENCE: 56
accatatcac catcttccaa aacggtgttc ttcagctcca gggg                    44

<210> SEQ ID NO 57

```
<211> LENGTH: 23
<212> TYPE: DNA
<213> ORGANISM: Artificial Sequence
<220> FEATURE:
<223> OTHER INFORMATION: Primer

<400> SEQUENCE: 57
gttacctctg actcccagtt gtt                                           23

<210> SEQ ID NO 58
<211> LENGTH: 26
<212> TYPE: DNA
<213> ORGANISM: Artificial Sequence
<220> FEATURE:
<223> OTHER INFORMATION: Primer

<400> SEQUENCE: 58
tccagtatct accatatcac catctt                                        26

<210> SEQ ID NO 59
<211> LENGTH: 47
<212> TYPE: DNA
<213> ORGANISM: Artificial Sequence
<220> FEATURE:
<223> OTHER INFORMATION: Primer

<400> SEQUENCE: 59
gatggtgata tggtagatac tggatacggc gccatggact tcagcac                 47

<210> SEQ ID NO 60
<211> LENGTH: 47
<212> TYPE: DNA
<213> ORGANISM: Artificial Sequence
<220> FEATURE:
<223> OTHER INFORMATION: Primer

<400> SEQUENCE: 60
aacaactggg agtcagaggt aacgatgctg ccgctggggc tggggct                 47

<210> SEQ ID NO 61
<211> LENGTH: 21
<212> TYPE: DNA
<213> ORGANISM: Artificial Sequence
<220> FEATURE:
<223> OTHER INFORMATION: Primer

<400> SEQUENCE: 61
gatgttatgt cctatattca t                                             21

<210> SEQ ID NO 62
<211> LENGTH: 23
<212> TYPE: DNA
<213> ORGANISM: Artificial Sequence
<220> FEATURE:
<223> OTHER INFORMATION: Primer

<400> SEQUENCE: 62
tattgttaaa ttggtactgc gag                                           23

<210> SEQ ID NO 63
<211> LENGTH: 45
<212> TYPE: DNA
<213> ORGANISM: Artificial Sequence
<220> FEATURE:
<223> OTHER INFORMATION: Primer

<400> SEQUENCE: 63
```
ctcgcagtac caatttaaca atatgcgcca gcacccagaa ccccg    45

<210> SEQ ID NO 64
<211> LENGTH: 45
<212> TYPE: DNA
<213> ORGANISM: Artificial Sequence
<220> FEATURE:
<223> OTHER INFORMATION: Primer

<400> SEQUENCE: 64
ctatgaatat aggacataac atcggcggtc agggtgatgg tgcac    45

<210> SEQ ID NO 65
<211> LENGTH: 23
<212> TYPE: DNA
<213> ORGANISM: Artificial Sequence
<220> FEATURE:
<223> OTHER INFORMATION: Primer

<400> SEQUENCE: 65
gcataccaat atagagtatt tag    23

<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66
atatggatta ccaacagtta ataat    25

<210> SEQ ID NO 67
<211> LENGTH: 44
<212> TYPE: DNA
<213> ORGANISM: Artificial Sequence
<220> FEATURE:
<223> OTHER INFORMATION: Primer

<400> SEQUENCE: 67
tattaactgt tggtaatcca tatttcaagg tgcccaaggg cggc    44

<210> SEQ ID NO 68
<211> LENGTH: 46
<212> TYPE: DNA
<213> ORGANISM: Artificial Sequence
<220> FEATURE:
<223> OTHER INFORMATION: Primer

<400> SEQUENCE: 68
cctaaatact ctatattggt atgcgctcac cttgggcacg tcctgc    46

<210> SEQ ID NO 69
<211> LENGTH: 23
<212> TYPE: DNA
<213> ORGANISM: Artificial Sequence
<220> FEATURE:
<223> OTHER INFORMATION: Primer

<400> SEQUENCE: 69
ttgggctgtg ccccgccat cgg    23

<210> SEQ ID NO 70
<211> LENGTH: 25
<212> TYPE: DNA

```
<213> ORGANISM: Artificial Sequence
<220> FEATURE:
<223> OTHER INFORMATION: Primer

<400> SEQUENCE: 70
agcacaggcc cacactaaac gttgt                                        25

<210> SEQ ID NO 71
<211> LENGTH: 45
<212> TYPE: DNA
<213> ORGANISM: Artificial Sequence
<220> FEATURE:
<223> OTHER INFORMATION: Primer

<400> SEQUENCE: 71
caacgtttag tgtgggcctg tgctggcgtg gagatcggca ggggc                  45

<210> SEQ ID NO 72
<211> LENGTH: 47
<212> TYPE: DNA
<213> ORGANISM: Artificial Sequence
<220> FEATURE:
<223> OTHER INFORMATION: Primer

<400> SEQUENCE: 72
gccgatggcg ggggcacagc ccaagatgca cagctgggtc tgcttgt                47

<210> SEQ ID NO 73
<211> LENGTH: 23
<212> TYPE: DNA
<213> ORGANISM: Artificial Sequence
<220> FEATURE:
<223> OTHER INFORMATION: Primer

<400> SEQUENCE: 73
ggctctattg ttacctctga ctc                                          23

<210> SEQ ID NO 74
<211> LENGTH: 25
<212> TYPE: DNA
<213> ORGANISM: Artificial Sequence
<220> FEATURE:
<223> OTHER INFORMATION: Primer

<400> SEQUENCE: 74
aagctgctca cgccgtaagc aaaaa                                        25

<210> SEQ ID NO 75
<211> LENGTH: 44
<212> TYPE: DNA
<213> ORGANISM: Artificial Sequence
<220> FEATURE:
<223> OTHER INFORMATION: Primer

<400> SEQUENCE: 75
tgcttacggc gtgagcagct tttcgccagg cacttctgga acag                   44

<210> SEQ ID NO 76
<211> LENGTH: 47
<212> TYPE: DNA
<213> ORGANISM: Artificial Sequence
<220> FEATURE:
<223> OTHER INFORMATION: Primer

<400> SEQUENCE: 76
ggagtcagag gtaacaatag agccgctggg gctggggctg tacaggt                47
```

<210> SEQ ID NO 77
<211> LENGTH: 22
<212> TYPE: DNA
<213> ORGANISM: Artificial Sequence
<220> FEATURE:
<223> OTHER INFORMATION: Primer

<400> SEQUENCE: 77
cagtatagca gacatgttga gg                                              22

<210> SEQ ID NO 78
<211> LENGTH: 23
<212> TYPE: DNA
<213> ORGANISM: Artificial Sequence
<220> FEATURE:
<223> OTHER INFORMATION: Primer

<400> SEQUENCE: 78
tattgttaaa ttggtactgc gag                                             23

<210> SEQ ID NO 79
<211> LENGTH: 47
<212> TYPE: DNA
<213> ORGANISM: Artificial Sequence
<220> FEATURE:
<223> OTHER INFORMATION: Primer

<400> SEQUENCE: 79
actcgcagta ccaatttaac aatatgcgcc agcaccacca gcagcat                   47

<210> SEQ ID NO 80
<211> LENGTH: 44
<212> TYPE: DNA
<213> ORGANISM: Artificial Sequence
<220> FEATURE:
<223> OTHER INFORMATION: Primer

<400> SEQUENCE: 80
ttcctcaaca tgtctgctat actgcttgaa gctggtgggg gtgt                      44

<210> SEQ ID NO 81
<211> LENGTH: 23
<212> TYPE: DNA
<213> ORGANISM: Artificial Sequence
<220> FEATURE:
<223> OTHER INFORMATION: Primer

<400> SEQUENCE: 81
gcataccaat atagagtatt tag                                             23

<210> SEQ ID NO 82
<211> LENGTH: 26
<212> TYPE: DNA
<213> ORGANISM: Artificial Sequence
<220> FEATURE:
<223> OTHER INFORMATION: Primer

<400> SEQUENCE: 82
attaccaaca gttaataatc tagagc                                          26

<210> SEQ ID NO 83
<211> LENGTH: 46
<212> TYPE: DNA
<213> ORGANISM: Artificial Sequence
<220> FEATURE:

<223> OTHER INFORMATION: Primer

<400> SEQUENCE: 83
gattattaac tgttggtaat ccctacttca aggtgcccaa gggcgg                46

<210> SEQ ID NO 84
<211> LENGTH: 47
<212> TYPE: DNA
<213> ORGANISM: Artificial Sequence
<220> FEATURE:
<223> OTHER INFORMATION: Primer

<400> SEQUENCE: 84
atttgggtca ggtaactgca ccctgaacac cctgtactgg taggcgc               47

<210> SEQ ID NO 85
<211> LENGTH: 25
<212> TYPE: DNA
<213> ORGANISM: Artificial Sequence
<220> FEATURE:
<223> OTHER INFORMATION: Primer

<400> SEQUENCE: 85
ttatgtattt tgggctgtgc ccctg                                       25

<210> SEQ ID NO 86
<211> LENGTH: 23
<212> TYPE: DNA
<213> ORGANISM: Artificial Sequence
<220> FEATURE:
<223> OTHER INFORMATION: Primer

<400> SEQUENCE: 86
agcacaggcc cacactaaac gtt                                         23

<210> SEQ ID NO 87
<211> LENGTH: 47
<212> TYPE: DNA
<213> ORGANISM: Artificial Sequence
<220> FEATURE:
<223> OTHER INFORMATION: Primer

<400> SEQUENCE: 87
gtttagtgtg ggcctgtgct ggcgtggaga tcggcagggg ccagccc               47

<210> SEQ ID NO 88
<211> LENGTH: 47
<212> TYPE: DNA
<213> ORGANISM: Artificial Sequence
<220> FEATURE:
<223> OTHER INFORMATION: Primer

<400> SEQUENCE: 88 gcagggcac agcccaaaat acataactgg gtctgcttgt agtccac                47

<210> SEQ ID NO 89
<211> LENGTH: 25
<212> TYPE: DNA
<213> ORGANISM: Artificial Sequence
<220> FEATURE:
<223> OTHER INFORMATION: Primer

<400> SEQUENCE: 89
aaaaacacag ttttggaaga tggtg                                       25

```
<210> SEQ ID NO 90
<211> LENGTH: 23
<212> TYPE: DNA
<213> ORGANISM: Artificial Sequence
<220> FEATURE:
<223> OTHER INFORMATION: Primer

<400> SEQUENCE: 90
ggcacagccc aaaatacata act                                           23

<210> SEQ ID NO 91
<211> LENGTH: 44
<212> TYPE: DNA
<213> ORGANISM: Artificial Sequence
<220> FEATURE:
<223> OTHER INFORMATION: Primer

<400> SEQUENCE: 91
ttatgtattt tgggctgtgc ccccgccatc ggcgagcact ggac                    44

<210> SEQ ID NO 92
<211> LENGTH: 47
<212> TYPE: DNA
<213> ORGANISM: Artificial Sequence
<220> FEATURE:
<223> OTHER INFORMATION: Primer

<400> SEQUENCE: 92
accatcttcc aaaactgtgt ttttcagctc caggggggg cagtcgc                  47

<210> SEQ ID NO 93
<211> LENGTH: 22
<212> TYPE: DNA
<213> ORGANISM: Artificial Sequence
<220> FEATURE:
<223> OTHER INFORMATION: Primer

<400> SEQUENCE: 93
cagtatagca gacatgttga gg                                            22

<210> SEQ ID NO 94
<211> LENGTH: 26
<212> TYPE: DNA
<213> ORGANISM: Artificial Sequence
<220> FEATURE:
<223> OTHER INFORMATION: Primer

<400> SEQUENCE: 94
tattgttaaa ttggtactgc ggtggt                                        26

<210> SEQ ID NO 95
<211> LENGTH: 46
<212> TYPE: DNA
<213> ORGANISM: Artificial Sequence
<220> FEATURE:
<223> OTHER INFORMATION: Primer

<400> SEQUENCE: 95
cagtaccaat ttaacaatat gcgccagcac caccagcagc atcccc                  46

<210> SEQ ID NO 96
<211> LENGTH: 47
<212> TYPE: DNA
<213> ORGANISM: Artificial Sequence
<220> FEATURE:
<223> OTHER INFORMATION: Primer
```

<400> SEQUENCE: 96
atattcctca acatgtctgc tatactgctt gaagctggtg ggggtgt   47

<210> SEQ ID NO 97
<211> LENGTH: 22
<212> TYPE: DNA
<213> ORGANISM: Artificial Sequence
<220> FEATURE:
<223> OTHER INFORMATION: Primer

<400> SEQUENCE: 97
cagtatagca gacatgttga gg   22

<210> SEQ ID NO 98
<211> LENGTH: 23
<212> TYPE: DNA
<213> ORGANISM: Artificial Sequence
<220> FEATURE:
<223> OTHER INFORMATION: Primer

<400> SEQUENCE: 98
tattgttaaa ttggtactgc gag   23

<210> SEQ ID NO 99
<211> LENGTH: 47
<212> TYPE: DNA
<213> ORGANISM: Artificial Sequence
<220> FEATURE:
<223> OTHER INFORMATION: Primer

<400> SEQUENCE: 99
actcgcagta ccaatttaac aatatgcgcc agcaccacca gcagcat   47

<210> SEQ ID NO 100
<211> LENGTH: 44
<212> TYPE: DNA
<213> ORGANISM: Artificial Sequence
<220> FEATURE:
<223> OTHER INFORMATION: Primer

<400> SEQUENCE: 100
ttcctcaaca tgtctgctat actgcttgaa gctggtgggg gtgt   44

<210> SEQ ID NO 101
<211> LENGTH: 22
<212> TYPE: DNA
<213> ORGANISM: Artificial Sequence
<220> FEATURE:
<223> OTHER INFORMATION: Primer

<400> SEQUENCE: 101
cagtatagca gacatgttga gg   22

<210> SEQ ID NO 102
<211> LENGTH: 23
<212> TYPE: DNA
<213> ORGANISM: Artificial Sequence
<220> FEATURE:
<223> OTHER INFORMATION: Primer

<400> SEQUENCE: 102
tattgttaaa ttggtactgc gag   23

<210> SEQ ID NO 103
<211> LENGTH: 47

```
<212> TYPE: DNA
<213> ORGANISM: Artificial Sequence
<220> FEATURE:
<223> OTHER INFORMATION: Primer

<400> SEQUENCE: 103
actcgcagta ccaatttaac aatatgcgcc agcaccacca gcagcat                    47

<210> SEQ ID NO 104
<211> LENGTH: 44
<212> TYPE: DNA
<213> ORGANISM: Artificial Sequence
<220> FEATURE:
<223> OTHER INFORMATION: Primer

<400> SEQUENCE: 104
ttcctcaaca tgtctgctat actgcttgaa gctggtgggg gtgt                       44

<210> SEQ ID NO 105
<211> LENGTH: 23
<212> TYPE: DNA
<213> ORGANISM: Artificial Sequence
<220> FEATURE:
<223> OTHER INFORMATION: Primer

<400> SEQUENCE: 105
cagttacctg acccaaataa att                                              23

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
agtcacgtaa tcatcggtat                                                  20

<210> SEQ ID NO 107
<211> LENGTH: 44
<212> TYPE: DNA
<213> ORGANISM: Artificial Sequence
<220> FEATURE:
<223> OTHER INFORMATION: Primer

<400> SEQUENCE: 107
taaataccga tgattacgtg actaggacca gcatcttcta ccac                       44

<210> SEQ ID NO 108
<211> LENGTH: 45
<212> TYPE: DNA
<213> ORGANISM: Artificial Sequence
<220> FEATURE:
<223> OTHER INFORMATION: Primer

<400> SEQUENCE: 108
aatttatttg ggtcaggtaa ctgcaccctg aacaccctgt actgg                      45

<210> SEQ ID NO 109
<211> LENGTH: 9
<212> TYPE: PRT
<213> ORGANISM: Human papillomavirus type 45

<400> SEQUENCE: 109

Asn Pro Val Pro Ser Thr Tyr Asp Pro
1               5
```

<210> SEQ ID NO 110
<211> LENGTH: 22
<212> TYPE: PRT
<213> ORGANISM: Human papillomavirus type 59

<400> SEQUENCE: 110

Leu Tyr Asn Lys Leu Asp Asp Thr Glu Asn Ser His Val Ala Ser Ala
1               5                   10                  15

Val Asp Thr Lys Asp Thr
            20

<210> SEQ ID NO 111
<211> LENGTH: 27
<212> TYPE: PRT
<213> ORGANISM: Human papillomavirus type 59

<400> SEQUENCE: 111

Ser Gly Thr Met Gly Asp Gln Leu Pro Glu Ser Leu Tyr Ile Lys Gly
1               5                   10                  15

Thr Asp Ile Arg Ala Asn Pro Gly Ser Tyr Leu
            20                  25

<210> SEQ ID NO 112
<211> LENGTH: 12
<212> TYPE: PRT
<213> ORGANISM: Human papillomavirus type 59

<400> SEQUENCE: 112

Thr Lys Gly Thr Ala Cys Lys Pro Thr Thr Val Val
1               5                   10

<210> SEQ ID NO 113
<211> LENGTH: 504
<212> TYPE: PRT
<213> ORGANISM: Human papillomavirus type 18

<400> SEQUENCE: 113

Met Arg Pro Ser Asp Asn Thr Val Tyr Leu Pro Pro Ser Val Ala
1               5                   10                  15

Arg Val Val Asn Thr Asp Asp Tyr Val Thr Arg Thr Ser Ile Phe Tyr
            20                  25                  30

His Ala Gly Ser Ser Arg Leu Leu Thr Val Gly Asn Pro Tyr Phe Arg
        35                  40                  45

Val Pro Ala Gly Gly Gly Asn Lys Gln Asp Ile Pro Lys Val Ser Ala
    50                  55                  60

Tyr Gln Tyr Arg Val Phe Arg Val Gln Leu Pro Asp Pro Asn Lys Phe
65                  70                  75                  80

Gly Leu Pro Asp Thr Ser Ile Tyr Asn Pro Glu Thr Gln Arg Leu Val
                85                  90                  95

Trp Ala Cys Ala Gly Val Glu Ile Gly Arg Gly Gln Pro Leu Gly Val
            100                 105                 110

Gly Leu Ser Gly His Pro Phe Tyr Asn Lys Leu Asp Asp Thr Glu Ser
        115                 120                 125

Ser His Ala Ala Thr Ser Asn Val Ser Glu Asp Val Arg Asp Asn Val
    130                 135                 140

Ser Val Asp Tyr Lys Gln Thr Gln Leu Cys Ile Leu Gly Cys Ala Pro
145                 150                 155                 160

Ala Ile Gly Glu His Trp Ala Lys Gly Thr Ala Cys Lys Ser Arg Pro

```
                165                 170                 175
Leu Ser Gln Gly Asp Cys Pro Pro Leu Glu Leu Lys Asn Thr Val Leu
            180                 185                 190

Glu Asp Gly Asp Met Val Asp Thr Gly Tyr Gly Ala Met Asp Phe Ser
            195                 200                 205

Thr Leu Gln Asp Thr Lys Cys Glu Val Pro Leu Asp Ile Cys Gln Ser
            210                 215                 220

Ile Cys Lys Tyr Pro Asp Tyr Leu Gln Met Ser Ala Asp Pro Tyr Gly
225                 230                 235                 240

Asp Ser Met Phe Phe Cys Leu Arg Arg Glu Gln Leu Phe Ala Arg His
                245                 250                 255

Phe Trp Asn Arg Ala Gly Thr Met Gly Asp Thr Val Pro Gln Ser Leu
            260                 265                 270

Tyr Ile Lys Gly Thr Gly Met Arg Ala Ser Pro Gly Ser Cys Val Tyr
            275                 280                 285

Ser Pro Ser Pro Ser Gly Ser Ile Val Thr Ser Asp Ser Gln Leu Phe
            290                 295                 300

Asn Lys Pro Tyr Trp Leu His Lys Ala Gln Gly His Asn Asn Gly Val
305                 310                 315                 320

Cys Trp His Asn Gln Leu Phe Val Thr Val Val Asp Thr Thr Arg Ser
                325                 330                 335

Thr Asn Leu Thr Ile Cys Ala Ser Thr Gln Ser Pro Val Pro Gly Gln
            340                 345                 350

Tyr Asp Ala Thr Lys Phe Lys Gln Tyr Ser Arg His Val Glu Glu Tyr
            355                 360                 365

Asp Leu Gln Phe Ile Phe Gln Leu Cys Thr Ile Thr Leu Thr Ala Asp
            370                 375                 380

Val Met Ser Tyr Ile His Ser Met Asn Ser Ser Ile Leu Glu Asp Trp
385                 390                 395                 400

Asn Phe Gly Val Pro Pro Pro Thr Thr Ser Leu Val Asp Thr Tyr
                405                 410                 415

Arg Phe Val Gln Ser Val Ala Ile Ala Cys Gln Lys Asp Ala Ala Pro
            420                 425                 430

Ala Glu Asn Lys Asp Pro Tyr Asp Lys Leu Lys Phe Trp Asn Val Asp
            435                 440                 445

Leu Lys Glu Lys Phe Ser Leu Asp Leu Asp Gln Tyr Pro Leu Gly Arg
            450                 455                 460

Lys Phe Leu Val Gln Ala Gly Leu Arg Arg Lys Pro Thr Ile Gly Pro
465                 470                 475                 480

Arg Lys Arg Ser Ala Pro Ser Ala Thr Thr Ala Ser Lys Pro Ala Lys
                485                 490                 495

Arg Val Arg Val Arg Ala Arg Lys
            500

<210> SEQ ID NO 114
<211> LENGTH: 1515
<212> TYPE: DNA
<213> ORGANISM: Human papillomavirus type 18

<400> SEQUENCE: 114
atgcggccta gtgacaatac cgtatatctt ccacctcctt ctgtggcaag agttgtaaat     60
accgatgatt acgtgactcg cacaagcata ttttatcatg ctggcagctc tagattatta    120
actgttggta atccatattt tagggttcct gcaggtggtg gcaataagca ggatattcct    180
```

```
aaggtttctg cataccaata tagagtattt agggtgcagt tacctgaccc aaataaattt      240
ggtttacctg atactagtat tttataatcct gaaacacaac gtttagtgtg ggcctgtgct     300
ggagtggaaa ttggccgtgg tcagcctta ggtgttggcc ttagtgggca tccattttat       360
aataaattag atgacactga agttcccat gccgccacgt ctaatgtttc tgaggacgtt       420
agggacaatg tgtctgtaga ttataagcag acacagttat gtattttggg ctgtgcccct     480
gctattgggg aacactgggc taaaggcact gcttgtaaat cgcgtccttt atcacagggc      540
gattgccccc ctttagaact taaaaacaca gttttggaag atggtgatat ggtagatact     600
ggatatggtg ccatggactt tagtacattg caagatacta atgtgaggt accattggat      660
atttgtcagt ctatttgtaa atatcctgat tatttacaaa tgtctgcaga tccttatggg     720
gattccatgt ttttttgctt acggcgtgag cagcttttg ctaggcattt ttggaataga      780
gcaggtacta tgggtgacac tgtgcctcaa tccttatata ttaaaggcac aggtatgcgt     840
gcttcacctg gcagctgtgt gtattctccc tctccaagtg gctctattgt tacctctgac    900
tcccagttgt ttaataaacc atattggtta cataaggcac agggtcataa caatggtgtt     960
tgctggcata atcaattatt tgttactgtg gtagatacca ctcgcagtac caatttaaca   1020
atatgtgctt ctacacagtc tcctgtacct gggcaatatg atgctaccaa atttaagcag   1080
tatagcagac atgttgagga atatgattg cagtttatttt ttcagttgtg tactattact    1140
ttaactgcag atgttatgtc ctatattcat agtatgaata gcagtatttt agaggattgg   1200
aactttggtg ttccccccccc gccaactact agtttggtgg atacatatcg ttttgtacaa   1260
tctgttgcta ttgcctgtca aaaggatgct gcaccggctg aaaataagga tccctatgat   1320
aagttaaagt tttggaatgt ggatttaaag gaaaagtttt ctttagactt agatcaatat   1380
cccccttggac gtaaattttt ggttcaggct ggattgcgtc gcaagcccac cataggccct   1440
cgcaaacgtt ctgctccatc tgccactacg gcttctaaac ctgccaagcg tgtgcgtgta   1500
cgtgccagga agtaa                                                    1515

<210> SEQ ID NO 115
<211> LENGTH: 513
<212> TYPE: PRT
<213> ORGANISM: Human papillomavirus type 45

<400> SEQUENCE: 115

Met Ala Leu Trp Arg Pro Ser Asp Ser Thr Val Tyr Leu Pro Pro Pro
1               5                   10                  15

Ser Val Ala Arg Val Val Ser Thr Asp Asp Tyr Val Ser Arg Thr Ser
            20                  25                  30

Ile Phe Tyr His Ala Gly Ser Ser Arg Leu Leu Thr Val Gly Asn Pro
        35                  40                  45

Tyr Phe Arg Val Val Pro Asn Gly Ala Gly Asn Lys Gln Ala Val Pro
    50                  55                  60

Lys Val Ser Ala Tyr Gln Tyr Arg Val Phe Arg Val Ala Leu Pro Asp
65                  70                  75                  80

Pro Asn Lys Phe Gly Leu Pro Asp Ser Thr Ile Tyr Asn Pro Glu Thr
                85                  90                  95

Gln Arg Leu Val Trp Ala Cys Val Gly Met Glu Ile Gly Arg Gly Gln
            100                 105                 110

Pro Leu Gly Ile Gly Leu Ser Gly His Pro Phe Tyr Asn Lys Leu Asp
        115                 120                 125

Asp Thr Glu Ser Ala His Ala Ala Thr Ala Val Ile Thr Gln Asp Val
```

```
            130                 135                 140
Arg Asp Asn Val Ser Val Asp Tyr Lys Gln Thr Gln Leu Cys Ile Leu
145                 150                 155                 160

Gly Cys Val Pro Ala Ile Gly Glu His Trp Ala Lys Gly Thr Leu Cys
                165                 170                 175

Lys Pro Ala Gln Leu Gln Pro Gly Asp Cys Pro Pro Leu Glu Leu Lys
            180                 185                 190

Asn Thr Ile Ile Glu Asp Gly Asp Met Val Asp Thr Gly Tyr Gly Ala
                195                 200                 205

Met Asp Phe Ser Thr Leu Gln Asp Thr Lys Cys Glu Val Pro Leu Asp
210                 215                 220

Ile Cys Gln Ser Ile Cys Lys Tyr Pro Asp Tyr Leu Gln Met Ser Ala
225                 230                 235                 240

Asp Pro Tyr Gly Asp Ser Met Phe Phe Cys Leu Arg Arg Glu Gln Leu
                245                 250                 255

Phe Ala Arg His Phe Trp Asn Arg Ala Gly Val Met Gly Asp Thr Val
                260                 265                 270

Pro Thr Asp Leu Tyr Ile Lys Gly Thr Ser Ala Asn Met Arg Glu Thr
            275                 280                 285

Pro Gly Ser Cys Val Tyr Ser Pro Ser Pro Ser Gly Ser Ile Ile Thr
            290                 295                 300

Ser Asp Ser Gln Leu Phe Asn Lys Pro Tyr Trp Leu His Lys Ala Gln
305                 310                 315                 320

Gly His Asn Asn Gly Ile Cys Trp His Asn Gln Leu Phe Val Thr Val
                325                 330                 335

Val Asp Thr Thr Arg Ser Thr Asn Leu Thr Leu Cys Ala Ser Thr Gln
                340                 345                 350

Asn Pro Val Pro Ser Thr Tyr Asp Pro Thr Lys Phe Lys Gln Tyr Ser
            355                 360                 365

Arg His Val Glu Glu Tyr Asp Leu Gln Phe Ile Phe Gln Leu Cys Thr
            370                 375                 380

Ile Thr Leu Thr Ala Glu Val Met Ser Tyr Ile His Ser Met Asn Ser
385                 390                 395                 400

Ser Ile Leu Glu Asn Trp Asn Phe Gly Val Pro Pro Pro Pro Thr Thr
                405                 410                 415

Ser Leu Val Asp Thr Tyr Arg Phe Val Gln Ser Val Ala Val Thr Cys
            420                 425                 430

Gln Lys Asp Thr Thr Pro Pro Glu Lys Gln Asp Pro Tyr Asp Lys Leu
            435                 440                 445

Lys Phe Trp Thr Val Asp Leu Lys Glu Lys Phe Ser Ser Asp Leu Asp
450                 455                 460

Gln Tyr Pro Leu Gly Arg Lys Phe Leu Val Gln Ala Gly Leu Arg Arg
465                 470                 475                 480

Arg Pro Thr Ile Gly Pro Arg Lys Arg Pro Ala Ala Ser Thr Ser Thr
                485                 490                 495

Ala Ser Thr Ala Ser Arg Pro Ala Lys Arg Val Arg Ile Arg Ser Lys
            500                 505                 510

Lys

<210> SEQ ID NO 116
<211> LENGTH: 1542
<212> TYPE: DNA
<213> ORGANISM: Human papillomavirus type 45
```

```
<400> SEQUENCE: 116
atggccctgt ggaggcccag cgacagcacc gtgtacctgc cccccccag cgtggccagg      60
gtggtgagca ccgacgacta cgtgagcagg accagcatct tctaccacgc cggcagcagc    120
aggctgctga ccgtgggcaa ccctacttc agggtggtgc caacggcgc cggcaacaag     180
caggccgtgc ccaaggtgag cgcctaccag tacagggtgt tcagggtggc cctgcccgac    240
cccaacaagt tcggcctgcc cgacagcacc atctacaacc ccgagaccca gaggctggtg    300
tgggcctgcg tgggcatgga gatcggcagg ggccagcccc tgggcatcgg cctgagcggc    360
caccccttct acaacaagct ggacgacacc gagagcgccc acgccgccac cgccgtgatc    420
acccaggacg tgagggacaa cgtgagcgtg gactacaagc agacccagct gtgcatcctg    480
ggctgcgtgc ccgccatcgg cgagcactgg gccaagggca ccctgtgcaa gcccgcccag    540
ctgcagcccg gcgactgccc ccccctggag ctgaagaaca ccatcatcga ggacggcgac    600
atggtggaca ccggctacgg cgccatggac ttcagcaccc tgcaggacac caagtgcgag    660
gtgccctg acatctgcca gagcatctgc aagtaccccg actacctgca gatgagcgcc     720
gaccctacg cgacagcat gttcttctgc ctgaggaggg agcagctgtt cgccaggcac      780
ttctggaaca gggccggcgt gatgggcgac accgtgccca ccgacctgta catcaagggc    840
accagcgcca acatgaggga caccccggc agctgcgtgt acagcccag cccagcggc       900
agcatcatca ccagcgacag ccagctgttc aacaagccct actggctgca caaggcccag    960
ggccacaaca cggcatctg ctggcacaac cagctgttcg tgaccgtggt ggacaccacc    1020
aggagcacca acctgaccct gtgcgccagc acccagaacc ccgtgccag cacctacgac    1080
cccaccaagt tcaagcagta cagcaggcac gtggaggagt acgacctgca gttcatcttc    1140
cagctgtgca ccatcaccct gaccgccgag gtgatgagct acatccacag catgaacagc    1200
agcatcctgg agaactggaa cttcggcgtg ccccccccc ccaccaccag cctggtggac    1260
acctacaggt tcgtgcagag cgtggccgtg acctgccaga aggacaccac ccccccgag    1320
aagcaggacc cctacgacaa gctgaagttc tggaccgtgg acctgaagga agttcagc    1380
agcgacctgg accagtaccc cctgggcagg aagttcctgg tgcaggccgg cctgaggagg    1440
aggcccacca tcggccccag gaagaggccc gccgccagca ccagcaccgc cagcaccgcc    1500
agcaggcccg ccaagagggt gaggatcagg agcaagaagt ga                      1542
```